United States Patent
Lee et al.

(10) Patent No.: US 9,359,346 B2
(45) Date of Patent: Jun. 7, 2016

(54) BENZAMIDE DERIVATIVE AND USE THEREOF

(71) Applicant: VIVOZON, INC., Seoul (KR)

(72) Inventors: Doo Hyun Lee, Seoul (KR); Myung Soo Ham, Sejong-si (KR); Ji-Hyun Lee, Seoul (KR)

(73) Assignee: VIVOZON, INC., Seoul (KR)

( * ) Notice: Subject to any disclaimer, the term of this patent is extended or adjusted under 35 U.S.C. 154(b) by 0 days.

(21) Appl. No.: 14/361,638

(22) PCT Filed: Nov. 29, 2012

(86) PCT No.: PCT/KR2012/010257
§ 371 (c)(1),
(2) Date: May 29, 2014

(87) PCT Pub. No.: WO2013/081400
PCT Pub. Date: Jun. 6, 2013

(65) Prior Publication Data
US 2014/0336378 A1    Nov. 13, 2014

(30) Foreign Application Priority Data

Nov. 29, 2011 (KR) .................... 10-2011-0125851
Nov. 29, 2012 (KR) .................... 10-2012-0136814

(51) Int. Cl.

| | |
|---|---|
| *A61K 31/47* | (2006.01) |
| *C07D 295/12* | (2006.01) |
| *C07D 217/22* | (2006.01) |
| *C07D 211/26* | (2006.01) |
| *C07D 413/04* | (2006.01) |
| *C07D 211/58* | (2006.01) |
| *C07D 207/09* | (2006.01) |
| *C07D 455/02* | (2006.01) |
| *C07D 285/12* | (2006.01) |
| *C07D 405/04* | (2006.01) |
| *C07D 211/44* | (2006.01) |
| *C07D 207/14* | (2006.01) |
| *C07D 453/02* | (2006.01) |
| *C07D 309/14* | (2006.01) |
| *C07D 215/38* | (2006.01) |
| *C07C 235/50* | (2006.01) |

(Continued)

(52) U.S. Cl.
CPC .............. *C07D 453/02* (2013.01); *A61K 31/47* (2013.01); *C07C 235/50* (2013.01); *C07C 235/54* (2013.01); *C07D 207/09* (2013.01); *C07D 207/14* (2013.01); *C07D 211/26* (2013.01); *C07D 211/34* (2013.01); *C07D 211/44* (2013.01); *C07D 211/58* (2013.01); *C07D 215/38* (2013.01); *C07D 217/22* (2013.01); *C07D 285/12* (2013.01); *C07D 295/12* (2013.01); *C07D 295/15* (2013.01); *C07D 309/14* (2013.01); *C07D 405/04* (2013.01); *C07D 413/04* (2013.01); *C07D 455/02* (2013.01)

(58) Field of Classification Search
CPC .. C07D 453/02; C07D 295/15; C07D 211/34; C07D 471/08; C07D 215/16; C07D 295/12; C07D 215/38; C07D 413/04; C07D 211/58; C07D 207/09; C07D 455/02; C07D 309/14; C07D 217/22; C07D 285/12; C07D 405/04; C07D 211/26; C07D 211/44; C07D 207/14; C07C 235/54; C07C 235/50; A61K 31/47
See application file for complete search history.

(56) References Cited

U.S. PATENT DOCUMENTS

| | | |
|---|---|---|
| 3,963,745 A | 6/1976 | Cale, Jr. et al. |
| 4,035,373 A | 7/1977 | Roll |

(Continued)

FOREIGN PATENT DOCUMENTS

| | | |
|---|---|---|
| FR | 2264530 A1 | 3/1975 |
| JP | 2005112804 A | 4/2005 |

(Continued)

OTHER PUBLICATIONS

Khurana, N., "Pharmacological Evaluation of Rhizomes of Acorus Calamus for Analgesic Activity." International Journal of Pharmacy and Pharmaceutical Sciences 7.4 (2015) p. 411-413.*

(Continued)

*Primary Examiner* — Samantha Shterengarts
*Assistant Examiner* — Matt Mauro
(74) *Attorney, Agent, or Firm* — Novick, Kim & Lee, PLLC; Jae Youn Kim

(57) ABSTRACT

Disclosed are a novel benzamide derivative and pharmaceutical use thereof, and more particularly, a novel benzamide derivative having a structure of Formula 1 or pharmaceutically acceptable salts thereof, and a composition for prevention or treatment of pain or itching including the above material. The novel benzamide derivative and pharmaceutically acceptable salt thereof according to the present invention exhibit excellent pain-suppressive effect and, in particular, pain-suppressive effect in not only a neuropathic animal model but also other models such as a formalin model, and therefore, may be used in suppression of different pains such as nociceptive pain, chronic pain, etc. Further, since it was demonstrated that the present invention displays anti-pruritic efficacy even in an itching model, to which a mechanism and treatment concept established with respect to pain is applied, the present invention may also be effectively used in radical treatment of atopic dermatitis by applying the inventive product to an anti-pruritic composition in order to suppress an initial itching stage and treat symptoms thereof, thus preventing skin damage or inflammation after the scratching stage.

5 Claims, 28 Drawing Sheets

(51) Int. Cl.
  *C07C 235/54* (2006.01)
  *C07D 211/34* (2006.01)
  *C07D 295/15* (2006.01)

(56) References Cited

U.S. PATENT DOCUMENTS

| | | | |
|---|---|---|---|
| 5,237,066 | A | 8/1993 | Dorme et al. |
| 5,238,962 | A | 8/1993 | Da Prada et al. |
| 5,728,835 | A | 3/1998 | Aoki et al. |
| 2006/0264441 | A1 | 11/2006 | Dargazanli et al. |

FOREIGN PATENT DOCUMENTS

| | | | |
|---|---|---|---|
| KR | 10-2006-0087598 A | 8/2006 | |
| WO | 02/101007 A2 | 12/2002 | |
| WO | 03-010132 A1 | 2/2003 | |

OTHER PUBLICATIONS

Recommendation, J. P. C. "Bulletin 149 Extended-release tapentadol (Palexia® SR) for severe chronic pain." Update (2012) p. 1-14.*
Glowacki, D., "Effective Pain Management and Improvements in Patients' Outcome and Satisfaction." 35(3) (2015) p. 33-43.*
WebMD Pain Management 2015; accessed online Aug. 12, 2015 @htt.p://www.webmd.com/pain-managemeny/guide/pain-management-symptoms-types p. 1-2.*
Caulfield, Wilson L. et al. "The First Potent and Selective Inhibitors of the Glycine Transporter Type 2" Journal of Medicinal Chemistry, 2011, vol. 44, No. 17, pp. 2679-2682 (Aug. 16, 2011).
Tian, Haibin et al. "Radiosynthesis of 3-(3-[18F]fluoropropoxy)-4-(benzyloxy)-N-[(1-dimethylaminocyclopenty1)methyl]-5-methoxybenzamide, a potential PET radiotracer for the glycine transporter GlyT-2" Journal of Labelled Compounds and Radiopharmaceuticals, 2006, vol. 49, pp. 1247-1258 (2006).
Arora, Jalaj et al. "N-[(3S)-1-Benzylpyrrolidin-3-yl]-(2-thienyl)benzamides: Human dopamine D4 ligands with high affinity for the 5-HT2A receptor" Bioorganic & Medicinal Chemistry Letters, 2005, vol. 15, pp. 5253-5256 (Sep. 15, 2005).
Oku, Hisae et al. "Antipruritic Effects if the Fruits of Chaenomeles sinesis" Biol. Pharm. Bull., 2003, vol. 26, No. 7, pp. 1031-1034 (Jul. 2003).
Terriere, D. et al. "Radiosynthesis of a New Radiobrominated Ligand for 5HT2A Receptors, a Potential Tracer for PET" Journal of Labelled Compounds and Radiopharmaceuticals, 1996, vol. 39, No. 1, pp. 11-19.
Catafau, Ana M. et al. "Characterization of the SPECT 5-HT2A Receptor Ligand 123I-R91150 in Healthy Volunteers: Part 2-Ketanserin Displacement" The Journal of Nuclear Medicine, 2006, vol. 47, No. 6, pp. 929-937 (Jun. 2006).
Rose, M. A. et al. "Gabapentin: pharmacology and its use in pain management" Anaesthesia, 2002, vol. 57, pp. 451-462.
Yesudian, P. D. et al. "Efficacy of Gabapentin in the Management of Pruritus of Unknown Origin" Arch. Dermatol., 2005, vol. 141, pp. 1507-1509 (Dec. 2005).
AstraZeneca "Study to Evaluate the Efficacy, Safety, Tolerability and Pharmacokinetics of AZD1386 in Patients with Osteoarthritis(OA) of the Knee(OA19)" ClinicalTrials.gov, Identifier No. NCT00878501.
Gavva, Narender R. et al. "Pharmacological blockade of the vanilloid receptor TRPV1 elicits marked hyperthermia in humans" Pain 136, 2008, pp. 202-210.
Lehto, S.G. et al. "Antihyperalgesic effects of (R,E)-N-(2-hydroxy-2,3-dihydro-1H-inden-4-yl)-3-(2-(piperidin-1-yl)-4-(trifluoromethyl)phenyl)-acrylamide (AMG8562), a novel transient receptor potential vanilloid type 1 modulator that does not cause hyperthermia in rats" J. Pharmacol. Exp. Ther. vol. 326, No. 1, pp. 218-229 (2008).
Hill, R. "NK1 (substance P) receptor antagonists—why are they not analgesic in humans?" Trends in Pharmacol. Sci., vol. 21, pp. 244-246 (Jul. 2000).

Rahn, Elizabeth J. et al. "Cannabinoids as pharmacotherapies for neuropathic pain: from the bench to the bedside" Neurotherapeutics, vol. 6, pp. 713-737 (Oct. 2009).
Pang, Min-Hee et al. "Foundation review: A series of case studies: practical methodology for identifying antinociceptive multi-target drugs" Drug Discovery Today, vol. 17, No. 9/10, pp. 425-434 (May 2012).
Bundgaard, Hans. "Means to Enhance Penetration—Prodrugs as a means to improve the delivery of peptide drugs" Advanced Drug Delivery Reviews, vol. 8, pp. 1-38 (1992).
Nielsen, Niels Mork et al. "Glycolamide Esters as Biolabile Prodrugs of Carboxylic Acid Agents: Synthesis, Stability, Bioconversion, and Physicochemical Properties" Journal of Pharmaceutical Sciences, vol. 77, No. 4, pp. 285-298 (Apr. 1988).
Kakeya Nobuharu et al. "Studies on Prodrugs of Cephalosporins. I. Synthesis and Biological Properties of Glycyloxybenzoyloxymethyl and Glycylaminobenzoyloxymethyl Esters of 7b-[2-(2-Aminothiazol-4-yl)-(Z)-2-methoxyiminoacetamido]-3-methyl-3-cephem-4-carboxylic Acid" Chem. Pharm. Bull., vol. 32, No. 2, pp. 692-698 (1984).
Kim, Sun Ho et al. "An experimental model for peripheral neuropathy produced by segmental spinal nerve ligation in the rat" Pain, vol. 50, pp. 355-363 (1992).
Chaplan, S. R. et al. "Quantitaive assessment of tactile allodynia in the rat paw" J. Neurosci. Methods vol. 53, pp. 55-63 (1994).
Yang, D. et al., "Serotoninergic properties of new conformationally restricted benzamides" European Journal of Medicinal Chemistry, 1996, vol. 31, pp. 231-239.
"AGN-PC-0N5VS0; 4-amino-5chloro-N[[4-(dimenthylamino)oxan-4-yl]methyl]-2-methoxybenzamide . . . ", Open Chemistry Database, U.S. National Library of Medicine, National Center for Biotechnology Information, National Institute of Health, Compound Summary for CID 10521221 (Oct. 25, 2006).
"AGN-PC-01N6VN; N-(oxan-4-ylmethyl) benzamide; SCHEMBL 15389532; AKOS011611447; (tetrahydro-pyran-4-ylmethyl)-benzamide . . . ", Open Chemistry Database, U.S. National Library of Medicine, National Center for Biotechnology Information, National Institute of Health, Compound Summary for CID 17952017 (Dec. 4, 2007).
"AGN-PC-0OOGT9; Benzamide, 4-butoxy-N-[(tetrahydro-2,2-dimethyl-2H-pyran-4-yl)methyl]-;96822-02-5 . . . ", Open Chemistry Database, U.S. National Library of Medicine, National Center for Biotechnology Information, National Institute of Health, Compound Summary for CID 13380937 (Feb. 8, 2007).
Labanauskas, L et al., "Nucleophilic substitution of the acetoxy group in 3-methylbenzoylaminomethyl acetate", Russian Chemical Bulletin, Aug. 2006, vol. 60, No. 8, pp. 1672-1676.
Collin, Sonia et al. "QSAR of nortropane-substituted benzamindes: use of lipophilic (RP-HPLA) and electronic (1H NMR) parameters", Eurpoean Journal of Medicinal Chemistry, 1989, pp. 163-169, vol. 24.
Hoegberg, Thomas et al., "Potential Antipsychotic Agents. 7. Synthesis and Antidopaminergic Properties of the Atypical Highly Potent (S)-5-Bromo-2,3-dimethoxy-N-[(1-ethyl-2-pyrrolidinyl)methyl]benzamide and Related Compounds. A Comparative Study", Journal of Medicinal Chemistry, Jan. 16, 1990, vol. 33, pp. 2305-2309.
Leppard, D. et al., "Methylation of 2-Acylamido-1,3,4-thiadiazoles. An Infrared, Proton and Carbon Nmr Study", CIBA-GEIGY Photochemic AG, Jan. 21, 1980, pp. 1469-1472, vol. 17 No. 7.
Maris Vilums et al., "Understanding of Molecular Substructures that Contribute to hERG K+ Chanel Blockades: Synthesis and Biological Evaluation of E-4031 Analogues", ChemMedChem Wiley Online Library, 2012, vol. 7 No. 1, pp. 107-113.
Moore, Kevin W. et al., "4-N-linked-Heterocyclic Piperidine Derivatives with High Affinity and Selectivity for Human Dopamine D4 Receptors", Biorganic and Medicinal Chemistry Letters, Mar. 29, 1999, vol. 9, pp. 1285-1290.
Cromwell, Norman H. et al., "Amino Ketones. II. The Synthesis of α,β-Diamines from α-Amino Ketones", Contribution from the Avery Laboratory of Chemistry of the University of Nebraska, Jan. 6, 1944, pp. 870-871, vol. 66 No. 6.

(56) References Cited

OTHER PUBLICATIONS

Celanire, Sylvain et al., "Discovery of a New Class of Non-imidazole Oxazoline-Based Histamine H3 Receptor (H3R) Inverse Agonists", ChemMedChem, 2009, pp. 1063-1068, vol. 4.

Webster, Scott P. et al. "Discovery and biological evaluation of adamantyl amide 11 β-HSD1 inhibitors", Bioorganic and Medicinal Chemistry Letters, Feb. 25, 2007, pp. 1469-1472, vol. 17, pp. 2838-2843.

Yung, D.K. et al., "Potential Antiarrhythmis Agents I Synthesis and Pharmacological Evaluation of Some Piperazine and Ethylenediamine Analogs of Procaine Amine", Journal of Pharmaceutical Sciences, Dec. 1968, pp. 2073-2080, vol. 57 No. 12.

Zhang, Zhongxing et al., "Selective Monoacylation of Symmetrical Siamines vie Prior Complexation with Boron", Bristol-Meyers Squibb Pharmaceutical Research Institute, Organic Letters, Jun. 12, 2003, vol. 5 No. 19, pp. 3399-3402.

Gou, Fa-Rong et al. "Palladium-Catalyzed Aryl C-H Bonds Activation/Acetxylation Utilizing a Bidentate System", Organic Letters, Oct. 29, 2009, vol. 11, No. 24, pp. 5726-5729.

"CHEMBL37544; SCHEMBL3366793; (exo) 4-Amino-5-chloro-N-(hexahydro-pyrrolizin-1-ylmethyl(-2-methoxy-benzamide; BDBM50005837; PDSP1_000059 . . . " Open Chemistry Database U.S. National Library of Medicine, National Center for Biotechnology Information, National Institute of Health, Compound Summary for CID 15095972 (Feb. 9, 2007).

Suzuki, Takeshi et al. "Novel 5-Hydoxytryptamine 4 (5-HT4) Receptor Agonist. Synthesis and Gastroprokinetic Activity of 4-Amino-N-[2-(1-aminocycloalkan-1yl)ethyl]-5-chloro-2-methoxybenzamides", Chamical Pharmaceutical Bulletin, Apr. 27, 1998, vol. 46, No. 7, pp. 1116-1124.

Schoenenberger, H. et al., "Synthesis and Local Anesthetic Action of N-Piperidinomethyl-4-alkoxybenzamides", Archiv der Pharmazie, Dec. 1969, pp. 798-804, vol. 303 No. 10.

"AKOS001397048", Open Chemistry Database U.S. National Library of Medicine, National Center for Biotechnology Information, National Institute of Health, Compound Summary for CID 24633038 (Feb. 29, 2008).

* cited by examiner

BENZAMIDE DERIVATIVE AND USE THEREOF

ACKNOWLEDGMENT

This research was supported by a grant of the Korea Health Technology R&D Project through the Korea Health Industry Development Institute (KHIDI), funded by the Ministry of Health & Welfare, Republic of Korea (grant number: HI13C0912).

TECHNICAL FIELD

The present invention relates to a novel benzamide derivative and pharmaceutical use thereof, and more particularly, to a novel benzamide derivative having a structure of Formula 1 or pharmaceutically acceptable salts thereof, and a composition for prevention or treatment of pain or itching including the above material.

BACKGROUND ART

Although a variety of neuropathological studies on pain have been actively conducted and pain treatment methods have been extensively studied, pain treatment still mostly depends upon use of narcotic analgesics already developed in the art.

Currently developed pain relievers affect peripheral or central nerves to decrease pain, and may typically include non-steroidal anti-inflammatory drugs (NSAID), COX-2 inhibitors, opiates and morphinomimetics, flupirtin, etc.

Representative examples of NSAID are paracetamol, and acetaminophen, which are presumed to affect the central nervous system and to inhibit cyclooxygenase, thus suppressing production of prostaglandin, and therefore, are known to reduce inflammation as well as pain. In particular, paracetamol shows fewer side effects and is relatively safe, however, when administered in doses higher than recommended, has a problem of inducing potentially fatal damage to the liver. Especially, NSAIDs drugs entail side effects such as paracusis, allergies, vision defects, gastritis, etc., in addition to the above problem.

Meanwhile, COX-2 inhibitor is a substance targeting COX-2 of cyclooxygenase, which is known as a target of NSAIDs and has COX-1 and COX-2, wherein COX-2 is known to influence pain. Rofecoxib (Vioxx) and celecoxib are representative of the COX-2 inhibitor as described above. Compared to NSAIDs, the COX-2 inhibitor exhibits substantially the same pain relieving effect while having reduced side effects, however, may cause heart and cerebrovascular disorders. For this reason, rofecoxib has been prohibited from being commercially available in the market, and is still a controversial matter in view of safety.

Opiates and morphinomimetics may typically include; archetypal opioid, codeine, oxycodone, hydrocodone, dihydromorphine, pethidine, and so forth. These drugs generally affect opioid receptors in the cerebrum to express a pain relieving effect. Tramadol is a drug based on the above substance but is more similar to venlafaxine rather than codeine, in terms of structure. However, in addition to activity with respect to the opioid receptor, the above drug also has a feature of effectively inhibiting reuptake of serotonin and norepinephrine. Although the above substance-based drugs have excellent pain relieving effects, these may induce vomiting, pruritus and constipation after administration and, in case of over-dosing, side effects such as confusion, respiratory depression, spasms, etc. may be a concern.

Flupirtin is a K+ channel opener having specific activity as an NMDA antagonist and is known as a drug without toxicity. Further, amitriptyline, nefopam, carbamazepine, gabapentin and pregabalin are typically used, however, some drugs are still not clearly understood in terms of functional mechanisms thereof. Further, since targets of the above drugs relate to the nervous system, these drugs may also be used as a remedy for curing further symptoms such as epilepsy, insomnia, post-traumatic stress disorder (PTSD), depression, nocturnal enuresis, stroke, etc., other than pain relief. A number of side effects possibly induced by corresponding drugs including, for example; hypotension, stroke, visual degradation, drowsiness, muscle stiffness, change in appetite, change in weight, or the like, have been reported in the art.

Accordingly, there is a significant need to develop novel medicaments capable of solving different problems such as side effects and toxicity of conventional pain relievers and relieving symptoms specific to pains.

Although a molecular-biological mechanism of pain and functions of drug targets based on the above mechanism have been relatively clearly disclosed, there is still considerable lack of understanding about a mechanism which results in pruritus (itching). With regard to a mechanism which leads to pain and itching in various peripheral tissues and spinal cords, significantly similar aspects are observed. However, most of pain therapeutics do not have an affect on pruritus, and narcotic analgesics are known to even cause pruritus.

Accordingly, in order to develop a drug capable of curing pruritus while relieving pain, it is necessary to more preferably understand differences between these two mechanisms, i.e., between physiological and pharmacological mechanisms. Of course, according to some examples of conventional art, gabapentin, which is one of neuropathic pain therapeutics widely used in the art, has been applied for treatment of neuropathic pruritus, i.e., pruritus of unknown origin, and successfully cured the same (M. A. Rose & P. C. A. Kam, *Anaesthesia*, 57:451, 2002; Yesudian P D & Wilson N J, *Arch. Dermatol.*, 141(12):1507, 2005). However, neuropathic pruritus is a symptom caused by a disorder of the central nervous system and has a principal difference from typical itching.

Further, a cause of atopic dermatitis outbreak is unclear and it is known that genetic, environmental and immunological factors may be involved in the above disease. Since most of currently used atopic therapeutics are used only for relieving symptoms of the disease, there is still a strong need to develop a substantially essential and innovative therapeutic product. Developing a drug that can inhibit an initial itching stage and cure symptoms thereof, thus preventing skin damage or inflammation after a scratching stage, may be a basic treatment method of atopic dermatitis.

Meanwhile, a number of pain therapeutics have been developed in a form of an antagonist of a transient receptor potential vanilloid receptor 1 (TRPV1, 'VR-1'). However, since the above products exhibited no efficacy or had clinically significant toxicity such as an increase in body temperature, most of research and development thereof have ended in failure. (ClinicalTrials.gov ID: NCT00878501; Gavva, N. R. et al. (2008) Pharmacological blockade of the vanilloid receptor TRPV1 elicits marked hyperthermia in humans. Pain 136, 202-210; Lehto, S. G. et al. (2008) Antihyperalgesic effects of (R,E)-N-(2-hydroxy-2,3-dihydro-1H-inden-4-yl)-3-(2-(piperidin-1-yl)-4-(trifluoromethyl)phenyl)-acrylamide (AMG8562), a novel transient receptor potential vanilloid type 1 modulator that does not cause hyperthermia in rats. J. Pharmacol. Exp. Ther. 326, 218-229). Further, even for a target of other pain therapeutics, i.e., CB2 or NK1, similar results were obtained and met with ill success. (Hill, R. (2000) NK1 (substance P) receptor antagonists—why are they not analgesic in humans? Trends Pharmacol. Sci. 21, 244-246; Rahn, E. J. and Hohmann, A. G. (2009) Cannabinoids as pharmacotherapies for neuropathic pain: from the bench to the bedside. Neurotherapeutics 6, 713-737). As such, major reasons of the failure in the development of pain therapeutics without desired efficacy are because individual targets may take a share of the pain mechanism but never comprise a whole part of the same. Therefore, it is suggested that only a drug simultaneously functioning on several targets may thoroughly control an overall pain mechanism. (Pang et al., A series of case studies: practical methodology for identifying antinociceptive multi-target drugs, 2012, Drug Discovery Today, vol 17, 425-434).

GlyT2 (Glycine transporter type 2) is an electrogenic carrier participating in Na+/Cl– ion transportation and primarily distributed around the spinal cord where pain arises, to thus play an important role in transferring a pain signal in the spinal cord. This fact is already widely known in the art.

5HT2A is a receptor relating to transfer of the pain signal, which is distributed in primary sensory neurons and spinal neurons and known to participate in peripheral/central sensitization of both the spinal cord neuron and peripheral nociceptor.

Accordingly, as a result of intensive effort to develop pain therapeutics affecting multiple targets, the present inventors found that a novel benzamide derivative and pharmaceutically acceptable salt thereof according to the present invention act not only as a GlyT2 antagonist but also a 5HT2A antagonist, which in turn, derives synergistic effects of activities of two targets, to exhibit excellent efficacy in prevention or treatment of pruritus, thereby completing the present invention.

The information as described in the above background art is only provided to more understand a background technology of the present invention, however, other information with respect to prior art well known to persons having ordinary skill in the art to which the present invention pertains, may not be included therein.

DISCLOSURE

Technical Problem

An object of the present invention is to provide a novel benzamide derivative and pharmaceutically acceptable salt thereof.

Another object of the present invention is to provide a pharmaceutical composition with excellent analgesic or antipruritic efficacy, including the benzamide derivative or pharmaceutically acceptable salt thereof.

Technical Solution

In order to accomplish the above objects, the present invention generally provides a novel benzamide derivative and use thereof.

Specifically, the present invention provides a benzamide derivative represented by Formula 1 below or pharmaceutically acceptable salt thereof.

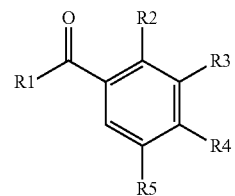

[Formula 1]

(wherein $R_1$ is $NHR_6$,

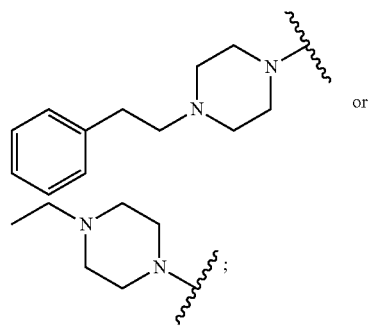

$R_2$ is hydrogen, $(C_1-C_6)$ alkyl or $(C_1-C_6)$ alkoxy;

$R_3$ is hydrogen, $(C_1-C_6)$ alkyl or $(C_1-C_6)$ alkoxy having at least one hydrogen atom substituted or unsubstituted with halogen;

$R_4$ is hydrogen, hydroxyl group, amino group ($NH_2$), $(C_1-C_6)$ alkoxy, $(C_3-C_6)$ aromatic cycloalkoxy, $(C_3-C_6)$ aliphatic cycloalkoxy, or $(C_1-C_6)$ alkylalkoxy having at least one $(C_3-C_6)$ aromatic ring or aliphatic ring;

$R_5$ is hydrogen, $(C_1-C_6)$ alkyl, $(C_1-C_6)$ alkoxy or halogen;

$R_6$ is $CH_2R_{11}$, $CH_2CHR_{12}R_{13}$, quinuclidine, naphthalene having at least one carbon atom substituted with N,

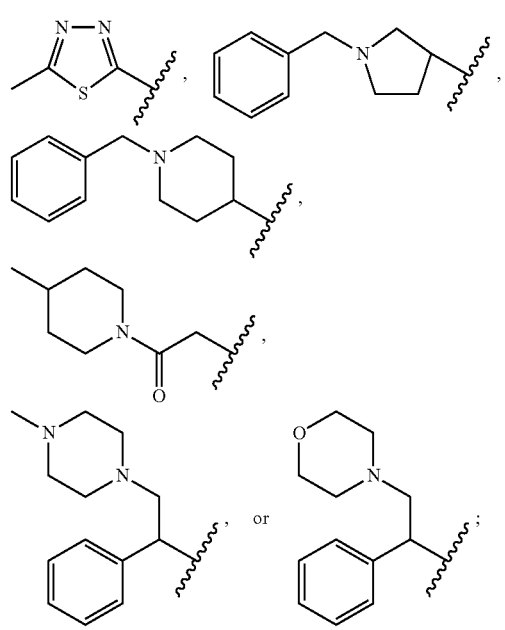

$R_{11}$ is a $(C_5-C_6)$ aliphatic cyclic or aromatic cyclic compound or $(C_5-C_6)$ aliphatic heterocyclic or aromatic heterocyclic compound having at least one carbon atom substituted with O or N, wherein the aliphatic ring, aromatic ring, aliphatic hetero-ring or aromatic hetero-ring of $R_{11}$ may be one substituted with at least one substituent selected from a group consisting of; $(C_1-C_6)$ alkyl, hydroxy, $NR_{21}R_{22}$, halogen and $(C_5-C_6)$ aliphatic heterocyclic or aromatic heterocyclic compound having at least one carbon atom substituted with O or N, wherein $R_{21}$ and $R_{22}$ are independently each hydrogen, $(C_1-C_6)$ alkyl or phenyl;

$R_{12}$ and $R_{13}$ are independently each hydrogen, $NR_{23}R_{24}$, an $(C_5-C_6)$ aliphatic cyclic or aromatic cyclic compound, or a $(C_5-C_6)$ aliphatic heterocyclic or aromatic heterocyclic compound having at least one carbon atom substituted with O or N, wherein the aliphatic ring, aromatic ring, aliphatic hetero-ring or aromatic hetero-ring of $R_{12}$ and $R_{13}$ may be one substituted with at least one substituent of $(C_1-C_6)$ alkyl or $(C_1-C_6)$ alkoxy, wherein $R_{23}$ and $R_{24}$ are independently each hydrogen or $(C_1-C_6)$ alkyl or, otherwise, are coupled together to form a $(C_5-C_6)$ aliphatic cyclic or heterocyclic compound or a $(C_5-C_6)$ aliphatic heterocyclic or aromatic heterocyclic compound having at least one carbon atom substituted with O.)

In addition, the present invention provides a composition for prevention or treatment of pain or pruritus, comprising the above mentioned benzamide derivative or pharmaceutically acceptable salt thereof.

Advantageous Effects

The novel benzamide derivative and pharmaceutically acceptable salt thereof according to the present invention exhibit excellent pain-suppressive effects and, in particular, pain-suppressive effects in not only a neuropathic animal model but also other models such as a formalin model, and therefore, may be used in suppression of different pains such as nociceptive pain, chronic pain, etc. Further, since it was demonstrated that the present invention displays anti-pruritic efficacy even in an itching model, to which a mechanism and treatment concept established with respect to pain is applied, the present invention may also be effectively used in radical treatment of atopic dermatitis by applying the inventive product to an anti-pruritic composition in order to suppress an initial itching stage and treat symptoms thereof, thus preventing skin damage or inflammation after the scratching stage.

BEST MODE

Figure 1:
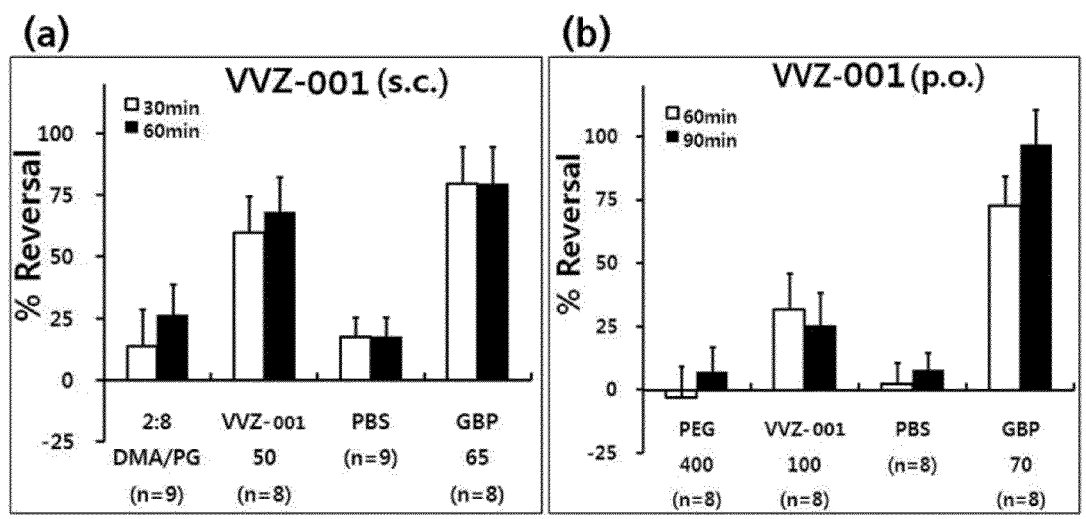
FIGS. 1 to 22 are graphs showing experimental results obtained by measuring extents of pain suppression when each of the compounds is administered to a representative neuropathic pain model, i.e., Chung model, through; (a) subcutaneous injection, or (b) oral administration (FIGS. 6 to 10, 13, 17, 18, 20 to 22 show graphs of experimental results obtained by measuring pain suppression extents in case of subcutaneous injection).
Figure 2:
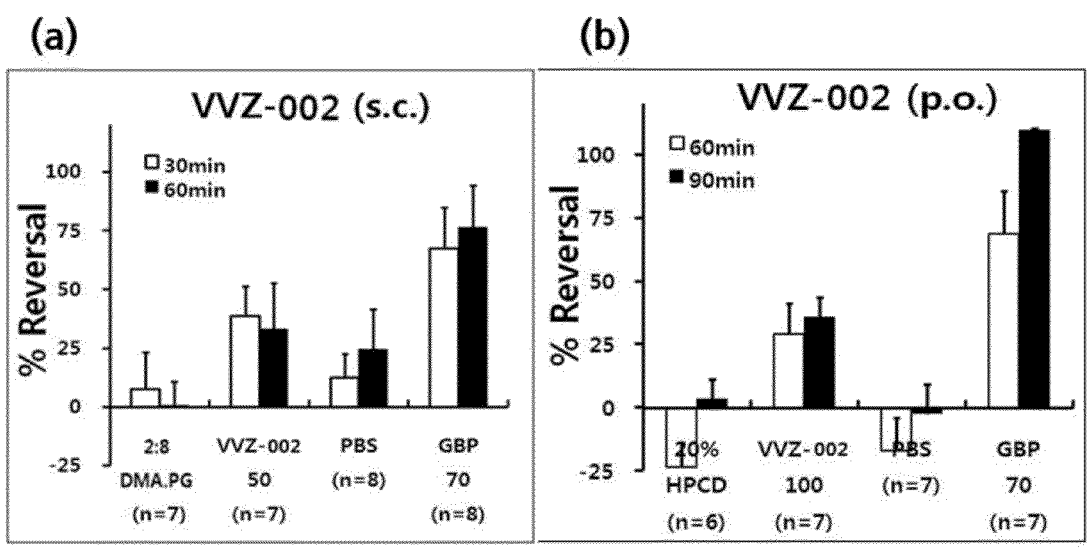
Figure 3:
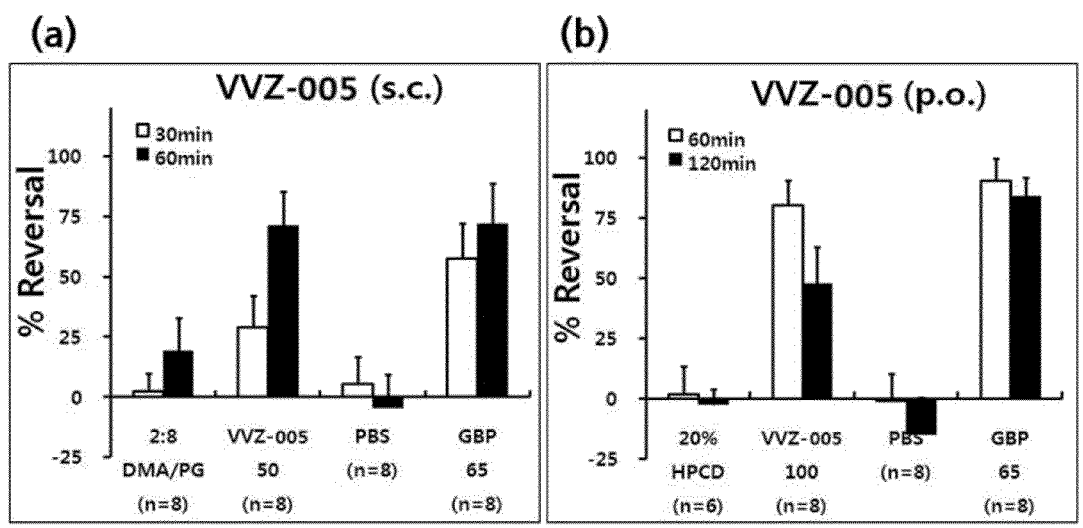
Figure 4:
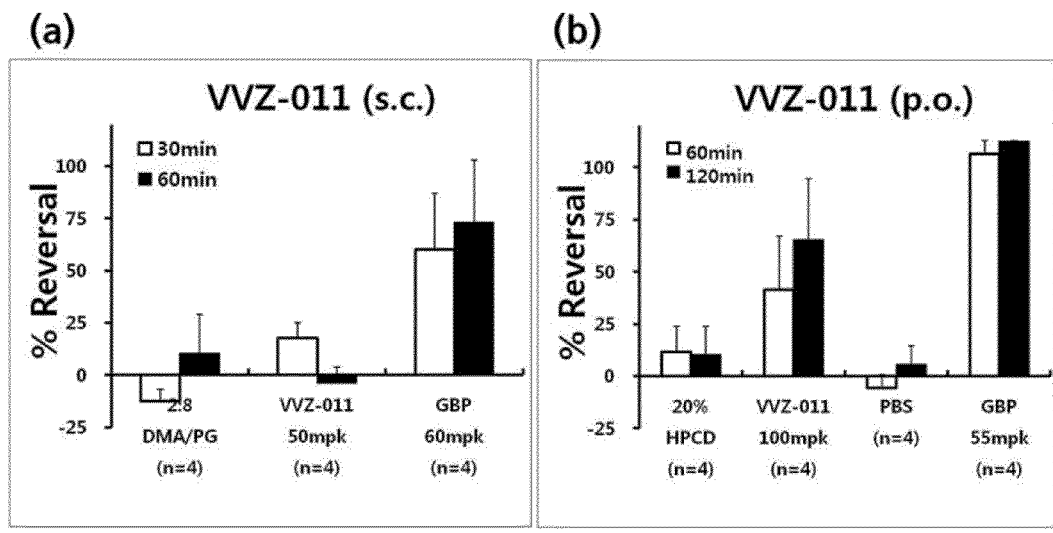
Figure 5:
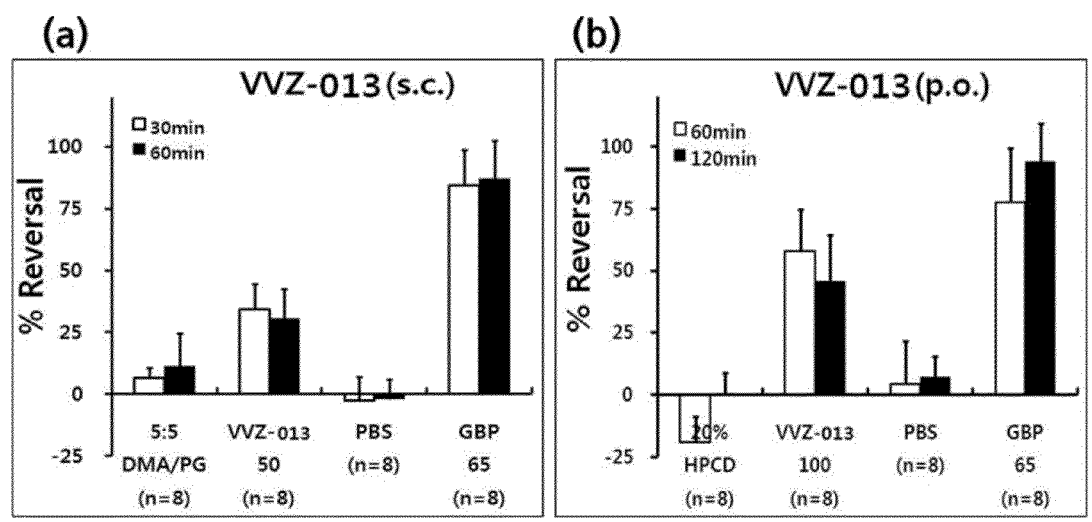
Figure 6:
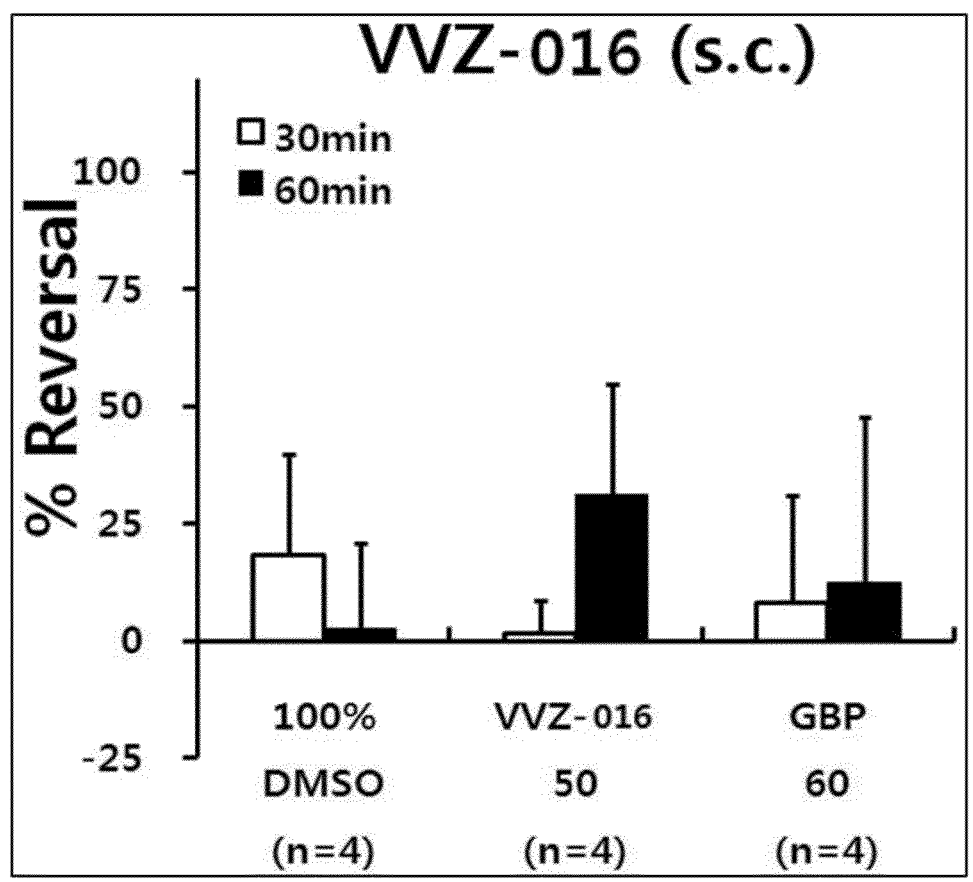
Figure 7:
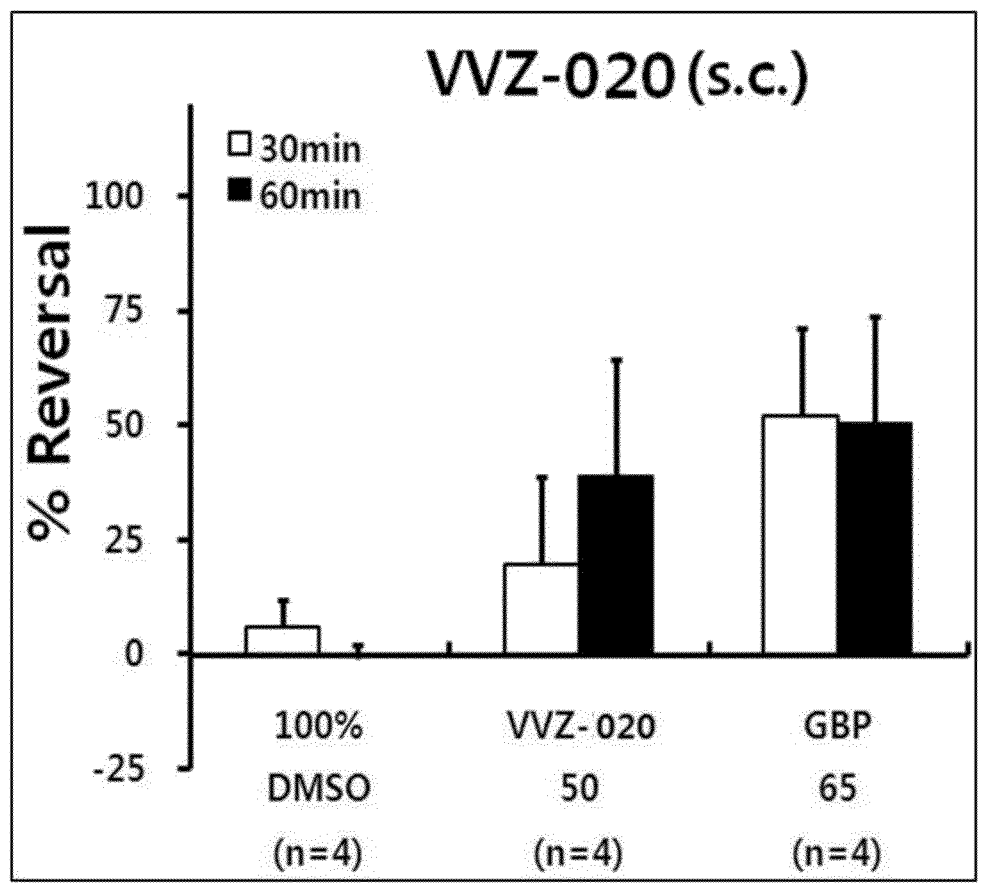
Figure 8:
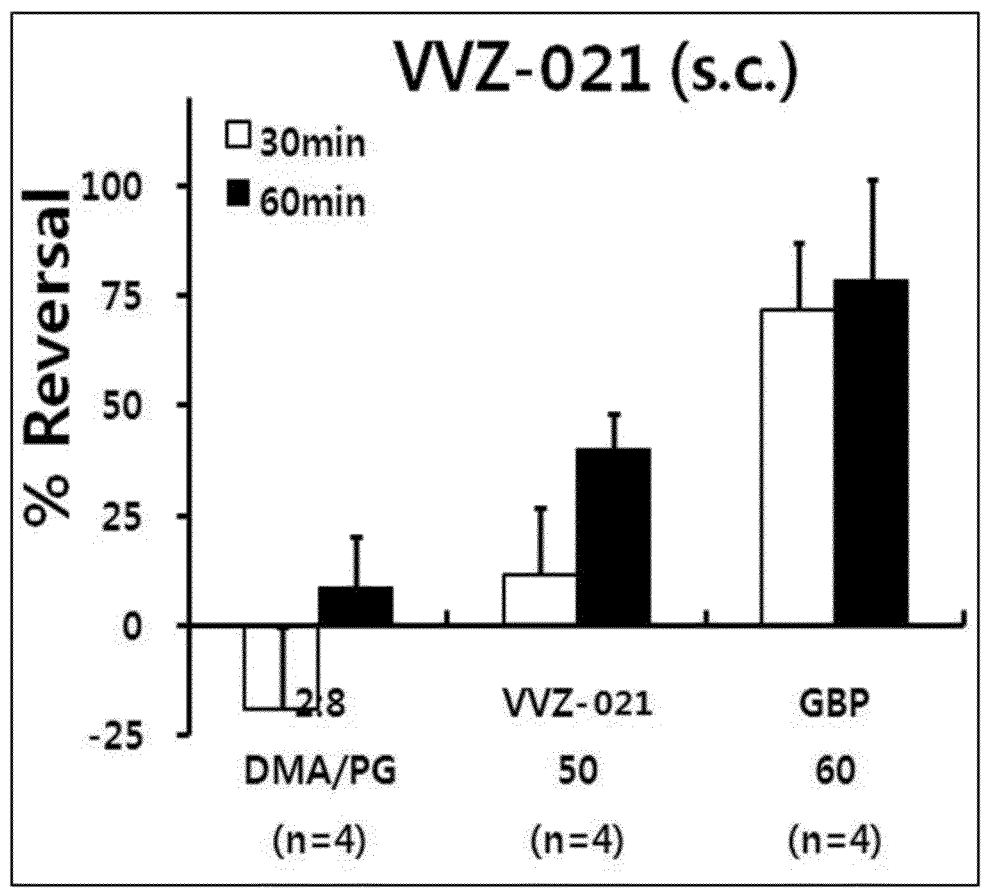
Figure 9:
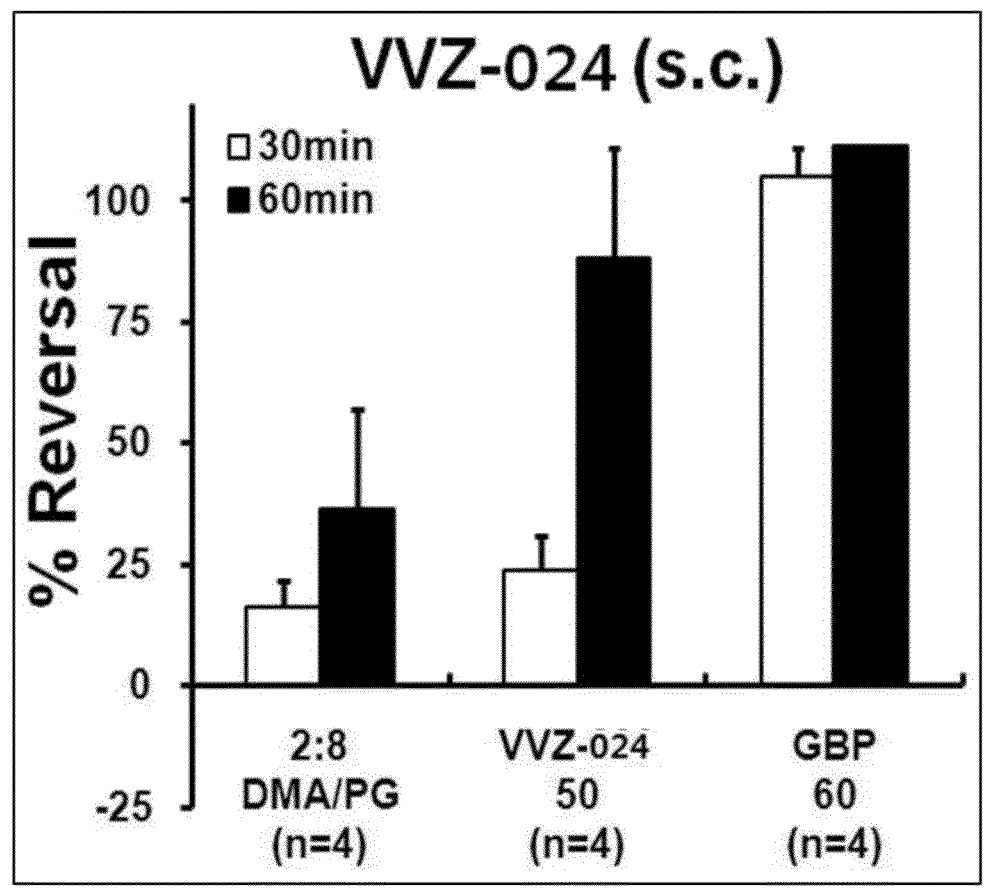
Figure 10:
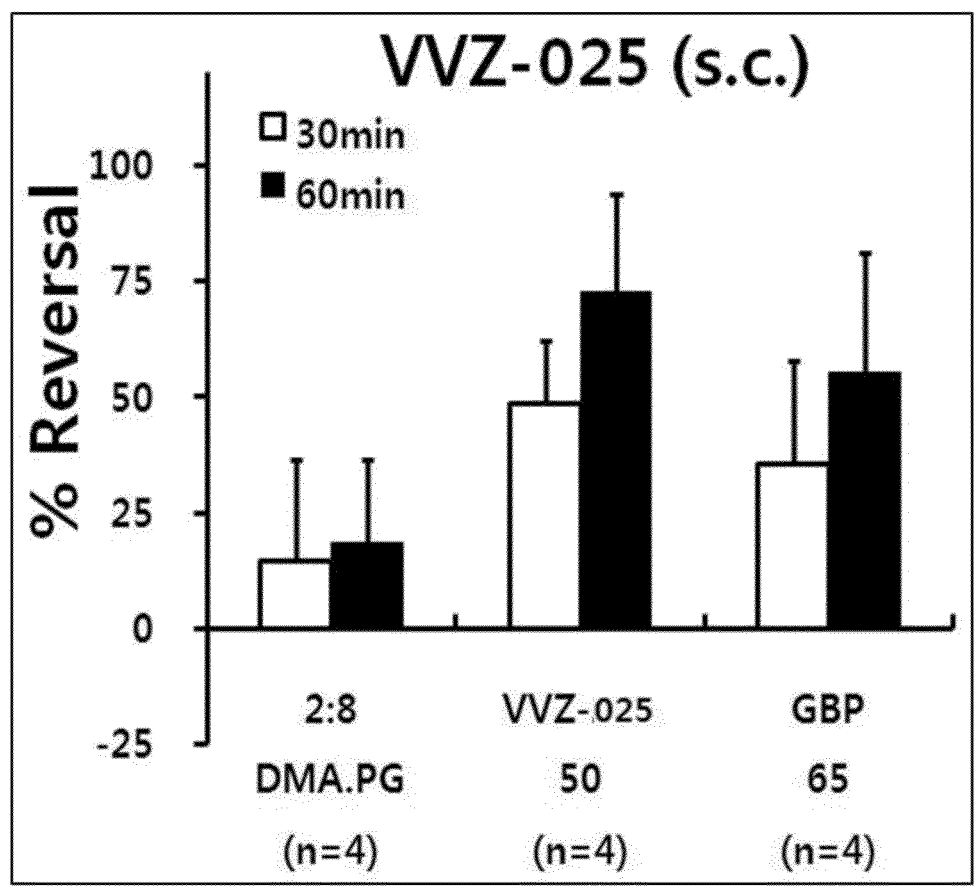
Figure 11:
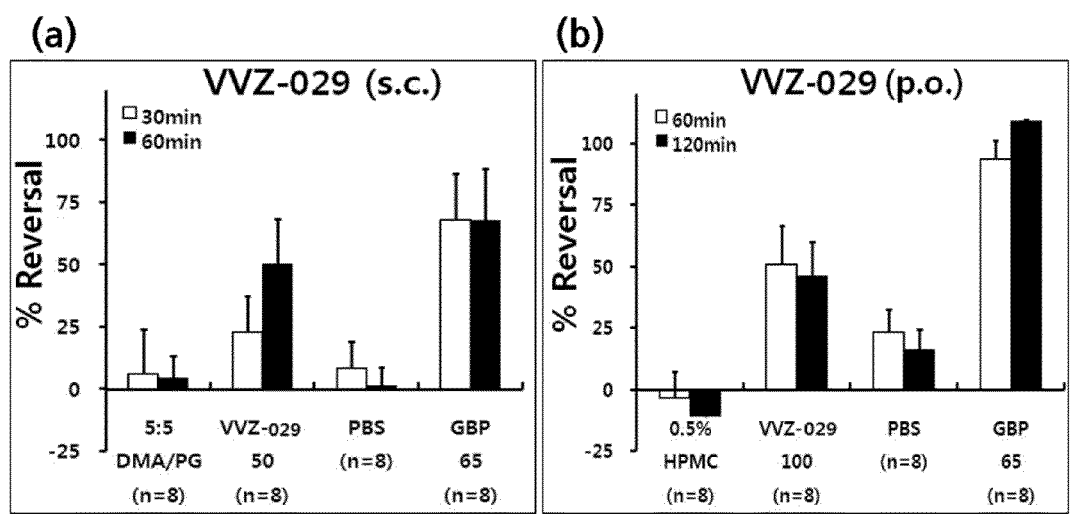
Figure 12:
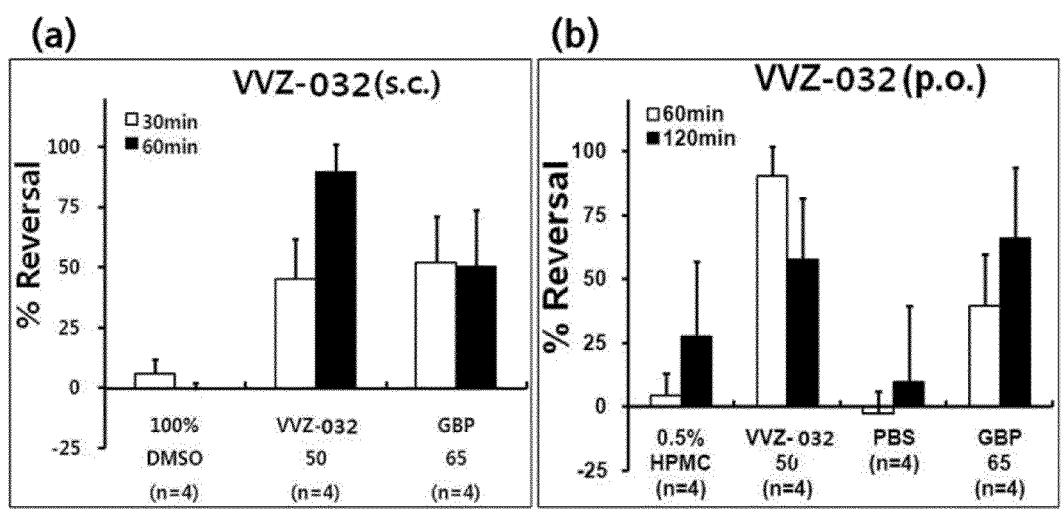
Figure 13:
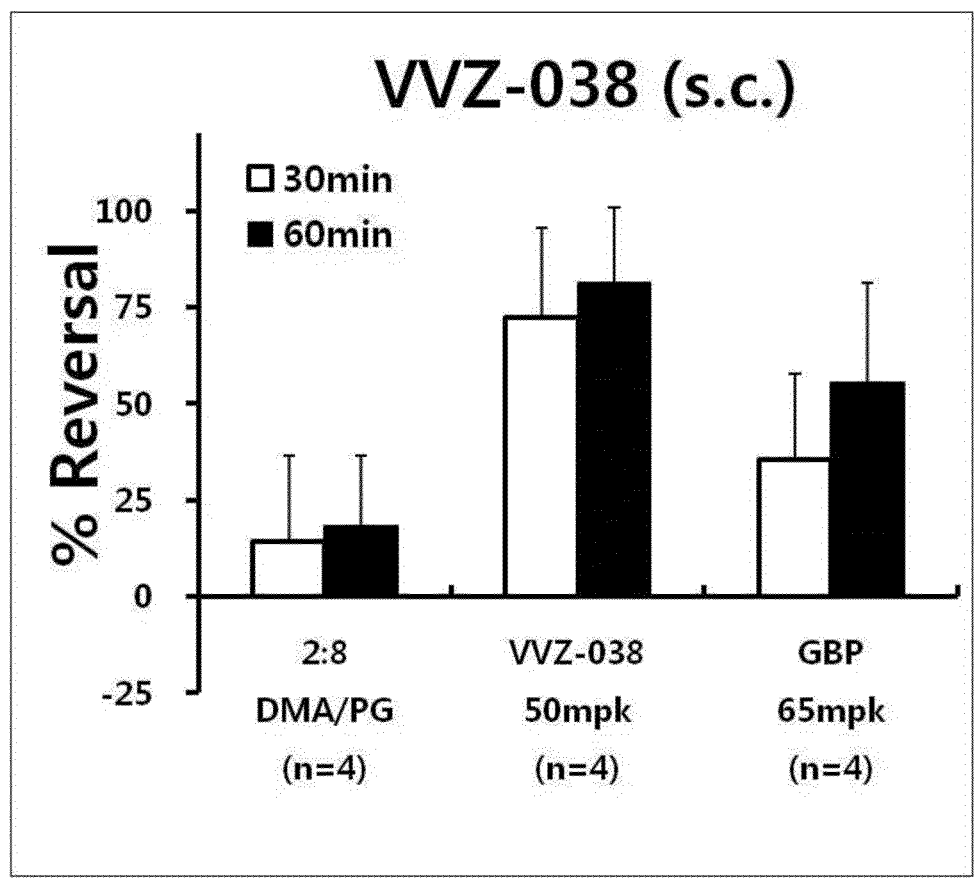
Figure 14:
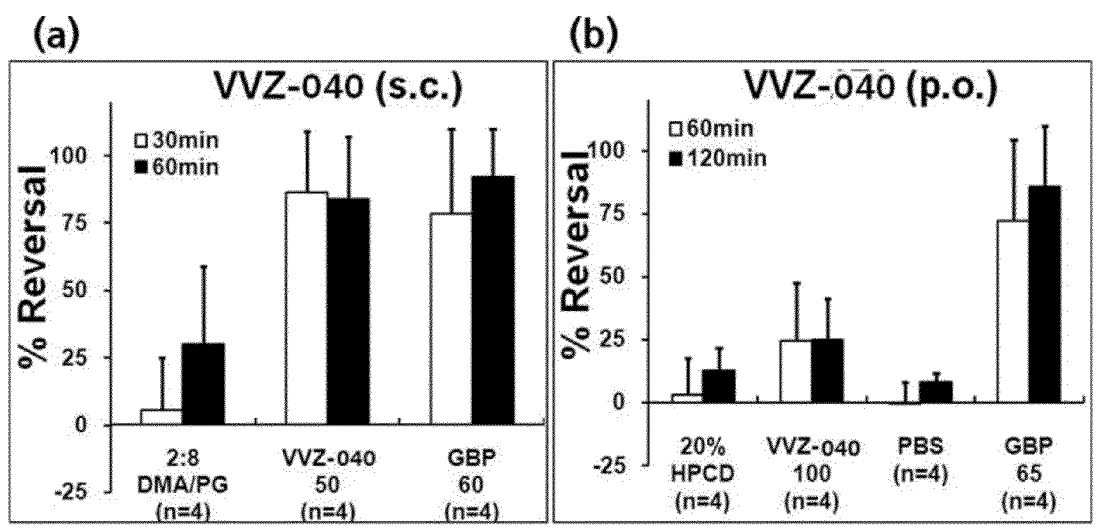
Figure 15:
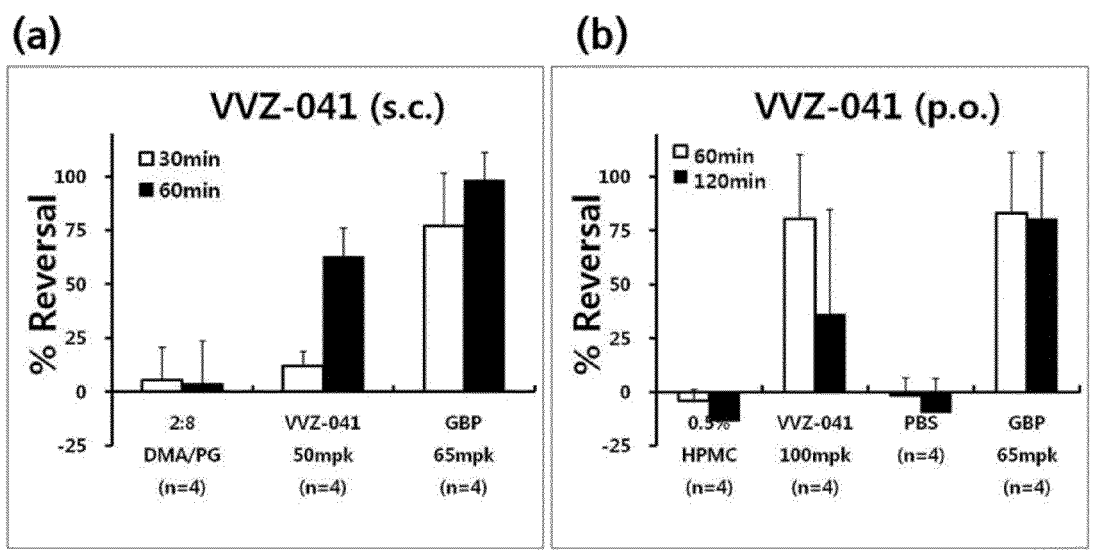
Figure 16:
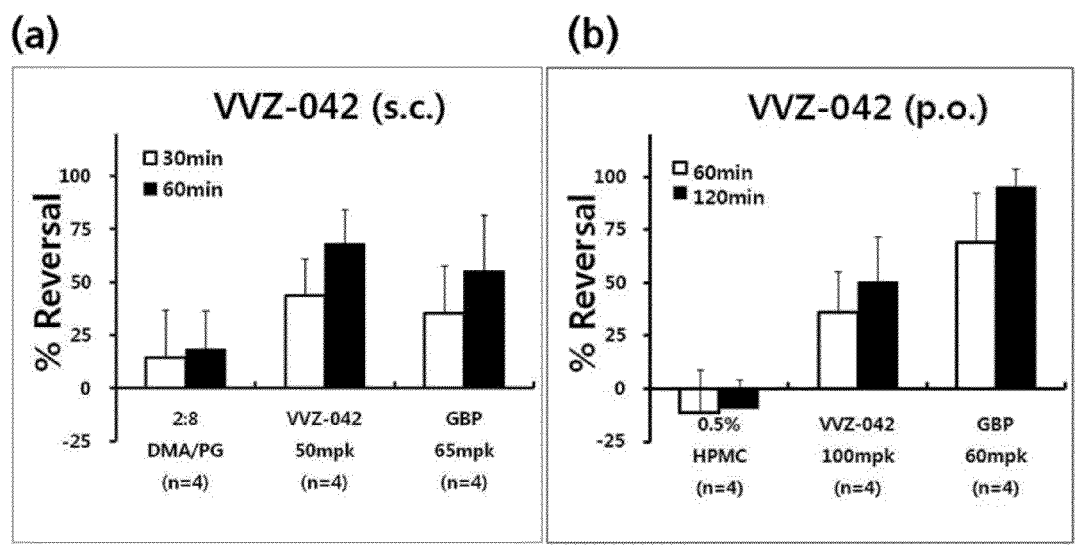
Figure 17:
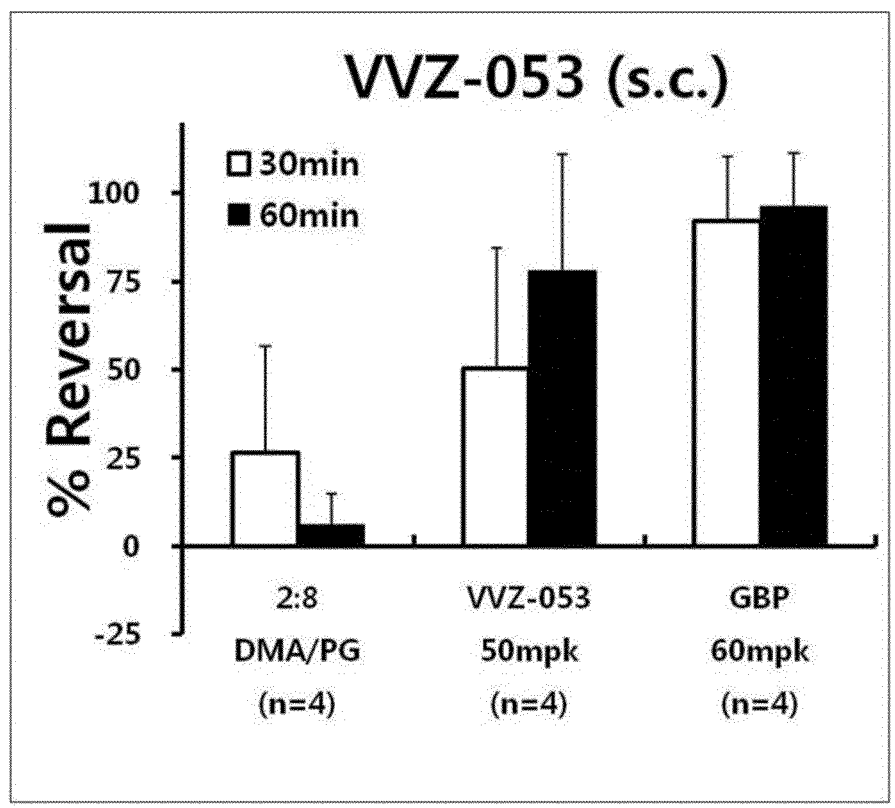
Figure 18:
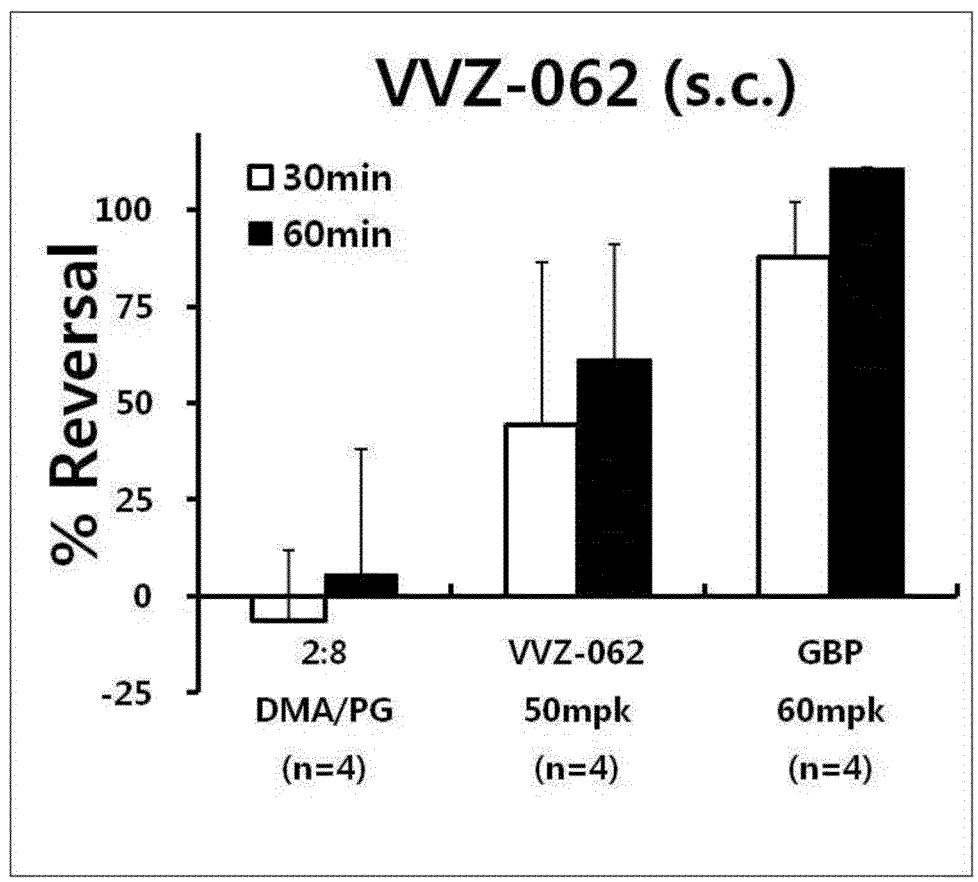
Figure 19:
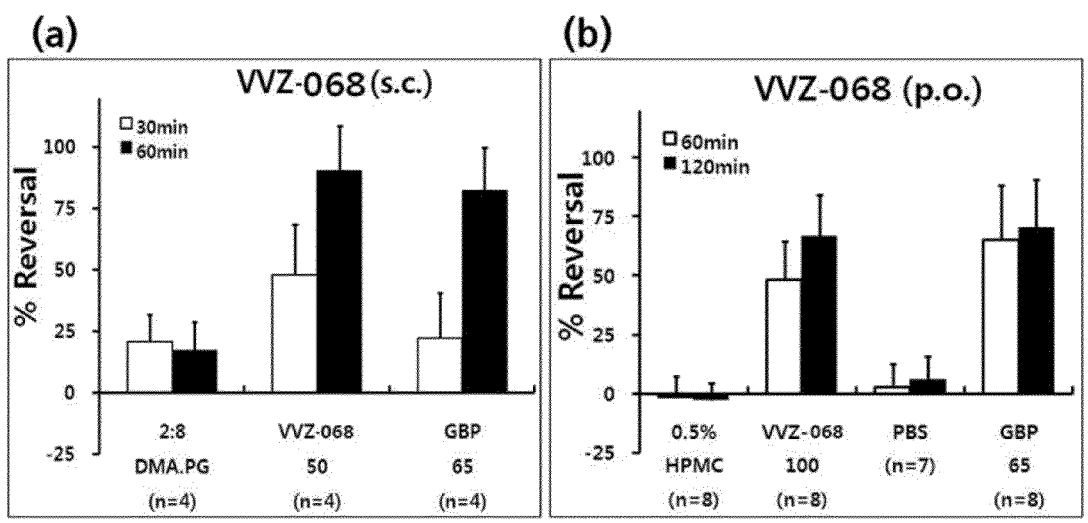
Figure 20:
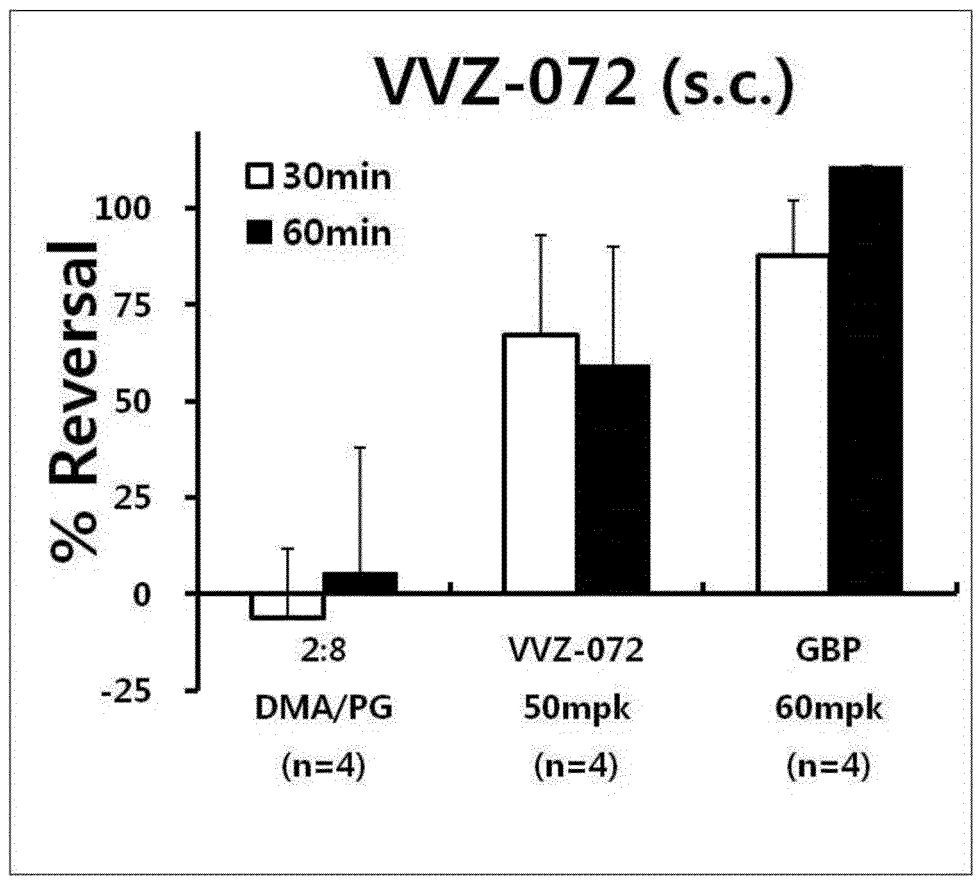
Figure 21:
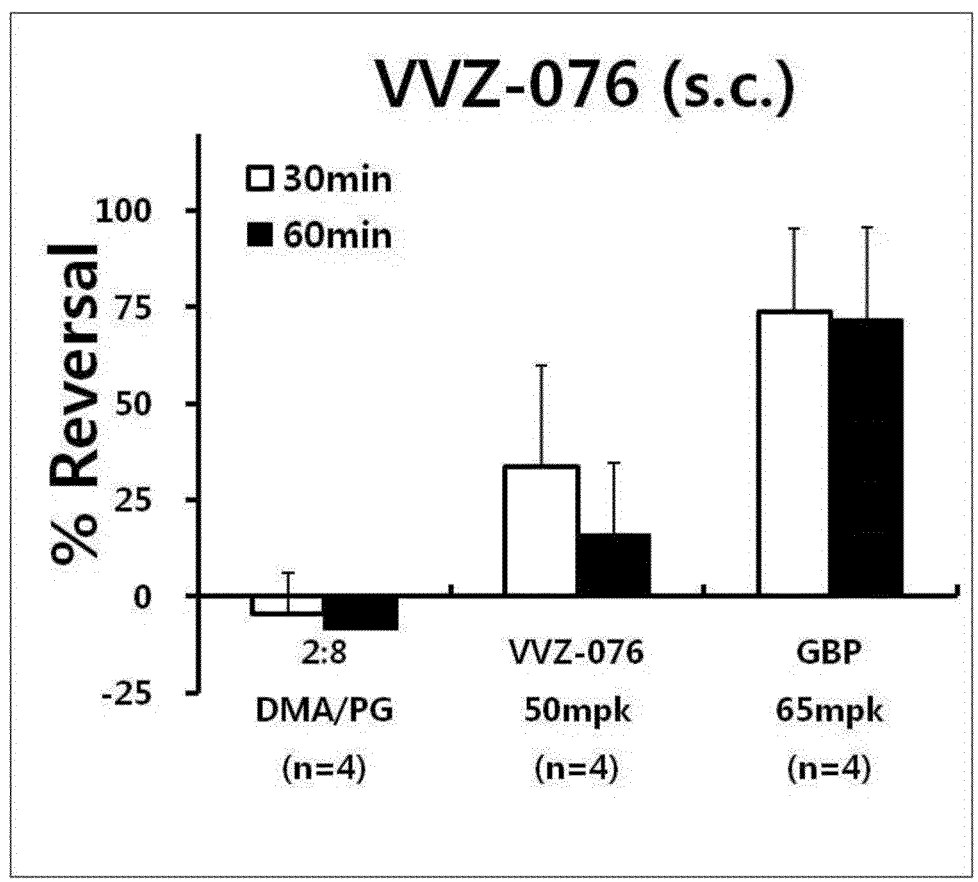
Figure 22:
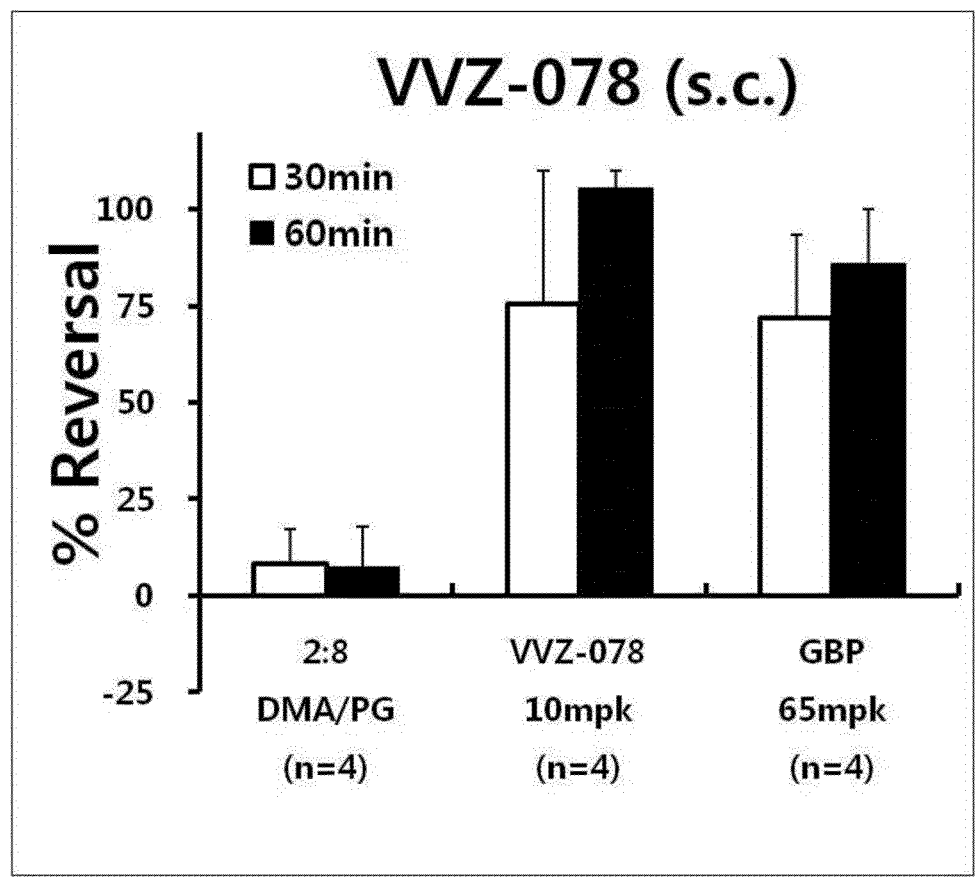

All technical and scientific terminologies used in the present text have the same meanings as commonly understood by those skilled in the art to which the present invention pertains, until further defined. In general, nomenclature guidelines used in the present invention are well known and commonly used in the art.

Major terms used in the detailed description of the present invention may include as follows. 'Pain' used herein may include acute pain, chronic pain, inflammatory pain, neuropathic pain and migraine pain, as well as nociceptive pain or neuropathic pain. A disease or condition requiring a composition of the present invention may include, but not be limited to, pains associated with trauma, traumatic amputation, neuralgia, fibromyalgia, burn, abrasion (scratches), infection, laceration, cutting, etc., and pains arising due to diabetes, shingles, AIDS, chemotherapy for cancer patients, etc.

'Pruritus' used herein may include systemic or local pruritus and causes thereof may include, but not be limited to, diabetes, biliary atresia, liver disease with jaundice, nephritis, renal disease with chronic renal failure, leukemia, hyperthyroidism, hypothyroidism, iron-deficiency anemia, autoimmune disease such as lupus (systemic lupus erythematodes), cancerous disease such as Hodgkin's disease or multiple myeloma, menopausal disorder, AIDS, parasite disease, psychogenic disorder, neurogenic dermatitis, otitis externa, allergic dermatitis, atopic dermatitis, or the like.

'Atopic dermatitis' used herein may be derived from genetic causes, express symptoms such as eczema, dry skin, and have features of chronic pruritus.

Hereinafter, the present invention will be described in detail.

According to an aspect of the present invention, there is provided a novel benzamide derivative or pharmaceutically acceptable salt thereof. Specifically, the benzamide derivative may be represented by Formula 1 below.

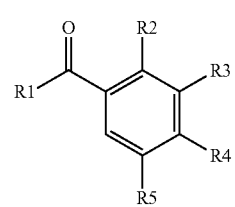

[Formula 1]

(wherein $R_1$ is $NHR_6$,

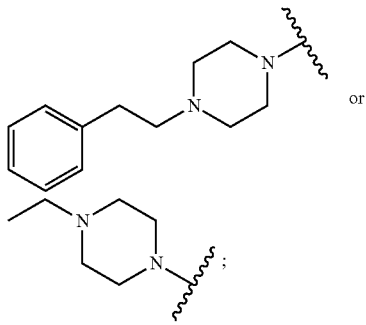

$R_2$ is hydrogen, $(C_1-C_6)$ alkyl or $(C_1-C_6)$ alkoxy;

$R_3$ is hydrogen, $(C_1-C_6)$ alkyl or $(C_1-C_6)$ alkoxy having at least one hydrogen atom substituted or unsubstituted with halogen;

$R_4$ is hydrogen, hydroxyl group, amino group ($NH_2$), $(C_1-C_6)$ alkoxy, $(C_3-C_6)$ aromatic cycloalkoxy, $(C_3-C_6)$ aliphatic cycloalkoxy, or $(C_1-C_6)$ alkylalkoxy having at least one $(C_3-C_6)$ aromatic ring or aliphatic ring;

$R_5$ is hydrogen, $(C_1-C_6)$ alkyl, $(C_1-C_6)$ alkoxy or halogen;

$R_6$ is $CH_2R_{11}$, $CH_2CHR_{12}R_{13}$, quinuclidine, naphthalene having at least one carbon atom substituted with N,

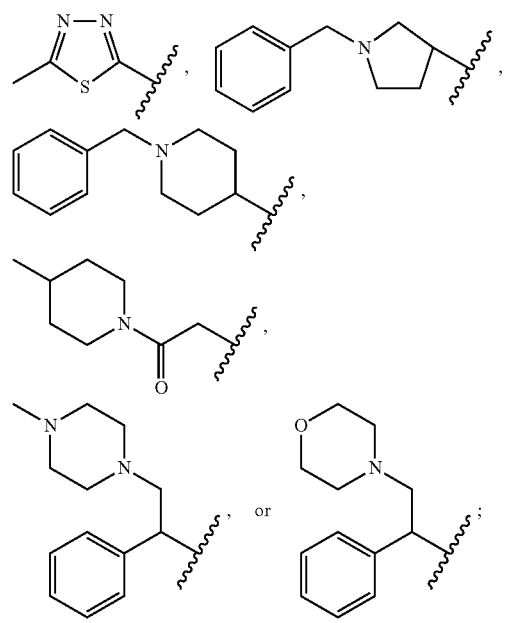

$R_{11}$ is a $(C_5-C_6)$ aliphatic cyclic or aromatic cyclic compound or $(C_5-C_6)$ aliphatic heterocyclic or aromatic heterocyclic compound having at least one carbon atom substituted with O or N, wherein the aliphatic ring, aromatic ring, aliphatic hetero-ring or aromatic hetero-ring of $R_{11}$ may be one substituted with at least one substituent selected from a group consisting of $(C_1-C_6)$ alkyl, hydroxy, $NR_{21}R_{22}$, halogen and $(C_5-C_6)$ aliphatic heterocyclic or aromatic heterocyclic compound having at least one carbon atom substituted with O or N, wherein $R_{21}$ and $R_{22}$ are independently each hydrogen, $(C_1-C_6)$ alkyl or phenyl;

$R_{12}$ and $R_{13}$ are independently each hydrogen, $NR_{23}R_{24}$, an $(C_5-C_6)$ aliphatic cyclic or aromatic cyclic compound, or a $(C_5-C_6)$ aliphatic heterocyclic or aromatic heterocyclic compound having at least one carbon atom substituted with O or N, wherein the aliphatic ring, aromatic ring, aliphatic hetero-ring or aromatic hetero-ring of $R_{12}$ and $R_{13}$ may be one substituted with at least one substituent of $(C_1-C_6)$ alkyl or $(C_1-C_6)$ alkoxy, wherein $R_{23}$ and $R_{24}$ are independently each hydrogen or $(C_1-C_6)$ alkyl or, otherwise, are coupled together to form a $(C_5-C_6)$ aliphatic cyclic or heterocyclic compound or a $(C_5-C_6)$ aliphatic heterocyclic or aromatic heterocyclic compound having at least one carbon atom substituted with O.)

The novel benzamide derivative according to the present invention may be used in a form of pharmaceutically acceptable salt and the pharmaceutically acceptable salt may include acid addition salts formed from pharmaceutically acceptable free acids. Such acid addition salts as described above may include, but not be limited to, methane sulfonate, ethane sulfonate, fumarate, succinate, hydrochloride, citrate, malate, tartrate and, less preferably, hydrobromide. In addition, a salt formed with hydrochloric acid, phosphoric acid and sulfuric acid may be properly used. Further, other preferred salts may include: alkaline salts, for example, salts of alkali-metal such as sodium, salts of alkali-earth metal such as calcium or magnesium; organic amine salts, for example, triethylamine, morpholine, N-methyl piperidine, N-ethyl piperidine, prokain, dibenzylamine, N,N-dibenzylethylamine, tris-(2-hydroxyethyl)amine, N-methyl d-glucamine, amino acid such as lysine, and so forth. According to the number of charged groups and atomic valence of cations or anions, at least one cation or anion may be contained. Pharmaceutically acceptable salts are sodium salts. However, in order to easily detach a salt during production, a salt less soluble in a selected solvent is preferably used in consideration of pharmaceutical acceptability. According to one embodiment of the present invention, with regard to a hydrochloric acid (HCl) salt of the novel benzamide derivative, pain model and itching model tests have been conducted, thus demonstrating that the above material has pain suppression and anti-pruritic efficacies.

Further, since the novel benzamide derivative according to the present invention can be prepared and used in any form of a prodrug, hydrate, solvate, isomer and/or pharmaceutically acceptable salt thereof in order to increase absorption in vivo or improve a solubility, such a prodrug, hydrate, solvate, isomer and/or pharmaceutically acceptable salt as described above may also be included within the scope of the present invention.

The benzamide derivative of the present invention may be present in a solvated form, for example, a hydrated form or non-solvate form. Moreover, the solvate of a benzamide derivative compound according to the present invention may include all of solvated forms having pharmaceutical activity.

The inventive benzamide derivative may be administered in a prodrug form which is decomposed in a human or animal body to provide the compound of the present invention. The prodrug may be used to modify or improve physical and/or pharmacokinetic profile of a parent compound, and be formed if the parent compound has a proper group (radical) or substituent to induce formation of the prodrug. Examples of the prodrug may include an in-vivo hydrolysable ester of the inventive compound and pharmaceutically acceptable salts thereof.

Various forms of the prodrug have been known in the art, for example:
a) Document [Design of Prodrugs, edited by H. Bundgaard, (Elsevier, 1985);
b) Document [A Textbook of Drug Design and Development, edited by Krogsgaard-Larsen and H. Bundgaard, Chapter 5 "Design and Application of Prodrugs", by H. Bundgaard p. 113-191 (1991)];
c) Document [H. Bundgaard, Advanced Drug Delivery Reviews, 8, 1-38 (1992)];
d) Document [H. Bundgaard, et al., Journal of Pharmaceutical Sciences, 77, 285 (1988)]; and
e) Document [N. Kakeya, et al., Chem Pharm Bull, 32, 692 (1984)], or the like, which are incorporated herein for reference.

Further, it is understood that all optical isomers (that is, enantiomers), diastereoisomers and racemic mixtures may also be included in the scope of the present invention. Preparation methods of optically active forms (for example, recrystallization, chiral synthesis, enzyme resolution, racemate isolation by bio-transformation or chromatographic separation) and measurement of antibiotic activity are well known in the art.

The compound represented by Formula 1 or its salt in the present invention may exhibit tautomer status and, although formulae or reaction schemes stated in the present text express a possible tautomer form alone, it is understood that the present invention includes any tautomer forms having pain suppression and anti-pruritic activities without particular limitation to only the tautomer form used in the formulae or reaction schemes described above.

A specific compound of the present invention may further exhibit polymorphism and any of polymorphisms having antibiotic activity may also be included in the present invention.

In the present invention, preferably, $R_2$ may be hydrogen or methoxy (—$OCH_3$), $R_3$ may be hydrogen, methyl (—$CH_3$), methoxy (—$OCH_3$) or trifluoromethyl (—$CF_3$), $R_4$ may be hydrogen, amino group (—$NH_2$), butoxy (—$O(CH_2)_3CH_3$) or benzyloxy (—$OCH_2C_6H_5$), and $R_5$ may be hydrogen, methyl (—$CH_3$), methoxy (—$OCH_3$) or chlorine (—Cl).

According to one aspect of the present invention, in the benzamide derivative represented by above Formula 1, $R_1$ may be $NHR_6$, $R_2$ may be hydrogen, $R_3$ and $R_5$ may be each methoxy (—$OCH_3$), $R_4$ may be butoxy (—$O(CH_2)_3CH_3$) or benzyloxy (—$OCH_2C_6H_5$). Preferably, the present invention may provide the benzamide derivative or pharmaceutically acceptable salt thereof represented by Formula 2 to Formula 46 below.

[Formula 2]

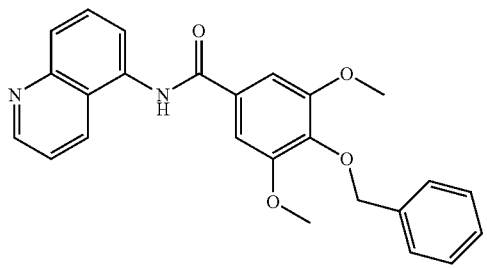

[Formula 3]

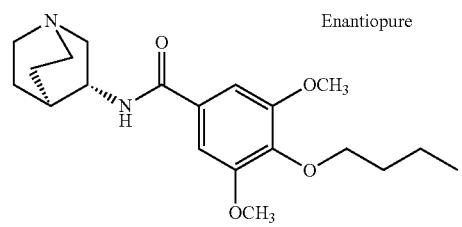

[Formula 4]

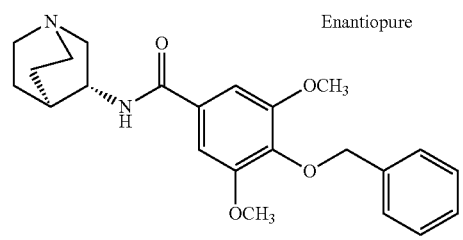

[Formula 5]

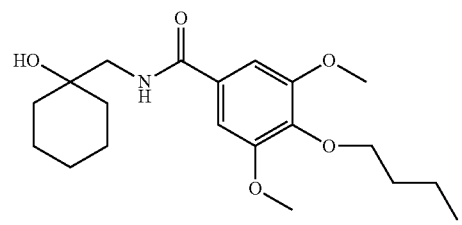

[Formula 6]

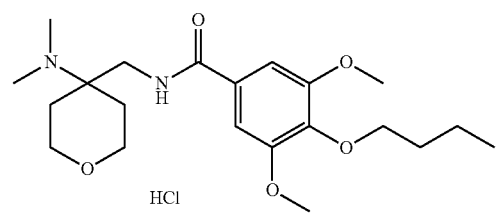

[Formula 7]

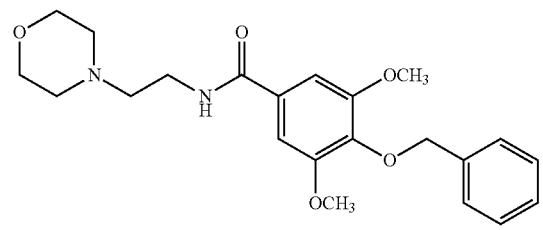

[Formula 8]

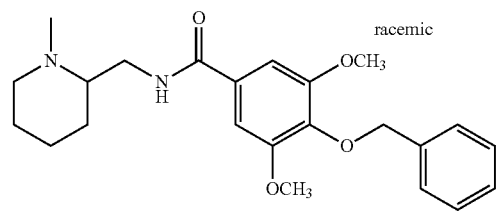

[Formula 9]
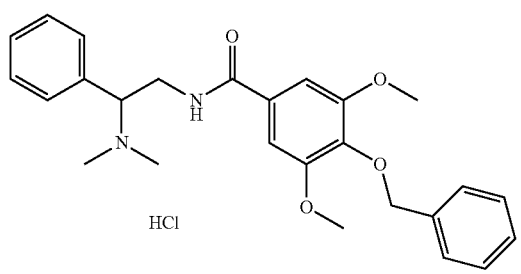
HCl
[Formula 10]
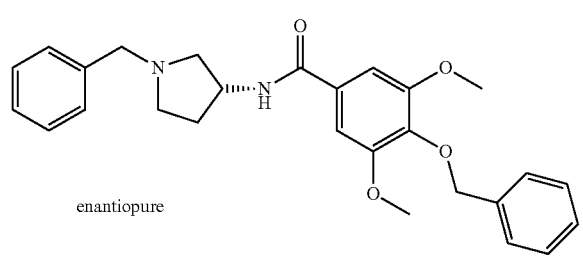
enantiopure
[Formula 11]
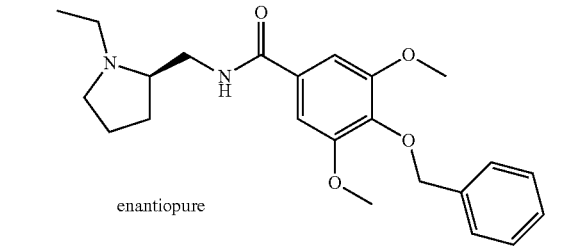
enantiopure
[Formula 12]
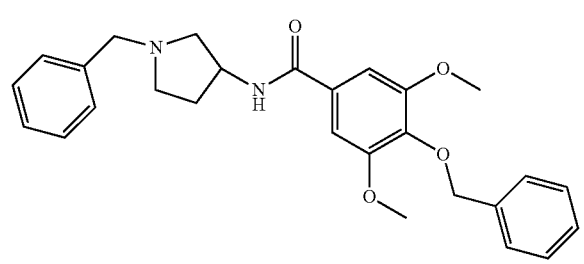
[Formula 13]
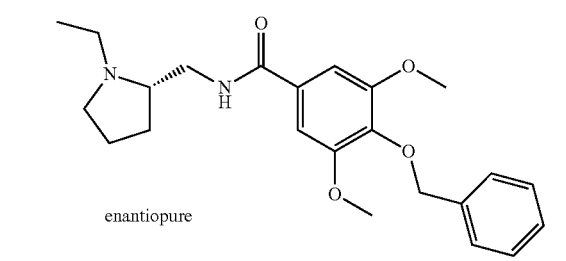
enantiopure
[Formula 14]
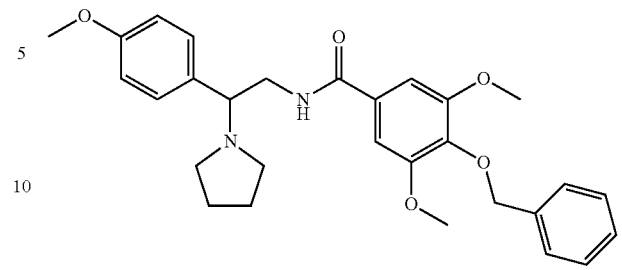
[Formula 15]
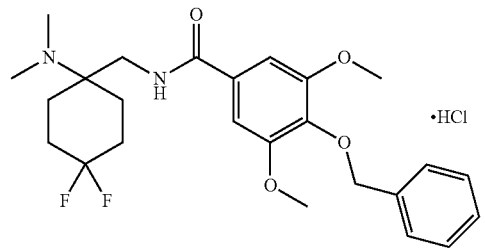
·HCl
[Formula 16]
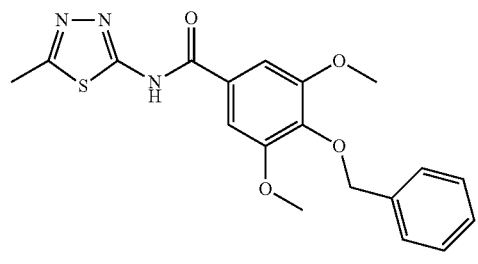
[Formula 17]
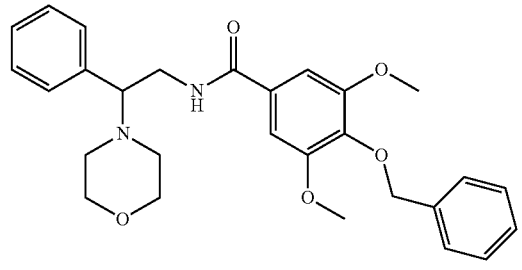
[Formula 18]
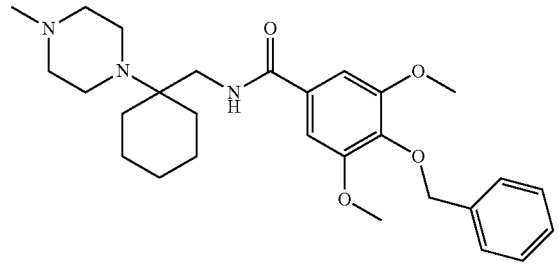

[Formula 19]
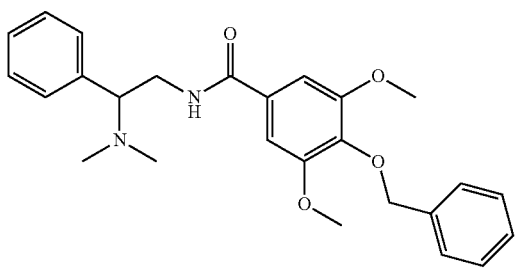
[Formula 20]
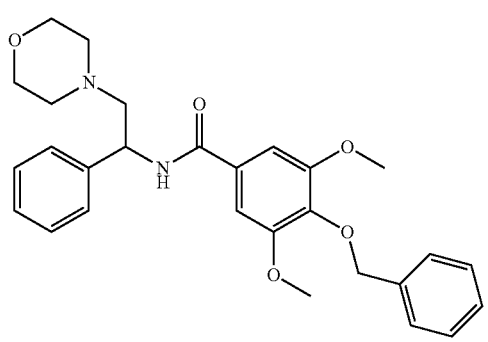
[Formula 21]
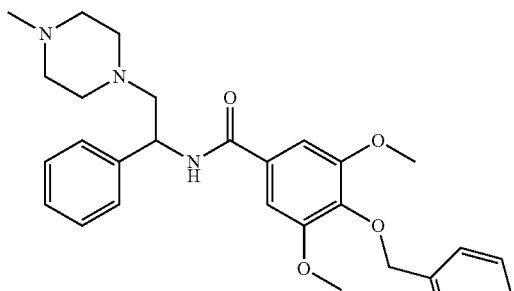
[Formula 22]
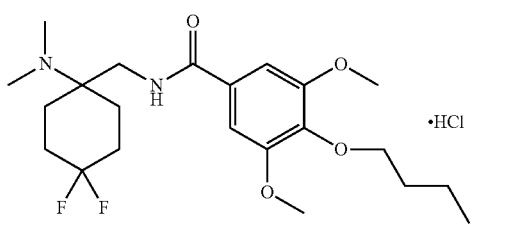
·HCl
[Formula 23]
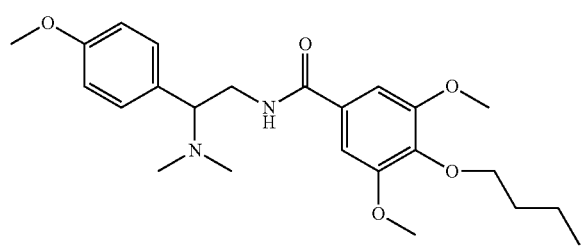
[Formula 24]
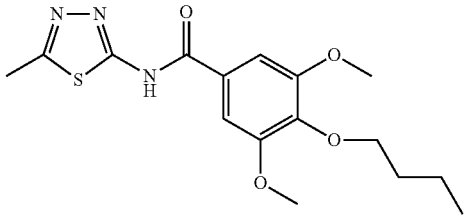
[Formula 25]
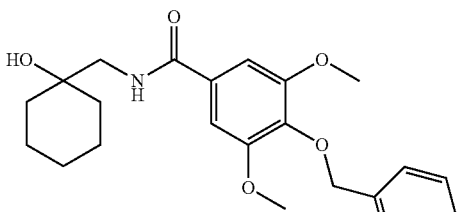
[Formula 26]
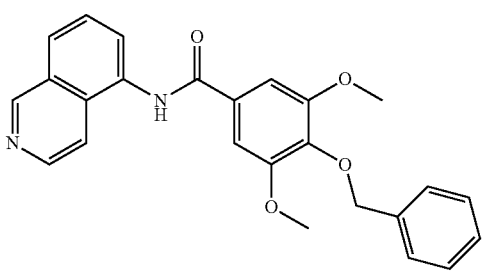
[Formula 27]
racemic
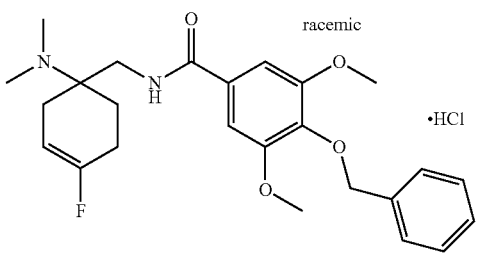
·HCl
[Formula 28]
enantiopure
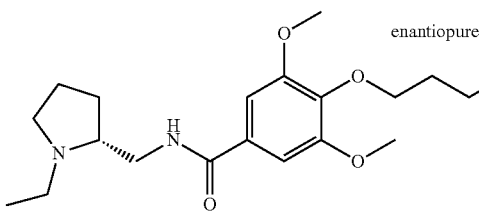
[Formula 29]
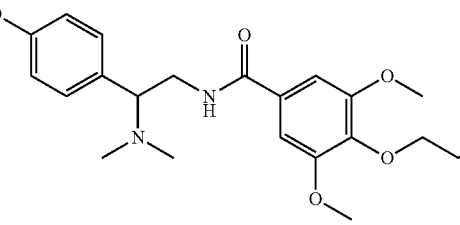

[Formula 30]
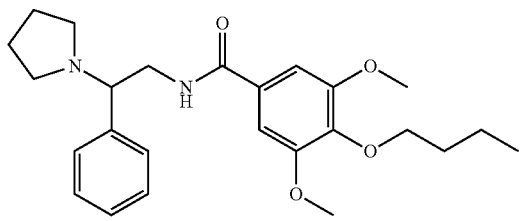
[Formula 31]
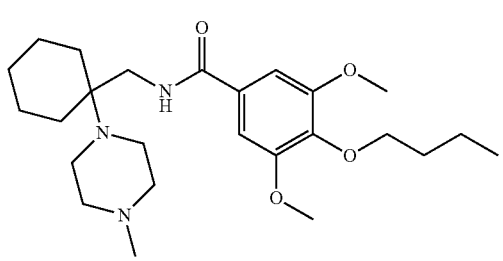
[Formula 32]
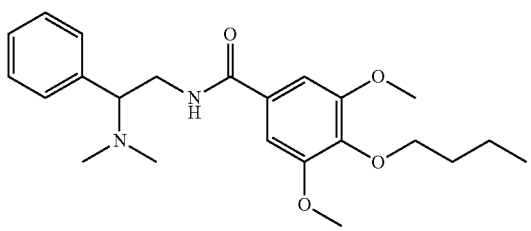
[Formula 33]
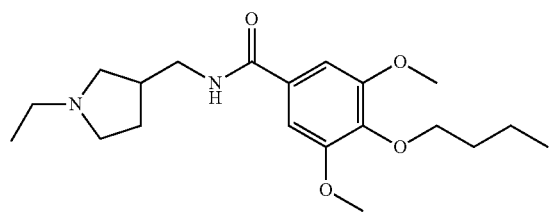
[Formula 34]
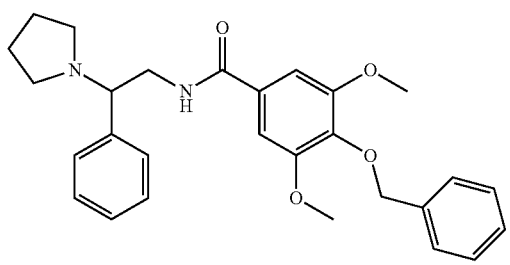
[Formula 35]
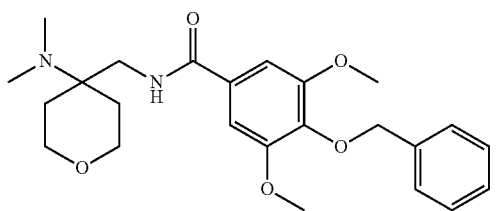
[Formula 36]
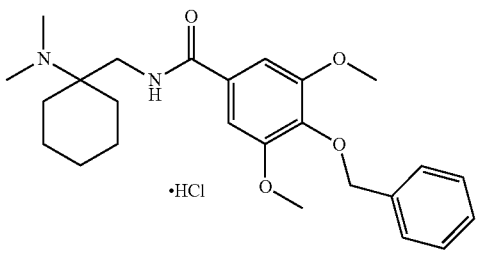
·HCl
[Formula 37]
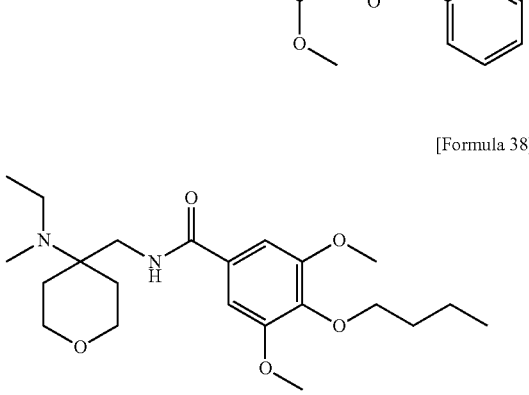
[Formula 38]
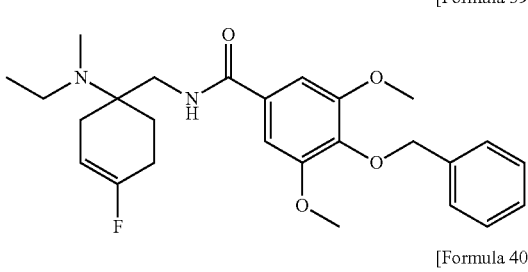
[Formula 39]
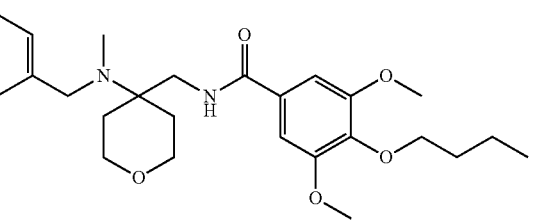
[Formula 40]
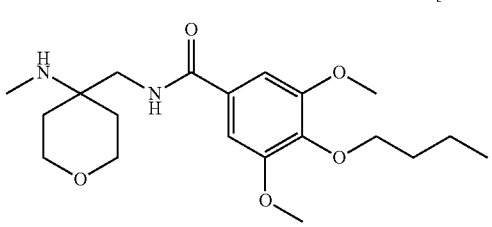
[Formula 41]

-continued

[Formula 42]

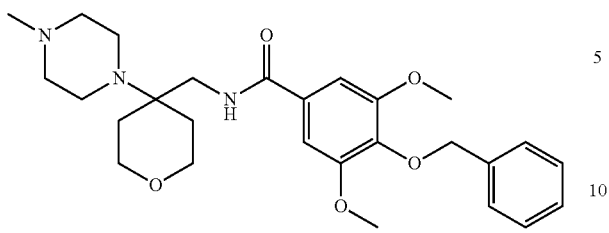

[Formula 43]

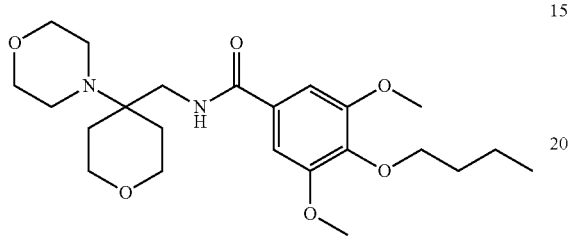

[Formula 44]

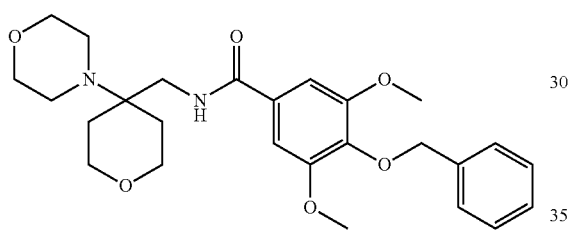

[Formula 45]

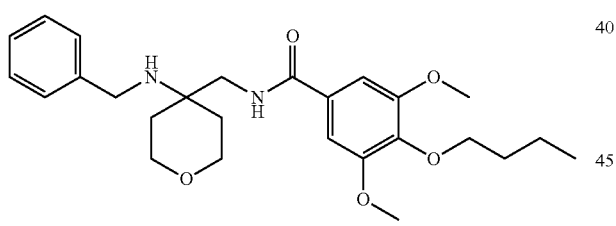

[Formula 46]

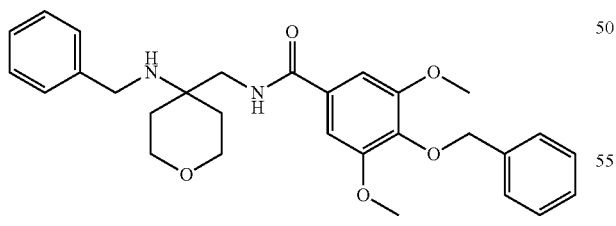

According to another aspect of the present invention, in the benzamide derivative represented by above Formula 1, $R_1$ may be $NHR_6$, $R_2$, $R_3$ and $R_5$ may be each hydrogen, and $R_4$ may be butoxy (—O(CH$_2$)$_3$CH$_3$) or benzyloxy (—OCH$_2$C$_6$H$_5$). Preferably, the present invention may provide the benzamide derivative or pharmaceutically acceptable salt thereof represented by Formula 47 to Formula 62 below.

[Formula 47]

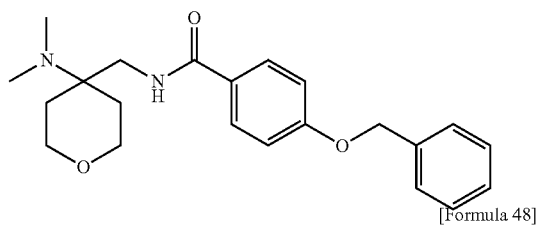

[Formula 48]

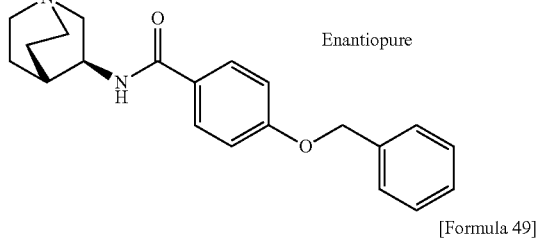

Enantiopure

[Formula 49]

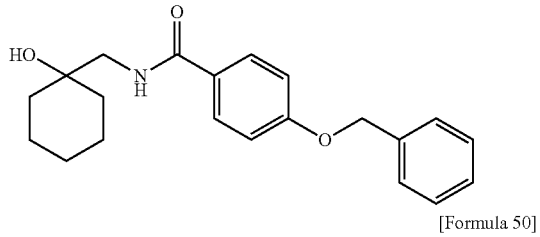

[Formula 50]

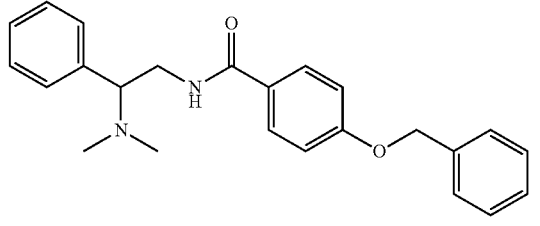

[Formula 51]

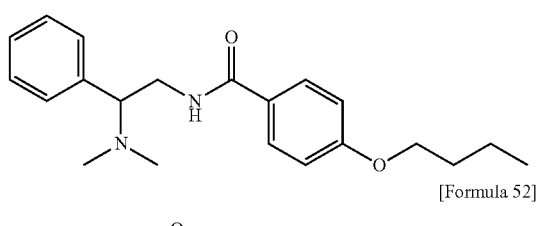

[Formula 52]

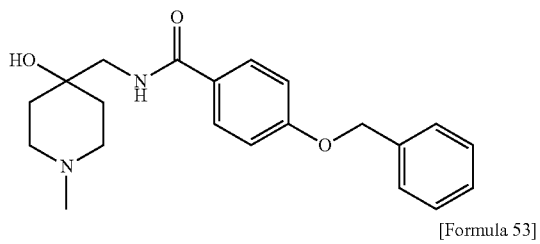

[Formula 53]

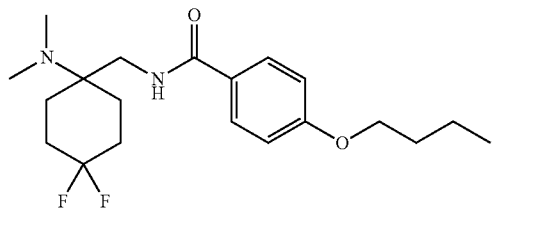

[Formula 54]
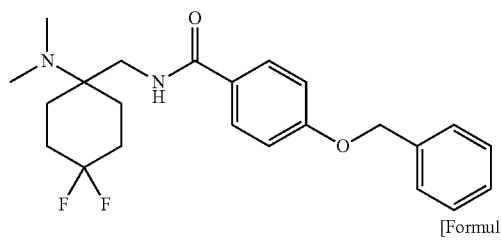

[Formula 55]
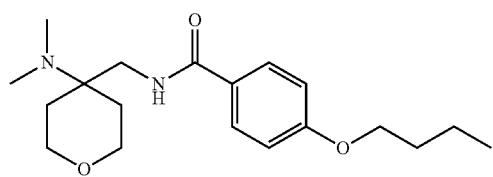

[Formula 56]
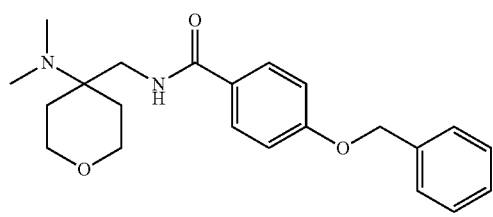

[Formula 57]
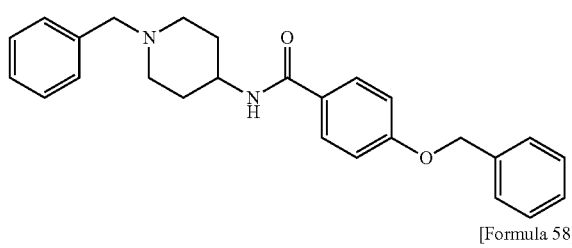

[Formula 58]
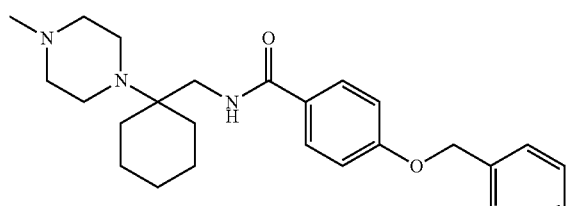

[Formula 59]
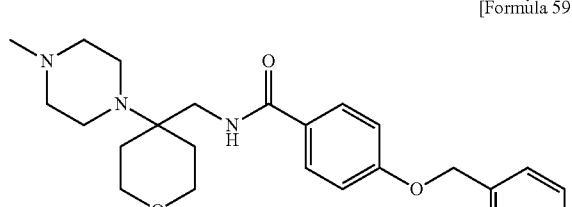

[Formula 60]
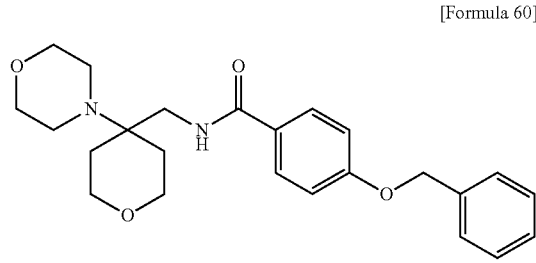

[Formula 61]
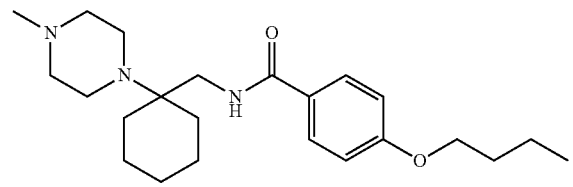

[Formula 62]
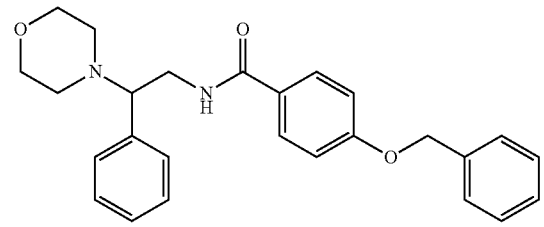

According to another aspect of the present invention, in the benzamide derivative represented by above Formula 1, $R_1$ may be $NHR_6$, $R_2$ may be hydrogen, $R_3$ and $R_5$ may be each methyl (—$CH_3$), $R_4$ may be butoxy (—$O(CH_2)_3CH_3$) or benzyloxy (—$OCH_2C_6H_5$). Preferably, the present invention may provide the benzamide derivative or pharmaceutically acceptable salt thereof represented by Formula 63 to Formula 75 below.

[Formula 63]
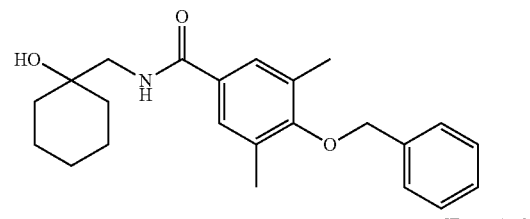

[Formula 64]
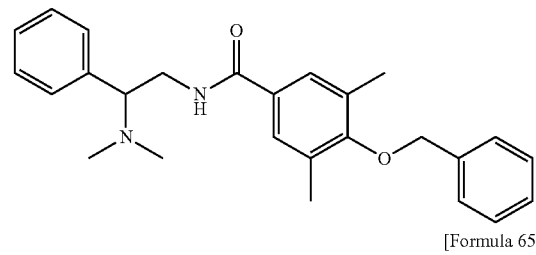

[Formula 65]
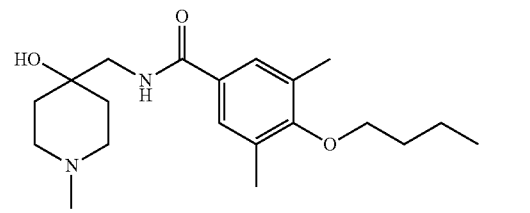

[Formula 66]
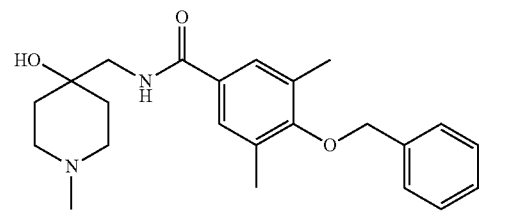

[Formula 67]
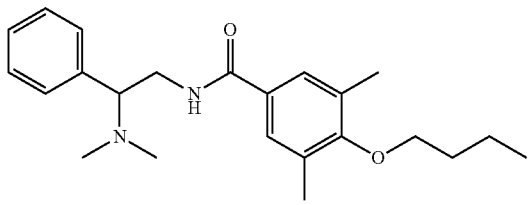

[Formula 73]
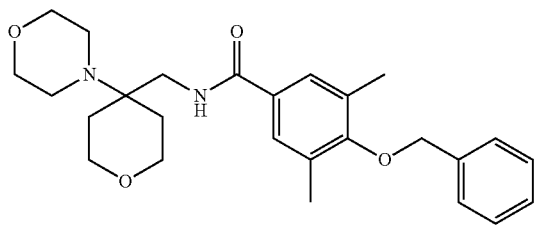

[Formula 68]
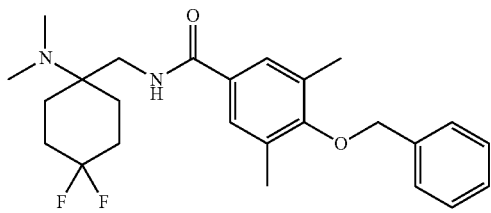

[Formula 74]
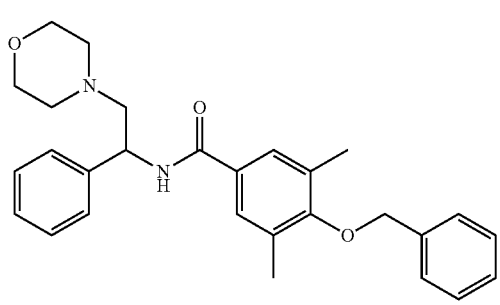

[Formula 69]
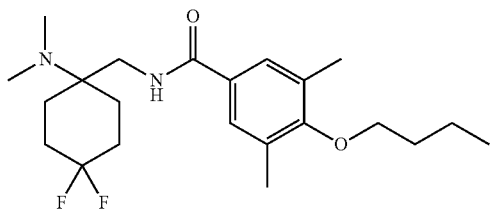

[Formula 75]
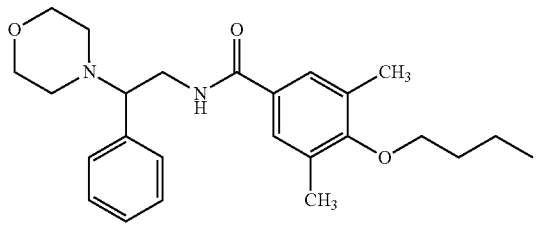

[Formula 70]
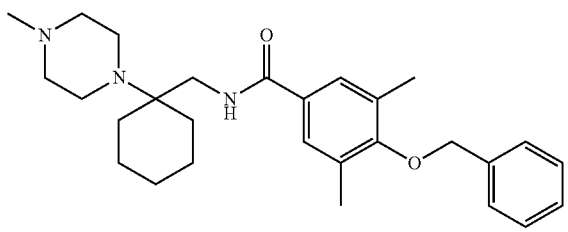

According to another aspect of the present invention, in the benzamide derivative represented by above Formula 1, $R_1$ may be $NHR_6$, $R_2$ may be methoxy (—$OCH_3$), $R_3$ may be hydrogen, $R_4$ may be amino group (—$NH_2$), and $R_5$ may be chlorine (—Cl). Preferably, the present invention may provide the benzamide derivative or pharmaceutically acceptable salt thereof represented by Formula 76 to Formula 80 below.

[Formula 71]
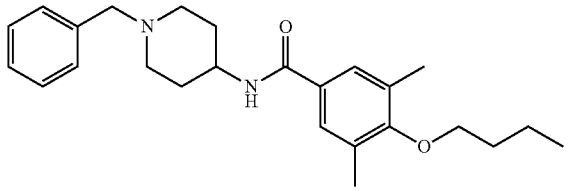

[Formula 76]
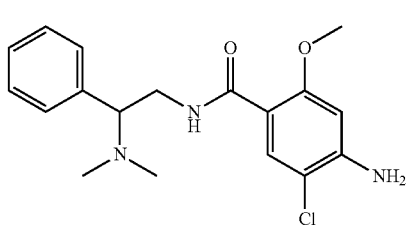

[Formula 72]
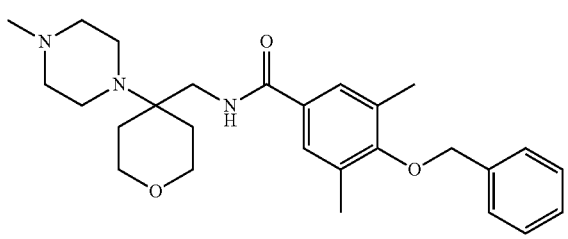

[Formula 77]
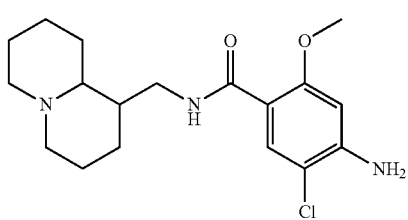

-continued

[Formula 78]

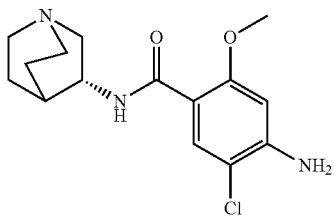
Enantiopure

[Formula 79]

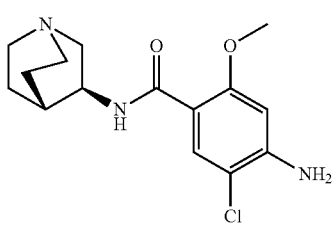
Enantiopure

[Formula 80]

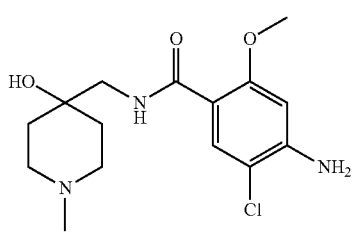

According to another aspect of the present invention, in the benzamide derivative represented by above Formula 1, $R_2$, $R_4$ and $R_5$ may be each hydrogen, and $R_3$ may be trifluoromethyl (—$CF_3$). Preferably, the present invention may provide the benzamide derivative or pharmaceutically acceptable salt thereof represented by Formula 81 to Formula 83 below.

[Formula 81]

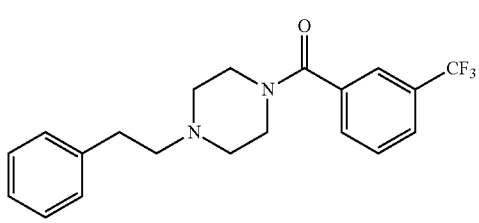

[Formula 82]

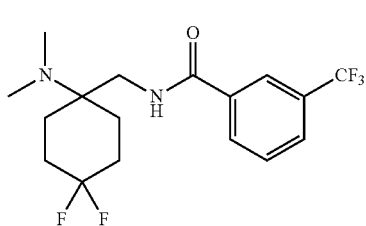

[Formula 83]

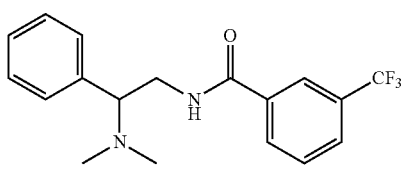

According to another aspect of the present invention, in the benzamide derivative represented by above Formula 1, $R_1$ may be

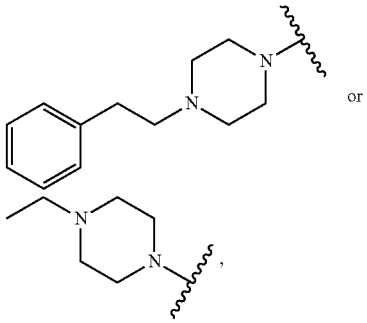

or $R_2$ may be hydrogen, $R_3$ and $R_5$ may be each methoxy (—$OCH_3$), $R_4$ may be butoxy (—$O(CH_2)_3CH_3$) or benzyloxy (—$OCH_2C_6H_5$). Preferably, the present invention may provide the benzamide derivative or pharmaceutically acceptable salt thereof represented by Formula 155 to Formula 157 below.

[Formula 155]

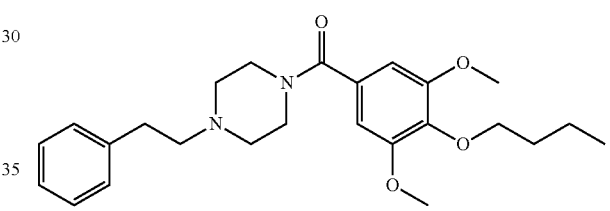

[Formula 156]

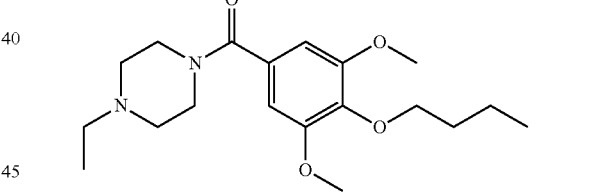

[Formula 157]

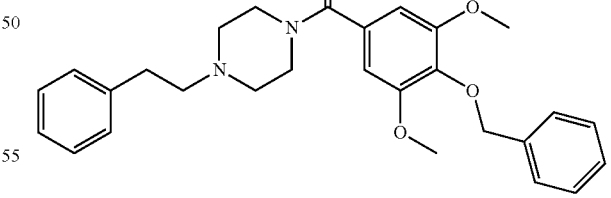

A novel benzamide derivative compound according to the present invention may be prepared by conventionally known methods depending upon types of substituents of the compound, for instance, by a method illustrated in the following reaction scheme. Since the preparation method with the following reaction scheme is proposed for illustration only and it is obviously understood that those skilled in the art can easily form modifications using specific substituents, a method for preparation of the benzamide derivative compound according to the present invention is not particularly limited to the method illustrated by the following reaction scheme and definition of the substituent in Reaction scheme 1 is substantially the same as that described in Formula 1 above, until further defined.

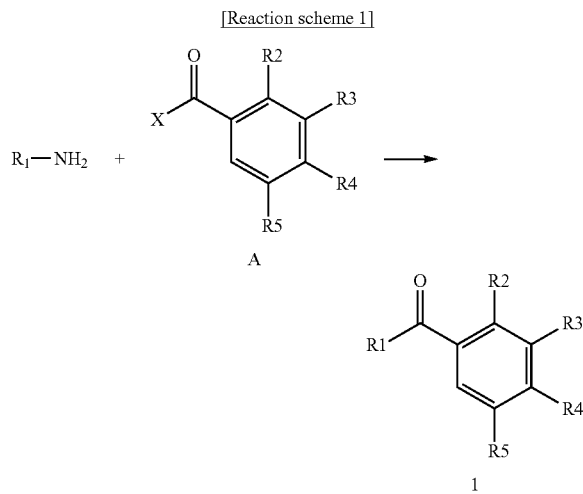

[Reaction scheme 1]

wherein X is OH or Cl.

According to one embodiment of the present invention, as described in Reaction schemes 2 to 86, after reacting an amine compound represented by R₁—NH₂ with a benzoic acid compound represented by Formula A in an organic solvent, the organic solvent is removed under reduced pressure to obtain an organic layer, followed by separation and purification through chromatography, thus resulting in a novel benzamide derivative. The organic solvent used herein may include, but not be limited to, diisopropylethylamine, triethylamine, N,N-dimethylformamide, tetrahydrofuran, etc.

According to another embodiment of the present invention, it is demonstrated that a novel compound and pharmaceutically acceptable salts thereof according to the present invention have activity simultaneously affecting both a GlyT2 target and a 5HT2A target, thereby attaining multi-target effects.

According to another embodiment of the present invention, it is demonstrated that the novel benzamide derivative and pharmaceutically acceptable salts thereof according to the present invention have excellent efficacy in neuropathic pain suppression with pain model experiments for tissue and living body. In particular, with regard to development of a compound of suppressing central neuropathic pain, Chung model (SNL-spinal nerve ligation model) widely used as a gold standard exhibited excellent pain suppression efficacy (see FIGS. 1 to 22). In addition, according to another embodiment of the present invention, since a desired effect was obtained even in a pain experiment using a formalin model, it was demonstrated that the inventive compound may effectively function in suppressing various pains including nociceptive pain, chronic pain, etc. as well as neuropathic pain (see FIGS. 23 and 24).

According to another embodiment of the present invention, it is demonstrated that the novel benzamide derivative and pharmaceutically acceptable salt thereof according to the present invention have multi-target activity simultaneously affecting both a GlyT2 target and a 5HT2A target, thereby exhibiting synergistic effects in terms of pain suppression efficacy. In order to identify synergistic effects in terms of multi-target activity, each of the pain animal models (Chung model and formalin model) is treated using MDL11939 as a 5-HT2A antagonist and ORG2553 as a GlyT2 antagonist, respectively, or as a combination thereof. As a result, when the 5-HT2A antagonist or GlyT2 antagonist is used alone, no or very little pain relieving effect is exhibited. On the other hand, using a combination of both the antagonists demonstrates remarkably improved pain relieving effect (see FIGS. 25 and 26).

Further, according to another embodiment of the present invention, a mechanism and treatment concept established with regard to pain are applied to itching. As a result of additional experiments conducted in an itching model, it is demonstrated that a compound and pharmaceutically acceptable salt thereof according to the present invention exhibit itching-suppressive effect, that is, anti-pruritic efficacy as well as pain-suppressive effect, and therefore, may effectively function as a composition for treatment or prevention of pruritus including atopic dermatitis (see FIGS. 27 and 28).

Accordingly, an aspect of the present invention relates to a composition for treatment or prevention of pain or pruritus.

Administration of the composition for treatment or prevention according to the present invention may include administering the benzamide derivative or pharmaceutically acceptable salt thereof according to the present invention alone. However, the above composition may further be generally administered in a pharmaceutical mixture form, which is suitably prepared into a formulation for specific uses and preferable purposes by mixing the above composition with any additive such as an excipient, binder, lubricant, disintegrant, coating material, emulsifier, suspension, solvent, stabilizer, absorption enhancer and/or ointment source. The mixture may be used for oral administration, injection, rectal administration or external remedy. Herein, "pharmaceutically acceptable" means a composition that is psychologically permitted and, when administered to the human, generally does not induce gastrointestinal disorders, allergic responses such as dizziness, or other similar responses.

An oral administering formulation may include, for example, tablets, coated tablets, dragees, hard or soft gelatin capsules, liquids, emulsions or suspensions. Administration may include: rectal administration, for example, using a suppository; local or transdermal administration, for example, in the form of ointment, cream, patch, gel or liquid; or non-oral administration, for example, using an injection solution for systemic administration or spinal administration.

For manufacturing a tablet, coated tablet, dragee, or hard or soft gelatin capsule, the benzamide derivative or pharmaceutically acceptable salt according to the present invention may further be mixed with a pharmaceutically inert inorganic or organic excipient (or pharmaceutically acceptable carrier). Examples of the excipient suitable for manufacturing the tablet, coated tablet, dragee, hard or soft gelatin capsule, or the like may include lactose, maize starch or derivatives thereof, talc, stearic acid, or salts thereof. Examples of an excipient suitable for manufacturing the soft gelatin capsule may include a vegetable oil, wax, fat, semi-solid or liquid polyol. However, the soft gelatin capsule optionally does not need any excipient depending upon features of active ingredients. For manufacturing liquid and syrup products, the excipient useable herein may include, for example, water, polyol, sucrose, invert sugar and glucose. Examples of the excipient useable in manufacturing a solution for injection may include water, alcohol, polyol, glycerin and vegetable oil. Examples of the excipient useable in manufacturing locally or transdermally applicable formulations as well as suppositories may include natural oil or hardened oil, wax, fat and semi-solid or liquid polyol.

The composition of the present invention may further include a preservative, solvent, stabilizer, wetting agent, emulsifier, sweetener, colorant, aromatic, osmotic pressure controlling salt, buffer, coating agent, tension relieving agent, isotonic regulating agent or antioxidant, and may further include other therapeutically valuable medicaments.

Consequently, a pharmaceutical formulation for oral administration may include granulates, tablets, sugar coating tablets, capsules, pills, suspensions or emulsions, while a formulation for non-oral administration may include, for example, a formulation in a sterile solution for intravenous, intramuscular or subcutaneous administration, and may further include other substances, for example, salts or glucoses in order to prepare an isotonic solution. Alternatively, a suppository or pessary formulation may be administered, or other formulations for external use in any form of patch, lotion, cream, ointment or dusting powder may also be adopted.

It is understood that a proper dosage of the inventive composition may be determined according to different related parameters including, for example, formulation method, manner of administration, age, gender, body weight and/or condition of illness, severity of patient, food, administering time, administering route, excretory speed, reaction sensibility, etc. Therefore, the dosage does not restrict the scope of the present invention under any conditions or aspects.

EXAMPLE

Hereinafter, the present invention will be described in detail by means of examples. However, the following examples are given for more concretely describing the present invention and may not be construed as a limitation of the scope of the present invention.

Example 1

Preparative Example 1

Preparation of Compound Represented by Formula 2 (VVZ-001)

[Reaction scheme 2]

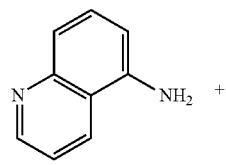

84

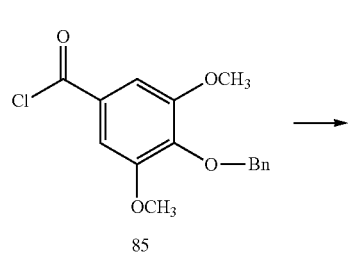

85

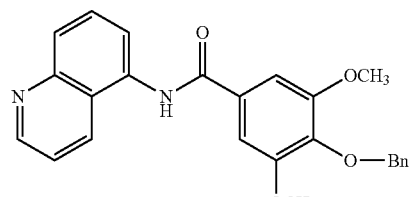

2

As shown in reaction scheme 2 above, after cooling a solution of 5-aminoquinoline represented by Formula 84 (439.93 mg, 3.05 mmol, purchased from TCI Co.) and triethylamine (0.95 mL, 6.78 mmol) in THF (10 mL) at 0° C. under a nitrogen atmosphere, a solution of 4-n-benzyloxy-3,5-dimethoxybenzoic acid chloride represented by Formula 85 (1.04 g, 3.39 mmol) in THF (15 mL) was slowly added to the above cold solution. After agitating the prepared solution at the same temperature for 30 minutes, this solution was left at room temperature for 18 hours. After filtering and removing a precipitate generated during the reaction, the remaining solution was diluted with chloroform and washed with a potassium carbonate solution, followed by separation and drying with (anhydrous) sodium sulfate. A concentrate remaining after removing the solvent under reduced pressure was recrystallized using ethyl acetate and hexane, resulting in a benzamide compound represented by Formula 2 as a desired product (VVZ-001; 1.08 g, 77% yield).

Analysis data of the produced benzamide compound is provided as follows.

$R_f$ (ethyl acetate/hexane/triethylamine, 2:1:0.1, v/v/v) 0.3;

HRMS (EI+) calcd for $C_{25}H_{22}N_2O_4$ ([M+]) 414.1580.

$^1$H NMR (500 MHz, DMSO-$d_6$) d 3.89 (s, 6H), 5.02 (s, 2H), 7.32 (t, 1H, J=7.5 Hz), 7.38 (t, 2H, J=7.5 Hz), 7.43 (s, 2H), 7.48 (d, 2H, J=7.5 Hz), 7.56 (dd, 1H, J=8.5 Hz, 8.5 Hz), 7.66 (d, 1H, J=7.5 Hz), 7.81 (t, 1H, J=7.5 Hz), 7.97 (d, 1H, J=8.5 Hz), 8.35 (d, 1H, J=8.0 Hz), 8.94 (dd, 1H, J=4.0 Hz, 4.0 Hz), 10.48 (s, 1H).

The compound represented by Formula 85 used herein was synthesized through the following four (4)-step chemical reaction after starting from methyl 3,4,5-trimethoxybenzoate purchased from Sigma-Aldrich Co.

Step 1: Preparation of methyl 3,5-dimethoxy-4-hydroxybenzoate

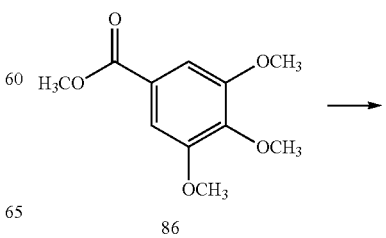

86

-continued

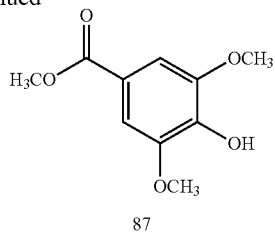

87

Aluminum chloride (III) (7.22 g, 54.1 mmol) was slowly added to methyl 3,4,5-trimethoxybenzoate represented by Formula 86 (3.50 g, 15.5 mmol, purchased from Sigma-Aldrich Co.) in dichloromethane (200 mL) at room temperature. After agitating the reaction mixture at room temperature, the solution was diluted with chloroform, washed with a 2N hydrochloric acid solution, followed by separation to form an organic layer. The organic layer was dried with sodium sulfate and the solvent was removed under reduced pressure. The remaining vacuum-concentrated mixture was subjected to separation and purification through column chromatography (chloroform/methanol, 20:1, v/v) using silica gel (SiO$_2$), resulting in a phenol compound represented by Formula 87 as a desired product (3.20 g, 98%). Analysis data of the above product is provided as follows.

$R_f$ (ethyl acetate <55>/hexane, 1:1) 0.4;

$^1$H NMR (500 MHz, DMSO-d$_6$) d 3.81 (s, 9H), 7.22 (s, 2H).

Step 2: Preparation of methyl 4-benzyloxy-3,5-dimethoxybenzoate

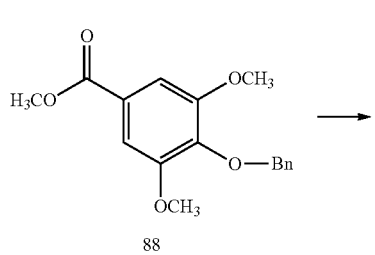

A mixture of methyl 3,5-dimethoxy-4-hydroxybenzoate represented by Formula 87 (7.00 g, 33.00 mmol), benzyl bromide (4.31 mL, 36.29 mmol), potassium carbonate (5.02 mg, 36.29 mmol) and potassium iodide (547.60 mg, 3.30 mmol) in DMF (60 mL) was agitated at 80° C. for 24 hours. After decreasing a temperature of the reaction mixture to room temperature, removing solids through filtration, (washing the same with acetone) and adding ethyl acetate to the remaining concentrate, the concentrate was consecutively washed with water and a 5N-hydrochloric acid solution. After separating an organic layer, drying the same with (anhydrous) magnesium sulfate and removing the solvent under reduced pressure, the obtained concentrate mixture was subjected to separation and purification through column chromatography (ethyl acetate/hexane, 1:5) using silica gel (SiO$_2$), resulting in an n-benzylether compound represented by Formula 88 (8.28 g, 83%) as a desired product. Analysis data of the product is provided as follows.

$R_f$ (ethyl acetate <60>/hexane, 1:5) 0.4;

$^1$H NMR (500 MHz, DMSO-d$_6$) d 3.82 (s, 6H), 3.84 (s, 3H), 4.99 (2, 2H), 7.23 (s, 2H), 7.30 (t, 1H, J=7.0 Hz), 7.35 (t, 2H, J=7.0 Hz), 7.44 (d, 2H, J=6.0 Hz).

Step 3: Preparation of 4-benzyloxy-3,5-dimethoxybenzoic acid

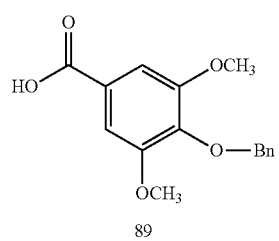

After agitating a solution of methyl 4-n-benzyloxy-3,5-dimethoxybenzoate represented by Formula 88 (8.61 g, 28.46 mmol) dissolved in potassium hydroxide (KOH, 44%, 20 mL) solution and methanol (185 mL) at 65° C. for 2 hours, the solution was cooled to room temperature and the solvent was removed under reduced pressure. The remaining concentrate mixture was dissolved again in water and washed with ethyl ether (×3) to form an aqueous solution. Adding a 5N-hydrochloric acid solution to the formed solution to reach pH 1 and a precipitate generated during this process was obtained through filtration. The obtained precipitate was washed with water and dried, followed by recrystallization in methanol (20 mL). As a result, bezoic acid represented by Formula 89 was obtained as a desired product (6.98 g, 85%). Analysis data of this product is provided as follows:

$R_f$ (ethyl acetate <65>/hexane, 1:2) 0.1;

$^1$H NMR (500 MHz, DMSO-d$_6$) d 3.82 (s, 6H), 4.98 (s, 2H), 7.23 (s, 2H), 7.30 (t, 1H, J=7.5 Hz), 7.36 (t, 2H, J=7.5 Hz), 7.44 (d, 2H, J=7.5 Hz).

Step 4: Preparation of 4-n-benzyloxy-3,5-dimethoxybenzoic acid chloride

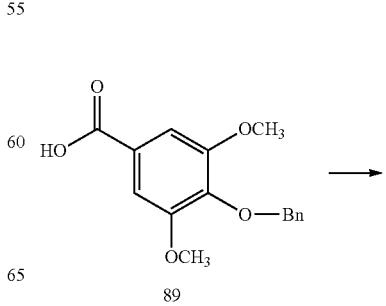

31

-continued

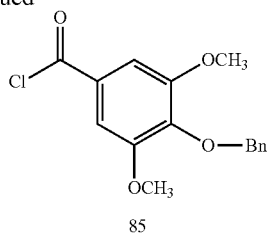
85

After agitating a reaction mixture prepared by adding one droplet of DMF to a solution of 4-benzyloxy-3,4-dimethoxybenzoic acid represented by Formula 89 (1.0 g, 3.47 mmol) and oxalic acid chloride (1.51 mL, 17.34 mmol) in dichloromethane (11 mL) at room temperature for 3 hours under a nitrogen atmosphere, the solvent was removed under reduced pressure to form a concentrate (1.04 g, 98%). This concentrate was used in the above reaction scheme 2 without further purification.

Preparative Example 2

Preparation of Compound Represented by Formula 3 (VVZ-002)

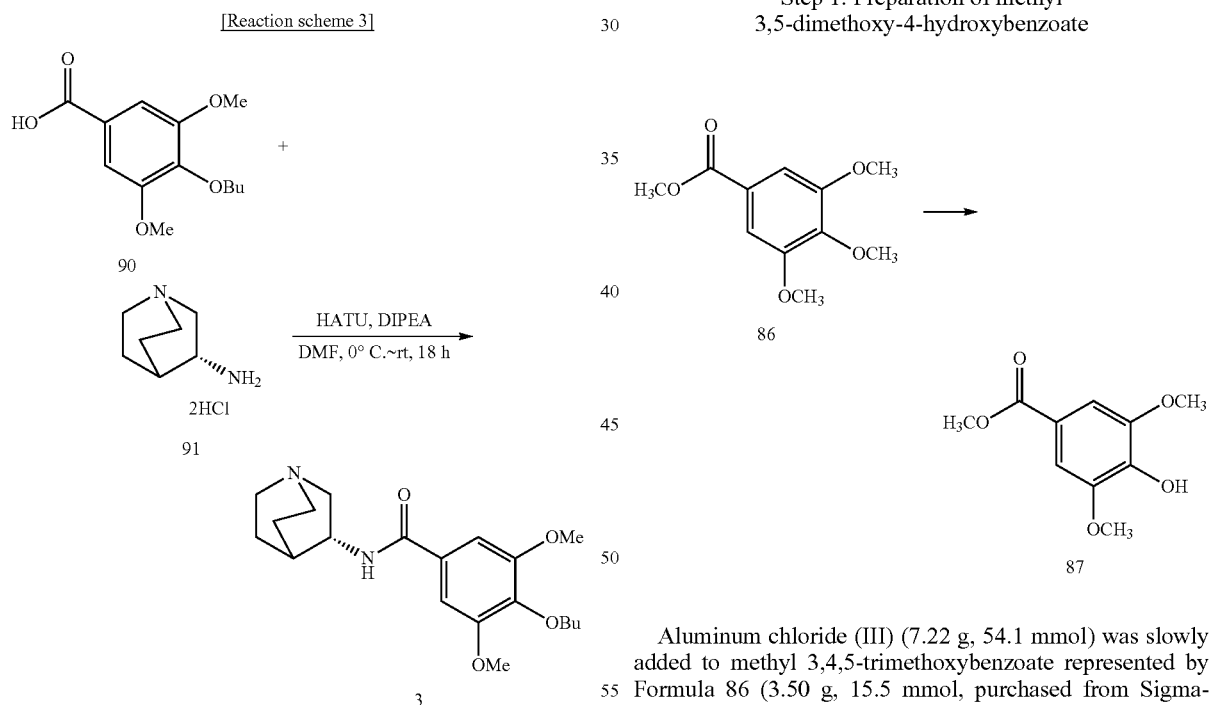

4-n-butoxy-3,5-dimethoxybenzoic acid represented by Formula 90 (2 g, 7.87 mmol) was slowly added to a solution of (R)-3-aminoquinuclidine chloride represented by Formula 91 (1.57 g, 7.87 mmol, purchased from Sigma-Aldrich Co.) and diisopropylethylamine (4.11 mL, 23.60 mmol) in DMF (5 mL) at room temperature. The reaction mixture was cooled to 0° C. and, after adding 2-(1H-7-azabenzotriazol-1-yl)-1,1,3,3-tetramethyluronium hexafluorophosphate methanaminium (HATU, 2.84 g, 7.47 mmol) thereto, the mixture was agitated at room temperature for 18 hours. After remov-

32 ing the reaction solvent under reduced pressure, chloroform/methanol (9:1) was added to the remaining concentrate to prepare a solution and the solution was washed with a potassium carbonate solution, followed by separation to form an organic layer. After drying the organic layer with magnesium sulfate (MgSO$_4$), the solvent was removed again under reduced pressure. The obtained vacuum-concentrated mixture was subjected to separation and purification through column chromatography (chloroform/methanol/ammonia solution, 10:1:0.01) using silica gel (SiO$_2$), resulting in a benzamide compound represented by Formula 3 (VVZ-002; 2.63 g, 92% yield).

Analysis data of the provided benzamide compound is provided as follows.

$R_f$ (chloroform/methanol/triethylamine, 10:1:0.1, v/v/v) 0.14;

HRMS (EI+) calcd for $C_{20}H_{30}N_2O_4$ ([M+]) 362.2205. found 362.2209.

$^1$H NMR (500 MHz, DMSO-d$_6$) δ 0.91 (t, 3H, J=7.3 Hz), 1.28-1.33 (m, 1H), 1.39-1.47 (m, 2H), 1.56-1.62 (m, 4H), 1.76-1.78 (m, 1H), 1.86-1.87 (m, 1H), 2.62-2.73 (m, 4H), 2.85-2.89 (m, 1H), 3.08-3.13 (m, 1H), 3.82 (s, 6H), 3.88 (t, 2H, J=6.5 Hz), 7.14 (s, 2H), 8.12 (d, 1H, J=7.0 Hz).

The compound represented by Formula 90 used herein was synthesized through the following three (3)-step chemical reaction after starting from methyl 3,4,5-trimethoxybenzoate purchased from Sigma-Aldrich Co.

Step 1: Preparation of methyl 3,5-dimethoxy-4-hydroxybenzoate

Aluminum chloride (III) (7.22 g, 54.1 mmol) was slowly added to methyl 3,4,5-trimethoxybenzoate represented by Formula 86 (3.50 g, 15.5 mmol, purchased from Sigma-Aldrich Co.) in dichloromethane (200 mL) at room temperature. After agitating the reaction mixture at room temperature for 4 hours, the obtained solution was diluted with chloroform and washed with 2N-hydrochloric acid solution, followed by separation to form an organic layer. The organic layer was dried with sodium sulfate and the solvent was removed under reduced pressure. The obtained vacuum-concentrated mixture was subjected to separation and purification through column chromatography (chloroform/methanol, 20:1, v/v) using silica gel (SiO$_2$), resulting in a phenol compound represented by Formula 87 as a desired product (3.20 g, 98%). Analysis data of the product is provided as follows.

$R_f$ (ethyl acetate <55>/hexane, 1:1) 0.4;

$^1$H NMR (500 MHz, DMSO-$d_6$) δ 3.81 (s, 9H), 7.22 (s, 2H).

Step 2: Preparation of methyl 4-n-butoxy-3,5-dimethoxybenzoate

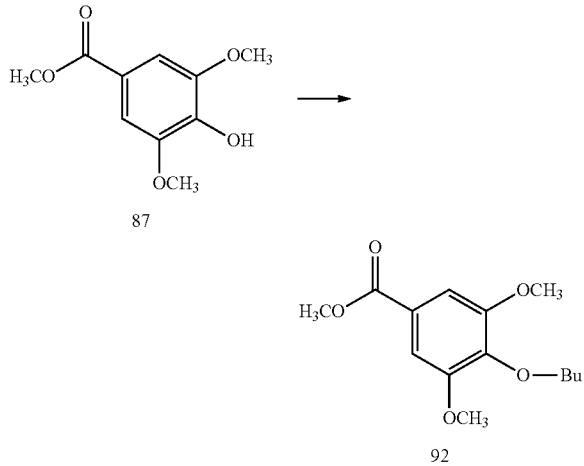

A mixture of methyl 3,5-dimethoxy-4-hydroxybenzoate represented by Formula 87 (5 g, 23.56 mmol), 1-bromobutane (2.80 mL, 25.92 mmol), potassium carbonate (3.58 mg, 25.92 mmol) and potassium iodide (547.60 mg, 3.30 mmol) in DMF (50 mL) was agitated at 80° C. for 24 hours. After decreasing a temperature of the reaction mixture to room temperature, removing solids through filtration and adding ethyl acetate to the remaining filtrate, the filtrate was consecutively washed with water and a 5N-hydrochloric acid solution. After separating an organic layer and drying the same with magnesium sulfate, the solvent was removed under reduced pressure to form a concentrate mixture, which in turn, was subjected to separation and purification through column chromatography (ethyl acetate/hexane, 1:5) using silica gel (SiO$_2$), resulting in an n-butylether compound represented by Formula 92 as a desired product (6.20 g, 94%). Analysis data of the product is provided as follows:

$R_f$ (ethyl acetate <60>/hexane, 1:5) 0.5;

$^1$H NMR (500 MHz, DMSO-$d_6$) δ 0.89 (t, 3H, J=7.3 Hz), 1.41 (m, 2H), 1.59 (m, 2H), 3.80 (s, 6H), 3.83 (s, 3H), 3.90 (t, 2H, J=6.5 Hz), 7.21 (s, 2H).

Step 3: Preparation of 4-n-butoxy-3,5-dimethoxybenzoic acid

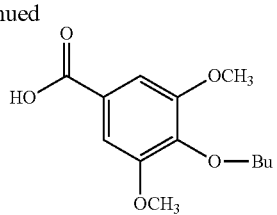

After agitating a solution of methyl 4-n-butoxy-3,5-dimethoxybenzoate represented by Formula 92 (5.83 g, 21.74 mmol) dissolved in a potassium hydroxide solution (KOH, 44%, 10 mL) and methanol (120 mL) at 65° C. for 2 hours, the prepared solution was cooled to room temperature and the solvent was removed under reduced pressure. The concentrate mixture was dissolved again in water and washed with ethylether (×3). Then, a 5N-hydrochloric acid solution was added to the above prepared solution to reach pH 1, and a precipitate generated during this process was obtained through filtration. The obtained precipitate was washed using water several times and dried, followed by recrystallization using methanol (20 mL), resulting in benzoic acid represented by Formula 90 as a desired product (4.28 g, 78%). Analysis data of the product is provided as follows:

$R_f$ (ethyl acetate <65>/hexane, 1:2) 0.2;

$^1$H NMR (500 MHz, DMSO-$d_6$) δ 0.91 (t, 3H, J=7.3 Hz), 1.43 (m, 2H), 1.60 (m, 2H), 3.81 (s, 6H), 3.91 (t, 2H, J=6.5 Hz), 7.22 (s, 2H).

Preparative Example 3

Preparation of Compound Represented by Formula 4 (VVZ-003)

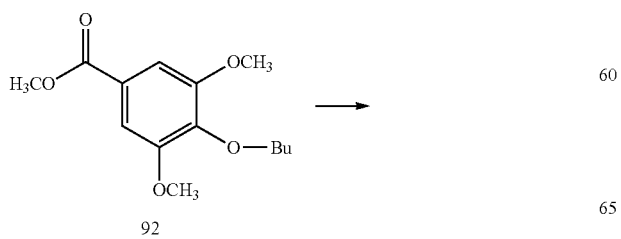

The same procedures as described in Preparative Example 2 were conducted, and 4-benzyloxy-3,4-dimethoxybenzoic acid represented by Formula 89 (100.00 mg, 0.347 mmol) prepared in Preparative Example 1 and (R)-3-aminoquinuclidine hydrochloride represented by Formula 91 (69.07 mg, 0.347 mmol) were used according to reaction scheme 4. As a result, a benzamide compound represented by Formula 4 was obtained as a desired product (VVZ-003; 46.40 mg, 33.7% yield).

Analysis data of the produced benzamide compound is provided as follows.

$^1$H-NMR (MeOD-d$_4$) d 1.55 (m, 1H), 1.79 (m, 2H), 1.92 (m, 1H), 2.04 (m, 1H), 2.85 (m, 4H), 3.02 (m, 2H), 3.89 (s, 6H), 4.13 (m, 1H), 5.02 (s, 2H), 7.18~7.48 (m, 7H).

Preparative Example 4

Preparation of Compound Represented by Formula 5 (VVZ-004)

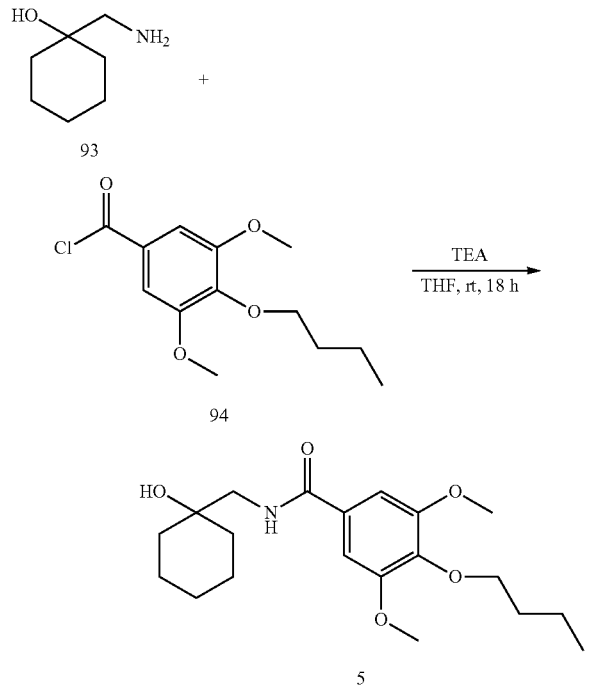

The same procedures as described in Preparative Example 1 were conducted, and 1-aminomethyl-1-cyclohexanol represented by Formula 93 (28 mg, 0.220 mmol) and 4-butoxy-3,5-dimethoxybenzoic acid chloride represented by Formula 94 (60 mg, 0.220 mmol) were used according to reaction scheme 5. As a result, a benzamide compound represented by Formula 5 was obtained as a desired product (VVZ-004; 61.00 g, 75.9% yield).

Analysis data of the benzamide compound is provided as follows.

$^1$H-NMR (MeOD-d$_4$) d 0.98 (t, 3H), 1.48~1.72 (m, 14H), 3.43 (s, 2H), 3.91 (s, 6H), 3.99 (t, 2H), 7.2 (s, 2H).

Preparative Example 5

Preparation of Compound Represented by Formula 6 (VVZ-005)

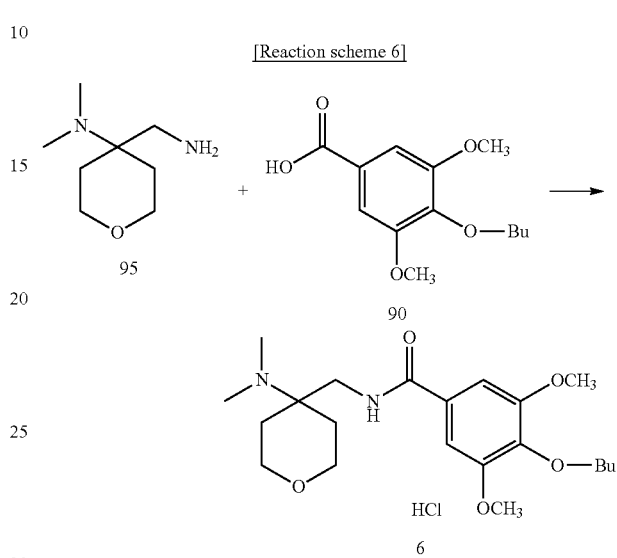

4-n-butoxy-3,5-dimethoxybenzoic acid represented by Formula 90 (6 g, 23.60 mmol) prepared in Preparative Example 2 above was slowly added to a solution of 4-(aminomethyl)-N,N-dimethyltetrahydro-2H-pyran-4-amine represented by Formula 95 (3.73 g, 23.60 mmol) and diisopropylethylamine (12.36 mL, 70.78 mmol) in DMF (80 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 8.97 g, 23.60 mmol) thereto, the mixture was agitated at room temperature for 24 hours. The reaction solvent was removed under reduced pressure and ethyl acetate was added to the remaining concentrate to prepare a solution. The prepared solution was washed with a potassium carbonate solution, followed by separation to form an organic layer. Then, after drying the organic layer with magnesium sulfate (MgSO$_4$), the solvent was removed again under reduced pressure. The obtained vacuum-concentrated mixture was subjected to separation and purification through column chromatography (chloroform/methanol, 10:1) using silica gel (SiO$_2$). After dissolving the obtained organic product in ethyl acetate, 2 M-ethylether chloride solution (14.16 mL, 28.31 mmol) was added thereto, followed by agitation at 45° C. for 15 minutes. Thereafter, the solvent was filtered to obtain a product in a powder form and the product was recrystallized in ethanol-methanol to thus produce a benzamide compound represented by Formula 6 as a desired product (VVZ-005; 6.77 g, 66% yield).

Analysis data of the produced benzamide compound is provided as follows.

R$_f$(chloroform/methanol, 10:1, v/v) 0.5;
HRMS (EI+) calcd for C$_{21}$H$_{35}$ClN$_2$O$_5$ ([M+]) 430.2234.
$^1$H NMR (500 MHz, MeOH-d$_4$) δ0.96 (t, 3H, J=5.8 Hz), 1.48-1.53 (m, 2H), 1.65-1.69 (m, 2H), 1.95-1.98 (m, 4H), 2.97 (s, 6H), 3.72-3.77 (m, 2H), 3.89 (s, 6H), 3.97-4.02 (m, 6H), 7.26 (s, 2H).

The compound represented by Formula 95 and used herein was synthesized through the following two (2)-step chemical reaction after starting from dimethylamine chloride purchased from Sigma-Aldrich Co., as well as tetrahydro-4H-pyran-4-one purchased from TCI Co.

Step 1: Preparation of 4-(dimethylamino)tetrahydro-2H-pyran-4-carbonitrile

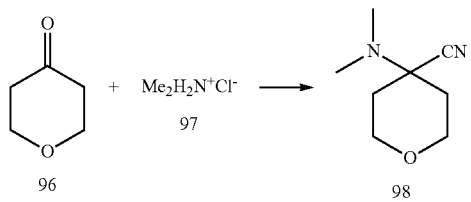

After mixing tetrahydro-4H-pyran-4-one represented by Formula 96 (10 g, 99.88 mmol) and dimethylamine chloride represented by Formula 97 (8.14 g, 99.88 mmol), 50 mL of a potassium cyanate solution (6.50 g, 99.88 mmol) was added thereto. The mixture was agitated at 0° C. for 10 minutes and, further, agitated at room temperature for 18 hours. After terminating the reaction and adding solid potassium carbonate thereto, the mixture was washed consecutively with ethylether and a potassium carbonate solution, followed by separation to form an organic layer. The organic layer was dried with sodium sulfate and the solvent was removed under reduced pressure. As a result, a nitrile compound represented by Formula 98 was produced (14.763 g, 96%). Analysis data of this product is provided as follows.

$R_f$ (ethyl acetate/hexane, 1:1, v/v) 0.6;
$^1$H NMR (500 MHz, MeOD-$d_4$) δ1.69 (dt, 2H, J=12.8, 4.0 Hz), 2.11 (dd, 2H, J=16.0, 2.5 Hz), 2.34 (s, 6H), 3.58 (td, 2H, J=12.1, 2.2 Hz), 3.99 (dt, 2H, J=12.5, 3.7 Hz).

Step 2: Preparation of 4-(aminomethyl)-N,N-dimethyltetrahydro-2H-pyran-4-amine

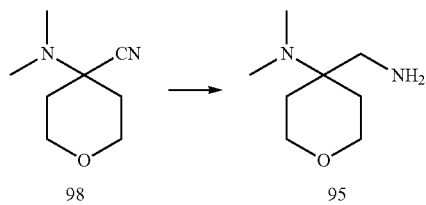

A solution of 4-(dimethylamino)tetrahydro-2H-pyran-4-carbonitrile represented by Formula 98 (5.79 g, 37.54 mmol) dissolved in ethylether (80 mL) was added to a solution of lithiumaluminum hydride (2.85 g, 75.07 mmol) in ethylether (300 mL) at room temperature. After reacting this mixture under refluxing for 2 days, cooling to room temperature and quenching the same using 15 mL water, the treated content was filtered to obtain a solution. From the solution, the solvent was removed under reduced pressure. As a result, an amine compound represented by Formula 95 was produced (4.65 g, 78%). Analysis data of the product is provided as follows.

$R_f$ (ethyl acetate/methanol, 10:1, v/v) 0.01;
$^1$H NMR (500 MHz, MeOD-$d_4$) δ1.51-1.54 (m, 2H), 1.74-1.79 (m, 2H), 2.29 (s, 6H), 2.82 (s, 2H), 3.52-3.57 (m, 2H), 3.78-3.83 (m, 2H).

Preparative Example 6

Preparation of Compound Represented by Formula 7 (VVZ-006)

[Reaction scheme 7]

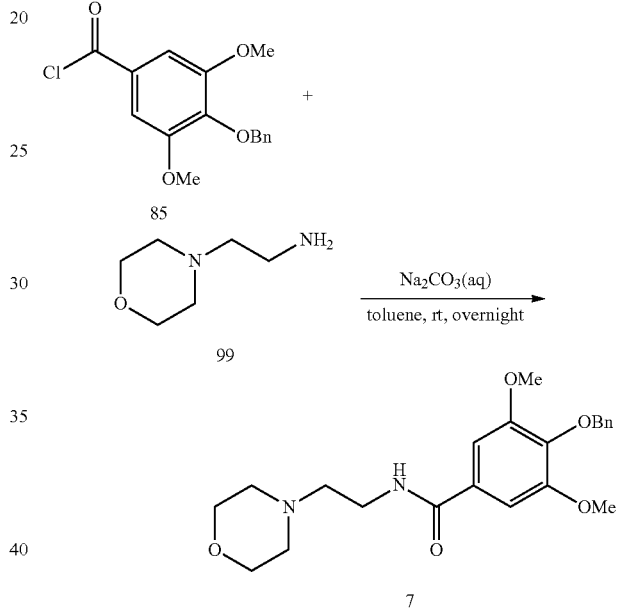

First, 4-benzyloxy-3,5-dimethoxybenzoic acid chloride represented by Formula 85 (61.30 mg, 0.200 mmol) prepared in Preparative Example 1 and 4-(2-aminoethyl)morpholine represented by Formula 99 (31.22 mg, 0.240 mmol) were prepared in 0.2 M solution, respectively, using a toluene solvent. After adding 1M sodium carbonate solution and 0.2 M acyl chloride solution to the above solutions, the mixture was vigorously shaken and agitated at room temperature overnight. After terminating the reaction, an aqueous layer was discarded using a tip while an organic layer was moved to a cartridge tube (6 mL, benzenesulfonic acid, 904030-WJ, UCT) using ethyl acetate. Impurities were removed using methanol (15 mL), while separation and purification using an elute solution (ethyl acetate/methanol/triethylamine, 20:2:1, v/v/v) was conducted to produce a benzamide compound represented by Formula 7 as a desired product (VVZ-006; 79.10 mg, 98.8% yield).

Analysis data of the produced benzamide compound is provided as follows.

$^1$H-NMR (MeOD-$d_4$) d 2.56 (m, 4H), 2.61 (t, 2H), 3.55 (t, 2H), 3.72 (m, 4H), 3.88 (s, 6H), 5.01 (s, 2H), 7.17~7.46 (m, 7H).

Preparative Example 7

Preparation of Compound Represented by Formula 8 (VVZ-009)

[Reaction scheme 8]

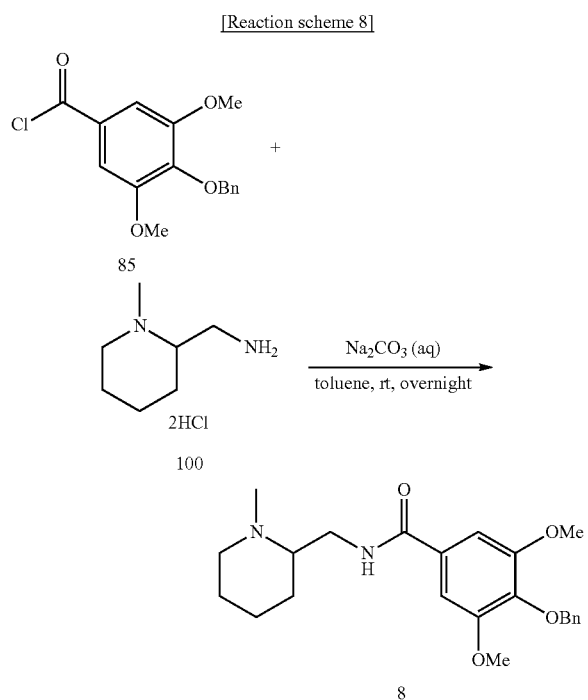

The same procedures as described in Preparative Example 2 were conducted, and 4-benzyloxy-3,5-dimethoxybenzoic acid chloride represented by Formula 85 (61.340 mg, 0.200 mmol) prepared in Preparative Example 1 and a compound represented by Formula 100 (48.27 mg, 0.240 mmol) were used according to reaction scheme 8. As a result, a benzamide compound represented by Formula 8 was obtained as a desired product (VVZ-009; 57.00 mg, 71.5% yield).

Analysis data of the produced benzamide compound is provided as follows.

$^1$H-NMR (MeOD-$d_4$) d 1.38 (m, 2H), 1.65 (m, 2H), 1.78 (m, 2H), 2.28 (m, 2H), 2.44 (s, 3H), 3.43 (s, 2H), 2.92 (m, 1H), 3.74 (m, 2H), 3.89 (s, 6H), 5.05 (s, 2H), 7.19~7.46 (m, 7H).

Preparative Example 8

Preparation of Compound Represented by Formula 9 (VVZ-010)

[Reaction scheme 9]

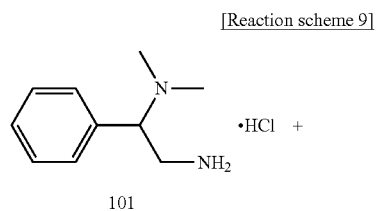

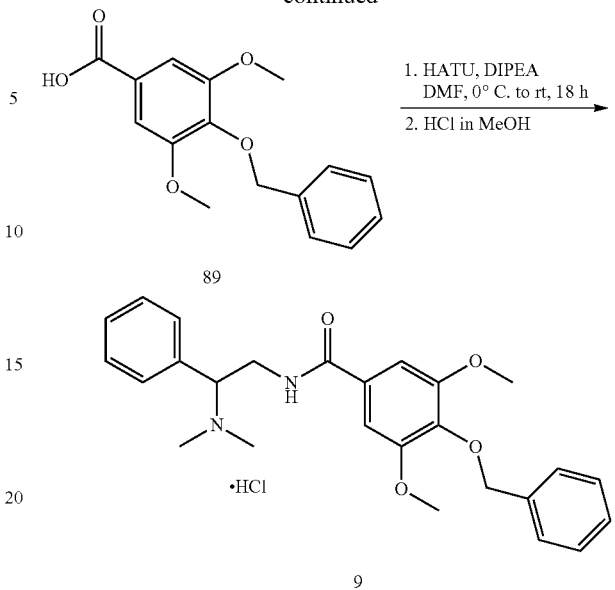

The same procedures as described in Preparative Example 2 were conducted, and a compound represented by Formula 101, i.e., N,N-dimethyl-1-phenyl-ethane-1,2-diamine chloride (40.14 mg, 0.200 mmol) as well as a compound represented by Formula 89 (57.660 mg, 0.200 mmol) prepared in Preparative Example 1 were used according to reaction scheme 9. As a result, a benzamide compound represented by Formula 9 was obtained as a desired product (VVZ-010; 52.70 mg, 55.9% yield).

Preparative Example 9

Preparation of Compound Represented by Formula 10 (VVZ-011)

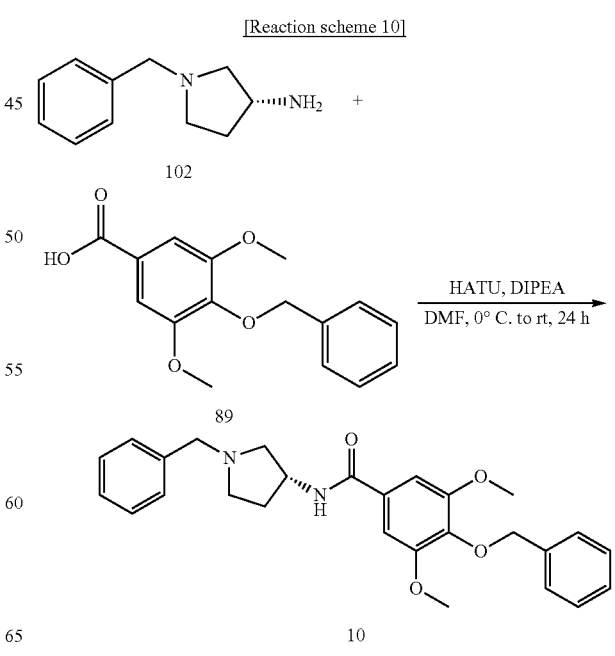

[Reaction scheme 10]

The same procedures as described in Preparative Example 2 were conducted, and a compound represented by Formula 102, i.e., (3R)-1-benzylpyrrolidine-3-amine (300 mg, 1.702 mmol) as well as a compound represented by Formula 89, that is, 4-benzyloxy-3,4-dimethoxybenzoic acid (539.77 mg, 1.872 mmol) prepared in Preparative Example 1 were used according to reaction scheme 10. As a result, a benzamide compound represented by Formula 10 was obtained as a desired product (VVZ-011; 756.00 mg, 99.5% yield).

Analysis data of the produced benzamide compound is provided as follows.

$^1$H-NMR (CDCl$_3$) d 1.85 (m, 1H), 2.35 (m, 1H), 2.57 (dd, 1H), 2.63 (dd, 1H), 2.82 (m, 1H), 2.88 (dd, 1H), 3.71 (dd, 2H), 3.87 (s, 6H), 4.56 (m, 1H), 5.02 (s, 2H) 7.15~7.43 (m, 12H).

Preparative Example 10

Preparation of Compound Represented by Formula 11 (VVZ-012)

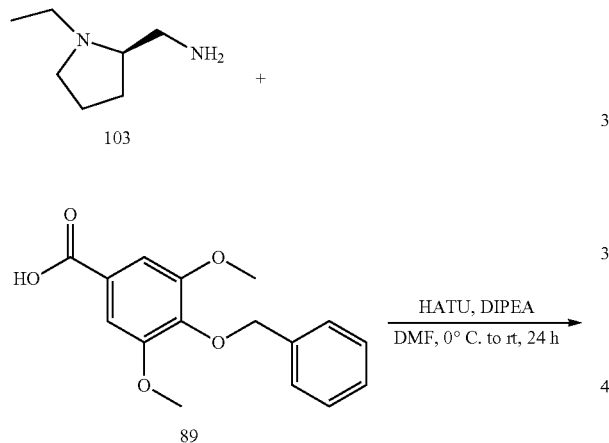

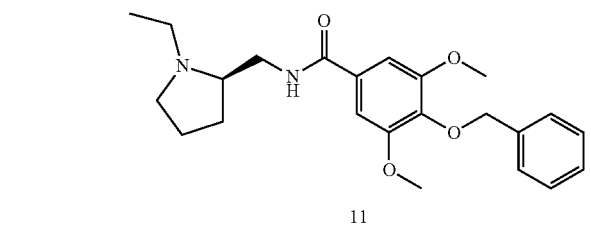

The same procedures as described in Preparative Example 2 was conducted, and a compound represented by Formula 103, i.e., [(2R)-1-ethylpyrrolidin-2-yl]methanamine (166.4 mg, 1.298 mmol) as well as a compound represented by Formula 89, that is, 4-benzyloxy-3,4-dimethoxybenzoic acid (411.59 mg, 1.428 mmol) prepared in Preparative Example 1 were used according to reaction scheme 11 above. As a result, a benzamide compound represented by Formula 11 was obtained as a desired product (VVZ-012; 476.20 mg, 92.1% yield).

Analysis data of the produced benzamide compound is provided as follows.

$^1$H-NMR (DMSO-d$_6$) d 1.16 (t, 3H), 1.70 (m, 1H), 1.78 (m, 2H), 1.97 (m, 1H), 2.26 (m, 1H), 2.38 (m, 1H), 2.72 (m, 1H), 2.99 (m, 1H), 3.17 (m, 1H), 3.25 (dd, 1H), 3.64 (dd, 1H), 3.87 (s, 6H), 5.02 (s, 2H), 7.15~7.43 (m, 7H).

Preparative Example 11

Preparation of Compound Represented by Formula 12 (VVZ-013)

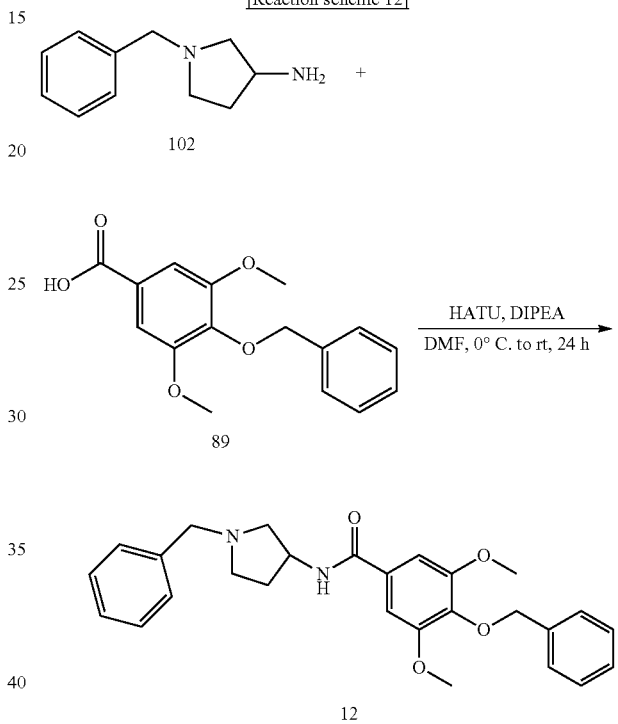

1-benzylpyrrolidine-3-amine represented by Formula 102 (180 mg, 1.02 mmol) was slowly added to a solution of 4-benzyloxy-3,4-dimethoxybenzoic acid represented by Formula 89 (323.88 mg, 1.12 mmol) prepared in Preparative Example 1 as well as diisopropylamine (0.71 mL, 4.09 mmol) in DMF (7 mL) at room temperature. The reaction mixture was cooled to 0° C. and, after adding 2-(1H-7-azabenzotriazol-1-yl)-1,1,3,3-tetramethyluronium hexafluorophosphate methanaminium (HATU, 388.29 mg, 1.02 mmol) thereto, the mixture was agitated at room temperature for 24 hours. After removing the reaction solvent under reduced pressure, chloroform (20 mL) was added to the remaining concentrate to form a solution, the solution was washed with a potassium carbonate solution, followed by separation to form an organic layer. The organic layer was dried with sodium sulfate (Na$_2$SO$_4$) and the solvent was removed again under reduced pressure. The obtained vacuum-concentrated mixture was subjected to separation and purification through column chromatography (ethyl acetate/hexane/triethylamine, 2:1:0.1, v/v/v) using silica gel (SiO$_2$), resulting in a benzamide compound represented by Formula 12 as a desired product (VVZ-013; 392.9 mg, 86% yield).

Analysis data of the produced benzamide compound is provided as follows.

$R_f$ (ethyl acetate/hexane/triethylamine, 2:1:0.1, v/v/v) 0.5; HRMS (EI+) calcd for $C_{27}H_{30}N_2O_4$ ([M+]) 446.2206.

$^1$H NMR (500 MHz, MeOH-$d_4$) d 1.80-1.87 (m, 1H), 2.32-2.40 (m, 1H), 2.57 (dd, 1H, J=16.5 Hz, 8.5 Hz), 2.63 (dd, 1H, J=10.0 Hz, 5.0 Hz), 2.80-2.85 (m, 1H), 2.89 (dd, 1H, J=7.0 Hz, 3.0 Hz), 3.36 (s, 2H), 3.87 (s, 6H), 4.53-4.59 (m, 1H), 5.01 (s, 2H), 7.16 (s, 2H), 7.26-7.38 (m, 8H), 7.45 (d, 2H, J=8.0 Hz).

Preparative Example 12

Preparation of Compound Represented by Formula 13 (VVZ-014)

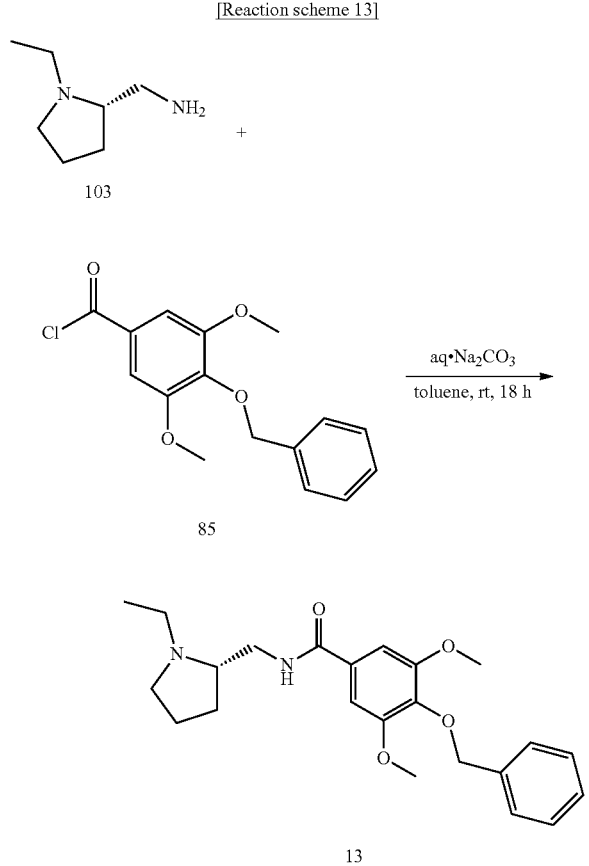

First, 4-benzyloxy-3,5-dimethoxybenzoic acid chloride represented by Formula 85 and [(2S)-1-ethylpyrrolidin-2-yl] methanamine represented by Formula 103 were prepared in 0.2 M solution, respectively, using a toluene solvent. An amine solution (1.2 mL, 0.240 mmol) entered 10 mL vial and a sodium carbonate solution (0.4 mL, 0.200 mmol) was added thereto. Thereafter, a benzoic acid chloride solution (1.0 mL, 0.200 mmol) entered the vial, vigorously shaken and agitated at room temperature for 18 hours. After terminating the reaction, an organic layer was moved to a cartridge tube (6 mL, benzenesulfonic acid, 904030-WJ, UCT) using ethyl acetate. Impurities were removed using methanol (15 mL) while separation and purification were conducted using an elute solution (ethyl acetate/methanol/triethylamine, 20:2:1, v/v/v), resulting in a benzamide compound represented by Formula 13 as a desired product (VVZ-014; 66 mg, 83% yield).

Analysis data of the produced benzamide compound is provided as follows.

$^1$H-NMR (MeOD-$d_4$) d 1.22 (t, 3H), 1.73 (m, 1H), 1.80 (m, 2H), 1.98 (m, 1H), 2.30 (m, 1H), 2.41 (m, 1H), 2.76 (m, 1H), 3.02 (m, 1H), 3.28 (m, 2H), 3.65 (dd, 1H), 3.88 (s, 6H), 5.02 (s, 2H), 7.17~7.46 (m, 7H).

Preparative Example 13

Preparation of Compound Represented by Formula 14 (VVZ-015)

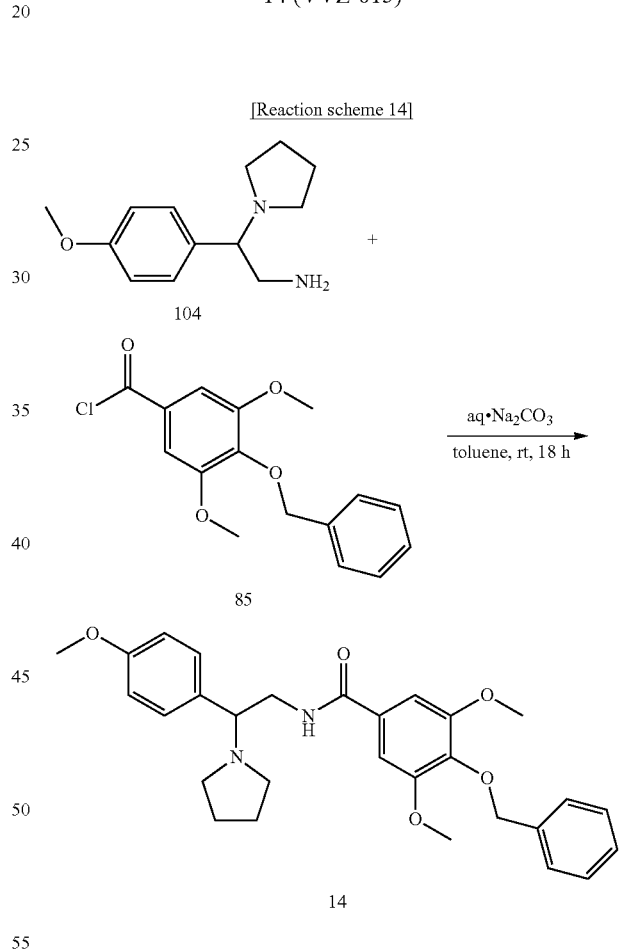

The same procedures as described in Preparative Example 12 were conducted, and 4-benzyloxy-3,5-dimethoxybenzoic acid chloride represented by Formula 85 and a compound represented by Formula 104, that is, 2-(4-methoxyphenyl)-2-(pyrrolidin-1-yl)ethane-1-amine were used according to reaction scheme 14. As a result, a benzamide compound represented by Formula 14 was obtained as a desired product (VVZ-015; 97.00 mg, 98.9% yield).

Analysis data of the produced benzamide compound is provided as follows.

$^1$H-NMR (MeOD-d$_4$) d 1.80 (m, 4H), 2.52 (m, 2H), 2.68 (m, 2H), 3.51 (m, 2H), 3.77 (s, 3H), 3.79 (s, 6H), 2.74 (m, 1H), 4.10 (dd, 1H), 4.98 (s, 2H), 6.85~7.43 (m, 11H).

Preparative Example 14

Preparation of Compound Represented by Formula 15 (VVZ-016)

[Reaction scheme 15]

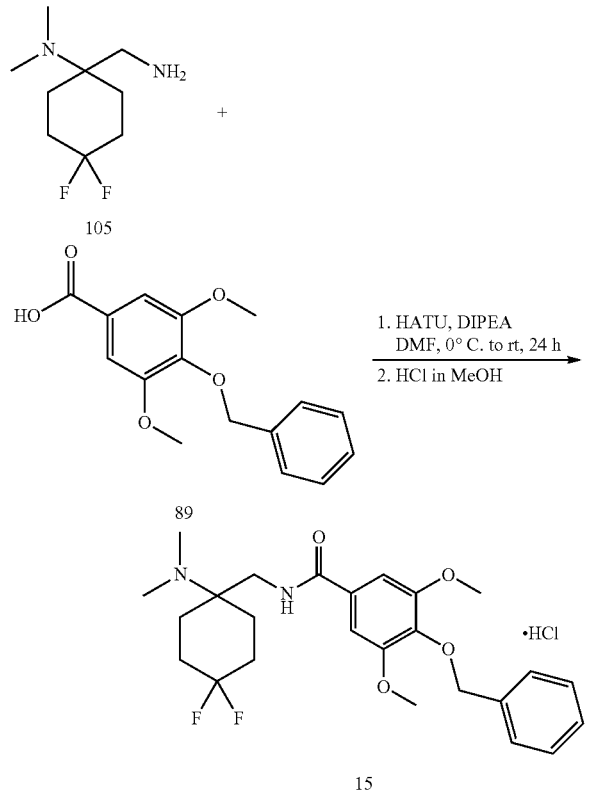

1-(aminomethyl)-4,4-difluoro-N,N-dimethylcyclohexanamine represented by Formula 105 (190 mg, 0.99 mmol) was slowly added to a solution of 4-benzyloxy-3,4-dimethoxybenzoic acid represented by Formula 89 (327.66 mg, 1.14 mmol) and diisopropylethylamine (0.70 mL, 3.95 mmol) in DMF (7 mL) at room temperature. The reaction mixture was cooled to 0° C. and, after adding 2-(1H-7-azabenzotriazol-1-yl)-1,1,3,3-tetramethyluronium hexafluorophosphate methanaminium (HATU, 375.75 mg, 0.99 mmol) thereto, agitated at room temperature for 24 hours. The reaction solvent was removed under reduced pressure and chloroform (20 mL) was added to the remaining concentrate to prepare a solution. The solution was washed with a potassium carbonate solution, followed by separation to form an organic layer. After drying the organic layer with sodium sulfate (Na$_2$SO$_4$), the solvent was removed again under reduced pressure. The obtained vacuum-concentrated mixture was subjected to separation and purification through column chromatography (ethyl acetate/hexane/triethylamine, 2:1:0.1, v/v/v) using silica gel (SiO$_2$), resulting in an alkalinized benzamide compound represented by Formula 11. HCl in MeOH (1.25 M, 0.75 mL, 0.93 mmol) was added to the alkalinized benzamide compound (360 mg, 0.78 mmol) in MeOH (5 mL) at room temperature. The reaction mixture was agitated at room temperature for 3 hours, the reaction solvent was removed under reduced pressure, and the remaining solids were filtered and washed with hexane to produce a benzamide salt compound represented by Formula 15 as a desired product (VVZ-016; 370 mg, 75% yield).

Analysis data of the produced benzamide salt compound is provided as follows.

R$_f$ (if it is alkaline, ethyl acetate/hexane/triethylamine, 2:1: 0.1, v/v/v) 0.7;

HRMS (EI+) calcd for C$_{25}$H$_{33}$C$_1$F$_2$N$_2$O$_4$ ([M+]) 498.2097.

$^1$H NMR (500 MHz, MeOH-d$_4$) d 1.98-2.23 (m, 8H), 2.94 (br, 6H), 3.24 (s, 2H), 3.90 (s, 6H), 5.04 (s, 2H), 7.25 (s, 2H), 7.27-7.35 (m, 3H), 7.45 (d, 2H, J=9.0 Hz).

The compound represented by Formula 105 and used herein was synthesized through the following four (4)-step chemical reaction after starting from 1,4-dioxaspiro[4,5]decan-8-one purchased from TCI Co.

Step 1: Preparation of 8,8-difluoro-1,4-dioxaspiro[4,5]decane

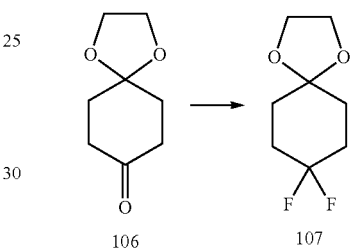

Under a nitrogen atmosphere, deoxofluor (3.07 mL, 16.65 mmol) in dichloromethane (3 mL) was added to 1,4-dioxaspiro[4,5]decan-8-one (2 g, 12.81 mmol, purchased from TCI Co.) represented by Formula 106 in dichloromethane (7 mL) at room temperature. Also, ethanol (0.15 mL, 2.56 mmol) as a catalyst was added thereto. The reaction mixture was agitated at room temperature for 2 hours, washed with a sodium bicarbonate solution, followed by separation to form an organic layer. After drying the organic layer with sodium sulfate (Na$_2$SO$_4$), the solvent was removed again under reduced pressure. The resultant crude product (3.5 g) was directly used as a reactant for further process (since it is difficult to separate this product from a monofluoro compound).

Analysis data of the produced difluoro acetal compound is provided as follows.

R$_f$ (ethyl acetate <55>/hexane, 1:5) 0.5;

Step 2: Preparation of 4,4-difluorocyclohexanone

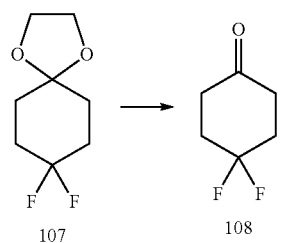 [SMILES: FC1(F)CCC2(CC1)OCCO2 ; O=C1CCC(F)(F)CC1]

3,8-difluoro-1,4-dioxaspiro[4,5]decane crude product represented by Formula 107 (3.5 g) and p-toluene sulfonic acid monohydrate (1.09 g, 5.72 mmol) in acetone (60 mL) were added with water (8 mL). After refluxing the reaction mixture for 24 hours, the mixture was cooled to room temperature. After adding a sodium bicarbonate solution (20 mL) to the mixture, the mixture was agitated for 20 minutes. After adding ethylether thereto, the prepared mixture was washed again with a sodium bicarbonate solution, followed by separation to form an organic layer. After drying the organic layer with magnesium sulfate, the solvent was removed in iced water under reduced pressure. The resultant crude product (2.5 g) was directly used as a reactant for further process (since a ketone compound is extremely volatile).

Analysis data of the produced ketone compound is provided as follows.

$R_f$ (ethyl acetate <60>/hexane, 1:5) 0.5;

Step 3: Preparation of 1-(dimethylamino)-4,4-difluorocyclohexane carbonitrile

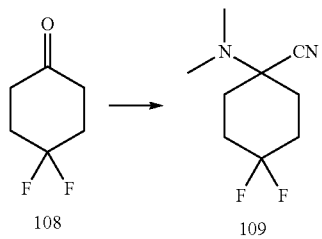

Potassium cyanate (1.31 g, 20.14 mmol) in water (50 mL) was added to the 4,4-difluorocyclohexanone crude product represented by Formula 108 (2.5 g) and dimethylamine hydrochloride (1.642 g, 20.14 mmol) at 0° C. After agitating the reaction mixture at room temperature for 24 hours, potassium carbonate solids (1 g) were added thereto and agitation was further conducted for 30 minutes. After adding ethylether to the reaction mixture, the mixture was washed with a potassium carbonate solution, followed by separation to form an organic layer. After drying the organic layer with sodium sulfate (Na$_2$SO$_4$), the solvent was removed again under reduced pressure. The obtained vacuum-concentrated mixture was subjected to separation and purification through column chromatography (ethyl acetate/hexane/triethylamine, 20:1:0.1, v/v/v) using silica gel (SiO$_2$), resulting in an aminonitrile compound represented by Formula 109 as a desired product (1.296 g, 68% yield).

$R_f$ (ethyl acetate <65>/hexane, 1:5) 0.7;
$^1$H NMR (500 MHz, CDCl$_3$) d 1.94-2.18 (m, 8H), 2.37 (s, 6H).

Step 4: Preparation of 1-(aminomethyl)-4,4-difluoro-N,N-dimethylcyclohexanamine

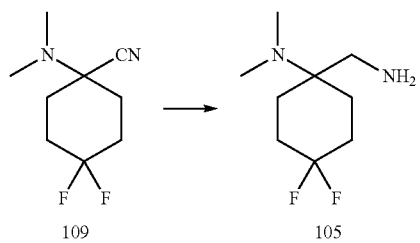

Under a nitrogen atmosphere, 1-(dimethylamino)-4,4-difluorocyclohexane carbonitrile represented by Formula 109 (233.3 mg, 1.24 mmol) in ethylether (4 mL) was slowly added to lithiumaluminum hydride (141 mg, 3.72 mmol) in ethylether (10 mL) at 0° C. The reaction mixture was refluxed for 3 days, ethylether (20 mL) was added to the mixture at 0° C. then water (0.8 mL) was further slowly added thereto at 0° C., followed by agitation for 1 hour. After filtering the reaction mixture using celite, the filtrate was washed with ethylether and the solvent was removed from the filtrate under reduced pressure, resulting in a diamine compound represented by Formula 105 as a desired product (206.8 mg, 87% yield).

Analysis data of the produced diamine compound is provided as follows.

$R_f$ (ethyl acetate <60>/hexane, 1:1) 0.1;
$^1$H NMR (500 MHz, CDCl$_3$) d 1.56-1.64 (m, 2H), 1.75-1.87 (m, 4H), 1.98-2.12 (m, 2H), 2.31 (s, 6H), 2.55 (s, 2H).

Preparative Example 15

Preparation of Compound Represented by Formula 16 (VVZ-017)

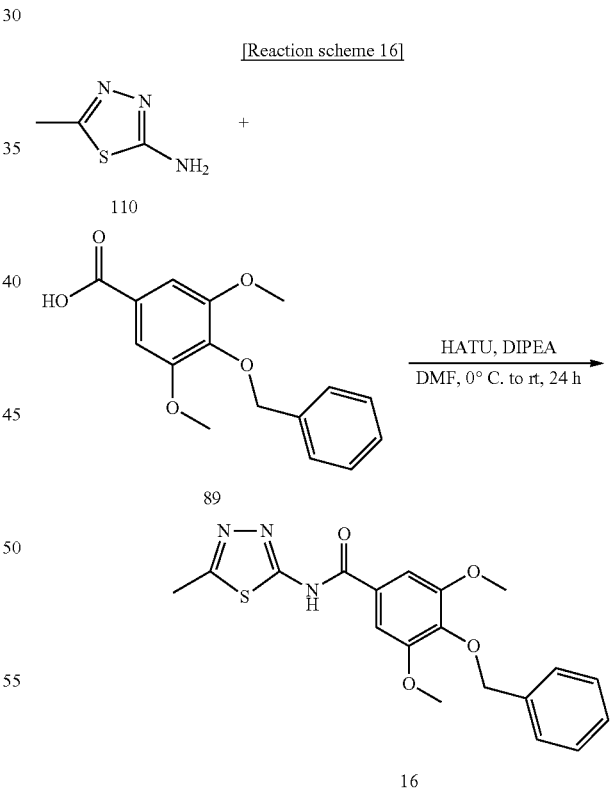

The same procedures as described in Preparative Example 2 were conducted, and a compound, i.e., 2-amino-5-methyl-1,3,4-thiadiazole represented by Formula 110 (76.5 mg, 0.764 mmol) and 4-benzyloxy-3,4-dimethoxybenzoic acid represented by Formula 89 (220.24 mg, 0.764 mmol) prepared in Preparative Example 1 were used according to reaction scheme 16. As a result, a benzamide compound represented by Formula 16 was obtained as a desired product (VVZ-017; 196.50 mg, 76.7% yield).

Analysis data of the produced benzamide compound is provided as follows.

$^1$H-NMR (MeOD-d$_4$) d 2.70 (s, 3H), 3.93 (s, 6H), 5.07 (s, 2H), 7.28~7.46 (m, 7H).

Preparative Example 16

Preparation of Compound Represented by Formula 17 (VVZ-018)

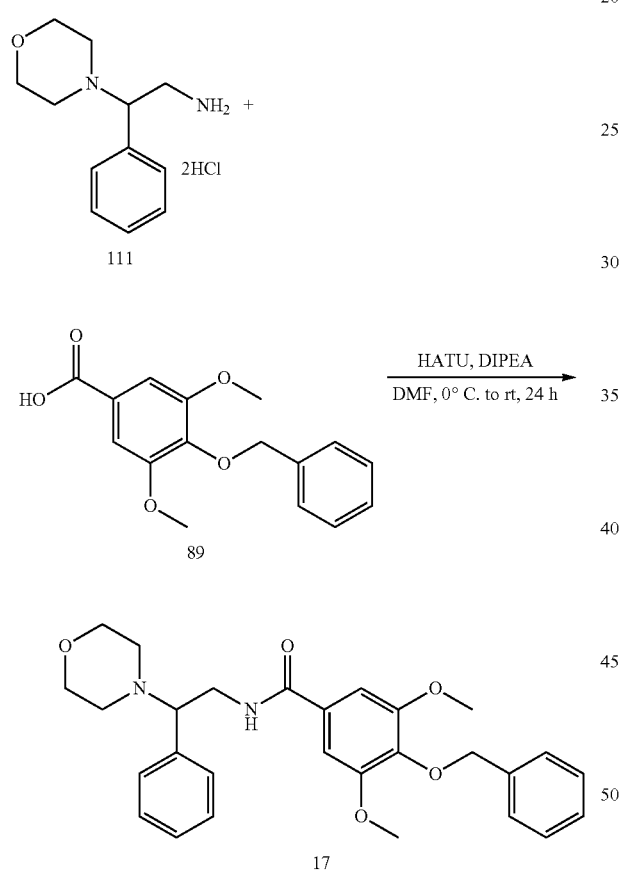

The same procedures as described in Preparative Example 2 were conducted, and 2-morphorin-4-yl-2-phenylethanamine dihydrochloride represented by Formula 111 (0.137 g, 0.491 mmol) and 4-benzyloxy-3,4-dimethoxybenzoic acid represented by Formula 89 (0.155 g, 0.540 mmol) prepared in Preparative Example 1 were used according to reaction scheme 17. As a result, a benzamide compound represented by Formula 17 was obtained as a desired product (VVZ-018; 0.248 g, 106.1% yield).

Analysis data of the produced benzamide compound is provided as follows.

$^1$H-NMR (MeOD-d$_4$) d 2.51 (m, 4H), 3.59 (m, 1H), 3.68 (m, 4H), 3.72 (m, 1H), 3.81 (s, 6H), 4.08 (dd, 1H), 5.99 (s, 2H), 6.91 (s, 2H), 7.03~7.44 (m, 10H).

Preparative Example 17

Preparation of Compound Represented by Formula 18 (VVZ-019)

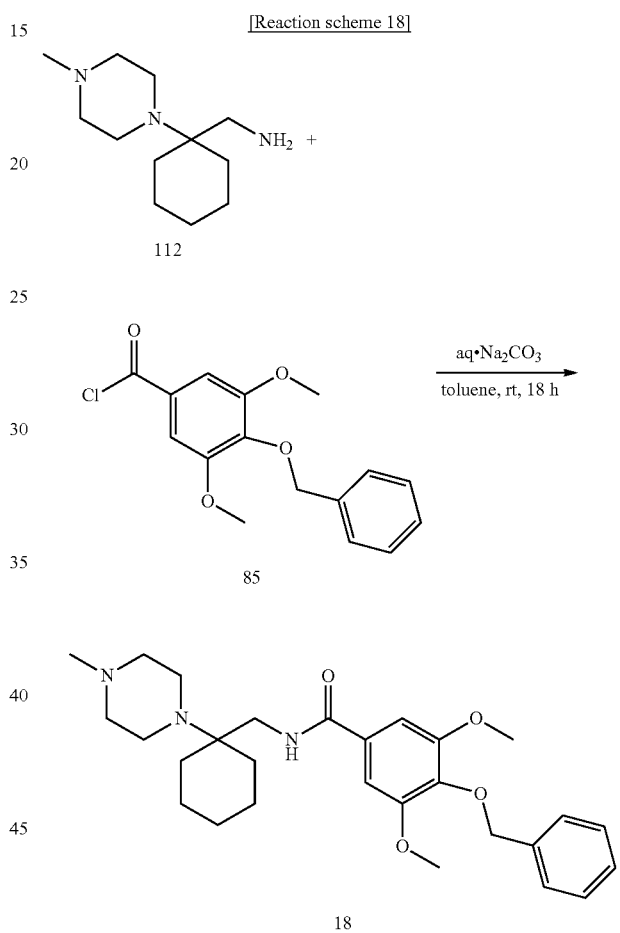

The same procedures as described in Preparative Example 12 were conducted, and 4-benzyloxy-3,5-dimethoxybenzoic acid chloride represented by Formula 85 (61.350 mg, 0.200 mmol) prepared in Preparative Example 1 and 1-[1-(4-methylpiperazin-1-yl)cyclohexyl]methanamine represented by Formula 112 (50.73 mg, 0.240 mmol) were used according to reaction scheme 18. As a result, a benzamide compound represented by Formula 18 was obtained as a desired product (VVZ-019; 61.5 mg, 63.8% yield).

Analysis data of the produced benzamide compound is provided as follows.

$^1$H-NMR (MeOD-d$_4$) d 1.41 (m, 6H), 1.65 (m, 2H), 1.80 (m, 2H), 2.29 (s, 3H), 2.50 (m, 4H), 2.79 (m, 4H), 3.45 (s, 2H), 3.88 (s, 6H), 5.03 (s, 2H), 7.12~7.46 (m, 7H).

Preparative Example 18

Preparation of Compound Represented by Formula 19 (VVZ-020)

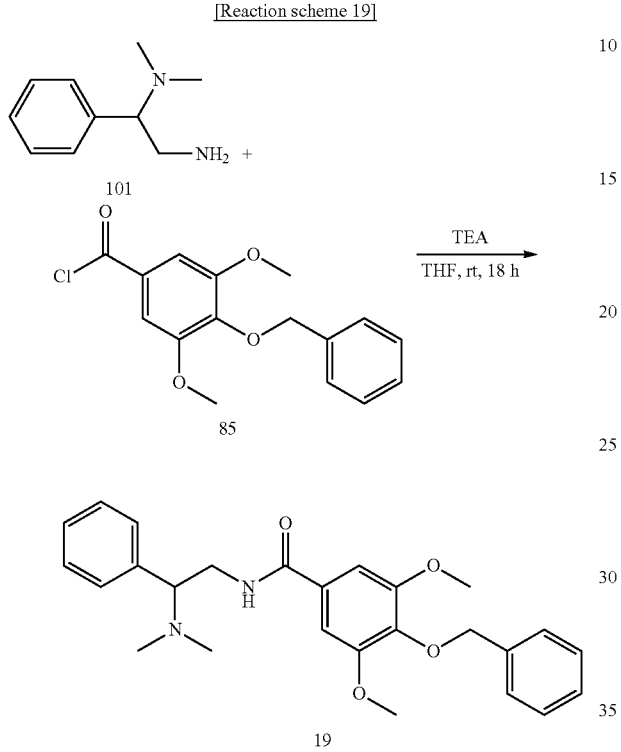

[Reaction scheme 19]

After cooling N,N-dimethyl-1-phenylethane-1,2-diamine represented by Formula 101 (292 mg, 1.78 mmol, purchased from Alfa Aesar Co.) and triethylamine (0.55 mL, 3.95 mmol) in THF (8 mL) at 0° C. under a nitrogen atmosphere, 4-n-benzyloxy-3,5-dimethoxybenzoic acid chloride represented by Formula 85 (606 mg, 1.98 mmol) prepared in Preparative Example 1 in THF (12 mL) was slowly added to the cooled solution. After agitating the above solution at the same temperature for 30 minutes, this was left alone at room temperature for 18 hours. A precipitate generated during the reaction was filtered and discarded, the remaining solution was diluted using chloroform and washed with a potassium carbonate solution, followed by separation and drying with sodium sulfate. The solvent was removed again under reduced pressure. The obtained vacuum-concentrated mixture was subjected to separation and purification through column chromatography (ethyl acetate/hexane/triethylamine, 2:1:0.1, v/v/v) using silica gel ($SiO_2$), resulting in a benzamide compound represented by Formula 19 as a desired product (VVZ-020; 451.3 mg, 52% yield).

Analysis data of the produced benzamide compound is provided as follows.

$R_f$ (ethyl acetate/hexane/triethylamine, 2:1:0.1, v/v/v) 0.1;

HRMS (EI+) calcd for $C_{26}H_{30}N_2O_4$ ([M+]) 434.2206.

$^1$H NMR (500 MHz, MeOH-$d_4$) d 2.27 (s, 6H), 3.61-3.70 (m, 2H), 3.80 (s, 6H), 4.00 (dd, 1H, J=12.0 Hz, 5.5 Hz), 4.98 (s, 2H), 6.90 (s, 2H), 7.27-7.43 (m, 10H).

Preparative Example 19

Preparation of Compound Represented by Formula 20 (VVZ-021)

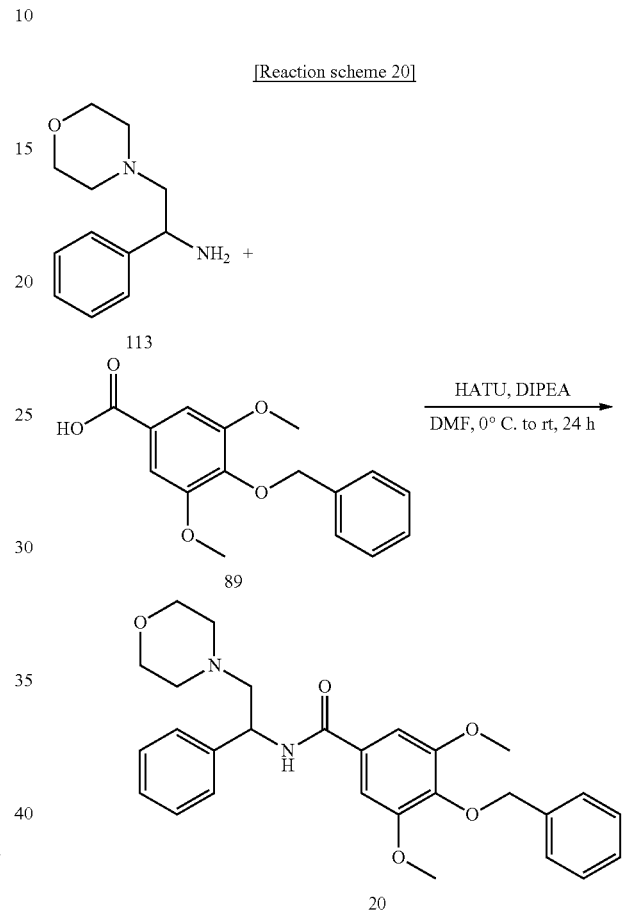

[Reaction scheme 20]

2-morpholino-1-phenylethanamine represented by Formula 113 (516.3 mg, 2.50 mmol, purchased from Enamine Co.) was slowly added to 4-benzyloxy-3,4-dimethoxybenzoic acid represented by Formula 89 (793.75 mg, 2.75 mmol) prepared in Preparative Example 1 and diisopropylethylamine (1.75 mL, 10.01 mmol) in DMF (12 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 1.05 g, 2.75 mmol) thereto, the mixture was agitated at room temperature for 24 hours. The reaction solvent was removed under reduced pressure and chloroform (25 mL) was added to the remaining concentrate to prepare a solution. The solution was washed with a potassium carbonate solution, followed by separation to form an organic layer. After drying the organic layer with sodium sulfate ($Na_2SO_4$), the solvent was removed again under reduced pressure. The obtained vacuum-concentrated mixture was subjected to separation and purification through column chromatography (ethyl acetate/hexane/triethylamine, 2:1:0.1, v/v/v) using silica gel ($SiO_2$), resulting in a benzamide compound represented by Formula 20 as a desired product (VVZ-021; 355.2 mg, 30% yield).

Analysis data of the produced benzamide compound is provided as follows.

$R_f$ (ethyl acetate/hexane/triethylamine, 2:1:0.1, v/v/v) 0.5; HRMS (EI+) calcd for $C_{28}H_{32}N_2O_5$ ([M+]) 476.2311.

$^1$H NMR (500 MHz, MeOH-$d_4$) d 2.50 (m, 2H), 2.61-2.63 (m, 3H), 2.91 (t, 1H, J=12.0 Hz), 3.68 (m, 4H), 3.88 (s, 6H), 5.02 (s, 2H), 5.31 (d, 1H, J=7.0 Hz), 7.20 (s, 2H), 7.30-7.35 (m, 6H), 7.40 (d, 2H, J=7.0 Hz), 7.44 (d, 2H, J=6.5 Hz).

Preparative Example 20

Preparation of Compound Represented by Formula 21 (VVZ-022)

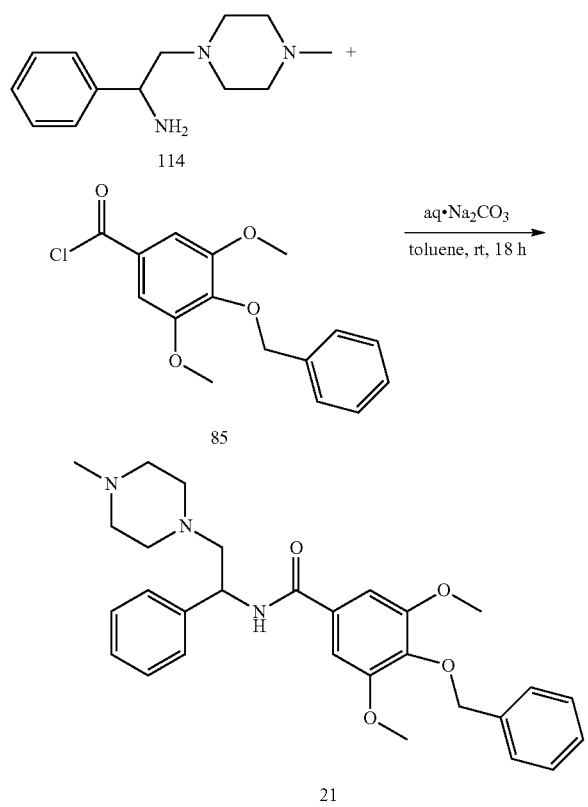

The same procedures as described in Preparative Example 12 were conducted, 4-benzyloxy-3,5-dimethoxybenzoic acid chloride represented by Formula 85 (61.350 mg, 0.200 mmol) and a compound represented by Formula 114, that is, 2-(4-methylpiperazinyl)-1-phenylethylamine represented by Formula 114 (52.64 mg, 0.240 mmol) were used according to reaction scheme 21. As a result, a benzamide compound represented by Formula 21 was obtained as a desired product (VVZ-022; 50.70 mg, 51.8% yield).

Analysis data of the produced benzamide compound is provided as follows.

$^1$H-NMR (MeOD-$d_4$) d 2.28 (s, 3H), 2.32 (m, 4H), 2.63 (m, 4H), 2.94 (m, 2H), 3.88 (s, 6H), 5.01 (s, 2H), 5.29 (m, 1H), 7.00~7.46 (m, 12H).

Preparative Example 21

Preparation of Compound Represented by Formula 22 (VVZ-023)

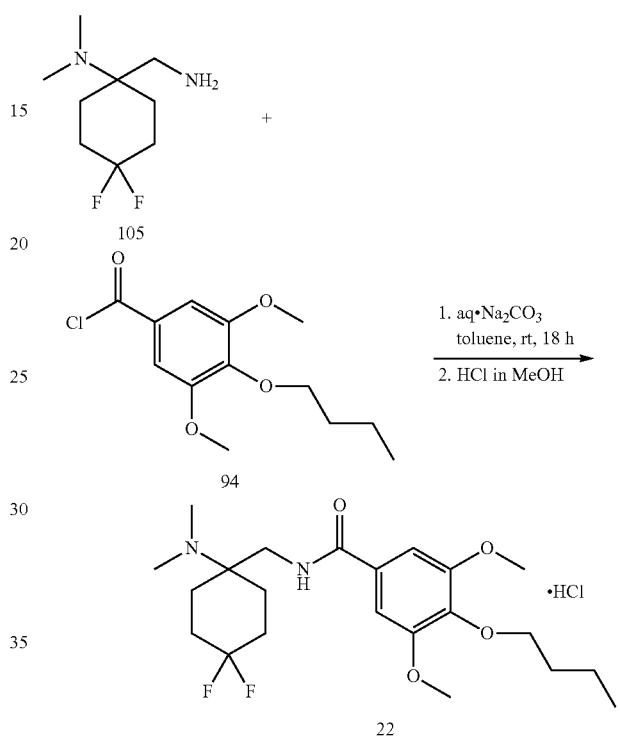

The same procedures as described in Preparative Example 12 were conducted, and 4-butoxy-3,5-dimethoxybenzoic acid chloride represented by Formula 94 (22.636 mg, 0.083 mmol) and the compound represented by Formula 105, that is, (1-aminomethyl-4,4-difluoro-cyclohexyl)-dimethylamine (15.96 mg, 0.083 mmol) prepared in Preparative Example 14 were used according to reaction scheme 22. As a result, a benzamide compound represented by Formula 22 was obtained as a desired product (VVZ-023; 16.90 mg, 43.8% yield).

Preparative Example 22

Preparation of Compound Represented by Formula 23 (VVZ-024)

[Reaction scheme 23]

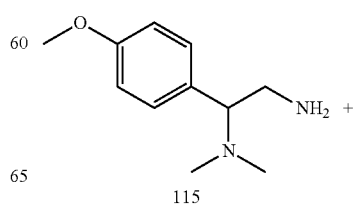

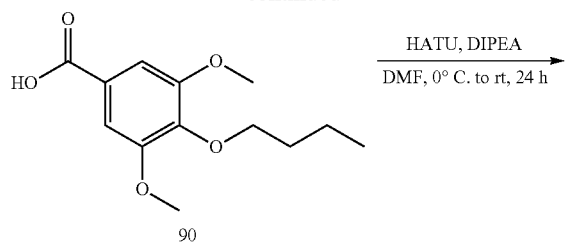

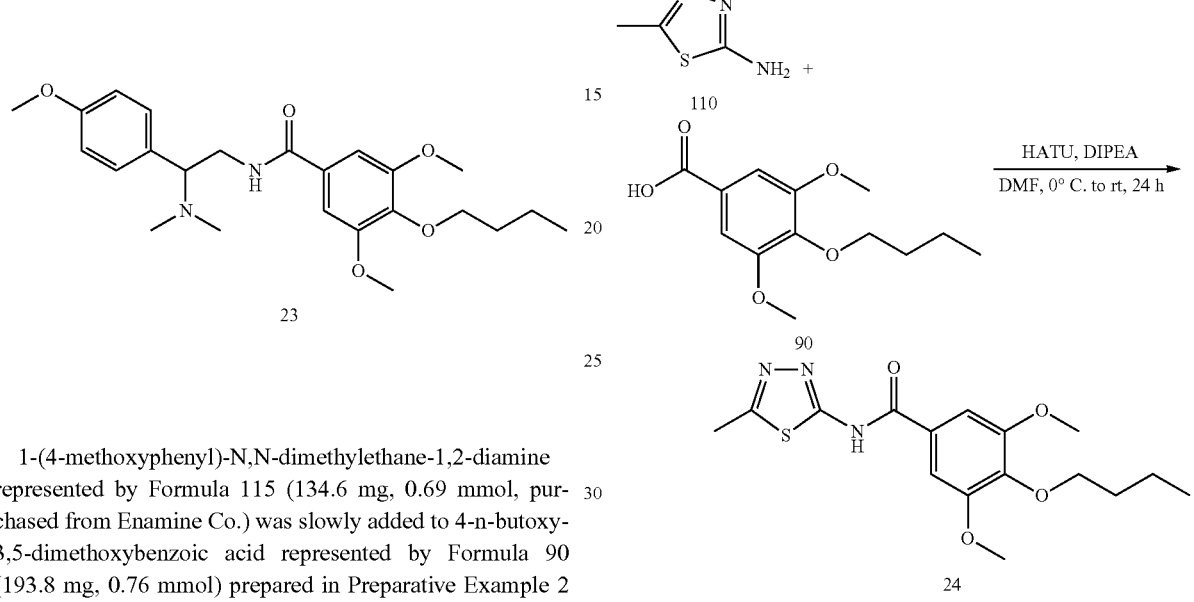

1-(4-methoxyphenyl)-N,N-dimethylethane-1,2-diamine represented by Formula 115 (134.6 mg, 0.69 mmol, purchased from Enamine Co.) was slowly added to 4-n-butoxy-3,5-dimethoxybenzoic acid represented by Formula 90 (193.8 mg, 0.76 mmol) prepared in Preparative Example 2 and diisopropylethylamine (0.48 mL, 2.77 mmol) in DMF (6 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 289.76 mg, 0.76 mmol) thereto, the mixture was agitated at room temperature for 24 hours. The reaction solvent was removed under reduced pressure and chloroform (15 mL) was added to the remaining concentrate to prepare a solution. The solution was washed with a potassium carbonate solution, followed by separation to form an organic layer. After drying the organic layer with sodium sulfate ($Na_2SO_4$), the solvent was removed again under reduced pressure. The obtained vacuum-concentrated mixture was subjected to separation and purification through column chromatography (ethyl acetate/hexane/triethylamine, 2:1:0.1, v/v/v) using silica gel ($SiO_2$), resulting in a benzamide compound represented by Formula 23 as a desired product (VVZ-024; 242.4 mg, 81% yield).

Analysis data of the produced benzamide compound is provided as follows.

$R_f$ (ethyl acetate/hexane/triethylamine, 2:1:0.1, v/v/v) 0.2; HRMS (EI+) calcd for $C_{24}H_{34}N_2O_5$ ([M+]) 430.5372.

$^1$H NMR (500 MHz, MeOH-$d_4$) d 0.95 (t, 3H, J=7.5 Hz), 1.47-1.51 (m, 2H), 1.63-1.69 (m, 2H), 2.25 (s, 6H), 3.58-3.66 (m, 2H), 3.76-3.81 (m, 9H), 3.93 (t, 2H, J=6.5 Hz), 3.97 (q, 1H, J=5.5 Hz), 6.90 (s, 2H), 6.92 (d, 2H, J=8.5 Hz), 7.24 (d, 2H, J=8.5 Hz).

Preparative Example 23

Preparation of Compound Represented by Formula 24 (VVZ-025)

[Reaction scheme 24]

A compound represented by Formula 110, that is, 2-amino-5-methyl-1,3,4-thiadiazole (314.6 mg, 2.73 mmol, purchased from TCI Co.) was slowly added to 4-n-butoxy-3,5-dimethoxybenzoic acid represented by Formula 90 (772 mg, 3.04 mmol) prepared in Preparative Example 2 and diisopropylethylamine (1.64 mL, 10.92 mmol) in DMF (15 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 1.15 g, 3.04 mmol) thereto, the mixture was agitated at room temperature for 24 hours. The reaction solvent was removed under reduced pressure and chloroform (30 mL) was added to the remaining concentrate to prepare a solution. The solution was washed with a potassium carbonate solution, followed by separation to form an organic layer. After drying the organic layer with sodium sulfate ($Na_2SO_4$), the solvent was removed again under reduced pressure. The obtained vacuum-concentrated mixture was subjected to separation and purification through column chromatography (ethyl acetate/hexane/triethylamine, 2:1:0.1, v/v/v) using silica gel ($SiO_2$), resulting in a benzamide compound represented by Formula 24 as a desired product (VVZ-025; 545.7 mg, 56.8% yield).

Analysis data of the produced benzamide compound is provided as follows.

$R_f$ (ethyl acetate/hexane/triethylamine, 2:1:0.1, v/v/v) 0.2; HRMS (EI+) calcd for $C_{16}H_{21}N_3O_4S$ ([M+]) 351.1253.

$^1$H NMR (500 MHz, MeOH-d$_4$) d 0.98 (t, 3H, J=7.5 Hz), 1.50-1.55 (m, 2H), 1.67-1.72 (m, 2H), 2.70 (s, 3H), 3.92 (s, 6H), 4.02 (t, 2H, J=6.5 Hz), 7.41 (s, 2H).

Preparative Example 24

Preparation of Compound Represented by Formula 25 (VVZ-026)

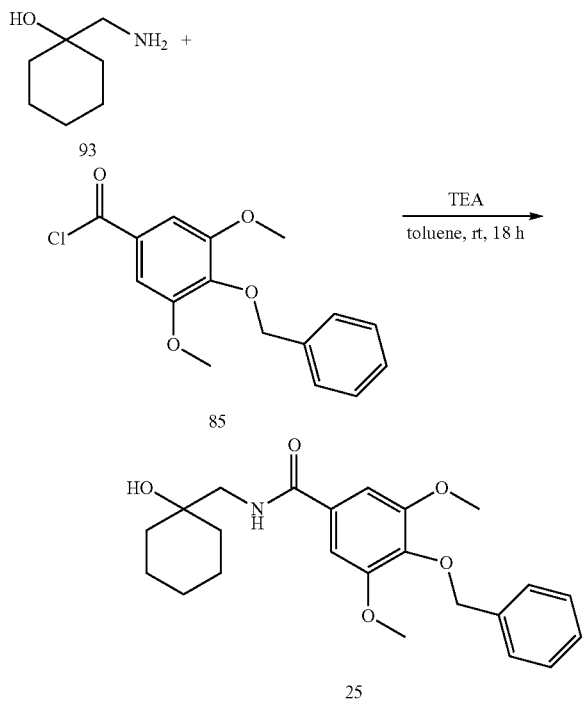

The same procedures as described in Preparative Example 1 were conducted, and 1-aminomethyl-1-cyclohexanol represented by Formula 93 (111.62 mg, 0.864 mmol) and 4-benzyloxy-3,5-dimethoxybenzoic acid chloride represented by Formula 85 (265 mg, 0.864 mmol) prepared in Preparative Example 1 were used according to reaction scheme 25. As a result, a benzamide compound represented by Formula 25 was obtained as a desired product (VVZ-026; 216.50 g, 62.7% yield).

Preparative Example 25

Preparation of Compound Represented by Formula 26 (VVZ-027)

[Reaction scheme 26]

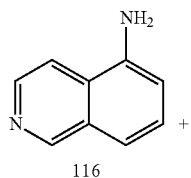

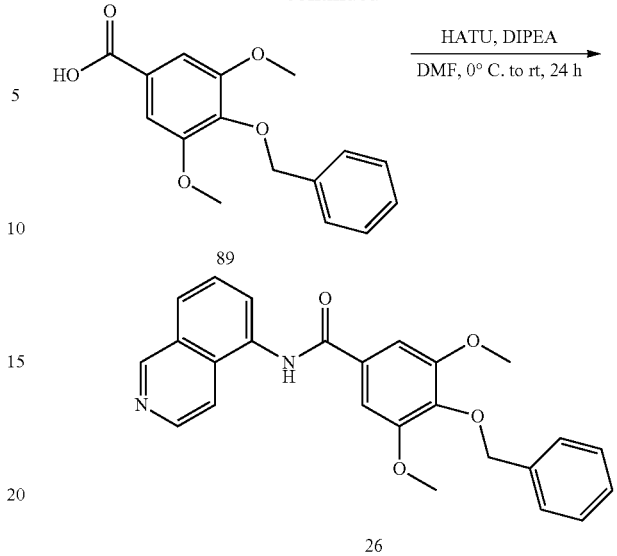

The same procedures as described in Preparative Example 2 were conducted, and a compound represented by Formula 116, that is, 5-aminoisoquinoline (50.00 mg, 0.347 mmol) and 4-benzyloxy-3,4-dimethoxybenzoic acid represented by Formula 89 (114.98 mg, 0.399 mmol) prepared in Preparative Example 1 were used according to reaction scheme 26. As a result, a benzamide compound represented by Formula 26 was obtained as a desired product (VVZ-027; 36.40 mg, 25.3% yield).

Analysis data of the produced benzamide compound is provided as follows.

$^1$H-NMR (MeOD-d$_4$) d 3.33 (s, 6H), 5.02 (s, 2H), 7.33~9.37 (m, 12H).

Preparative Example 26

Preparation of Compound Represented by Formula 27 (VVZ-028)

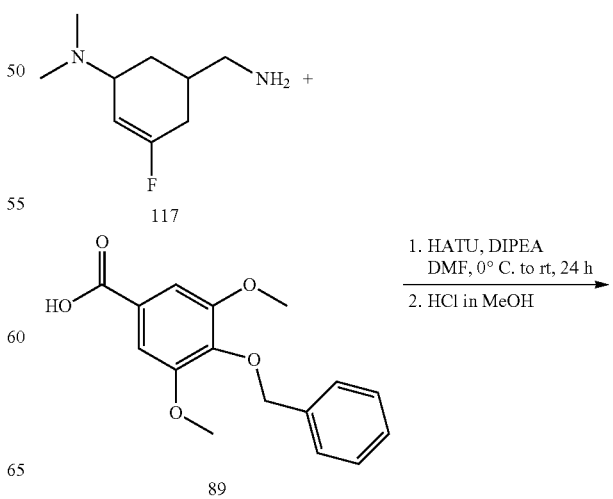

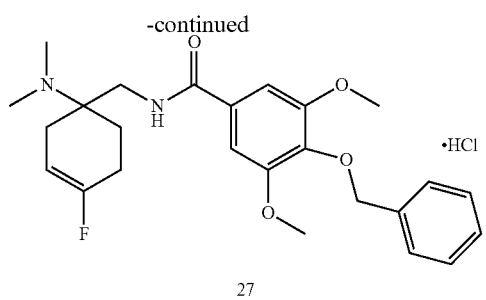

27

The same procedures as described in Preparative Example 2 were conducted, and a compound represented by Formula 117, that is, (1-aminomethyl-4-fluoro-cyclohex-3-enyl)-dimethyl-amine (60.00 mg, 0.348 mmol) and 4-benzyloxy-3,4-dimethoxybenzoic acid represented by Formula 89 (115.49 mg, 0.401 mmol) prepared in Preparative Example 1 were used according to reaction scheme 27. As a result, a benzamide compound represented by Formula 27 was obtained as a desired product (VVZ-028; 88.00 mg, 52.7% yield).

Analysis data of the produced benzamide compound is provided as follows.

$^1$H-NMR (MeOD-$d_4$) d 2.15 (m, 1H), 2.24 (m, 1H), 2.39 (m, 2H), 2.68 (m, 2H), 2.95 (s, 3H), 3.08 (s, 3H), 3.73 (d, 1H), 3.89 (s, 6H), 3.99 (d, 1H), 5.03 (s, 2H), 7.23~7.46 (m, 7H).

Preparative Example 27

Preparation of Compound Represented by Formula 28 (VVZ-029)

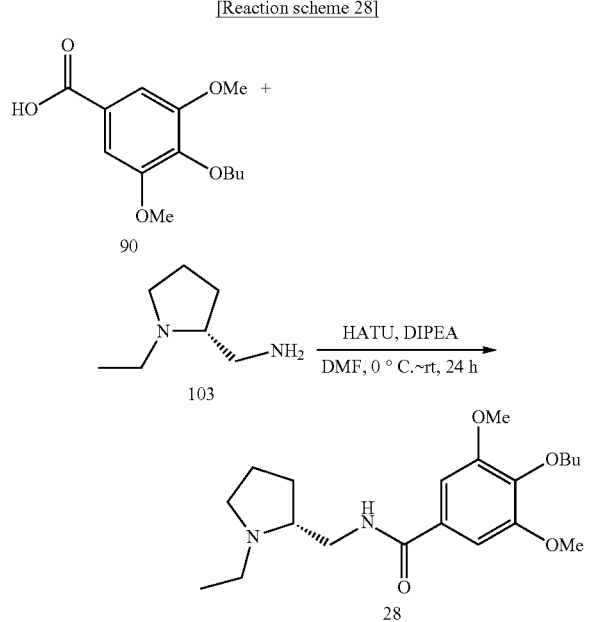

3,5-dimethoxy-4-butoxybenzoic acid represented by Formula 90 (450 mg, 1.77 mmol) prepared in Preparative Example 2 was slowly added to a compound represented by Formula 103, that is, [(2R)-1-ethylpyrrolidin-2-yl]methanamine (226.91 mg, 1.77 mmol, purchased from TCI Co.) and diisopropylethylamine (0.93 mL, 5.309 mmol) in DMF (20 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 672.84 mg, 1.77 mmol) thereto, the mixture was agitated at room temperature for 24 hours. The reaction solvent was removed under reduced pressure and chloroform/methanol (9:1) was added to the remaining concentrate to prepare a solution. The solution was washed with a potassium carbonate solution, followed by separation to form an organic layer. After drying the organic layer with magnesium sulfate (MgSO$_4$), the solvent was removed again under reduced pressure. The obtained vacuum-concentrated mixture was subjected to separation and purification through column chromatography (chloroform/methanol, 10:1) using silica gel (SiO$_2$). As a result, a benzamide compound represented by Formula 28 was obtained as a desired product (563.00 mg, 87% yield).

Analysis data of the produced benzamide compound is provided as follows.

R$_f$ (chloroform/methanol, 10:1, v/v) 0.3;
HRMS (EI+) calcd for C$_{20}$H$_{32}$N$_2$O$_4$ ([M+]) 746.4830.
$^1$H NMR (500 MHz, MeOH-d$_4$) δ 0.98 (t, 3H, J=7.3 Hz), 1.21 (t, 3H, J=7.0 Hz), 1.47-1.54 (m, 2H), 1.65-1.73 (m, 3H), 1.76-1.83 (m, 2H), 1.95-2.01 (m, 1H), 2.30-2.42 (m, 2H), 2.76 (br, 1H), 3.21 (br, 1H), 3.66 (dd, 1H, J=13.3, 4.3 Hz), 3.89 (s, 6H), 4.01 (t, 2H, 11.5 Hz), 7.18 (s, 2H).

Preparative Example 28

Preparation of Compound Represented by Formula 29 (VVZ-030)

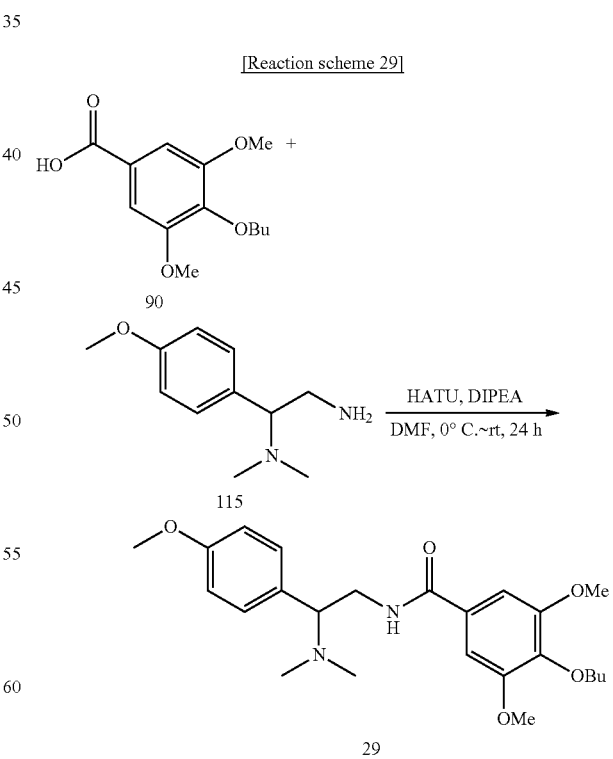

The same procedures as described in Preparative Example 2 were conducted, and 3,5-dimethoxy-4-butoxybenzoic acid represented by Formula 90 (150.00 mg, 0.590 mmol) and 1-(4-methoxyphenyl)-N,N-dimethylethane-1,2-diamine represented by Formula 115 (114.60 mg, 0.590 mmol) were used according to reaction scheme 29. As a result, a benzamide compound represented by Formula 29 was obtained as a desired product (VVZ-030; 250.40 mg, 98.6% yield).

Analysis data of the produced benzamide compound is provided as follows.

$^1$H-NMR (MeOD-d$_4$) d 0.95 (t, 3H), 1.49 (m, 2H), 1.64 (m, 2H), 2.37 (s, 6H), 3.62 (m, 2H), 3.76 (s, 3H), 3.78 (s, 6H), 3.95 (t, 2H), 3.97 (m, 1H), 6.88 (s, 2H), 6.89~7.24 (dd, 4H).

Preparative Example 29

Preparation of Compound Represented by Formula 30 (VVZ-031)

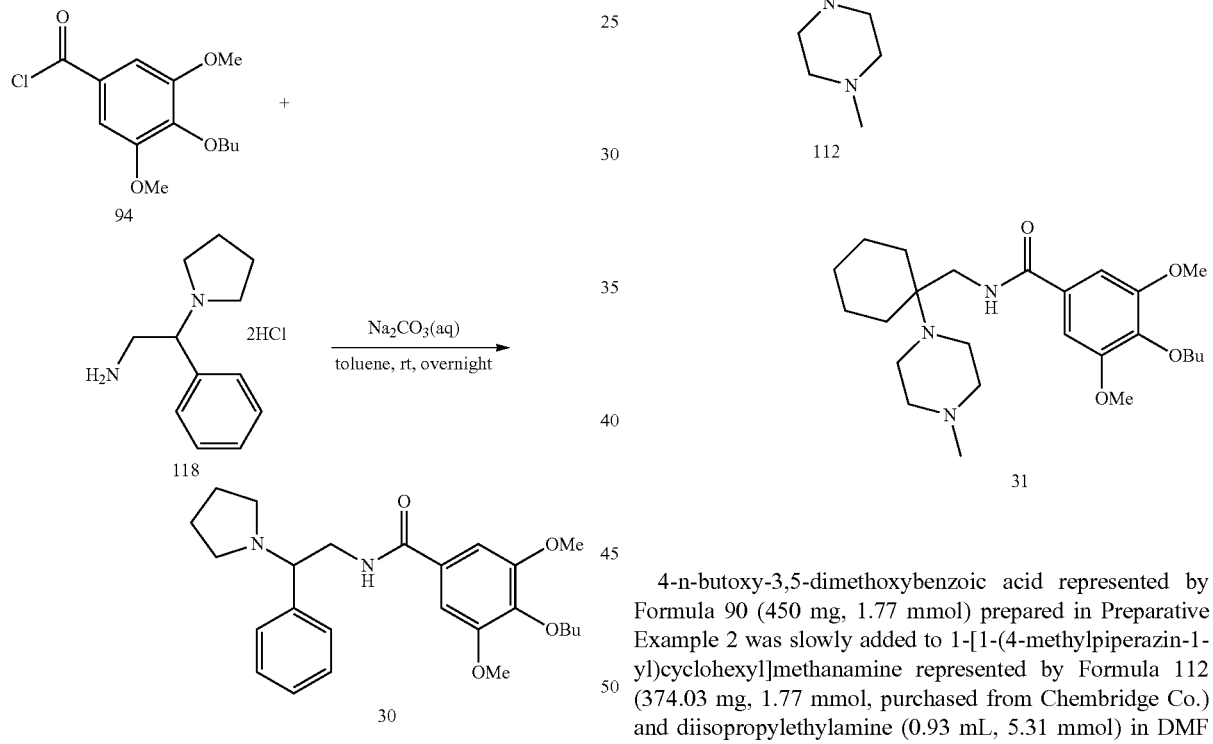

The same procedures as described in Preparative Example 12 were conducted, and 4-butoxy-3,5-dimethoxybenzoic acid chloride represented by Formula 94 (54.544 mg, 0.200 mmol) and a compound represented by Formula 118 (63.17 mg, 0.240 mmol) were used according to reaction scheme 30. As a result, a benzamide compound represented by Formula 30 was obtained as a desired product (VVZ-031; 68.60 mg, 80.4% yield).

Analysis data of the produced benzamide compound is provided as follows.

$^1$H-NMR (MeOD-d$_4$) d 0.95 (t, 3H), 1.49 (m, 2H), 1.66 (m, 2H), 1.82 (m, 4H), 2.52 (m, 2H), 2.72 (m, 2H), 3.55 (m, 2H), 3.85 (s, 6H), 3.85 (t, 2H), 4.06 (dd, 1H), 7.27~7.39 (m, 7H).

Preparative Example 30

Preparation of Compound Represented by Formula 31 (VVZ-032)

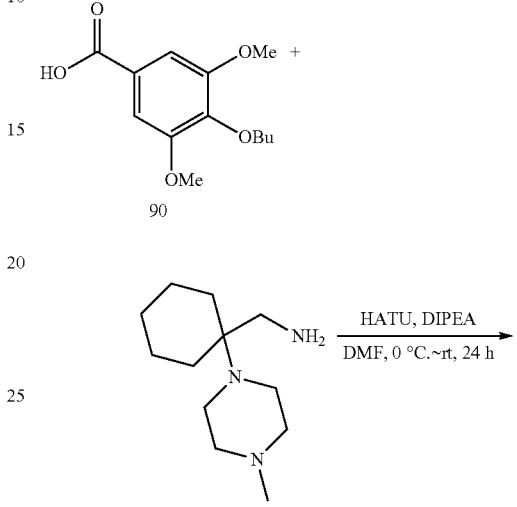

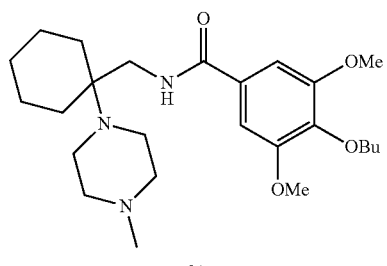

4-n-butoxy-3,5-dimethoxybenzoic acid represented by Formula 90 (450 mg, 1.77 mmol) prepared in Preparative Example 2 was slowly added to 1-[1-(4-methylpiperazin-1-yl)cyclohexyl]methanamine represented by Formula 112 (374.03 mg, 1.77 mmol, purchased from Chembridge Co.) and diisopropylethylamine (0.93 mL, 5.31 mmol) in DMF (20 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 672.84 mg, 1.77 mmol) thereto, the mixture was agitated at room temperature for 24 hours. The reaction solvent was removed under reduced pressure and chloroform/methanol (9:1) was added to the remaining concentrate to prepare a solution. The concentration was washed with a potassium carbonate solution, followed by separation to form an organic layer. After drying the organic layer with magnesium sulfate (MgSO$_4$), the solvent was removed again under reduced pressure. The obtained vacuum-concentrated mixture was subjected to separation and purification through column chromatography (chloroform/methanol, 10:1) using silica gel (SiO$_2$). As a result, a benzamide compound represented by Formula 31 was produced (VVZ-032; 672.00 mg, 85% yield).

Analysis data of the produced benzamide compound is provided as follows.

R$_f$ (chloroform/methanol, 10:1, v/v) 0.3;

HRMS (EI+) calcd for C$_{25}$H$_{41}$N$_3$O$_4$ ([M+]) 447.3097. found xxx.xxxx.

$^1$H NMR (500 MHz, MeOH-d$_4$) δ0.98 (t, 3H, J=7.3 Hz), 1.37-1.45 (m, 5H), 1.50-1.54 (m, 3H), 1.63-1.72 (m, 4H), 1.80-1.83 (br, 2H), 2.29 (s, 3H), 2.80 (br, 3H), 2.87 (s, 2H), 3.00 (s, 2H), 3.46 (s, 2H), 3.89 (s, 6H), 3.99 (t, 2H, J=6.5 Hz), 7.14 (s, 2H).

Preparative Example 31

Preparation of Compound Represented by Formula 32 (VVZ-033)

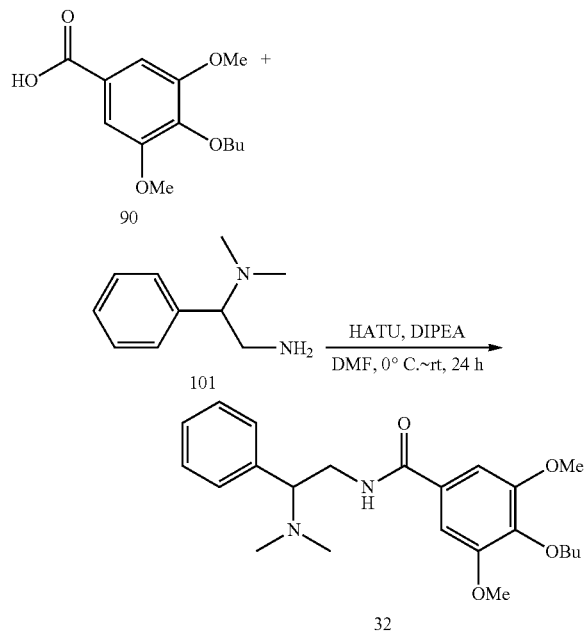

The same procedures as described in Preparative Example 2 were conducted, and a compound represented by Formula 101, that is, N,N-dimethyl-1-phenylethan-1,2-diamine (150 mg, 0.590 mmol) and 3,5-dimethoxy-4-butoxybenzoic acid represented by Formula 90 (96.89 mg, 0.590 mmol) prepared in Preparative Example 2 were used according to reaction scheme 32. As a result, a benzamide compound represented by Formula 32 was obtained as a desired product (VVZ-033; 182.40 mg, 77.2% yield).

Analysis data of the produced benzamide compound is provided as follows.

$^1$H-NMR (MeOD-d$_4$) d 0.96 (t, 3H), 1.50 (m, 2H), 1.67 (m, 2H), 2.27 (s, 6H), 3.66 (m, 2H), 3.80 (s, 6H), 3.95 (t, 2H), 4.01 (m, 1H), 6.91 (s, 2H), 7.34 (m, 5H).

Preparative Example 32

Preparation of Compound Represented by Formula 33 (VVZ-034)

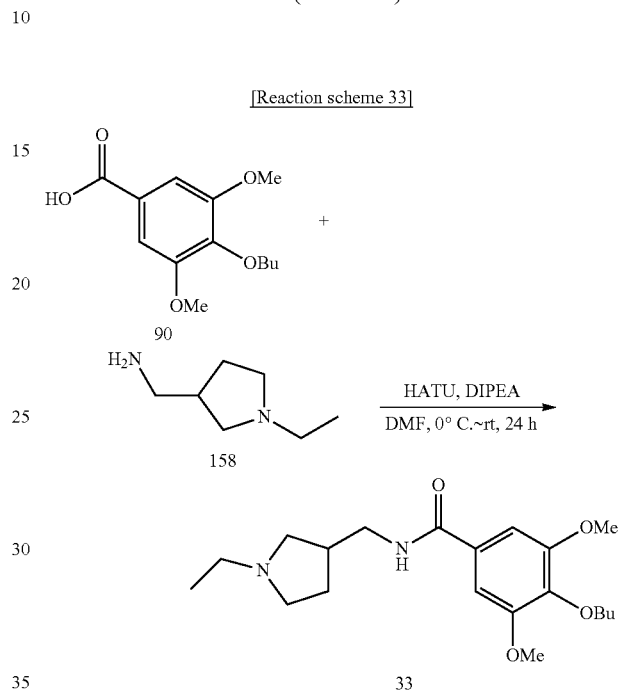

The same procedures as described in Preparative Example 2 were conducted, and a compound represented by Formula 158, that is, (+/−)-N-ethyl-3-(aminomethyl)pyrrolidine (75.64 mg, 0.590 mmol) and 3,5-dimethoxy-4-butoxybenzoic acid represented by Formula 90 (150 mg, 0.590 mmol) prepared in Preparative Example 2 were used according to reaction scheme 33. As a result, a benzamide compound represented by Formula 33 was obtained as a desired product (VVZ-034; 116.20 mg, 54% yield).

Preparative Example 33

Preparation of Compound Represented by Formula 34 (VVZ-035)

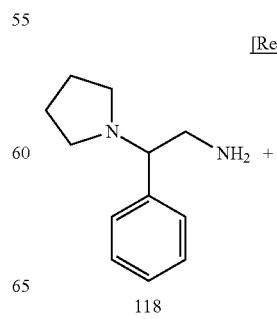

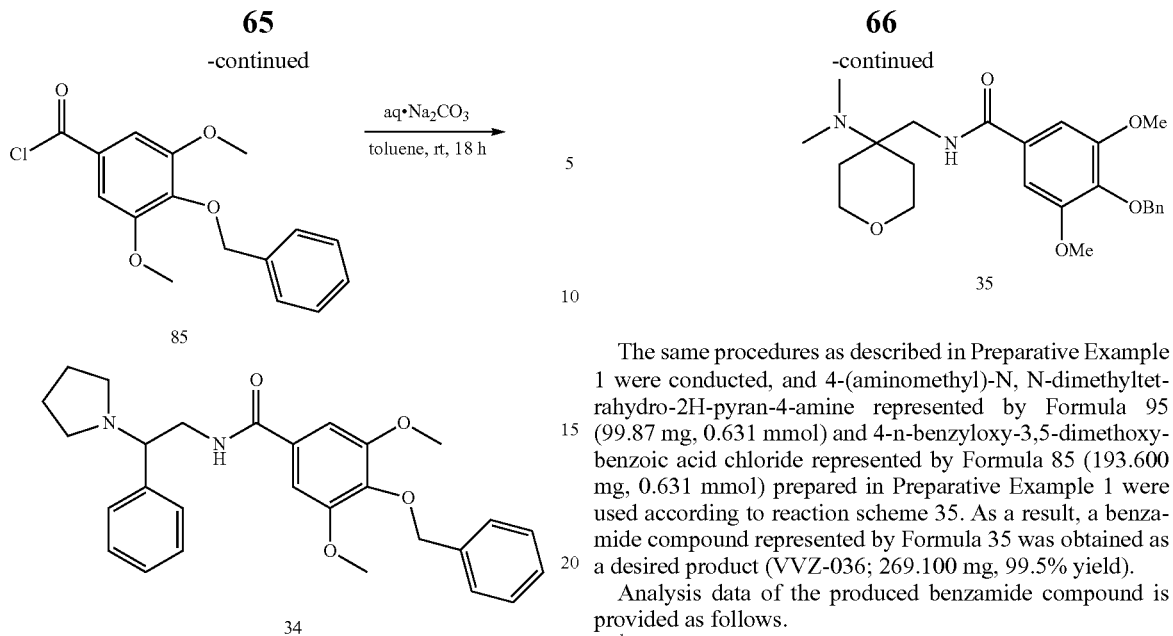

The same procedures as described in Preparative Example 12 were conducted, and 4-benzyloxy-3,5-dimethoxybenzoic acid chloride represented by Formula 85 (0.755 mL, 0.2 M, 0.181 mmol) prepared in Preparative Example 1 and a compound represented by Formula 118 (0.903 mL, 0.2 M, 0.181 mmol) were used according to reaction scheme 34. As a result, a benzamide compound represented by Formula 34 was obtained as a desired product (VVZ-035; 47.50 mg, 68.5% yield).

Preparative Example 34

Preparation of Compound Represented by Formula 35 (VVZ-036)

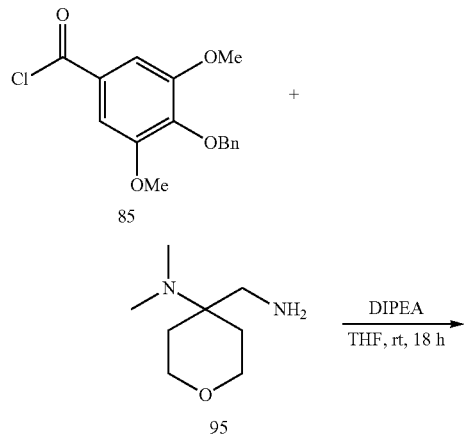

The same procedures as described in Preparative Example 1 were conducted, and 4-(aminomethyl)-N, N-dimethyltetrahydro-2H-pyran-4-amine represented by Formula 95 (99.87 mg, 0.631 mmol) and 4-n-benzyloxy-3,5-dimethoxybenzoic acid chloride represented by Formula 85 (193.600 mg, 0.631 mmol) prepared in Preparative Example 1 were used according to reaction scheme 35. As a result, a benzamide compound represented by Formula 35 was obtained as a desired product (VVZ-036; 269.100 mg, 99.5% yield).

Analysis data of the produced benzamide compound is provided as follows.

$^1$H-NMR (MeOD-$d_4$) d 1.65 (m, 2H), 1.84 (m, 2H), 2.47 (s, 6H), 3.67 (m, 2H), 3.84 (m, 2H), 3.85 (s, 6H), 5.02 (s, 2H), 7.16~7.44 (m, 7H).

Preparative Example 35

Preparation of Compound Represented by Formula 36 (VVZ-037)

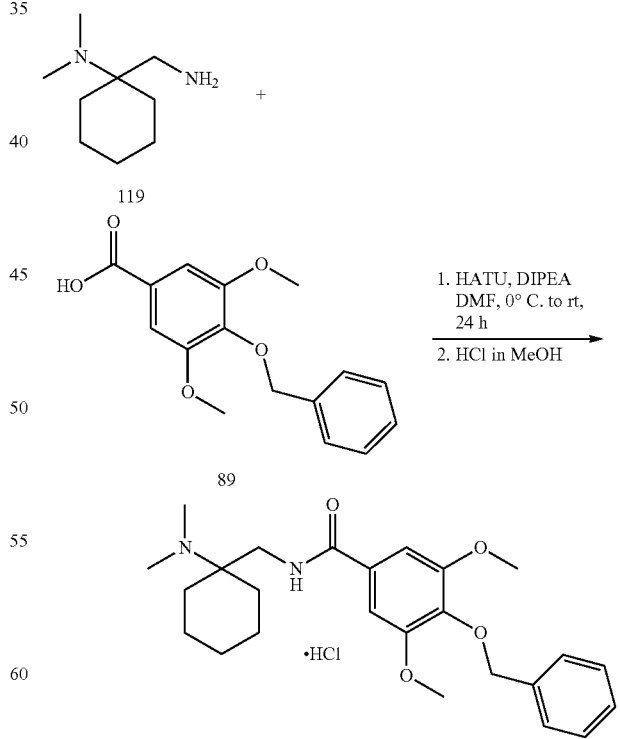

The same procedures as described in Preparative Example 2 were conducted, and a compound represented by Formula 119, that is, (1-aminomethyl-cyclohexyl)dimethylamine (89.70 mg, 0.574 mmol) and 4-benzyloxy-3,4-dimethoxybenzoic acid represented by Formula 89 (190.31 mg, 0.660 mmol) prepared in Preparative Example 1 were used according to reaction scheme 36. As a result, a benzamide compound represented by Formula 36 was obtained as a desired product (VVZ-037; 147.60 mg, 55.5% yield).

Analysis data of the produced benzamide compound is provided as follows.

$^1$H-NMR (MeOD-d$_4$) d 1.3~2.0 (m, 10H), 2.70 (s, 6H), 3.89 (s, 6H), 5.02 (s, 2H), 7.25~7.45 (m, 7H).

Preparative Example 36

Preparation of Compound Represented by Formula 37 (VVZ-040)

[Reaction scheme 37]

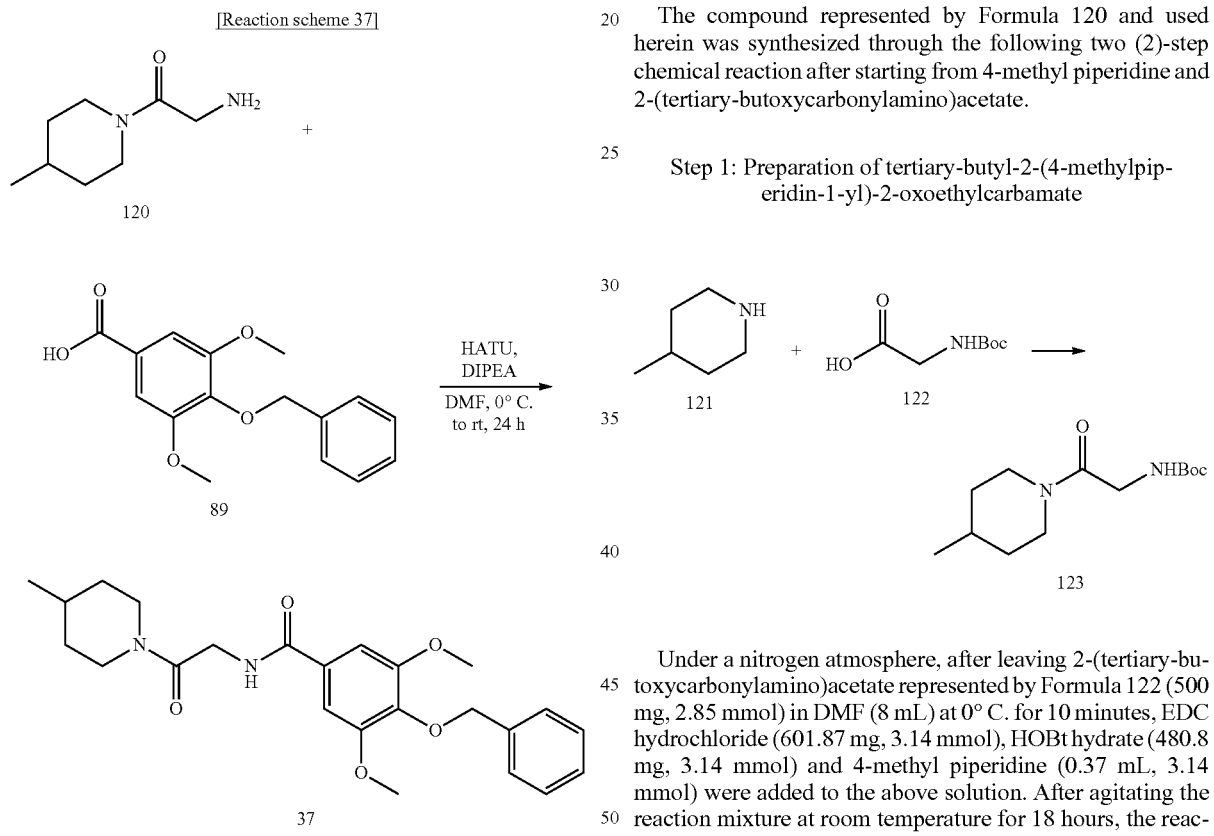

2-amino-1-(4-methylpiperidin-1-yl)ethanone represented by Formula 120 (24 mg, 0.15 mmol) was slowly added to 4-benzyloxy-3,4-dimethoxybenzoic acid represented by Formula 89 (48.72 mg, 0.17 mmol) prepared in Preparative Example 1 and diisopropylethylamine (0.11 mL, 0.61 mmol) in DMF (3 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 58.41 mg, 0.15 mmol) thereto, the mixture was agitated for 24 hours. The reaction solvent was removed under reduced pressure and chloroform (5 mL) was added to the remaining concentrate to prepare a solution. The solution was washed with a potassium carbonate solution, followed by separation to form an organic layer. After drying the organic layer with sodium sulfate (Na$_2$SO$_4$), the solvent was removed again under reduced pressure and the concentrate mixture was recrystallized using chloroform and hexane, resulting in a benzamide compound represented by Formula 37 as a desired product (VVZ-040; 27.2 mg, 42% yield).

Analysis data of the produced benzamide compound is provided as follows.

R$_f$ (ethyl acetate/hexane/triethylamine, 2:1:0.1, v/v/v) 0.7;
HRMS (EI+) calcd for C$_{24}$H$_{30}$N$_2$O$_5$ ([M+]) 426.2155.

$^1$H NMR (500 MHz, MeOH-d$_4$) d 0.98 (d, 3H, J=6.0 Hz), 1.06-1.14 (m, 1H), 1.16-1.25 (m, 1H), 1.64-1.72 (m, 2H), 1.77 (1H, J=13.0 Hz), 2.68 (t, 1H, J=13.0 Hz), 3.11 (t, 1H, J=13.0 Hz), 3.87 (s, 6H), 3.93 (d, 1H, J=13.5 Hz), 4.24 (q, 2H, J=16.5 Hz), 4.48 (d, 1H, J=13.0 Hz), 5.02 (s, 2H), 7.20 (s, 2H), 7.26-7.34 (m, 3H), 7.44 (d, 2H, J=7.0 Hz).

The compound represented by Formula 120 and used herein was synthesized through the following two (2)-step chemical reaction after starting from 4-methyl piperidine and 2-(tertiary-butoxycarbonylamino)acetate.

Step 1: Preparation of tertiary-butyl-2-(4-methylpiperidin-1-yl)-2-oxoethylcarbamate

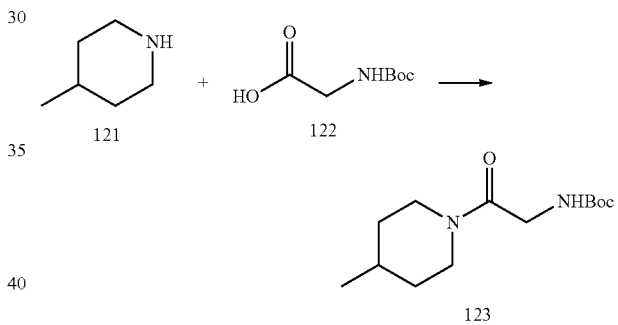

Under a nitrogen atmosphere, after leaving 2-(tertiary-butoxycarbonylamino)acetate represented by Formula 122 (500 mg, 2.85 mmol) in DMF (8 mL) at 0° C. for 10 minutes, EDC hydrochloride (601.87 mg, 3.14 mmol), HOBt hydrate (480.8 mg, 3.14 mmol) and 4-methyl piperidine (0.37 mL, 3.14 mmol) were added to the above solution. After agitating the reaction mixture at room temperature for 18 hours, the reaction solvent was removed under reduced pressure and dichloromethane (20 mL) was added to the remaining concentrate to prepare a solution. The solution was washed, followed by separation to form an organic layer. After drying the organic layer with sodium sulfate (Na$_2$SO$_4$), the solvent was removed again under reduced pressure. The obtained vacuum-concentrated mixture was subjected to separation and purification through column chromatograph (ethyl acetate/hexane, 1:5, v/v) using silica gel (SiO$_2$), resulting in a carbamate compound represented by Formula 123 as a desired product (698.5 mg, 96% yield).

Analysis data of the produced carbamate compound is provided as follows.

R$_f$ (ethyl acetate <55>/hexane, 1:5) 0.5;
$^1$H NMR (500 MHz, CDCl$_3$) 0.95 (d, 3H, J=6.5 Hz), 1.05-1.13 (m, 2H), 1.45 (s, 9H), 1.57-1.65 (m, 1H), 1.66-1.72 (m, 2H), 2.61 (t, 1H, J=12.5 Hz), 2.97 (t, 1H, J=13.5 Hz), 3.65 (d, 1H, J=13.5 Hz), 3.90-3.99 (m, 2H), 4.53 (d, 1H, J=13.0 Hz), 5.57 (br, 1H).

Step 2: Preparation of 2-amino-1-(4-methylpiperidin-1-yl)ethanone

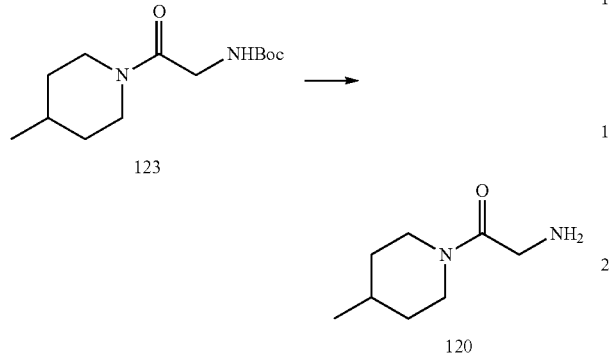

Trifluoroacetate (TFA, 0.12 mL, 1.61 mmol) was added to tertiary-butyl-2-(4-methylpiperidin-1-yl)-2-oxoethylcarbamate represented by Formula 123 (82.3 mg, 0.32 mmol) in dichloromethane (3.5 mL) at 0° C. After agitating the reaction mixture at room temperature for 18 hours and adding 5% sodium bicarbonate solution to the mixture at 0° C., dichloromethane (10 mL) was further added, followed by washing and separation to form an organic layer. After drying the organic layer with sodium sulfate (Na$_2$SO$_4$), the solvent was removed again under reduced pressure to produce an acetamide compound represented by Formula 120 as a desired product (34 mg, 68% yield).

Analysis data of the produced acetamide compound is provided as follows.

R$_f$ (ethyl acetate <60>/hexane, 2:1) 0.1;

$^1$H NMR (500 MHz CDCl$_3$) d 0.97 (d, 3H, J=8.5 Hz), 1.07-1.15 (m, 2H), 1.59-1.67 (m, 1H), 1.68-1.74 (m, 2H), 2.63 (t, 1H, J=14.5 Hz), 2.99 (t, 1H, J=15.5 Hz), 3.67 (d, 1H, J=15.5 Hz), 3.92-4.01 (m, 2H), 4.55 (t, 1H, J=15.0 Hz), 5.59 (br, 2H).

Preparative Example 37

Preparation of Compound Represented by Formula 38 (VVZ-041)

[Reaction scheme 38]

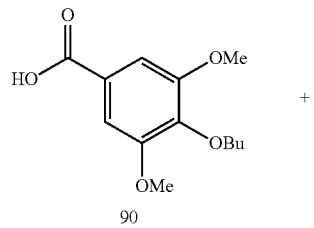

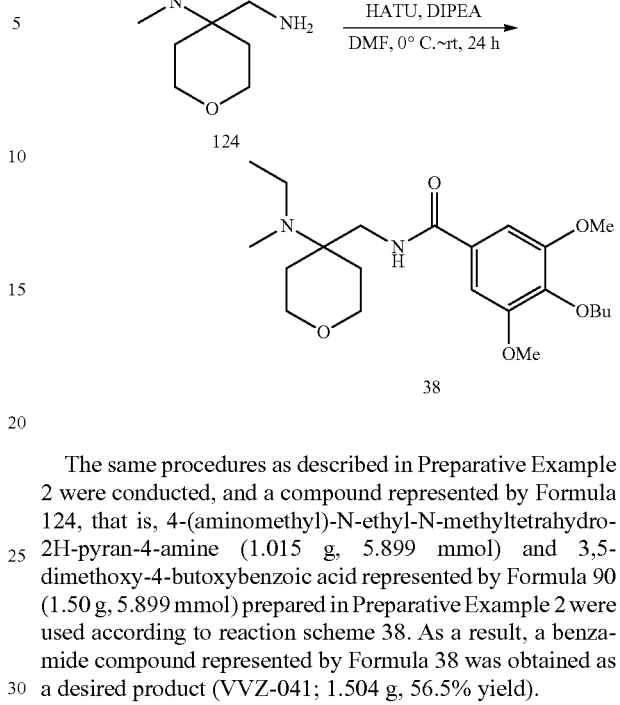

The same procedures as described in Preparative Example 2 were conducted, and a compound represented by Formula 124, that is, 4-(aminomethyl)-N-ethyl-N-methyltetrahydro-2H-pyran-4-amine (1.015 g, 5.899 mmol) and 3,5-dimethoxy-4-butoxybenzoic acid represented by Formula 90 (1.50 g, 5.899 mmol) prepared in Preparative Example 2 were used according to reaction scheme 38. As a result, a benzamide compound represented by Formula 38 was obtained as a desired product (VVZ-041; 1.504 g, 56.5% yield).

Analysis data of the produced benazmide compound is provided as follows.

$^1$H-NMR (MeOD-d$_4$) d 0.96 (t, 3H), 1.09 (t, 3H), 1.52 (m, 2H), 1.66 (m, 4H), 1.82 (m, 2H), 2.36 (s, 3H), 2.68 (q, 2H), 3.54 (s, 2H), 3.64 (m, 2H), 3.84 (m, 2H), 3.88 (s, 6H), 3.97 (t, 2H), 7.13 (s, 2H).

Preparative Example 38

Preparation of Compound Represented by Formula 39 (VVZ-050)

[Reaction scheme 39]

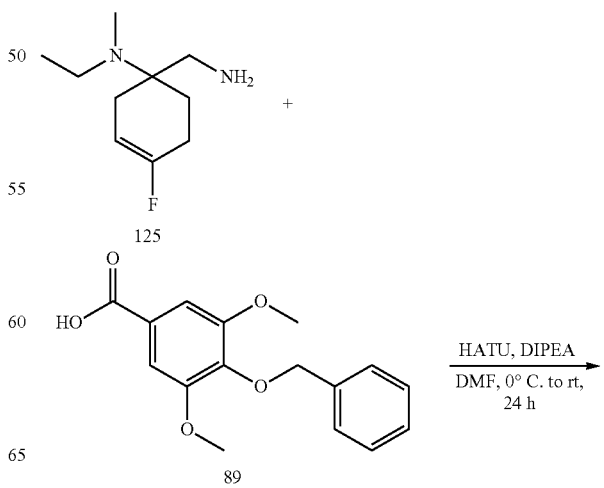

-continued

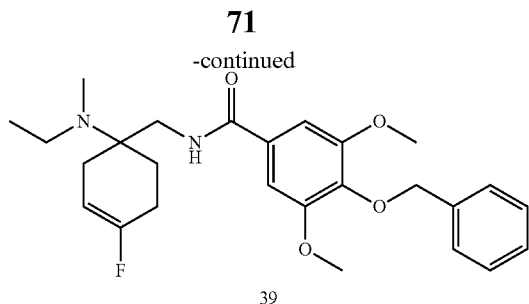

39

The same procedures as described in Preparative Example 2 were conducted, and 4-benzyloxy-3,4-dimethoxybenzoic acid represented by Formula 89 (33.88 mg, 0.118 mmol) prepared in Preparative Example 1 and a compound represented by Formula 125, that is, (1-aminomethyl-4-fluoro-cyclohex-3-enyl)-ethylmethylamine (19.9 mg, 0.107 mmol) were used according to reaction scheme 39. As a result, a benzamide compound represented by Formula 39 was obtained as a desired product (VVZ-050; 16.00 mg, 32.8% yield).

Analysis data of the produced benzamide compound is provided as follows.

$^1$H-NMR (MeOD-$d_4$) d 0.95 (t, 3H), 1.67 (m, 1H), 1.88 (m, 2H), 2.15 (m, 3H), 2.25 (s, 3H), 2.45 (m, 1H), 2.63 (m, 1H), 3.41 (dd, 2H), 3.78 (s, 6H), 4.92 (s, 2H), 5.02 (d, 1H), 7.15 (s, 2H), 7.16~7.36 (m, 5H).

Preparative Example 39

Preparation of Compound Represented by Formula 40 (VVZ-067)

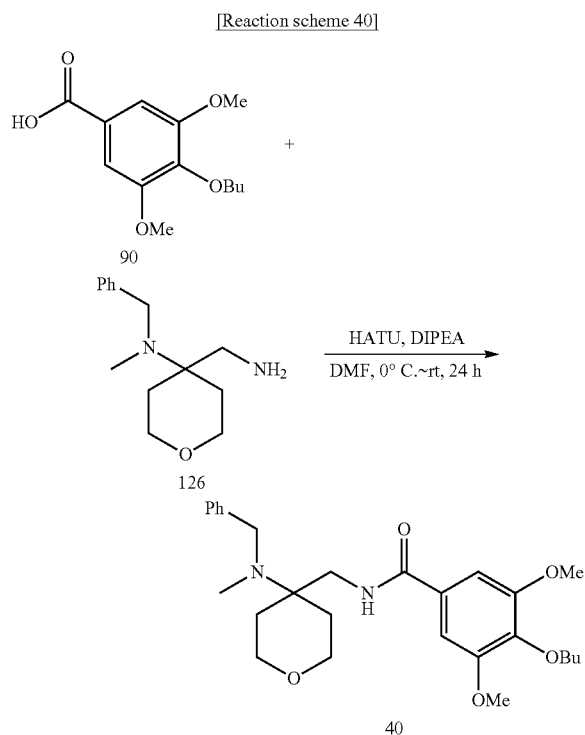

The same procedures as described in Preparative Example 2 were conducted, and 3,5-dimethoxy-4-butoxybenzoic acid represented by Formula 90 (150.00 mg, 0.590 mmol) and a compound represented by Formula 126, that is, 4-(aminomethyl)-N-benzyl-N-methyltetrahydro-2H-pyran-4-amine (138.24 mg, 0.590 mmol) were used according to reaction scheme 40. As a result, a benzamide compound represented by Formula 40 was obtained as a desired product (VVZ-067; 158.50 mg, 57.1% yield).

Analysis data of the produced benzamide compound is provided as follows.

$^1$H-NMR (MeOD-$d_4$) d 0.98 (t, 3H), 1.52 (m, 2H), 1.68 (m, 2H), 1.75 (m, 2H), 1.97 (m, 2H), 2.29 (s, 3H), 3.65 (s, 2H), 3.95 (s, 6H), 3.97 (m, 2H), 3.99 (t, 2H), 7.17~7.38 (m, 7H).

Preparative Example 40

Preparation of Compound Represented by Formula 41 (VVZ-068)

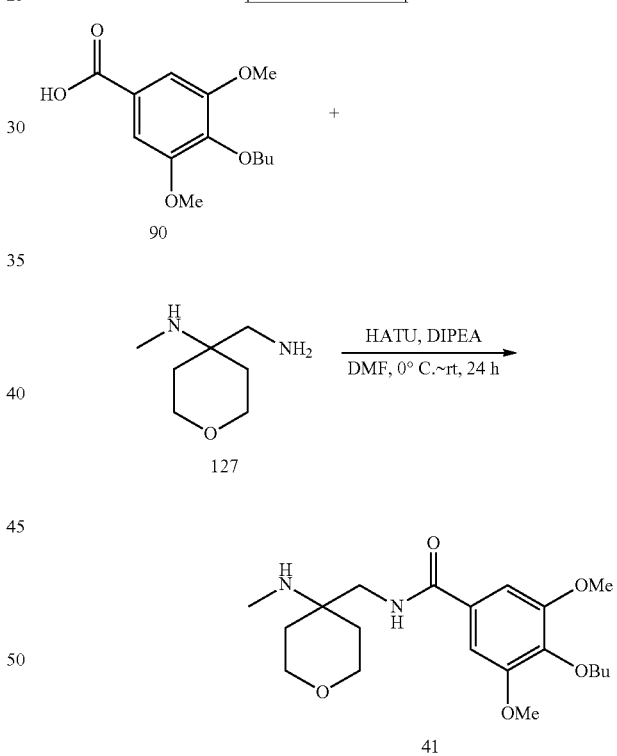

4-n-butoxy-3,5-dimethoxybenzoic acid represented by Formula 90 (1.5 g, 5.90 mmol) prepared in Preparative Example 2 was slowly added to 4-(aminomethyl)-N-methyltetrahydro-2H-pyran-4-amine represented by Formula 127 (0.85 g, 5.90 mmol) and diisopropylethylamine (3.09 mL, 17.70 mmol) in DMF (40 mL) at room temperature. After cooling the reaction mixture to or and adding 2-(1H-7-azabenzotriazol-1-yl)-1,1,3,3-tetramethyluronium hexafluorophosphate methanaminium (HATU, 2.24 g, 5.90 mmol) thereto, the mixture was agitated at room temperature for 24 hours. The reaction solvent was removed under reduced pressure and ethyl acetate was added to the remaining concentrate to prepare a solution. The solution was washed with a potassium carbonate solution, followed by separation to form an organic layer. After drying the organic layer under magnesium sulfate (MgSO$_4$), the solvent was removed again under reduced pressure. The obtained vacuum-concentrated mixture was subjected to separation and purification through column chromatography (chloroform/methanol, 10:1) using silica gel (SiO$_2$), resulting in an organic material. After dissolving the organic material in methanol, 1.25 M-hydrochloride in methanol solution (5.66 mL, 7.08 mmol) was added to the mixture, followed by agitation at 45° C. for 15 minutes. Thereafter, the solvent was removed again under reduced pressure and a benzamide compound represented by Formula 41 was produced (VVZ-068; 1.54 g, 63% yield).

Analysis data of the produced benzamide compound is provided as follows.

R$_f$ (chloroform/methanol, 10:1, v/v) 0.1;

HRMS (EI+) calcd for C$_{20}$H$_{33}$ClN$_2$O$_5$ ([M+]) 416.2078.

$^1$H NMR (500 MHz, MeOH-d$_4$) δ0.98 (t, 3H, 7.5 Hz), 1.50-1.54 (m, 2H), 1.68-1.71 (m, 2H), 1.85-1.92 (m, 4H), 2.79 (s, 3H), 3.75 (t, 2H, 11.5 Hz), 3.87 (s, 2H), 3.91 (s, 6H), 3.94-4.01 (m, 4H), 7.28 (s, 2H).

The compound represented by Formula 127 and used herein was synthesized through the following two (2)-step chemical reaction after starting from N-methylamine hydrochloride purchased from Sigma-Aldrich Co. and tetrahydro-4H-pyran-4-one purchased from TCl Co.

Step 1: Preparation of 4-(methylamino)tetrahydro-2H-pyran-4-carbonitrile

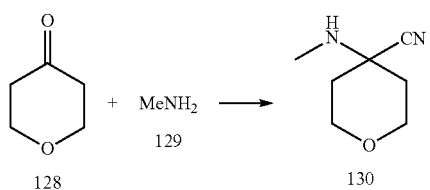

To N-methylamine hydrochloride represented by Formula 129 (8.60 mL, 99.88 mmol), 1.25 M hydrochloride in methanol solution was added and, after agitating this mixture at room temperature overnight, the solvent was removed under reduced pressure. Tetrahydro-4H-pyran-4-on represented by Formula 128 was added to the obtained amine hydrochloride and 50 mL of a potassium cyanate solution (6.50 g, 99.88 mmol) was further mixed thereto. This mixture was agitated at 0° C. for 10 minutes and, further agitated at room temperature for 18 hours. After terminating the reaction, solid potassium carbonate was added, followed by washing using ethylether and a potassium carbonate solution, and separation to form an organic layer. After drying the organic layer with sodium sulfate, the solvent was removed under reduced pressure. As a result, a nitrile compound represented by Formula 130 was obtained (9.11 g, 65%). Analysis data of the product is provided as follows.

R$_f$ (ethyl acetate/hexane, 1:1, v/v) 0.2;

$^1$H NMR (500 MHz, MeOD-d$_4$) δ1.67 (td, 2H, J=12.1, 3.8 Hz), 2.02 (d, 2H, J=12.0 Hz), 2.45 (s, 3H), 3.61 (t, 2H, J=11.7 Hz), 3.95 (dt, 2H, J=12.5, 3.9 Hz).

Step 2: Preparation of 4-(aminomethyl)-N-methyltetrahydro-2H-pyran-4-amine

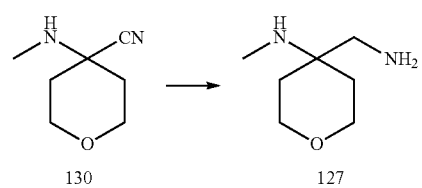

A solution of 4-(methylamino)tetrahydro-2H-pyran-4-carbonitrile represented by Formula 130 (9.28 g, 66.25 mmol) in ethylether (80 mL) was added to lithiumaluminum hydride (5.03 g, 132.50 mmol) in ethylether (300 mL) at room temperature. After reacting this mixture under refluxing for 2 days and cooling the same to room temperature, the treated mixture was quenched using 20 mL water then filtered to prepare a solution. The solvent was removed from the solution under reduced pressure. As a result, an amine compound represented by Formula 127 (8.02 g, 84%) was produced. Analysis data of the produced compound is provided as follows.

R$_f$ (ethyl acetate/methanol, 10:1, v/v) 0.01;

$^1$H NMR (500 MHz, MeOD-d$_4$) δ1.51-1.54 (br, 2H), 1.74-1.79 (m, 2H), 2.93 (s, 3H), 2.82 (s, 2H), 3.52-3.57 (m, 2H), 3.78-3.83 (m, 2H).

Preparative Example 41

Preparation of Compound Represented by Formula 42 (VVZ-071)

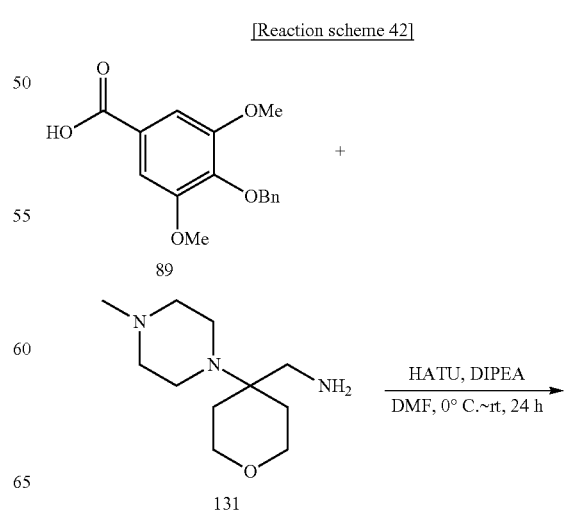

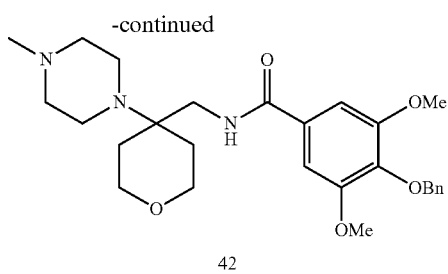

42

The same procedures as described in Preparative Example 2 were conducted, and 4-benzyloxy-3,5-dimethoxybenzoic acid represented by Formula 89 (50.00 mg, 0.173 mmol) prepared in Preparative Example 1 and a compound represented by Formula 131, that is, (4-(4-methylpiperazin-1-yl)tetrahydro-2H-pyran-4-yl)methanamine (37.00 mg, 0.173 mmol) were used according to reaction scheme 42. As a result, a benzamide compound represented by Formula 42 was obtained as a desired product (VVZ-071; 55.40 mg, 66.1% yield).

Analysis data of the produced benzamide compound is provided as follows.

$^1$H-NMR (MeOD-d$_4$) d 1.53 (m, 2H), 1.78 (m, 2H), 2.22 (s, 3H), 2.43 (m, 4H), 2.73 (m, 4H), 3.41 (s, 2H), 3.54 (m, 2H), 3.72 (m, 2H), 3.77 (s, 6H), 4.92 (s, 2H), 7.03~7.34 (m, 4H).

Preparative Example 42

Preparation of Compound Represented by Formula 43 (VVZ-073)

[Reaction scheme 43]

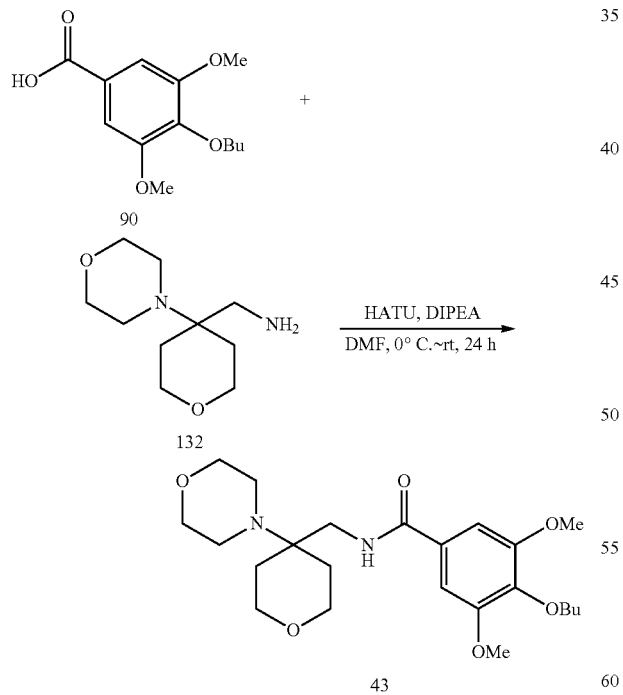

The same procedures as described in Preparative Example 2 were conducted, and 3,5-dimethoxy-4-butoxybenzoic acid represented by Formula 90 (50.00 mg, 0.197 mmol) prepared in Preparative Example 2 and a compound represented by Formula 132, that is, (4-morpholinotetrahydro-2H-pyran-4-yl)methanamine (39.38 mg, 0.197 mmol) were used according to reaction scheme 43. As a result, a benzamide compound represented by Formula 43 was obtained as a desired product (VVZ-073; 74.60 mg, 86.9% yield).

Analysis data of the produced benzamide compound is provided as follows.

$^1$H-NMR (MeOD-d$_4$) d 0.95 (t, 3H), 1.52 (m, 2H), 1.60 (m, 2H), 1.64 (m, 2H), 1.75 (m, 2H), 2.76 (m, 4H), 3.51 (s, 2H), 3.62 (m, 2H), 3.68 (m, 4H), 3.83 (m, 2H), 3.87 (s, 6H), 3.96 (t, 2H), 7.13 (s, 2H).

The compound represented by Formula 132 and used herein was synthesized through the following two (2)-step chemical reaction after starting from morpholine purchased from TCI Co. and tetrahydro-4H-pyran-4-one.

Step 1: Preparation of 4-morpholinotetrahydro-2H-pyran-4-carbonitrile

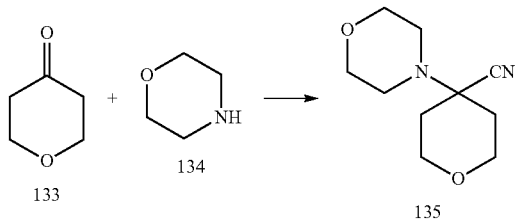 [SMILES: O=C1CCOCC1 ; C1COCCN1 ; N#CC1(N2CCOCC2)CCOCC1]

1.25 M-hydrochloride in methanol solution (39.95 mL) was added to morpholine represented by Formula 134 (4.32 mL, 49.94 mmol) and, after agitating the mixture at room temperature overnight, the solvent was removed under reduced pressure. Tetrahydro-4H-pyran-4-one represented by Formula 133 (5.0 g, 49.94 mmol) was added to the obtained amine hydrochloride and a potassium cyanate solution (KCN, 3.25 g, 49.94 mmol, 40 mL) was further mixed thereto. This mixture was agitated at 0° C. for 10 minutes and further agitated at room temperature for 18 hours. After terminating the reaction, solid potassium carbonate (K$_2$CO$_3$) was added, followed by washing using ethylether and a potassium carbonate (K$_2$CO$_3$) solution, and separation to form an organic layer. After drying the organic layer with sodium sulfate (Na$_2$SO$_4$), the solvent was removed under reduced pressure. As a result, a nitrile compound represented by Formula 135 (2.94 g, 30%) was produced. Analysis data of the produced compound is provided as follows.

R$_f$ (ethyl acetate/hexane, 1:1, v/v) 0.42;
$^1$H NMR (500 MHz, MeOD-d$_4$) δ 1.70 (td, 2H, J=12.5, 4.0 Hz), 2.13 (d, 2H, J=12.0 Hz), 2.64 (s, 4H), 3.60 (t, 2H, J=12.0 Hz), 3.73 (t, 4H, J=4.5 Hz), 4.0 (dt, 2H, J=12.5, 3.5 Hz).

Step 2: Preparation of (4-morpholinotetrahydro-2H-pyran-4-yl)methanamine

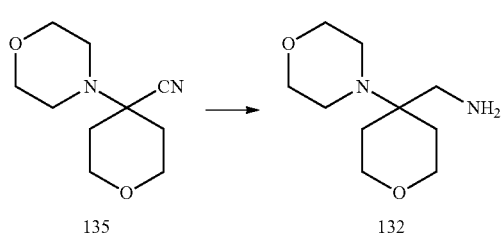 [SMILES: N#CC1(N2CCOCC2)CCOCC1 ; NCC1(N2CCOCC2)CCOCC1]

A solution of 4-morpholinotetrahydro-2H-pyran-4-carbonitrile represented by Formula 135 (2.94 g, 14.97 mmol) in ethylether/tetrahydrofuran (20 mL/30 mL, v/v) was added to lithiumaluminum hydride (LiAlH$_4$, 1.14 g, 29.95 mmol) in ethylether (150 mL) at room temperature. After refluxing this mixture for 2 days and cooling the same to room temperature, water (6 mL) was added and the mixture was filtered to prepare a solution. The solvent was removed from the solution under reduced pressure. As a result, an amine compound represented by Formula 132 (1.83 g, 61%) was produced. Analysis data of the produced compound is provided as follows.

R$_f$ (ethyl acetate/methanol, 10:1, v/v) 0.01;

$^1$H NMR (500 MHz, MeOD-d$_4$) δ 1.50-1.54 (br, 2H), 1.77-1.82 (m, 2H), 2.65 (t, 4H, J=4.5 Hz), 2.76 (s, 2H), 3.56-3.61 (m, 2H), 3.67 (t, 4H, J=4.5 Hz), 3.81-3.85 (m, 2H).

Preparative Example 43

Preparation of Compound Represented by Formula 44 (VVZ-074)

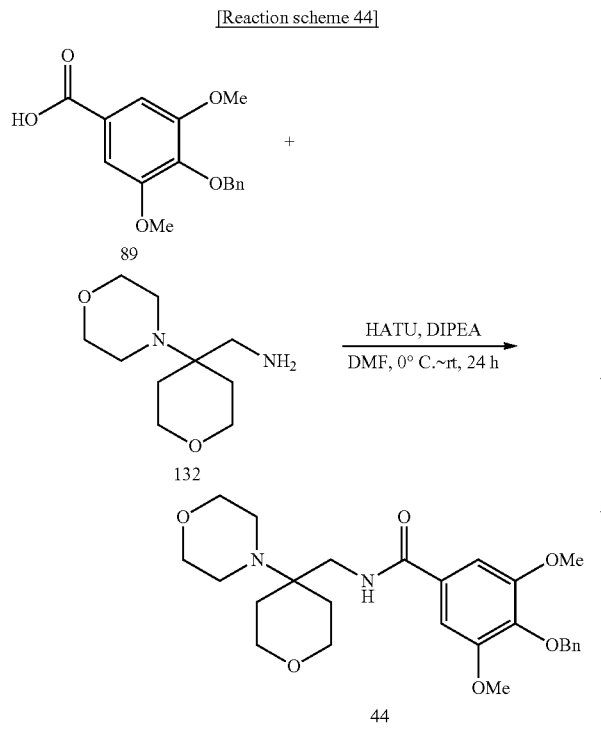

The same procedures as described in Preparative Example 2 were conducted, and 4-benzyloxy-3,5-dimethoxybenzoic acid represented by Formula 89 (50.00 mg, 0.173 mmol) prepared in Preparative Example 1 and (4-morpholinotetrahydro-2H-pyran-4-yl)methanamine represented by Formula 132 (34.73 mg, 0.173 mmol) prepared in Preparative Example 42 were used according to reaction scheme 44. As a result, a benzamide compound represented by Formula 44 was obtained as a desired product (VVZ-074; 78.80 mg, 96.6% yield).

Analysis data of the produced benzamide compound is provided as follows.

$^1$H-NMR (MeOD-d$_4$) d 1.60 (m, 2H), 1.83 (m, 2H), 2.76 (m, 4H), 3.51 (s, 2H), 3.62 (m, 2H), 3.67 (m, 4H), 3.83 (m, 2H), 3.87 (s, 6H), 5.01 (s, 2H), 7.12~7.44 (m, 7H).

Preparative Example 44

Preparation of Compound Represented by Formula 45 (VVZ-083)

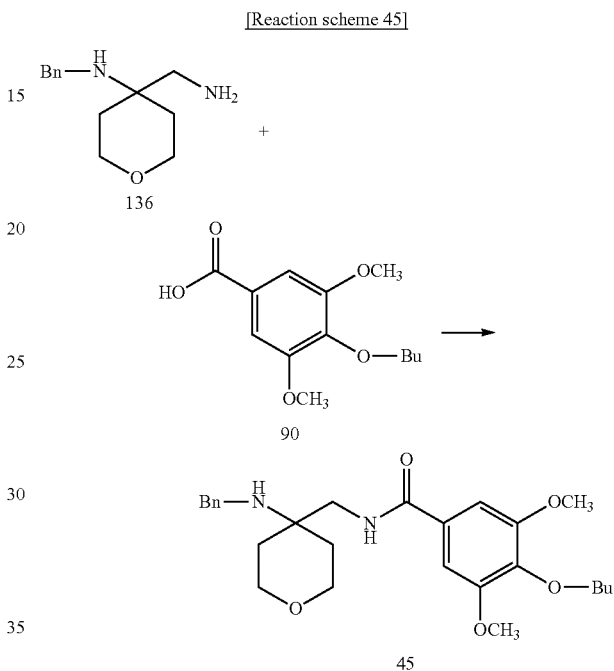

3,5-dimethoxy-4-butyloxybenzoic acid represented by Formula 90 (50 mg, 0.197 mmol) prepared in Preparative Example 2 was slowly added to 4-(aminomethyl)-N-benzyltetrahydro-2H-pyran-4-amine represented by Formula 136 (43.3 mg, 0.197 mmol) and diisopropylethylamine (0.103 mL, 0.590 mmol) in DMF (5 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 74.8 mg, 0.197 mmol) thereto, the mixture was agitated at room temperature for 18 hours. The reaction solvent was removed under reduced pressure and chloroform/methanol (9:1, v/v) was added to the remaining concentrate to prepare a solution. The solution was washed with a potassium carbonate (K$_2$CO$_3$) solution, followed by separation to form an organic layer. After drying the organic layer with magnesium sulfate (MgSO$_4$), the solvent was removed again under reduced pressure. The obtained vacuum-concentrated mixture was subjected to separation and purification through column chromatography (chloroform/methanol, 10:1, v/v) using silica gel (SiO$_2$). As a result, a benzamide compound represented by Formula 45 was produced (VVZ-083; 50.7 mg, 56.5% yield).

Analysis data of the produced benzamide compound is provided as follows.

R$_f$ (chloroform/methanol, 10:1, v/v) 0.34;

$^1$H NMR (500 MHz, MeOD-d$_4$) δ 0.97 (t, 3H, J=7.3 Hz), 1.50-1.54 (m, 2H), 1.68-1.72 (m, 6H), 3.60 (s, 2H), 3.70-3.72 (m, 2H), 3.81 (s, 2H), 3.88 (s, 8H), 3.99 (t, 2H, J=6.5 Hz), 7.16 (s, 2H), 7.21-7.31 (m, 3H), 7.41-7.43 (br, 2H).

The compound represented by Formula 136 and used herein was synthesized through the following two (2)-step chemical reaction after starting from benzylamine hydrochloride purchased from Sigma-Aldrich Co. and tetrahydro-4H-pyran-4-one purchased from TCI Co.

Step 1: Preparation of 4-(benzylamino)tetrahydro-2H-pyran-4-carbonitrile

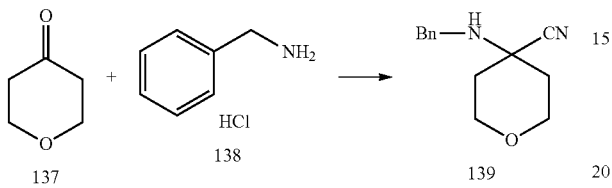

After mixing tetrahydro-4H-pyran-4-one represented by Formula 137 (5 g, 49.94 mmol) with benzylamine hydrochloride represented by Formula 138 (7.17 g, 49.94 mmol), a potassium cyanate solution (KCN, 3.25 g, 49.94 mmol, 50 mL) was added thereto. The mixture was agitated at 0° C. for 10 minutes and, further, agitated at room temperature for 18 hours. After terminating the reaction and adding solid potassium carbonate ($K_2CO_3$) thereto, the mixture was consecutively washed with ethylether and a potassium carbonate ($K_2CO_3$) solution, followed by separation to form an organic layer. After drying the organic layer with sodium sulfate ($Na_2SO_4$), the solvent was removed under reduced pressure. As a result, a nitrile compound represented by Formula 139 (10.79 g, 99%) was produced. Analysis data of the produced compound is provided as follows.

$R_f$ (ethyl acetate/hexane, 1:1, v/v) 0.73;
$^1$H NMR (500 MHz, MeOD-$d_4$) δ 1.74-1.79 (m, 2H), 2.06 (dd, 2H, J=13.5, 1.5 Hz), 3.62 (td, 2H, J=11.3, 1.8 Hz), 3.87 (s, 2H), 3.94-3.97 (m, 2H), 7.22-7.38 (m, 5H).

Step 2: Preparation of 4-(aminomethyl)-N-benzyltetrahydro-2H-pyran-4-amine

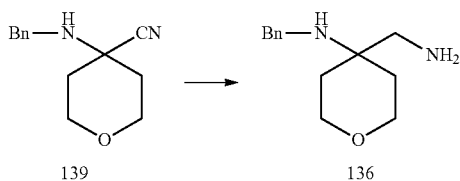 [SMILES: N#CC1(NCc2ccccc2)CCOCC1 ; NCC1(NCc2ccccc2)CCOCC1]

A solution of 4-(benzylamino)tetrahydro-2H-pyran-4-carbonitrile represented by Formula 139 (10.79 g, 49.89 mmol) in ethylether (80 mL) was added to lithiumaluminum hydride (LiAlH$_4$, 3.79 g, 99.78 mmol) in ethylether (300 mL) at room temperature. After refluxing this mixture for 2 days and cooling the same to room temperature, water (15 mL) was added thereto and the mixture was filtered to prepare a solution. The solvent was removed from the solution under reduced pressure. As a result, an amine compound represented by Formula 136 was produced (9.8 g, 89.2%). Analysis data of this product is provided as follows.

$R_f$ (ethyl acetate/methanol, 10:1, v/v) 0.1;
$^1$H NMR (500 MHz, MeOD-$d_4$) δ 1.54-1.66 (m, 4H), 2.68 (s, 2H), 3.62-3.67 (m, 4H), 3.81-3.86 (m, 2H), 7.21-7.41 (m, 5H).

Preparative Example 45

Preparation of Compound Represented by Formula 46 (VVZ-084)

[Reaction scheme 46]

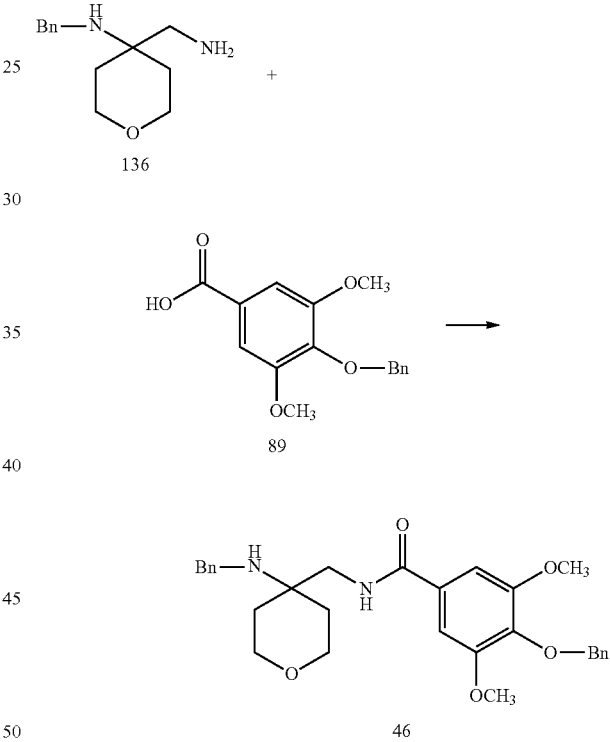

3,5-dimethoxy-4-benzyloxybenzoic acid represented by Formula 89 (50 mg, 0.173 mmol) prepared in Preparative Example 1 was slowly added to 4-(aminomethyl)-N-benzyltetrahydro-2H-pyran-4-amine represented by Formula 136 (38.2 mg, 0.173 mmol) prepared in Preparative Example 44 and diisopropylethylamine (0.091 mL, 0.520 mmol) in DMF (5 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 65.9 mg, 0.173 mmol) thereto, the mixture was agitated at room temperature for 18 hours. The reaction solvent was removed under reduced pressure and chloroform/methanol (9:1, v/v) was added to the remaining concentrate to prepare a solution. The solution was washed with a potassium carbonate (K$_2$CO$_3$) solution, followed by separation to form an organic layer. After drying the organic layer with magnesium sulfate (MgSO$_4$), the solvent was removed again under reduced pressure. The obtained vacuum-concentrated mixture was subjected to separation and purification through column chromatography (chloroform/methanol, 10:1, v/v) using silica gel (SiO$_2$). As a result, a benzamide compound represented by Formula 46 was produced (VVZ-084; 68.3 mg, 80.3% yield).

Analysis data of the produced benzamide compound is provided as follows.

R$_f$ (chloroform/methanol, 10:1, v/v) 0.39;

$^1$H NMR (500 MHz, MeOD-d$_4$) δ 1.71 (s, 4H), 3.60 (s, 2H), 3.70-3.72 (br, 2H), 3.80 (s, 2H), 3.87-3.90 (br, 8H), 5.03 (s, 2H), 7.15 (s, 2H), 7.22-7.45 (m, 10H).

Preparative Example 46

Preparation of Compound Represented by Formula 47 (VVZ-038)

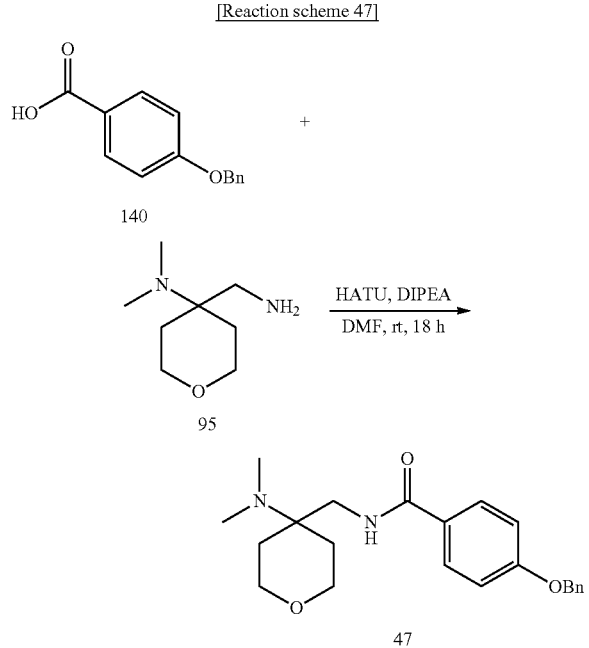

The same procedures as described in Preparative Example 2 were conducted, and a compound represented by Formula 140, that is, 4-benzyloxybenzoic acid (148.560 mg, 0.651 mmol) and 4-(aminomethyl)-N,N-dimethyltetrahydro-2H-pyran-4-amine represented by Formula 95 (103.00 mg, 0.651 mmol) were used according to reaction scheme 47. As a result, a benzamide compound represented by Formula 47 was obtained as a desired product (VVZ-038; 164.50 mg, 68.6% yield).

Analysis data of the produced benzamide compound is provided as follows.

$^1$H-NMR (MeOD-d$_4$) d 1.63 (m, 2H), 1.83 (m, 2H), 2.44 (s, 6H), 3.63 (s, 2H), 3.66 (m, 2H), 3.85 (m, 2H), 5.15 (s, 2H), 7.05~7.79 (m, 9H).

Preparative Example 47

Preparation of Compound Represented by Formula 48 (VVZ-039)

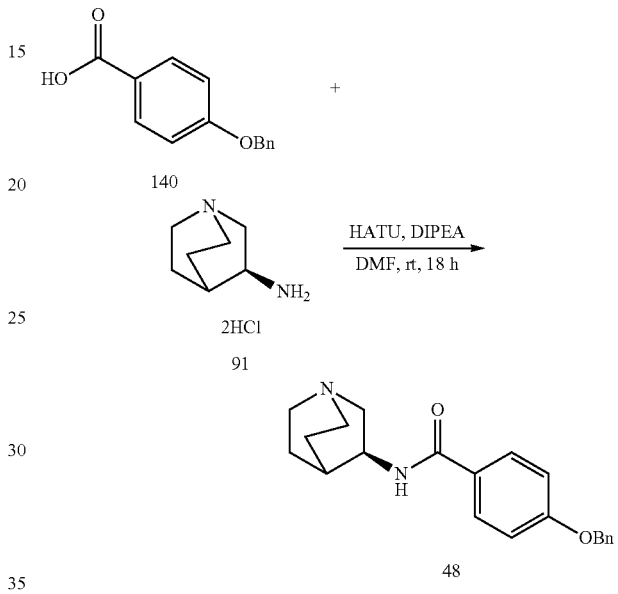

The same procedures as described in Preparative Example 2 were conducted, and a compound represented by Formula 140, that is, 4-benzyloxybenzoic acid (50.00 mg, 0.219 mmol) and a compound represented by Formula 91, that is, (S)-3-aminoquinuclidine hydrochloride (43.62 mg, 0.219 mmol) were used according to reaction scheme 48. As a result, a benzamide compound represented by Formula 48 was obtained as a desired product (VVZ-039; 66.20 mg, 89.8% yield).

Analysis data of the produced benzamide compound is provided as follows.

$^1$H-NMR (MeOD-d$_4$) d 1.53 (m, 1H), 1.76 (m, 2H), 1.88 (m, 1H), 2.07 (m, 1H), 2.82 (m, 4H), 3.02 (m, 2H), 4.13 (m, 1H), 5.16 (s, 2H), 7.04~7.81 (m, 9H).

Preparative Example 48

Preparation of Compound Represented by Formula 49 (VVZ-048)

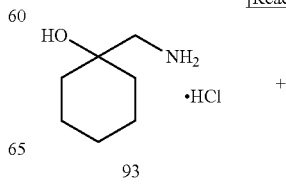

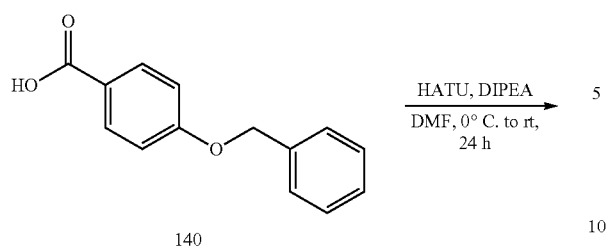

140

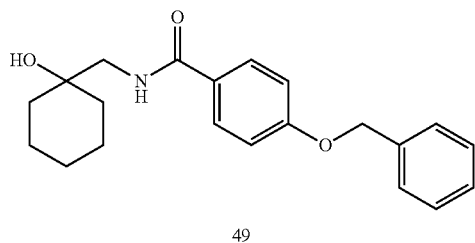

49

The same procedures as described in Preparative Example 2 were conducted, and a compound represented by Formula 140, that is, 4-benzyloxybenzoic acid (119.42 mg, 0.523 mmol) and 1-aminomethyl-1-cyclohexanol hydrochloride represented by Formula 93 (78.8 mg, 0.476 mmol) were used according to reaction scheme 49. As a result, a benzamide compound represented by Formula 49 was obtained as a desired product (VVZ-048; 142.10 mg, 88.0% yield).

Analysis data of the produced benzamide compound is provided as follows.

$^1$H-NMR (MeOD-d$_4$) d 1.32~1.69 (m, 10H), 3.40 (s, 2H), 5.16 (s, 2H), 7.05~7.83 (m, 9H).

Preparative Example 49

Preparation of Compound Represented by Formula 50 (VVZ-051)

[Reaction scheme 50]

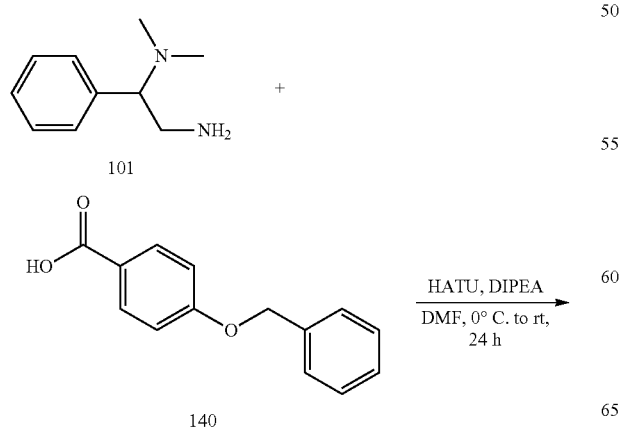

The same procedures as described in Preparative Example 2 were conducted, and a compound represented by Formula 140, that is, 4-benzyloxybenzoic acid (137.42 mg, 0.602 mmol) and a compound represented by Formula 101, that is, (2-amino-1-phenylethyl)dimethylamine (89.9 mg, 0.547 mmol) were used according to reaction scheme 50. As a result, a benzamide compound represented by Formula 50 was obtained as a desired product (VVZ-051; 116.70 mg, 56.9% yield).

Analysis data of the produced benzamide compound is shown a follows.

$^1$H-NMR (MeOD-d$_4$) d 2.26 (s, 6H), 3.68 (m, 2H), 3.97 (dd, 1H), 5.11 (s, 2H), 6.97~7.61 (m, 14H).

Preparative Example 50

Preparation of Compound Represented by Formula 51 (VVZ-052)

[Reaction scheme 51]

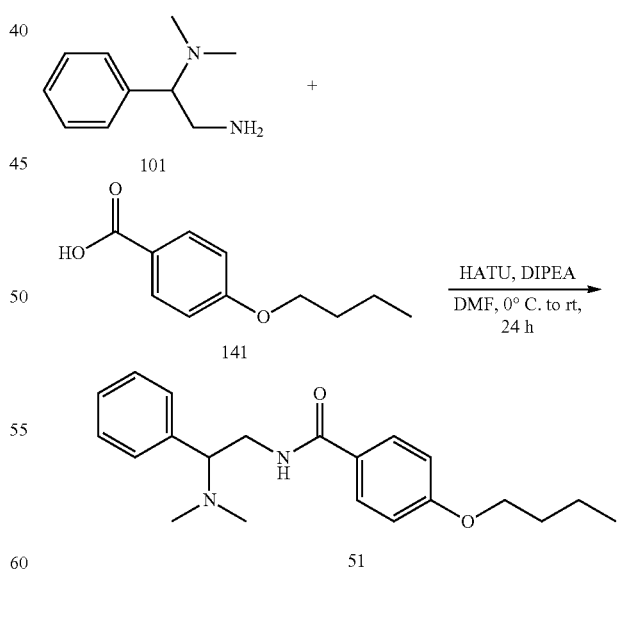

The same procedures as described in Preparative Example 2 were conducted, and a compound represented by Formula 141, that is, 4-butyloxybenzoic acid (82.86 mg, 0.427 mmol) and a compound represented by Formula 101, that is, (2-amino-1-phenylethyl)dimethylamine (63.7 mg, 0.388 mmol) were used according to reaction scheme 51. As a result, a benzamide compound represented by Formula 51 was obtained as a desired product (VVZ-052; 116.70 mg, 56.9% yield).

Analysis data of the produced benzamide compound is provided as follows.

$^1$H-NMR (MeOD-$d_4$) d 0.98 (t, 3H), 1.50 (m, 2H), 1.76 (m, 2H), 2.25 (s, 6H), 3.66 (m, 2H), 3.97 (dd, 1H), 4.00 (t, 2H), 3.95 (t, 2H), 3.97 (m, 1H), 6.88 (s, 2H), 6.89~7.62 (m, 9H).

Preparative Example 51

Preparation of Compound Represented by Formula 52 (VVZ-056)

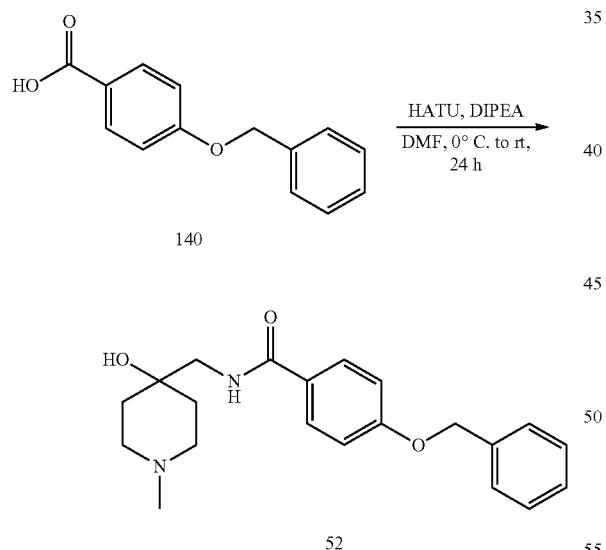

The same procedures as described in Preparative Example 2 were conducted, and a compound represented by Formula 140, that is, 4-benzyloxybenzoic acid (54.23 mg, 0.238 mmol) and a compound represented by Formula 142, that is, 4-(aminomethyl)-1-methylpiperidin-4-ol dihydrochloride (46.9 mg, 0.216 mmol) were used according to reaction scheme 52. As a result, a benzamide compound represented by Formula 52 was obtained as a desired product (VVZ-056; 56.00 mg, 73.1% yield).

Analysis data of the produced benzamide compound is provided as follows.

$^1$H-NMR (MeOD-$d_4$) d 1.67 (m, 4H), 2.29 (s, 3H), 2.41 (m, 2H), 2.62 (m, 2H), 3.32 (s, 2H), 5.16 (s, 2H), 7.05~7.83 (m, 9H).

Preparative Example 52

Preparation of Compound Represented by Formula 53 (VVZ-060)

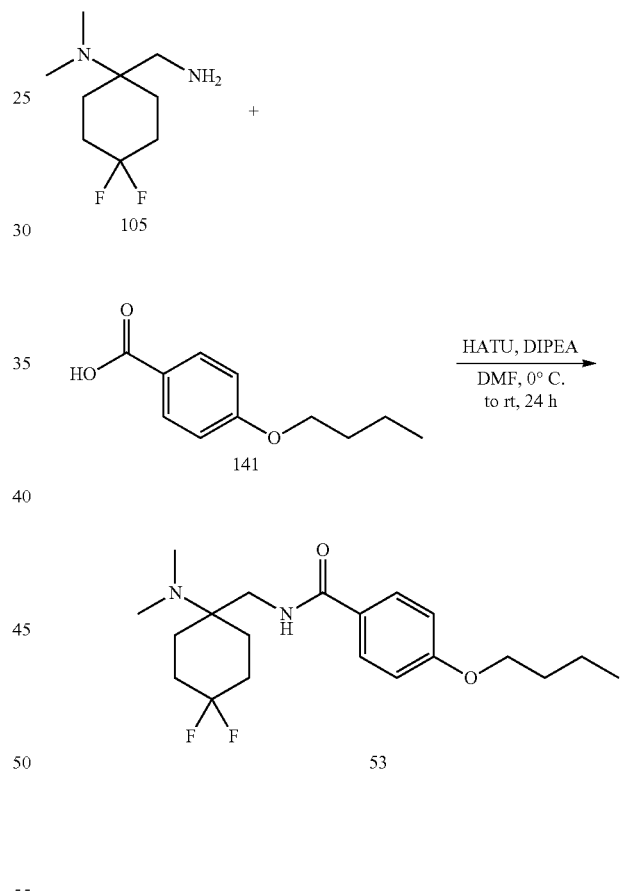

The same procedures as described in Preparative Example 2 were conducted, and a compound represented by Formula 141, that is, 4-butyloxybenzoic acid (40.67 mg, 0.209 mmol) and a compound represented by Formula 105, that is, (1-aminomethyl-4,4-difluoro-cyclohexyl)-dimethylamine (36.6 mg, 0.190 mmol) were used according to reaction scheme 53. As a result, a benzamide compound represented by Formula 53 was obtained as a desired product (VVZ-060; 56.40 mg, 80.4% yield).

Analysis data of the produced benzamide compound is provided as follows.

¹H-NMR (MeOD-d₄) d 0.89 (t, 3H), 1.41 (m, 2H), 1.48 (m, 2H), 1.66 (m, 2H), 1.85 (m, 2H), 2.30 (s, 6H), 3.4 (s, 2H), 3.93 (t, 2H), 6.82 (d, 2H), 7.66 (d, 2H).

¹H-NMR (MeOD-d₄) d 1.60 (m, 2H), 1.83 (m, 2H), 1.95 (m, 2H), 2.04 (m, 2H), 2.41 (s, 6H), 3.50 (s, 2H), 5.16 (s, 2H), 7.06~7.78 (m, 9H).

Preparative Example 53

Preparation of Compound Represented by Formula 54 (VVZ-061)

[Reaction scheme 54]

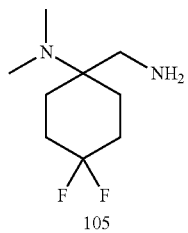

105

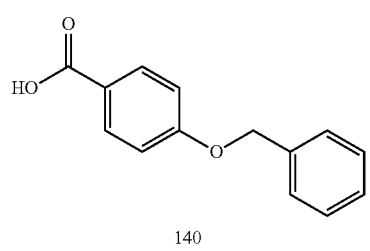

140

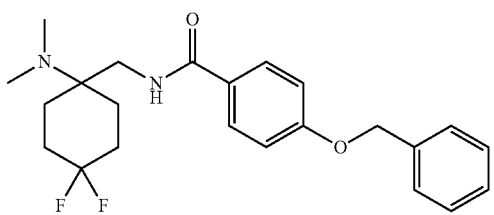

54

The same procedures as described in Preparative Example 2 were conducted, and a compound represented by Formula 140, that is, 4-benzyloxybenzoic acid (43.36 mg, 0.190 mmol) and a compound represented by Formula 105, that is, (1-aminomethyl-4,4-difluoro-cyclohexyl)-dimethylamine (33.2 mg, 0.173 mmol) were used according to reaction scheme 54. As a result, a benzamide compound represented by Formula 54 was obtained as a desired product (VVZ-061; 52.30 mg, 75.2% yield).

Analysis data of the produced benzamide compound is provided as follows.

Preparative Example 54

Preparation of Compound Represented by Formula 55 (VVZ-064)

[Reaction scheme 55]

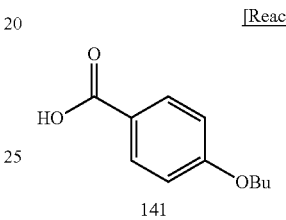

141

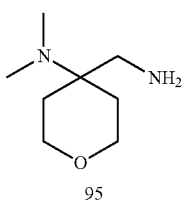

95

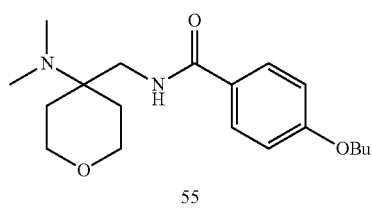

55

The same procedures as described in Preparative Example 2 were conducted, and a compound represented by Formula 141, that is, 4-butyloxybenzoic acid (50.00 mg, 0.257 mmol) and a compound represented by Formula 95, that is, 4-(aminomethyl)-N,N-dimethyltetrahydro-2H-pyran-4-amine (40.74 mg, 0.257 mmol) were used according to reaction scheme 55. As a result, a benzamide compound represented by Formula 55 was obtained as a desired product (VVZ-064; 56.50 mg, 65.6% yield).

Analysis data of the produced benzamide compound is provided as follows.

$^1$H-NMR (MeOD-d$_4$) d 1.00 (t, 3H), 1.52 (m, 2H), 1.64 (m, 2H), 1.78 (m, 2H), 1.82 (m, 2H), 2.42 (s, 6H), 3.62 (s, 2H), 3.67 (m, 2H), 3.83 (m, 2H), 4.04 (t, 2H), 6.67~7.79 (dd, 4H).

Preparative Example 55

Preparation of Compound Represented by Formula 56 (VVZ-065)

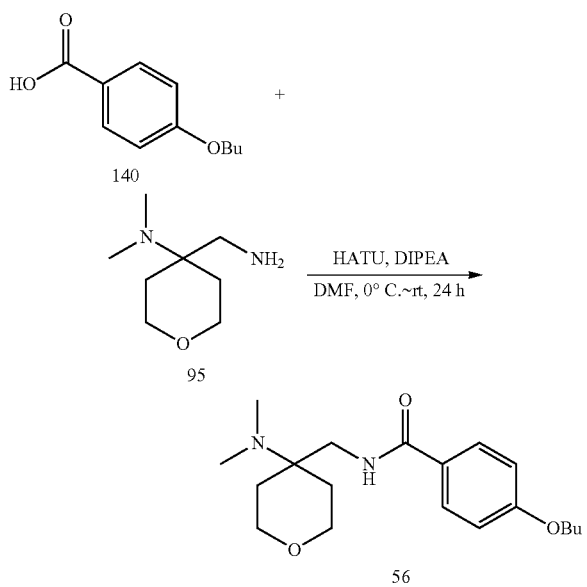

The same procedures as described in Preparative Example 2 were conducted, and a compound represented by Formula 140, that is, 4-benzyloxybenzoic acid (50.00 mg, 0.219 mmol) and a compound represented by Formula 95, that is, 4-(aminomethyl)-N,N-dimethyltetrahydro-2H-pyran-4-amine (34.67 mg, 0.219 mmol) were used according to reaction scheme 56. As a result, a benzamide compound represented by Formula 56 was obtained as a desired product (VVZ-065; 37.40 mg, 46.3% yield).

Analysis data of the produced benzamide compound is provided as follows.

$^1$H-NMR (MeOD-d$_4$) d 1.63 (m, 2H), 1.82 (m, 2H), 2.41 (s, 6H), 3.62 (s, 2H), 3.65 (m, 2H), 3.83 (m, 2H), 5.16 (s, 2H), 7.06~7.80 (m, 9H).

Preparative Example 56

Preparation of Compound Represented by Formula 57 (VVZ-066)

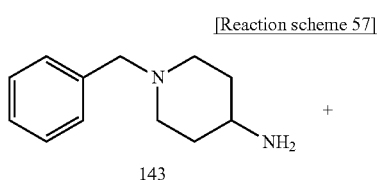

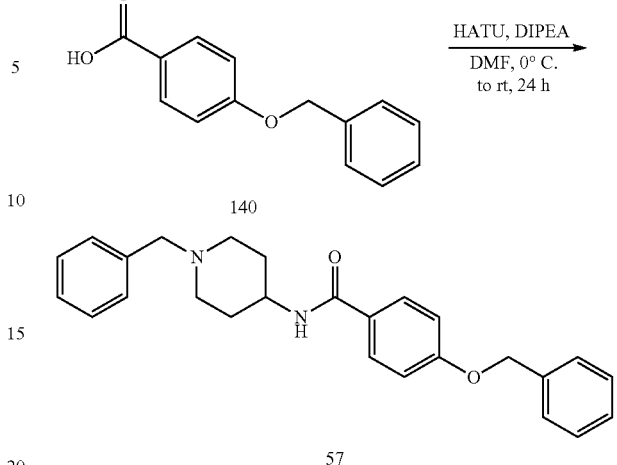

The same procedures as described in Preparative Example 2 were conducted, and a compound represented by Formula 140, that is, 4-benzyloxybenzoic acid (153.06 mg, 0.671 mmol) and a compound represented by Formula 143, that is, 1-benzylpiperidine-4-amine (116 mg, 0.610 mmol) were used according to reaction scheme 57. As a result, a benzamide compound represented by Formula 57 was obtained as a desired product (VVZ-066; 148.60 mg, 60.9% yield).

Analysis data of the produced benzamide compound is provided as follows.

$^1$H-NMR (MeOD-d$_4$) d 1.67 (m, 2H), 1.92 (m, 2H), 2.17 (m, 2H), 2.95 (m, 2H), 3.45 (s, 2H), 3.87 (m, 1H), 5.14 (s, 2H), 7.04~7.79 (dd, 14H).

Preparative Example 57

Preparation of Compound Represented by Formula 58 (VVZ-069)

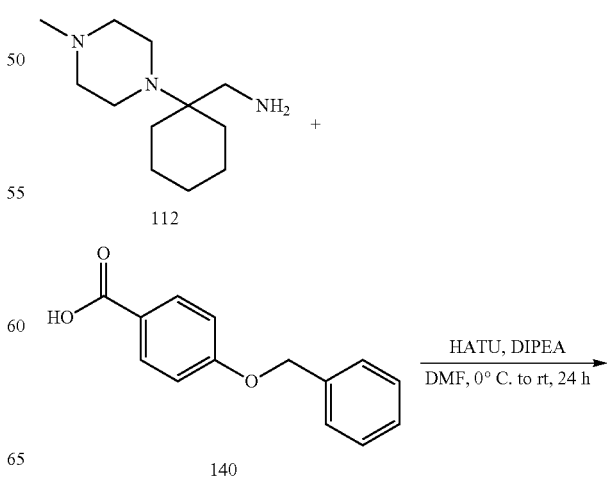

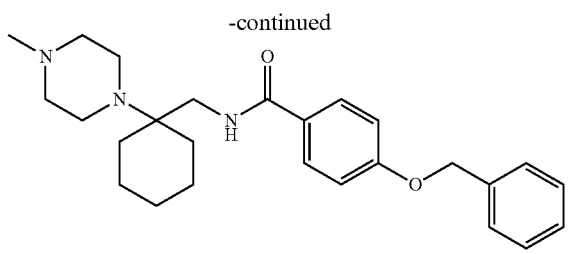

58

The same procedures as described in Preparative Example 2 were conducted, and a compound represented by Formula 140, that is, 4-benzyloxybenzoic acid (61.77 mg, 0.271 mmol) and a compound represented by Formula 112, that is, 1-[1-(4-methylpiperazin-1-yl)cyclohexyl]methanamine (52.00 mg, 0.271 mmol) were used according to reaction scheme 58. As a result, a benzamide compound represented by Formula 58 was obtained as a desired product (VVZ-069; 88.40 mg, 85.2% yield).

Analysis data of the produced benzamide compound is provided as follows.

$^1$H-NMR (MeOD-d$_4$) d 1.42 (m, 6H), 1.65 (m, 2H), 1.78 (m, 2H), 2.28 (s, 3H), 2.48 (m, 4H), 2.78 (m, 4H), 3.93 (s, 2H), 5.18 (s, 2H), 7.07~7.78 (m, 9H).

Preparative Example 58

Preparation of Compound Represented by Formula 59 (VVZ-072)

[Reaction scheme 59]

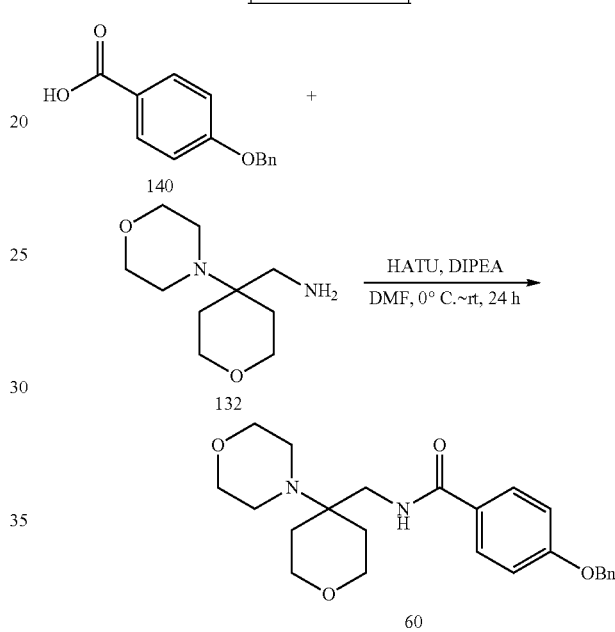

The same procedures as described in Preparative Example 2 were conducted, and a compound represented by Formula 140, that is, 4-benzyloxybenzoic acid (40.25 mg, 0.176 mmol) and a compound represented by Formula 131, that is, (4-(4-methylpiperazin-1-yl)tetrahydro-2H-pyran-4-yl)methanamine (34.20 mg, 0.160 mmol) were used according to reaction scheme 59. As a result, a benzamide compound represented by Formula 59 was obtained as a desired product (VVZ-072; 38.10 mg, 56.1% yield).

Analysis data of the produced benzamide compound is provided as follows.

$^1$H-NMR (MeOD-d$_4$) d 1.61 (m, 2H), 1.84 (m, 2H), 2.31 (s, 3H), 2.53 (m, 4H), 2.81 (m, 4H), 3.05 (s, 2H), 3.63 (m, 2H), 3.81 (m, 2H), 5.15 (s, 2H), 7.04~7.78 (m, 9H).

Preparative Example 59

Preparation of Compound Represented by Formula 60 (VVZ-076)

[Reaction scheme 60]

The same procedures as described in Preparative Example 2 were conducted, and a compound represented by Formula 140, that is, 4-benzyloxybenzoic acid (50 mg, 0.219 mmol) and a compound represented by Formula 132, that is, (4-morpholinotetrahydro-2H-pyran-4-yl)methanamine (43.87 mg, 0.219 mmol) were used according to reaction scheme 60. As a result, a benzamide compound represented by Formula 60 was obtained as a desired product (VVZ-076; 76 mg, 84.5% yield).

Preparative Example 60

Preparation of Compound Represented by Formula 61 (VVZ-077)

[Reaction scheme 61]

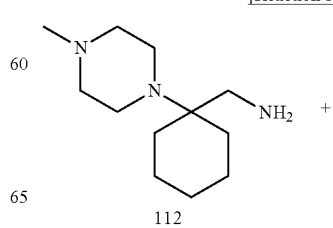

112

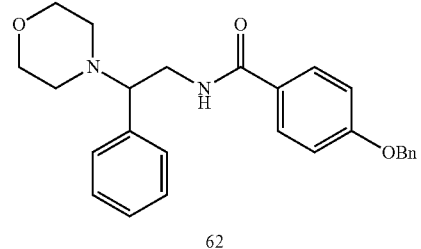

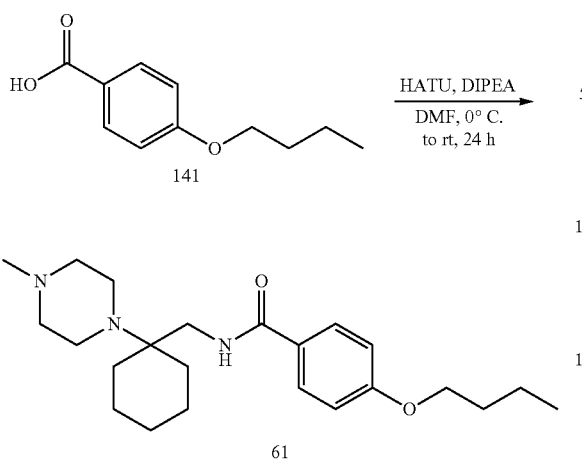

The same procedures as described in Preparative Example 2 were conducted, a compound represented by Formula 141, that is, 4-butyloxybenzoic acid (37.10 mg, 0.191 mmol) and a compound represented by Formula 112, that is, 1-[1-(4-methylpiperazin-1-yl)cyclohexyl]methanamine (36.70 mg, 0.174 mmol) were used according to reaction scheme 61. As a result, a benzamide compound represented by Formula 61 was obtained as a desired product (VVZ-077; 50.10 mg, 74.4% yield).

Analysis data of the produced benazmide compound is provided as follows.

$^1$H-NMR (MeOD-d$_4$) d 0.99 (t, 3H), 1.36~1.78 (m, 14H), 2.28 (s, 3H), 2.49 (m, 4H), 2.77 (m, 4H), 3.43 (s, 2H), 4.03 (t, 2H), 6.97 (d, 1H), 7.74 (d, 1H).

Preparative Example 61

Preparation of Compound Represented by Formula 62 (VVZ-081)

[Reaction scheme 62]

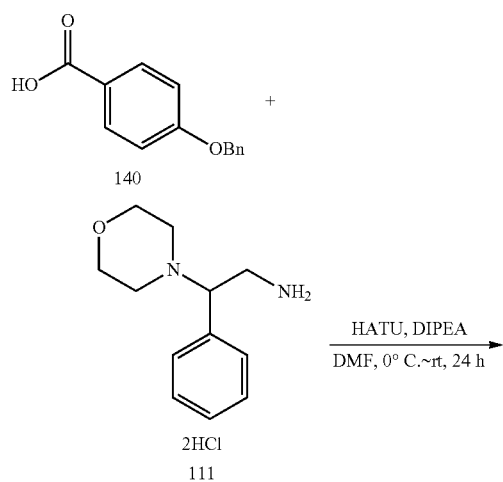

4-benzyloxybenzoic acid represented by Formula 140 (150 mg, 0.657 mmol, purchased from TCI Co.) was slowly added to 2-morpholin-2-yl-2-phenylethanamine dihydrochloride represented by Formula 111 (183.5 mg, 0.657 mmol, purchased from Matrix Co.) and diisopropylethylamine (0.344 mL, 1.972 mmol) in DMF (10 mL) at room temperature. After cooling the reaction mixture to 0° C. and adding 2-(1H-7-azabenzotriazol-1-yl)-1,1,3,3-tetramethyluronium hexafluorophosphate methanaminium (HATU, 249.9 mg, 0.657 mmol) thereto, the mixture was agitated at room temperature for 18 hours. The reaction solvent was removed under reduced pressure and chloroform/methanol (9:1, v/v) was added to the remaining concentrate to prepare a solution. The solution was washed with a potassium carbonate (K$_2$CO$_3$) solution, followed by separation to form an organic layer. After drying the organic layer with magnesium sulfate (MgSO$_4$), the solvent was removed again under reduced pressure. The obtained vacuum-concentrated mixture was subjected to separation and purification through column chromatography (chloroform/methanol, 10:1, v/v) using silica gel (SiO$_2$). As a result, a benzamide compound represented by Formula 62 was produced (VVZ-081; 196 mg, 71.6% yield).

Analysis data of the produced benzamide compound is provided as follows.

R$_f$ (ethyl acetate/n-hexane/triethylamine, 2:1/0.1, v/v/v) 0.47;

$^1$H NMR (500 MHz, MeOD-d$_4$) δ 2.51 (s, 4H), 3.57-3.62 (m, 1H), 3.67-3.73 (m, 5H), 3.98-4.02 (m, 1H), 5.15 (s, 2H), 7.00-7.02 (m, 2H), 7.28-7.44 (m, 10H), 7.61-7.64 (m, 2H).

Preparative Example 62

Preparation of Compound Represented by Formula 63 (VVZ-045)

[Reaction scheme 63]

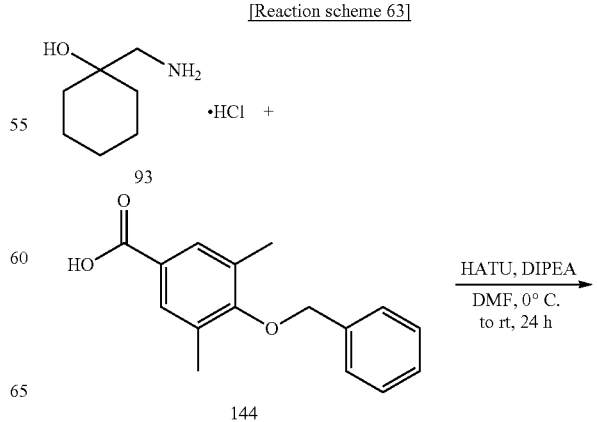

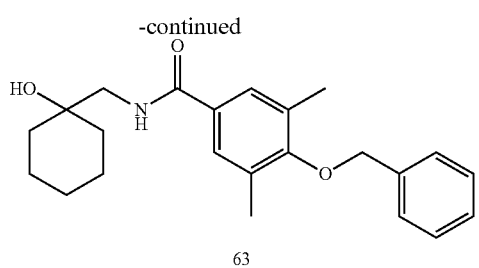

The same procedures as described in Preparative Example 2 were conducted, and 1-aminomethyl-1-cyclohexanol represented by Formula 93 (49.80 mg, 0.301 mmol) and a compound represented by Formula 144, that is, 4-benzyloxy-3,5-dimethylbenzoic acid (84.75 mg, 0.331 mmol) were used according to reaction scheme 63. As a result, a benzamide compound represented by Formula 63 was obtained as a desired product (VVZ-045; 98.30 mg, 89.0% yield).

Analysis data of the produced benzamide compound is provided as follows.

$^1$H-NMR (MeOD-d$_4$) d 1.03~1.66 (m, 10H), 2.28 (s, 6H), 3.38 (s, 2H), 4.83 (s, 2H), 7.31~7.54 (m, 7H).

Preparative Example 63

Preparation of Compound Represented by Formula 64 (VVZ-046)

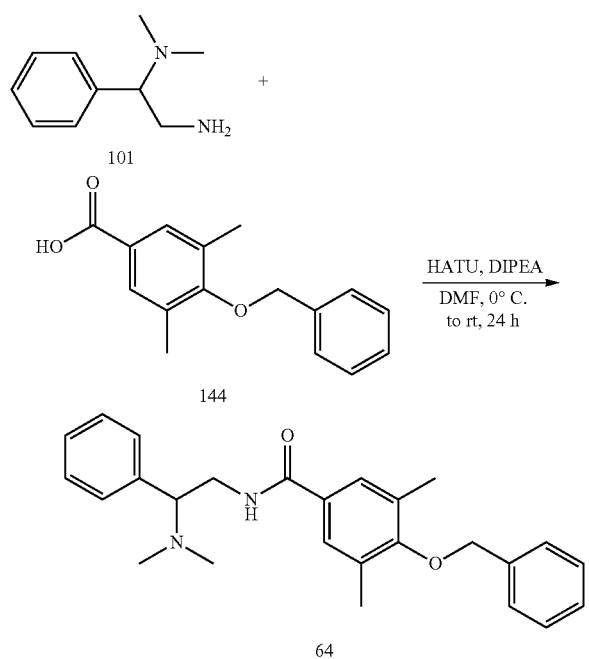

The same procedures as described in Preparative Example 2 were conducted, and a compound represented by Formula 101, that is, N,N-dimethyl-1-phenylethane-1,2-diamine (50.20 mg, 0.306 mmol) and a compound represented by Formula 144, that is, 4-benzyloxy-3,5-dimethylbenzoic acid (86.17 mg, 0.336 mmol) were used according to reaction scheme 64. As a result, a benzamide compound represented by Formula 64 was obtained as a desired product (VVZ-046; 104.80 mg, 85.2% yield).

Analysis data of the produced benzamide compound is provided as follows.

$^1$H-NMR (MeOD-d$_4$) d 2.26 (s, 12H), 3.65 (m, 2H), 3.96 (m, 1H), 3.48 (s, 2H), 7.29~7.99 (m, 12H).

Preparative Example 64

Preparation of Compound Represented by Formula 65 (VVZ-053)

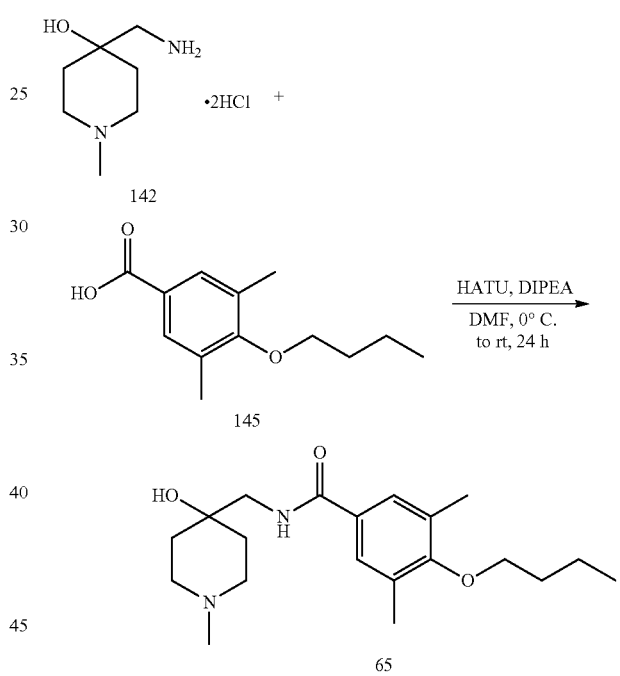

The same procedures as described in Preparative Example 2 were conducted, and 4-butyloxy-3,5-dimethylbenzoic acid represented by Formula 145 (45.49 mg, 0.205 mmol) prepared in Preparative Example 74 and a compound represented by Formula 142, that is, 4-(aminomethyl)-1-methylpiperidin-4-ol dihydrochloride (40.4 mg, 0.186 mmol) were used according to reaction scheme 65. As a result, a benzamide compound represented by Formula 65 was obtained as a desired product (VVZ-053; 60.20 mg, 92.8% yield).

Analysis data of the produced benzamide compound is provided as follows.

$^1$H-NMR (MeOD-d$_4$) d 1.02 (t, 3H), 1.58 (m, 2H), 1.81 (m, 6H), 2.30 (s, 6H), 2.54 (s, 3H), 2.82 (m, 2H), 2.96 (m, 2H), 3.43 (s, 2H), 3.81 (t, 2H), 7.53 (s, 2H).

The compound represented by Formula 145 and used herein was synthesized through two (2)-chemical reaction after starting from methyl 3,5-dimethyl-4-hydroxybenzoate purchased from Medizin Co. Ltd.

Step 1: Preparation of methyl 4-butoxy-3,5-dimethylbenzoate

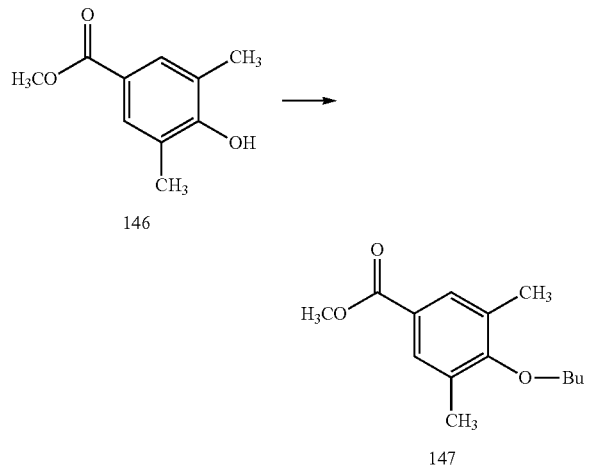

A mixture of methyl 3,5-dimethyl-4-hydroxybenzoate represented by Formula 146 (1.72 g, 9.52 mmol), 1-bromobutane (1.13 mL, 10.47 mmol), potassium carbonate ($K_2CO_3$, 1.45 g, 10.47 mmol) and potassium iodide (KI, 158 mg, 0.95 mmol) in DMF (20 mL) was agitated at 80° C. for 24 hours. After decreasing a temperature of the reaction mixture to room temperature, solids were removed through filtration (and washed with acetone) to obtain a filtrate. After adding ethyl acetate to the filtrate, the solution was consecutively washed with water and a 5N HCl solution. After separating an organic layer and drying the same with magnesium sulfate ($MgSO_4$), the solvent was removed under reduced pressure to prepare a concentrate mixture. This mixture was subjected to separation and purification through column chromatography (ethyl acetate/hexane, 1:5, v/v) using silica gel ($SiO_2$), resulting in a benzylether compound represented by Formula 147 as a desired product (2.1 g, 93%). Analysis data of the product is provided as follows:

$R_f$ (ethyl acetate/hexane, 1:5, v/v) 0.5;
$^1$H NMR (500 MHz, $CDCl_3$-$d_1$) δ 1.00 (t, 3H, J=7.0 Hz), 1.52-1.56 (m, 2H), 1.77-1.82 (m, 2H), 2.30 (s, 6H), 3.79 (t, 2H, J=6.5 Hz), 3.88 (s, 3H), 7.71 (s, 2H).

Step 2: Preparation of 4-butoxy-3,5-dimethyl benzoic acid

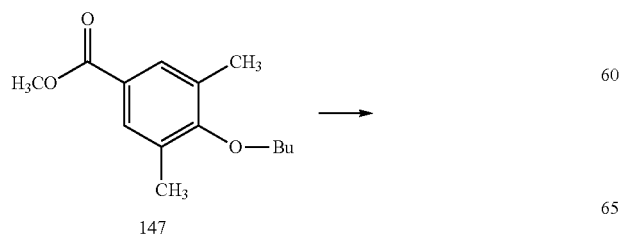

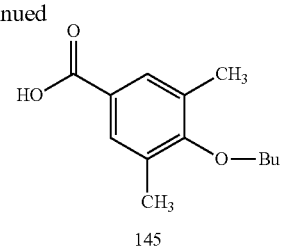

A solution of methyl 4-butoxy-3,5-dimethylbenzoate represented by Formula 147 (2.1 g, 8.89 mmol) dissolved in potassium hydroxide (KOH, 44%, 5 mL) and methanol (40 mL) was agitated at 65° C. for 2 hours and cooled to room temperature, and the solvent was removed under reduced pressure. After dissolving the concentrate mixture in water then washing the mixture with ethylether (×3), 5N HCl aqueous solution was added to the obtained solution to reach pH 1. A precipitate generated during this process was obtained through filtration. After washing the obtained precipitate with water several times and drying the same, the dried precipitate was subjected to recrystallization in an ethyl acetate/hexane solvent. As a result, benzoic acid represented by Formula 145 was obtained as a desired product (907 mg, 46%). Analysis data of the product is provided as follows:

$R_f$ (ethyl acetate/hexane, 1:2, v/v) 0.2;
$^1$H NMR (500 MHz, $CDCl_3$-$d_1$) δ 1.00 (t, 3H, J=7.5 Hz), 1.53-1.57 (m, 2H), 1.79-1.82 (m, 2H), 2.32 (s, 6H), 3.81 (t, 2H, J=6.5 Hz), 7.78 (s, 2H).

Preparative Example 65

Preparation of Compound Represented by Formula 66 (VVZ-054)

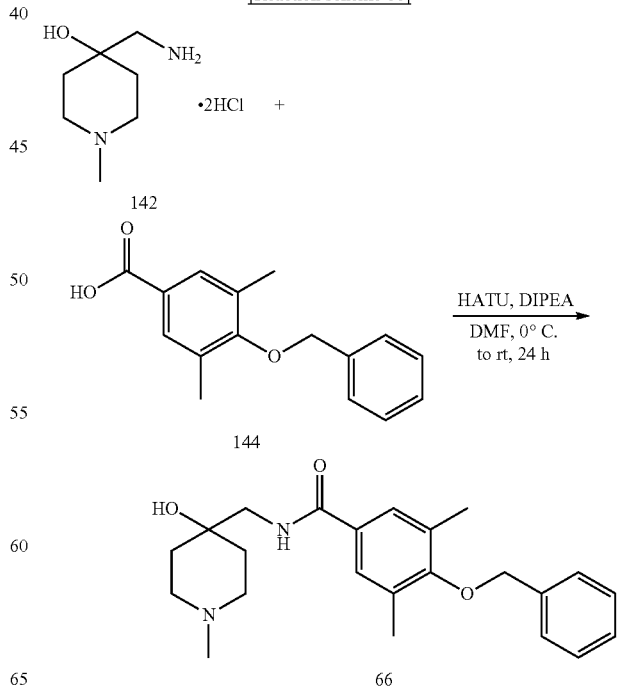

The same procedures as described in Preparative Example 2 were conducted, and a compound represented by Formula 142, that is, 4-(aminomethyl)-1-methylpiperidin-4-ol dihydrochloride (44.30 mg, 0.204 mmol) and a compound represented by Formula 144, that is, 4-benzyloxy-3,5-dimethylbenzoic acid (57.52 mg, 0.224 mmol) were used according to reaction scheme 66. As a result, a benzamide compound represented by Formula 66 was obtained as a desired product (VVZ-054; 72.80 mg, 93.3% yield).

Analysis data of the produced benzamide compound is provided as follows.

$^1$H-NMR (MeOD-d$_4$) d 1.82 (m, 4H), 2.35 (s, 6H), 2.62 (s, 3H), 3.05 (m, 4H), 3.45 (s, 2H), 4.86 (s, 2H), 6.33~7.57 (m, 7H).

Preparative Example 66

Preparation of Compound Represented by Formula 67 (VVZ-057)

[Reaction scheme 67]

The same procedures as described in Preparative Example 2 were conducted, 4-butyloxy-3,5-dimethylbenzoic acid represented by Formula 145 (54.48 mg, 0.245 mmol) prepared in Preparative Example 74 and a compound represented by Formula 101, that is, (2-amino-1-phenylethyl)dimethylamine (36.6 mg, 0.223 mmol) were used according to reaction scheme 67. As a result, a benzamide compound represented by Formula 67 was obtained as a desired product (VVZ-057; 67.80 mg, 82.6% yield).

Analysis data of the produced benzamide compound is provided as follows.

$^1$H-NMR (MeOD-d$_4$) d 1.01 (t, 3H), 1.55 (m, 2H), 1.78 (m, 2H), 2.24 (s, 6H), 2.24 (s, 6H), 3.65 (m, 2H), 3.78 (t, 2H), 3.96 (dd, 1H), 7.35 (m, 7H).

Preparative Example 67

Preparation of Compound Represented by Formula 68 (VVZ-058)

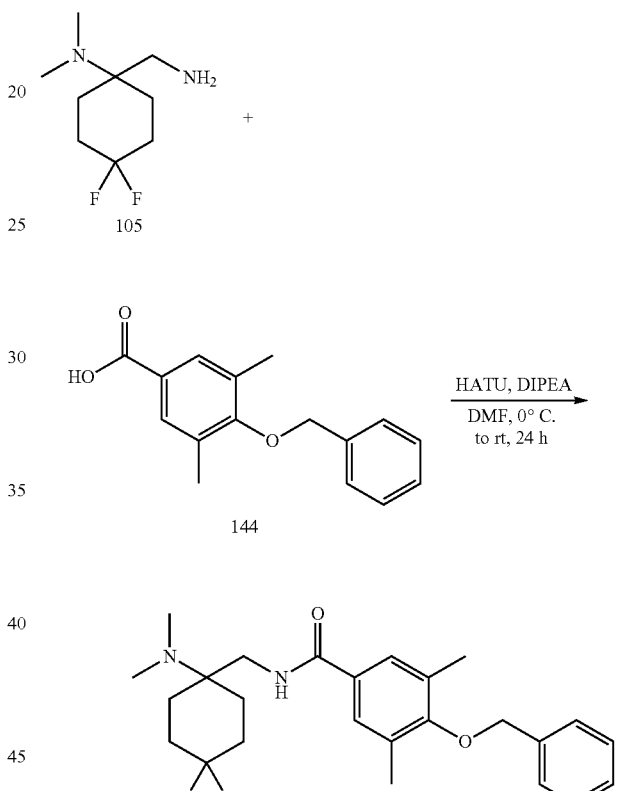

[Reaction scheme 68]

The same procedures as described in Preparative Example 2 were conducted, and 1-(aminomethyl)-4,4-difluoro-N,N-dimethylcyclohexanamine represented by Formula 105 (33.40 mg, 0.174 mmol) and a compound represented by Formula 144, that is, 4-benzyloxy-3,5-dimethylbenzoic acid (48.98 mg, 0.191 mmol) were used according to reaction scheme 68. As a result, a benzamide compound represented by Formula 68 was obtained as a desired product (VVZ-058; 59.10 mg, 79.0% yield).

Analysis data of the produced benzamide compound is provided as follows.

$^1$H-NMR (MeOD-d$_4$) d 1.64 (m, 2H), 1.85 (m, 2H), 1.96 (m, 2H), 2.05 (m, 2H), 2.32 (s, 6H), 2.41 (s, 6H), 3.50 (s, 2H), 4.90 (s, 2H), 7.33~7.51 (m, 7H).

Preparative Example 68

Preparation of Compound Represented by Formula 69 (VVZ-059)

[Reaction scheme 69]

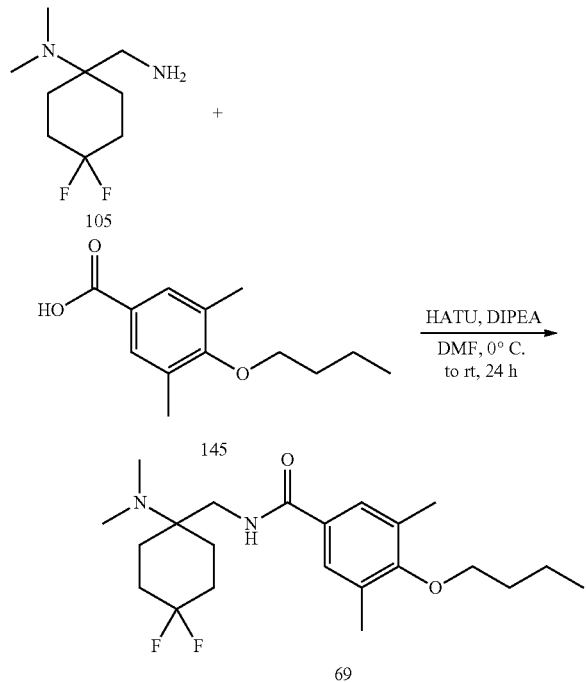

The same procedures as described in Preparative Example 2 were conducted, and 4-butyloxy-3,5-dimethylbenzoic acid represented by Formula 145 (39.30 mg, 0.177 mmol) prepared in Preparative Example 64 and a compound represented by Formula 105, that is, (1-aminomethyl-4,4-difluoro-cyclohexyl)-dimethylamine (30.9 mg, 0.177 mmol) were used according to reaction scheme 69. As a result, a benzamide compound represented by Formula 69 was obtained as a desired product (VVZ-059; 50.80 mg, 79.7% yield).

Analysis data of the produced benzamide compound is provided as follows.

$^1$H-NMR (MeOD-d$_4$) d 1.02 (t, 3H), 1.57 (m, 4H), 1.80 (m, 4H), 1.95 (m, 2H), 2.06 (m, 2H), 2.31 (s, 6H), 2.40 (s, 6H), 3.50 (s, 2H), 3.82 (t, 2H), 7.48 (s, 2H).

Preparative Example 69

Preparation of Compound Represented by Formula 70 (VVZ-063)

[Reaction scheme 70]

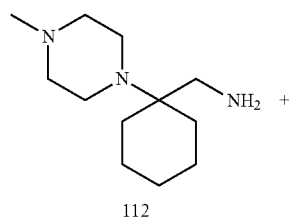

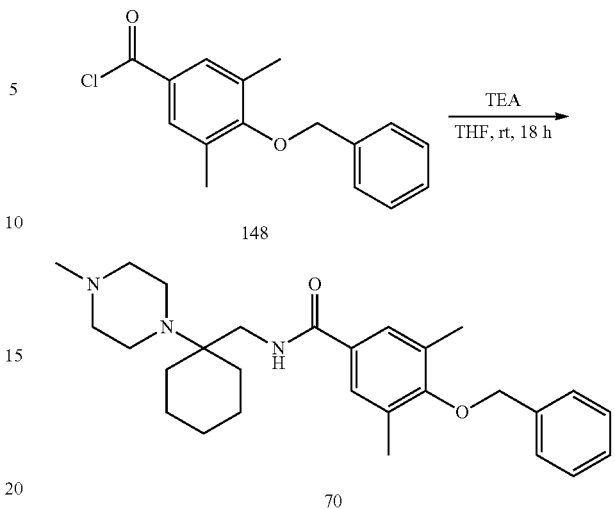

The same procedures as described in Preparative Example 1 were conducted, and a compound represented by Formula 112, that is, 1-[1-(4-methylpiperazin-1-yl)cyclohexyl]methanamine (36.60 mg, 0.187 mmol) and a compound represented by Formula 148, that is, 4-benzyloxy-3,5-dimethylbenzoic acid chloride (56.62 mg, 0.206 mmol) were used according to reaction scheme 70. As a result, a benzamide compound represented by Formula 70 was obtained as a desired product (VVZ-063; 72.30 mg, 85.8% yield).

Analysis data of the produced benzamide compound is provided as follows.

$^1$H-NMR (MeOD-d$_4$) d 1.41 (m, 6H), 1.65 (m, 2H), 1.80 (m, 2H), 2.28 (s, 3H), 2.31 (s, 6H), 2.48 (m, 4H), 2.78 (m, 4H), 3.35 (s, 2H), 7.35~7.51 (m, 7H).

Preparative Example 70

Preparation of Compound Represented by Formula 71 (VVZ-070)

[Reaction scheme 71]

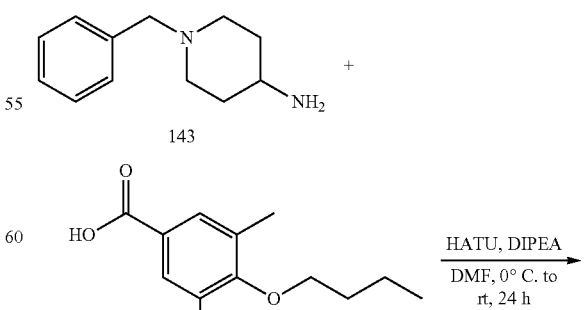

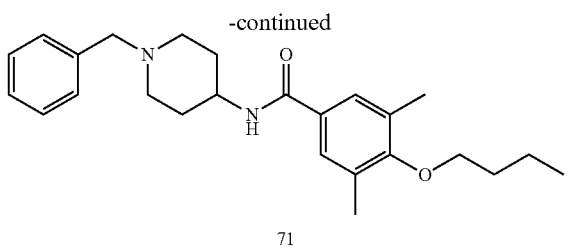

The same procedures as described in Preparative Example 2 were conducted, 4-butyloxy-3,5-dimethylbenzoic acid represented by Formula 145 (67.21 mg, 0.302 mmol) prepared in Preparative Example 74 and a compound represented by Formula 143, that is, 1-bezylpiperidine-4-amine (52.30 mg, 0.275 mmol) were used according to reaction scheme 71. As a result, a benzamide compound represented by Formula 71 was obtained as a desired product (VVZ-070; 75.80 mg, 69.9% yield).

Analysis data of the produced benzamide compound is provided as follows.

$^1$H-NMR (MeOD-$d_4$) d 0.92 (t, 3H), 1.49 (m, 2H), 1.57 (m, 2H), 1.69 (m, 2H), 1.82 (m, 2H), 2.07 (m, 2H), 2.20 (s, 6H), 2.87 (m, 2H), 3.46 (s, 2H), 3.72 (t, 2H), 3.77 (m, 1H), 4.04 (t, 2H), 7.18~7.40 (m, 7H).

Preparative Example 71

Preparation of Compound Represented by Formula 72 (VVZ-075)

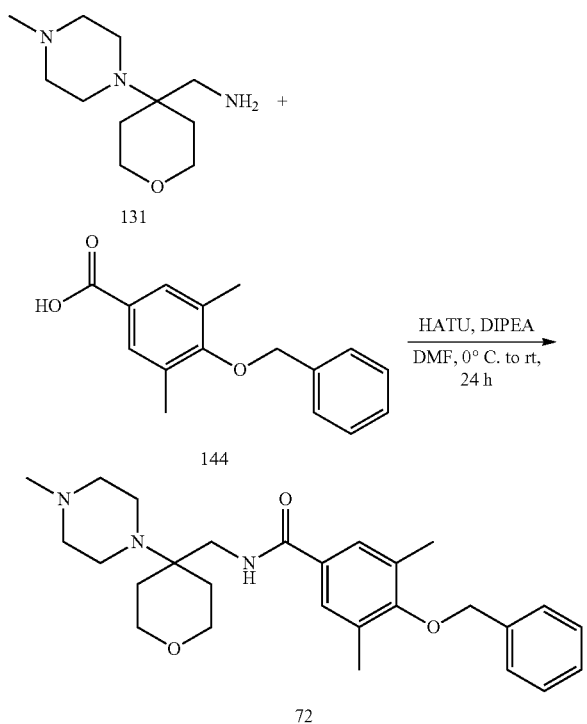

The same procedures as described in Preparative Example 2 were conducted, and a compound represented by Formula 131, that is, (4-(4-methylpiperazin-1-yl)tetrahydro-2H-pyran-4-yl)methanamine (47.7 mg, 0.224 mmol) and a compound represented by Formula 144, that is, 4-benzyloxy-3,5-dimethylbenzoic acid (63.04 mg, 0.246 mmol) were used according to reaction scheme 72. As a result, a benzamide compound represented by Formula 72 was obtained as a desired product (VVZ-075; 58.80 mg, 58.2% yield).

Analysis data of the produced benzamide compound is provided as follows.

$^1$H-NMR (MeOD-$d_4$) d 1.53 (m, 2H), 1.76 (m, 2H), 2.22 (s, 9H), 2.43 (m, 4H), 2.72 (m, 4H), 3.41 (s, 2H), 3.55 (m, 2H), 3.73 (m, 2H), 4.79 (s, 2H), 7.24~7.42 (m, 7H).

Preparative Example 72

Preparation of Compound Represented by Formula 73 (VVZ-079)

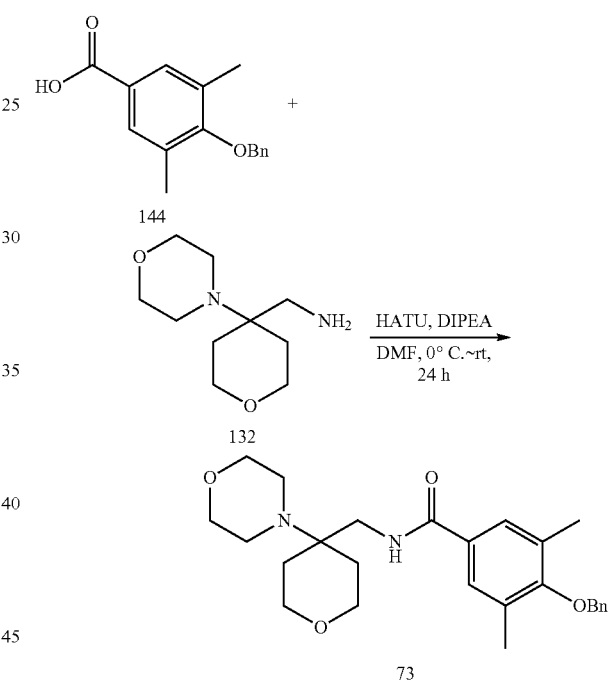

4-benzyloxy-3,5-dimethylbenzoic acid represented by Formula 144 (50 mg, 0.195 mmol, purchased from Medizin Co. Ltd.) was slowly added to (4-morpholinotetrahydro-2H-pyran-4-yl)methanamine represented by Formula 132 (39.09 mg, 0.195 mmol) prepared in Preparative Example 42 and diisopropylethylamine (0.102 mL, 0.585 mmol) in DMF (5 mL) solution at room temperature. After cooling the reaction mixture to 0° C. and adding 2-(1H-7-azabenzotriazol-1-yl)-1,1,3,3-tetramethyluronium hexafluorophosphate methanaminium (HATU, 70.46 mg, 0.185 mmol) thereto, the mixture was agitated at room temperature for 18 hours. The reaction solvent was removed under reduced pressure and chloroform was added to the remaining concentrate to prepare a solution. The solution was washed with a potassium carbonate ($K_2CO_3$) solution, followed by separation to form an organic layer. After drying the organic layer with magnesium sulfate ($MgSO_4$), the solvent was removed again under reduced pressure. The obtained vacuum-concentrated mixture was subjected to separation and purification using a silica gel (SiO$_2$) cartridge (ethyl acetate/methanol/ammonia solution, 10:1:0.5, v/v/v). As a result, a benzamide compound represented by Formula 73 was produced (VVZ-079; 67.9 mg, 79.4% yield).

Analysis data of the produced benzamide compound is provided as follows.

R$_f$ (Chloroform/methanol, 10:1, v/v) 0.54;
$^1$H NMR (500 MHz, MeOD-d4) δ 1.62 (t, 2H, J=11.8 Hz), 1.84-1.87 (m, 2H), 2.31 (s, 6H), 2.76 (t, 4H, J=4.5 Hz), 3.51 (s, 2H), 3.64-3.70 (m, 6H), 3.86 (t, 2H, J=10.3 Hz), 4.89 (s, 2H), 7.34-7.40 (m, 3H), 7.46 (d, 2H, J=7.0 Hz), 7.52 (s, 2H).

Preparative Example 73

Preparation of Compound Represented by Formula 74 (VVZ-080)

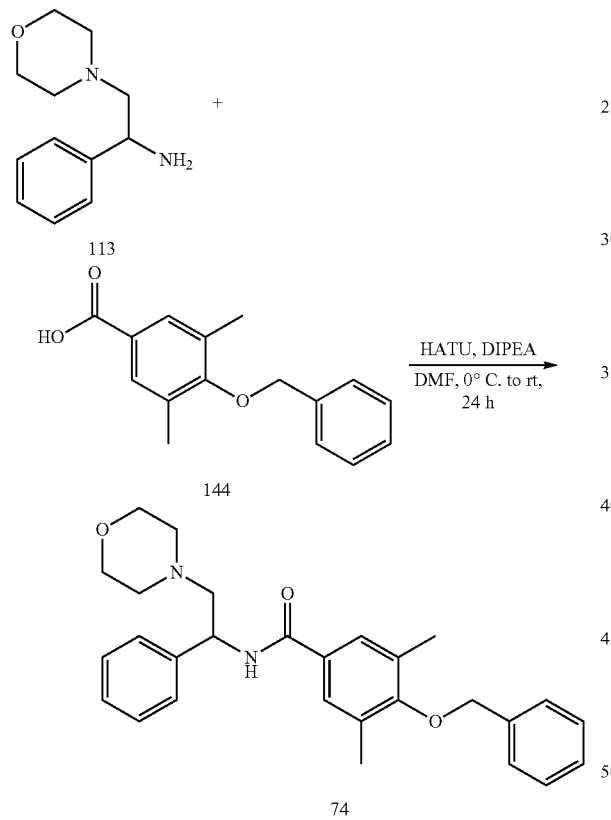

2-morpholino-1-phenylethanamine represented by Formula 113 (38.4 mg, 0.186 mmol) was slowly added to 4-benzyloxy-3,5-dimethylbenzoic acid represented by Formula 144 (52.5 mg, 0.205 mmol, purchased from Medizin Co. Ltd.) and diisopropylethylamine (0.13 mL, 0.745 mmol) in DMF (3 mL) solution at room temperature. After cooling the reaction mixture to 0° C. and adding 2-(1H-7-azabenzotriazol-1-yl)-1,1,3,3-tetramethyluronium hexafluorophosphate methanaminium (HATU, 77.9 mg, 0.205 mmol) thereto, the mixture was agitated at room temperature for 24 hours. The reaction solvent was removed under reduced pressure and chloroform (2 mL) was added to the remaining concentrate to prepare a solution. The solution was washed with a potassium carbonate (K$_2$CO$_3$) solution, followed by separation to form an organic layer. After drying the organic layer with sodium sulfate (Na$_2$SO$_4$), the solvent was removed again under reduced pressure. The obtained vacuum-concentrated mixture was moved to a cartridge tube (6 mL, benzenesulfonic acid, 904030-WJ, UCT) using a small amount of ethyl acetate. Impurities were eliminated using methanol (15 mL) then separation and purification were conducted (using ethyl acetate/methanol/triethylamine, 20:2:1, v/v/v) to produce a benzamide compound represented by Formula 74 as a desired product (VVZ-080; 31 mg, 37% yield).

Analysis data of the produced benzamide compound is provided as follows.

R$_f$ (ethyl acetate/hexane/triethylamine, 2:1:0.1, v/v/v) 0.3;
HRMS (EI+) calcd for C$_{28}$H$_{32}$N$_2$O$_3$ ([M+]) 444.2413.
$^1$H NMR (500 MHz, MeOH-d$_4$) d 2.32 (s, 6H), 2.50-2.51 (m, 2H), 2.58-2.63 (m, 4H), 3.68-3.72 (m, 4H), 4.88 (s, 2H), 5.30 (dd, 1H, J=5.0 Hz, 5.5 Hz), 7.25 (t, 1H, J=7.0 Hz), 7.32-7.40 (m, 7H), 7.47 (d, 2H, J=7.5 Hz), 7.58 (s, 2H).

Preparative Example 74

Preparation of Compound Represented by Formula 75 (VVZ-082)

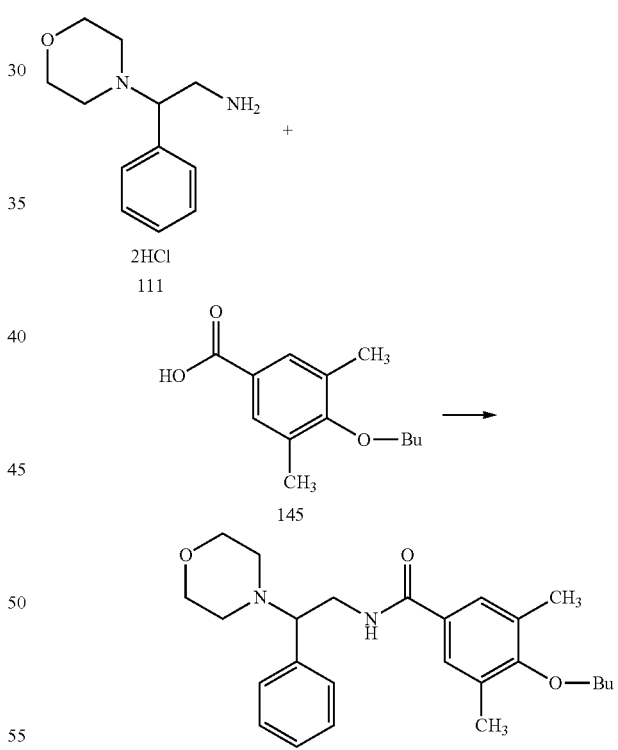

3,5-dimethyl-4-butyloxybenzoic acid represented by Formula 145 (150 mg, 0.675 mmol) was slowly added to 2-morpholin-4-yl-2-phenylethanamine dihydrochloride represented by Formula 111 (188.4 mg, 0.675 mmol, purchased from Matrix Co.) and diisopropylethylamine (0.344 mL, 1.972 mmol) in DMF (10 mL) solution at room temperature. After cooling the reaction mixture to 0° C. and adding 2-(1H-7-azabenzotriazol-1-yl)-1,1,3,3-tetramethyluronium hexafluorophosphate methanaminium (HATU, 256.6 mg, 0.675 mmol) thereto, the mixture was agitated at room temperature for 18 hours. The reaction solvent was removed under reduced pressure and chloroform/ethanol (9:1, v/v) was added to the remaining concentrate to prepare a solution. The solution was washed with a potassium carbonate ($K_2CO_3$) solution, followed by separation to form an organic layer. After drying the organic layer with magnesium sulfate ($MgSO_4$), the solvent was removed again under reduced pressure. The obtained vacuum-concentrated mixture was subjected to separation and purification through column chromatography (chloroform/methanol, 10:1, v/v) using silica gel ($SiO_2$). As a result, a benzamide compound represented by Formula 75 was obtained as a desired product (VVZ-082; 190.6 mg, 68.8% yield).

Analysis data of the produced benzamide compound is provided as follows.

$R_f$ (ethyl acetate/n-hexane/triethylamine, 2:1/0.1, v/v/v) 0.34;

$^1$H NMR (500 MHz, MeOD-$d_4$) δ 1.02 (t, 3H, J=7.2 Hz), 1.55-1.61 (m, 2H), 1.77-1.82 (m, 2H), 2.27 (s, 6H), 2.51 (br, 4H), 3.56-3.60 (m, 1H), 3.68-3.74 (m, 5H), 3.80 (t, 2H, J=6.5 Hz), 3.98-4.02 (m, 1H), 7.32-7.38 (m, 7H).

Preparative Example 75

Preparation of Compound Represented by Formula 76 (VVZ-043)

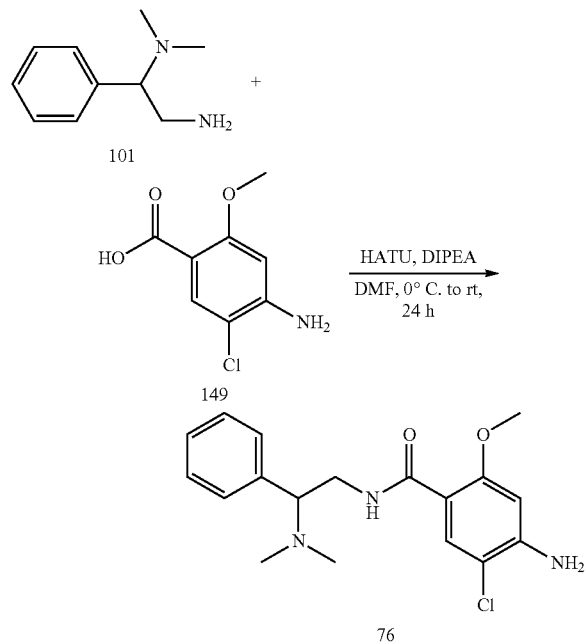

[Reaction scheme 76]

The same procedures as described in Preparative Example 2 were conducted, a compound represented by Formula 101, that is, N,N-dimethyl-1-phenylethane-1,2-diamine (98.10 mg, 0.597 mmol) and a compound represented by Formula 149, that is, 4-amino-5-chloro-2-methoxybenzoic acid (132.16 mg, 0.657 mmol) were used according to reaction scheme 76. As a result, a benzamide compound represented by Formula 76 was obtained as a desired product (VVZ-043; 77.00 mg, 37.1% yield).

Analysis data of the produced benzamide compound is provided as follows.

$^1$H-NMR (MeOD-$d_4$) d 2.23 (s, 6H), 3.46 (m, 1H), 3.56 (m, 1H), 3.60 (s, 3H), 4.03 (dd, 1H), 6.37 (s, 1H), 7.48 (m, 5H), 7.76 (s, 1H).

Preparative Example 76

Preparation of Compound Represented by Formula 77 (VVZ-044)

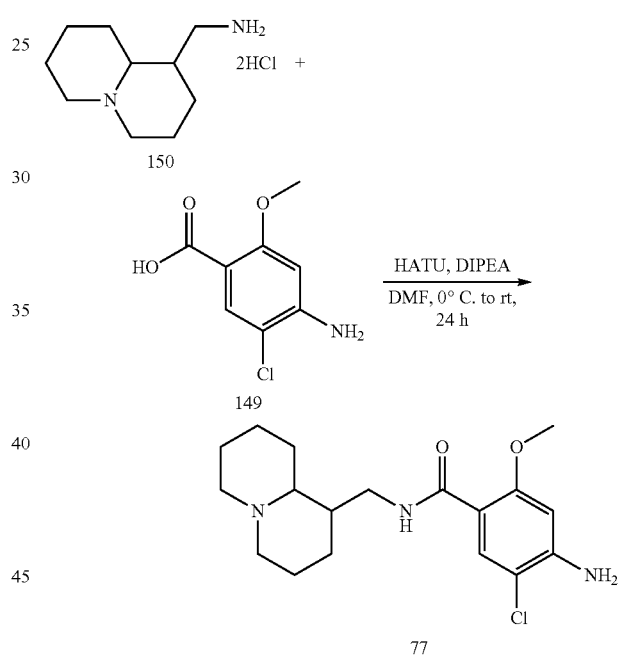

[Reaction scheme 77]

The same procedures as described in Preparative Example 2 were conducted, and a compound represented by Formula 150, that is, C-(octahydroquinolizin-1-yl)methylamine dihydrochloride (24.90 mg, 0.103 mmol) and a compound represented by Formula 149, that is, 4-amino-5-chloro-2-methoxybenzoic acid (22.84 mg, 0.114 mmol) were used according to reaction scheme 77. As a result, a benzamide compound represented by Formula 77 was obtained as a desired product (VVZ-044; 24.40 mg, 67.2% yield).

Analysis data of the produced benzamide compound is provided as follows.

$^1$H-NMR (MeOD-$d_4$) d 1.33 (m, 1H), 1.46 (m, 2H), 1.54 (m, 4H), 1.82 (m, 3H), 2.06 (m, 1H), 2.84 (m, 1H), 3.41 (m, 2H), 3.87 (s, 3H), 6.47 (s, 1H), 7.75 (s, 1H).

Preparative Example 77

Preparation of Compound Represented by Formula 78 (VVZ-047)

[Reaction scheme 78]

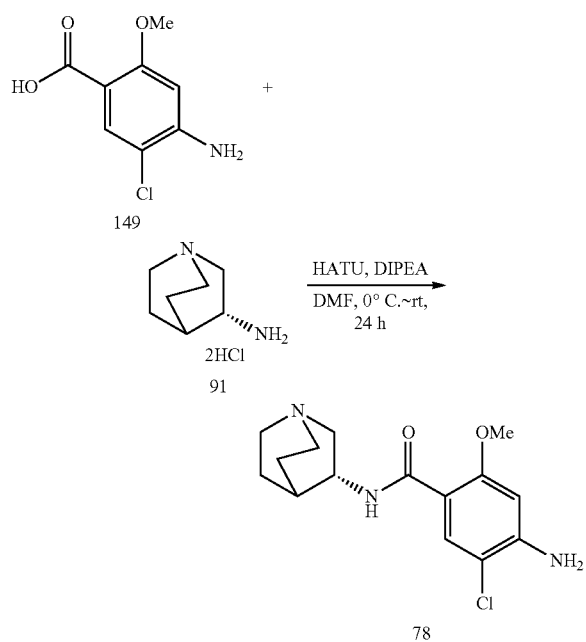

The same procedures as described in Preparative Example 2 were conducted, and a compound represented by Formula 91, that is, (R)-3-aminoquinuclidine hydrochloride (44.90 mg, 0.225 mmol) and a compound represented by Formula 149, that is, 4-amino-5-chloro-2-methoxybenzoic acid (50.01 mg, 0.248 mmol) were used according to reaction scheme 78. As a result, a benzamide compound represented by Formula 78 was obtained as a desired product (VVZ-047; 54.40 mg, 77.9% yield).

Analysis data of the produced benzamide compound is provided as follows.

$^1$H-NMR (MeOD-d$_4$) d 1.64 (m, 1H), 1.80 (m, 3H), 1.99 (m, 1H), 2.54 (m, 1H), 2.88 (m, 5H), 3.95 (s, 3H), 4.09 (m, 1H), 6.53 (s, 1H), 7.79 (m, 1H).

Preparative Example 78

Preparation of Compound Represented by Formula 79 (VVZ-049)

[Reaction scheme 79]

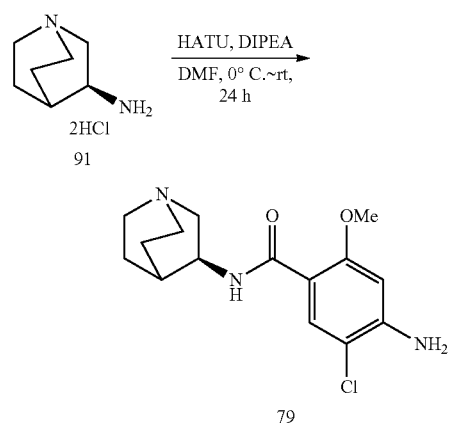

The same procedures as described in Preparative Example 2 were conducted, and a compound represented by Formula 91, that is, (S)-3-aminoquinuclidine hydrochloride (44.90 mg, 0.225 mmol) and a compound represented by Formula 149, that is, 4-amino-5-chloro-2-methoxybenzoic acid (50.01 mg, 0.248 mmol) were used according to Formula 79. A benzamide compound represented by Formula 79 was obtained as a desired product (VVZ-049; 47.50 mg, 68.0% yield).

Analysis data of the produced benzamide compound is provided as follows.

$^1$H-NMR (MeOD-d$_4$) d 1.64 (m, 1H), 1.80 (m, 3H), 1.99 (m, 1H), 2.64 (m, 1H), 2.78 (m, 1H), 2.86 (m, 2H), 2.91 (m, 2H), 3.95 (s, 3H), 4.09 (m, 1H), 6.53 (s, 1H), 7.79 (s, 1H).

Preparative Example 79

Preparation of Compound Represented by Formula 80 (VVZ-055)

[Reaction scheme 80]

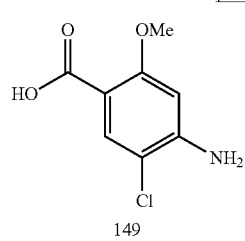

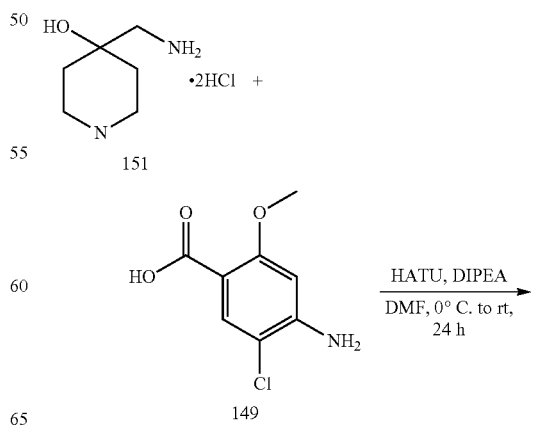

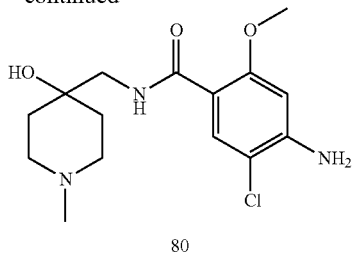

80

The same procedures as described in Preparative Example 2 were conducted, and a compound represented by Formula 151, that is, 4-aminomethyl-1-methylpiperidin-4-ol hydrochloride (58.90 mg, 0.271 mmol) and a compound represented by Formula 149, that is, 4-amino-5-chloro-2-methoxybenzoic acid (60.02 mg, 0.298 mmol) were used according to reaction scheme 80. As a result, a benzamide compound represented by Formula 80 was obtained as a desired product (VVZ-055; 44.70 mg, 50.3% yield).

Analysis data of the produced benzamide compound is provided as follows.

$^1$H-NMR (MeOD-$d_4$) d 1.75 (m, 4H), 2.51 (s, 3H), 2.79 (m, 2H), 2.88 (m, 2H), 3.45 (s, 2H), 3.97 (s, 3H), 6.51 (s, 1H), 7.83 (s, 1H).

Preparative Example 80

Preparation of Compound Represented by Formula 81 (VVZ-042)

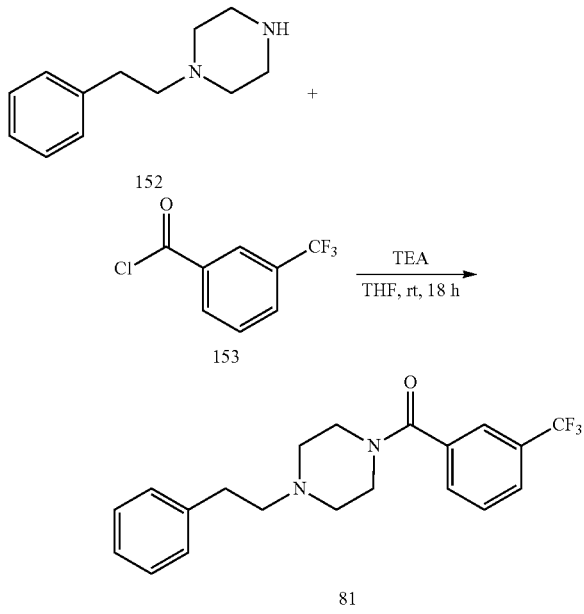

The same procedures as described in Preparative Example 1 were conducted, and a compound represented by Formula 152, that is, 1-(2-phenylethyl)piperazine (95.90 mg, 0.504 mmol) and 3-(trifluoromethyl)benzoic acid chloride represented by Formula 153 (105.11 mg, 0.504 mmol) were used according to reaction scheme 81. As a result, a benzamide compound represented by Formula 81 was obtained as a desired product (VVZ-042; 127.00 mg, 69.5% yield).

Analysis data of the produced benzamide compound is provided as follows.

$^1$H-NMR (MeOD-$d_4$) d 2.43 (m, 2H), 2.55 (m, 4H), 2.71 (m, 2H), 3.35 (m, 2H), 3.71 (m, 2H), 7.05~7.70 (m, 9H).

Preparative Example 81

Preparation of Compound Represented by Formula 82 (VVZ-062)

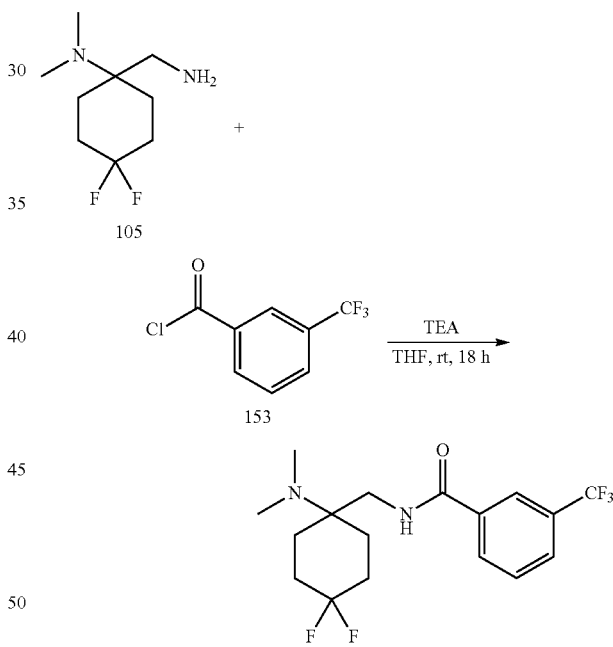

The same procedures as described in Preparative Example 1 were conducted, and a compound represented by Formula 105, that is, 1-(aminomethyl)-4,4-difluoro-N,N-dimethylcyclohexanamine (47.00 mg, 0.244 mmol) and 3-(trifluoromethyl)benzoic acid chloride represented by Formula 153 (56.09 mg, 0.269 mmol) were used according to reaction scheme 82. As a result, a benzamide compound represented by Formula 82 was obtained as a desired product (VVZ-062; 66.90 mg, 75.1% yield).

Analysis data of the produced benzamide compound is provided as follows.

¹H-NMR (MeOD-d₄) d 1.62 (m, 2H), 1.85 (m, 2H), 1.97 (m, 2H), 2.08 (m, 2H), 2.41 (s, 6H), 3.54 (s, 2H), 7.68~8.13 (m, 4H).

Preparative Example 82

Preparation of Compound Represented by Formula 83 (VVZ-078)

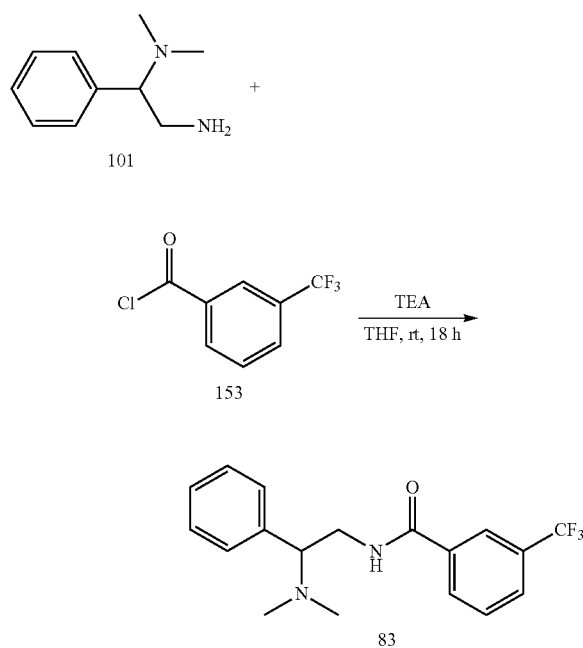

As shown in reaction scheme 83, N,N-dimethyl-1-phenylethane-1,2-diamine represented by Formula 101 (439.1 mg, 2.67 mmol, purchased from Alfa Aesar Co.) and triethylamine (0.75 mL, 5.35 mmol) in THF (10 mL) solution were cooled to 0° C. under a nitrogen atmosphere, then, 3-(trifluoromethyl)benzoic acid chloride represented by Formula 153 (613.17 mg, 2.94 mmol, purchased from TCI Co.) in THF (15 mL) solution was slowly added thereto. After agitating the mixture at the same time for 30 minutes, the mixture was left at room temperature for 18 hours. A precipitate generated during the reaction was removed through filtration. The remaining solution was diluted with chloroform and this diluted solution was washed with a potassium carbonate (K₂CO₃) solution, followed by separation and drying the same with sodium sulfate (Na₂SO₄). The obtained vacuum-concentrated mixture was subjected to separation and purification through column chromatography (ethyl acetate/hexane/triethylamine, 2:1:0.1, v/v/v) using silica gel (SiO₂), resulting in a benzamide compound represented by Formula 83 as a desired product (VVZ-078; 632.5 mg, 70% yield).

Analysis data of the produced benzamide compound is provided as follows.

R_f (ethyl acetate/hexane/triethylamine, 2:1:0.1, v/v/v) 0.4;
HRMS (EI+) calcd for C₁₈H₁₉F₃N₂O ([M+]) 336.1449.
¹H NMR (500 MHz, MeOH-d₄) d 2.27 (s, 6H), 3.70-3.72 (m, 2H), 4.00 (dd, 1H, J=4.5 Hz, 7.5 Hz), 7.28-7.37 (m, 5H), 7.60 (t, 1H, J=8.0 Hz), 7.79 (d, 1H, J=7.5 Hz), 7.87 (d, 1H, J=7.5 Hz), 7.91 (s, 1H).

Preparative Example 83

Preparation of Compound Represented by Formula 155 (VVZ-085)

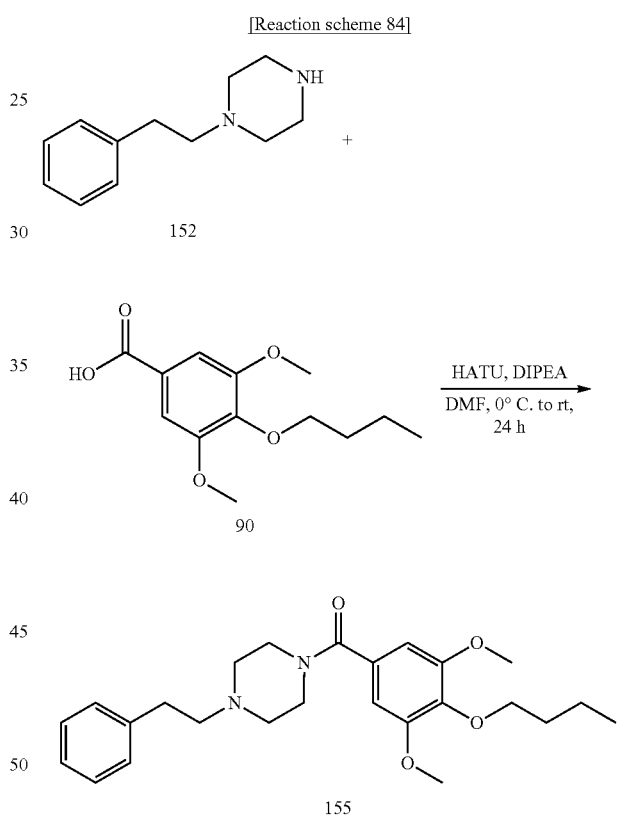

The same procedures as described in Preparative Example 2 were conducted, and a compound represented by Formula 152, that is, 1-(2-phenylethyl)piperazine (222.00 mg, 1.167 mmol) and a compound represented by Formula 90, that is, 3,5-dimethoxy-4-butoxybenzoic acid (326.34 mg, 1.283 mmol) were used according to reactive scheme 84. As a result, a benzamide compound represented by Formula 155 was obtained as a desired product (VVZ-085; 485.0 mg, 97.5% yield).

Analysis data of the produced benzamide compound is provided as follows.

$^1$H-NMR (MeOD-d$_4$+DMSO-d$_6$) d 0.96 (t, 3H), 1.53 (m, 2H), 1.68 (m, 2H), 2.54 (m, 2H), 2.64 (m, 4H), 2.84 (m, 2H), 3.53 (m, 2H), 3.79 (m, 2H), 3.82 (s, 6H), 3.95 (t, 2H), 6.70 (s, 2H), 7.15~7.27 (m, 5H).

Preparative Example 84

Preparation of Compound Represented by Formula 156 (VVZ-086)

[Reaction scheme 85]

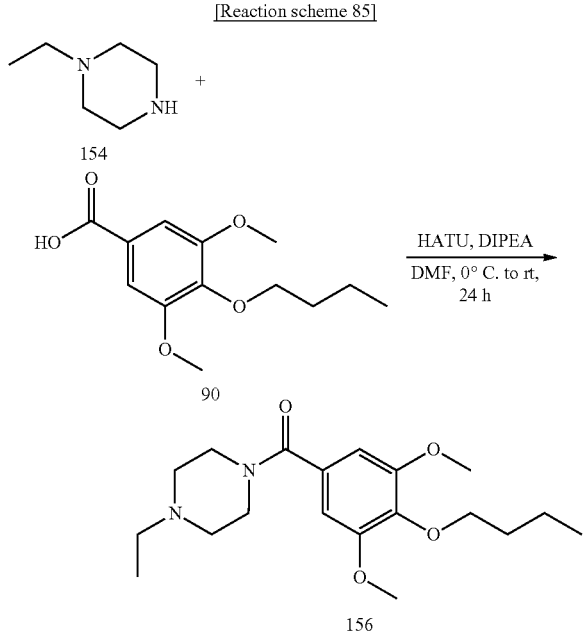

The same procedures as described in Preparative Example 2 were conducted, and a compound represented by Formula 154, that is, 1-ethylpiperazine (182.00 mg, 1.594 mmol) and 3,5-dimethoxy-4-butoxybenzoic acid represented by Formula 90 (445.81 mg, 1.753 mmol) were used according to reaction scheme 85. As a result, a benzamide compound represented by Formula 156 was obtained as a desired product (VVZ-086; 472.00 mg, 84.5% yield).

Analysis data of the produced benzamide compound is provided as follows.

$^1$H-NMR (MeOD-d$_4$) d 0.96 (t, 3H), 1.12 (t, 3H), 1.51 (m, 2H), 1.68 (m, 2H), 2.48 (q, 2H), 2.55 (m, 4H), 3.52 (m, 2H), 3.76 (m, 2H), 3.82 (s, 6H), 3.92 (t, 2H), 3.95 (m, 1H), 6.70 (s, 2H).

Preparative Example 85

Preparation of Compound Represented by Formula 157 (VVZ-087)

[Reaction scheme 86]

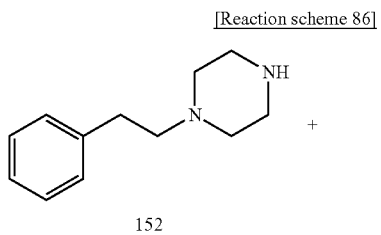

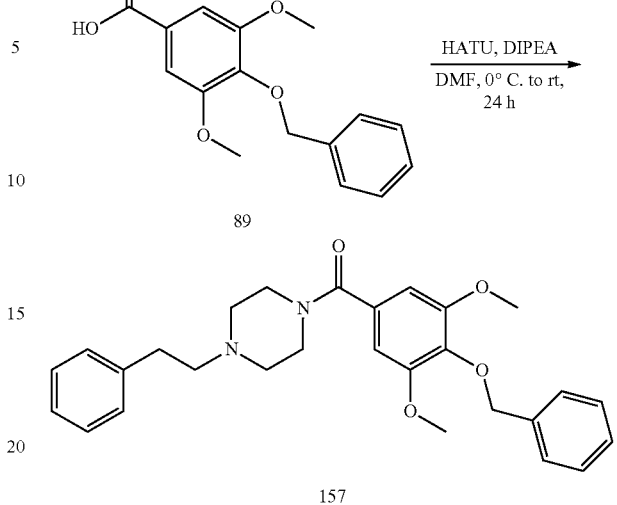

The same procedures as described in Preparative Example 2 were conducted, a compound represented by Formula 152, that is, 1-(2-phenylethyl)piperazine (134.5 mg, 0.707 mmol) and 4-benzyloxy-3,4-dimethoxybenzoic acid represented by Formula 89 (234.35 mg, 0.813 mmol) were used according to reaction scheme 86. As a result, a benzamide compound represented by Formula 157 was obtained as a desired product (VVZ-087; 312.90 mg, 96.1% yield).

Analysis data of the produced benzamide compound is provided as follows.

$^1$H-NMR (MeOD-d$_4$) d 2.5 (m, 2H), 2.64 (m, 4H), 2.82 (m, 2H), 3.49 (m, 2H), 3.76 (m, 2H), 3.84 (s, 6H), 4.98 (s, 2H), 6.69 (s, 2H), 7.15~7.45 (m, 8H).

Example 2

Determination of Multi-Target Activity

In the present example, it was demonstrated that the novel compound of the present invention simultaneously functions on both targets GlyT2 and 5HT2A which are well known as targets in association with pain.

2-1. Experiment for Determination of GlyT2 Target Activity

GlyT2 (Glycine transporter type 2) is an electrogenic carrier associated with Na$^+$/Cl$^-$ ion transportation, primarily distributed around the spinal cord part, and has an important role in the transfer of a pain signal in the spinal cord.

In order to identify the fact that the novel compound of the present invention has GlyT2 targeting activity, a membrane potential assay was performed. FLIPR Membrane Potential Assay is used to measure ion channel modulation caused by an increase or decrease in fluorescence signal due to variations of cellular membrane potential. This is based on a principle that, if (+) ions are introduced into the cell and the cellular membrane is depolarized, the fluorescence signal increases, while the fluorescence signal is reduced when (+) ions are released out of the cell to hence cause hyperpolarization.

First, pcDNA4/TO vector encoding GlyT2 of the rat in HEK293 cell was transfected to prepare a stable recombinant cell line, i.e., T-rex-293-rGlyT2. A 92 clear bottom well plate (Greiner #655090) coated with poly-D-lysine was prepared, and the above recombinant cells (T-rex-293-rGlyT2) were seeded at 3.2×10⁴/well therein using a medium containing 15 μg/ml of tetracycline. After this, incubation was conducted at 37° C. for 48 hours under 5% $CO_2$ conditions to express GlyT2. 10 ml of assay buffer (1×HBSS, 20 mM HEPES, pH 7.4) was added to a blue dye solution and sufficiently dissolved therein to prepare a membrane potential dye solution. After removing the medium from the well showing GlyT2 expression, the membrane potential dye solution was added to the well in an amount of 100 μl/well and incubated for 20 minutes.

According to the FLIPR Membrane Potential Assay kit's protocol, SoftMax Pro Software of FlexStation 3 software (Molecular Devices, US) was set up. An extent of GlyT2 expression was determined such that the extent of cellular membrane depolarization relative to an administered amount of glycine during glycine treatment is indicated in relative fluorescence units (RFU), and RFU (Max-Min) is calculated by subtracting the minimum value from the maximum value of RFU. After firstly treating 10 uM of the novel compound according to the present invention, glycine was treated and RFU (Max-Min) for glycine administration was determined. Then, with the determined result, the extent of depolarization inhibition (% inhibition) was assessed for each compound, compared to a positive control.

The positive control used herein was ORG25543 (500 nM) having strong inhibitory efficacy specific to GlyT2.

2-2. Experiment for Determination of 5HT2A Target Activity

Since 5HT2A is a G protein-coupled receptor (GPCR) included in a serotonin receptor family, an experiment using a calcium assay was performed. A calcium assay is based on a principle that, when a ligand is bonded to a receptor, a calcium ion ($Ca^{2+}$) is released into cytoplasm and combined with dye in a cell to generate a fluorescence signal.

First, HEK293 cells were seeded in a 92 clear bottom well plate (Greiner #655090) at 2.0-8.0×10⁴/well. After 24 hours, transfection was performed using lipofectamine 2000 (Introgen #11668-019). 24 hours after the transfection, a medium was removed from each well and a calcium dye put into the well with 100 μl per well, followed by incubation. According to the FLIPR Calcium Assay Kit's protocol, SoftMax Pro Software of FlexStation 3 software (Molecular Devices, US) was set up. After firstly treating 10 uM of the novel compound according to the present invention, serotonin was treated and the extent of calcium flux in the cell in relation to serotonin administration was determined in terms of RFU (Max-Min) value. Then, the extent of calcium flux inhibition (% inhibition) was assessed for each compound, compared to a positive control.

The positive control used herein was MDL11939 (100 nM) having strong inhibitory efficacy specific to 5HT2A.

2-3. Experimental Results: Determination of Multi-Target Activity

For GlyT2 inhibitory efficacy, the efficacy of the compound ORG25543 (500 nM) was defined as 100%. Similarly, for 5HT2A inhibitory efficacy, the efficacy of MDL11939 (100 nM) was defined as 100%. Therefore, the target inhibitory efficacy of each compound was indicated in a relative value compared to the above defined efficacy.

As shown in Table 1 below, it was demonstrated that the inventive compound simultaneously functioned on two targets. Accordingly, it may be understood that the novel compound of the present invention can be used as a novel pain therapeutic agent to overcome problems of a conventional drug containing a material strongly but selectively acting on a single target.

TABLE 1

| Formula | Compound Serial No. | GlyT2 % inhibition | 5HT2A % inhibition |
|---|---|---|---|
| Formula 4 | VVZ-003 | 78.2 | 31.6 |
| Formula 6 | VVZ-005 | 101.3 | 61.2 |
| Formula 7 | VVZ-006 | 48.9 | 89.8 |
| Formula 8 | VVZ-009 | 116.7 | 90.4 |
| Formula 9 | VVZ-010 | 102.5 | 108.1 |
| Formula 10 | VVZ-011 | 88.8 | 56.2 |
| Formula 11 | VVZ-012 | 117.9 | 76.1 |
| Formula 12 | VVZ-013 | 72.9 | 48.5 |
| Formula 13 | VVZ-014 | 75.0 | 93.6 |
| Formula 14 | VVZ-015 | 108.0 | 57.0 |
| Formula 15 | VVZ-016 | 109.3 | 97.5 |
| Formula 17 | VVZ-018 | 76.8 | 70.7 |
| Formula 19 | VVZ-020 | 102.6 | 94.1 |
| Formula 23 | VVZ-024 | 96.7 | 70.5 |
| Formula 27 | VVZ-028 | 87.9 | 93.9 |
| Formula 28 | VVZ-029 | 46.0 | 71.3 |
| Formula 32 | VVZ-033 | 104.9 | 97.1 |
| Formula 34 | VVZ-035 | 84.8 | 100.8 |
| Formula 35 | VVZ-036 | 103.2 | 66.1 |
| Formula 36 | VVZ-037 | 100.3 | 99.8 |
| Formula 47 | VVZ-038 | 108.2 | 96.1 |
| Formula 38 | VVZ-041 | 79.2 | 105.1 |
| Formula 81 | VVZ-042 | 34.4 | 107.2 |
| Formula 64 | VVZ-046 | 113.4 | 54.2 |
| Formula 78 | VVZ-047 | 23.4 | 78.8 |
| Formula 39 | VVZ-050 | 116.7 | 107.8 |
| Formula 50 | VVZ-051 | 110.5 | 95.0 |
| Formula 51 | VVZ-052 | 76.6 | 102.8 |
| Formula 65 | VVZ-053 | 59.6 | 31.4 |
| Formula 66 | VVZ-054 | 82.9 | 57.1 |
| Formula 80 | VVZ-055 | 55.3 | 146.1 |
| Formula 67 | VVZ-057 | 101.3 | 65.7 |
| Formula 68 | VVZ-058 | 101.7 | 134.0 |
| Formula 69 | VVZ-059 | 101.9 | 56.1 |
| Formula 53 | VVZ-060 | 59.3 | 77.0 |
| Formula 54 | VVZ-061 | 96.0 | 113.0 |
| Formula 70 | VVZ-063 | 112.3 | 76.7 |
| Formula 56 | VVZ-065 | 105.1 | 107.8 |
| Formula 41 | VVZ-068 | 105.4 | 69.1 |
| Formula 58 | VVZ-069 | 83.9 | 150.3 |
| Formula 42 | VVZ-071 | 78.8 | 60.8 |
| Formula 59 | VVZ-072 | 59.1 | 101.2 |
| Formula 44 | VVZ-074 | 73.5 | 154.9 |
| Formula 60 | VVZ-076 | 50.6 | 113.1 |
| Formula 61 | VVZ-077 | 42.2 | 121.4 |
| Formula 74 | VVZ-080 | 40.6 | 113.1 |
| Formula 62 | VVZ-081 | 45.3 | 71.5 |
| Formula 46 | VVZ-084 | 79.0 | 94.4 |

Example 3

Determination of Pain Suppression Efficacy of Each Compound in Neuropathic Pain Model (Chung Model)

3-1. Test Animal

In the present example, Sprague-Dawley male rats weighing 100 to 120 g were purchased from Core-tech (Pyeongtaek, Gyeonggi-do, Korea) and used. The rats were kept in a clean room at a constant temperature and humidity with a 12 hour lighting period. Feed and water were freely provided during the experiment.

3-2. Determination of Pain Suppression Efficacy of Each Compound in Neuropathic Pain Model (Chung Model)

Chung model (SNL model) is an animal model for neuropathic pain and widely used as a gold standard for pain animal models in worldwide global pharmaceutical companies.

After anesthetizing the test animal in Example 3-1, that is, the rat by isoflurane inhalation, left lumbar nerves L5 and L6 were tightly tied at ends of dorsal ganglia and at a front of an entrance to a sciatic nerve using a stitching fiber (6-0 silk suture) according to a known document (Kim and Chung (1992), *Pain* 50(3): 355-63)). After suturing a cut part of the rat, the rat was placed in a standard living environment to recover within 2 weeks. The above procedures induced physical abnormal pain at the left hind leg of the rat. In order to determine such a physical (tactile) abnormal pain, the rat was placed in a custody box having a wire mesh on the bottom. While applying gradually increased stimulus to the surface of the sole of the foot to which nerve injury was inflicted (using von Frey filament with a range of 0.41 to 15.8 g), a stimulus intensity at which a pain response (behavior such that the rat quickly takes its feet off, and licks or sucks its paws) was observed, and recorded. According to the study of Chaplan et al. (1994) (Chaplan et al. (1994) *J. Neurosci. Methods* 53(1): 55-63), paw withdrawal threshold (PWT) was determined while continuously increasing or decreasing the stimulus intensity. The determined results were assessed by applying Dixon's up-down manner. Only rats without behavior disorder (ex., feet dragging or dangling) were screened and used in the study and the rats used herein had PWT of not more than 3.16 g. Measurement was done before and 2 weeks after surgical operation.

After measuring an extent of basic response before drug injection, each of compounds represented by Formulae 2, 3, 6, 10, 12, 15, 19, 20, 23, 24, 28, 31, 37, 38, 41, 47, 59, 60, 65, 81, 82 and 83 (the compounds represented by Formulae 2, 6, 12, 15, 23, 24, 28, 31, 41 may use a hydrochloric acid salt) and a solvent were administered by subcutaneous injection (50 mg/kg) or oral administration (100 mg/kg) and, after drug injection, the measurement was repeated at constant intervals (30 minutes and 60 minutes for subcutaneous administration, and 60 minutes and 120 minutes or 60 minutes and 90 minutes for oral administration).

An examiner for PWT measurement carried out the measurement under a blind test condition that does not indicate which drugs are administered to which rats for testing and, during measurement, control rats administered with gabapentin (55 to 70 mg/kg, intraperitoneal administration) were also randomly mixed with the test rats. The measured PWT was used for calculating recovery from pain (% reversal) according to Equation 1 below, thus enabling statistical analysis. With high reversal (%), it means that abnormal pain is considerably alleviated after drug administration.

Recovery from Pain (% reversal)=[(PTW after drug administration)−(PTW before drug administration]*100/[(15 g as estimated PWT of normal animal)−(PWT before drug administration)]  <Equation 1>

PWT used herein is a logarithmic value of 'gram value' (as a measuring unit of force)×10,000, which is generally used in the art.

For PWT measurement, the examiner evaluated the extent of sedation of activity or sense in a five-point scale, in order to determine side effects of the administered drug to the central nervous system. Herein, the 0 point denotes normal sensory awareness so as to be normally active, while 5 points means significant sedation in activity or sensory awareness to such an extent that the test rat may almost fall asleep.

Although every experiment has been performed for a group of compounds, a group of solvents for the compounds, gabapentin (GBP) as a positive control, and a group of solvents for gabapentin (100% PBS), the experiment may be optionally omitted for the PBS group. For subcutaneous administration, a solvent for compounds may mostly comprise a solvent of DMA/PG in 2:8, that is, a solvent mixture of dimethylacetamide and propyleneglycol in 2:8. According to solubility, 5:5 DMA/PG or 100% DMSO was optionally used. For oral administration, a solvent for compounds used herein was 20% hydroxypropyl beta-cyclodextrin (HPCD), 0.5% hydroxypropyl methyl cellulose (HPMC) or PEC 400 (polyethyleneglycol 400).

Therefore, as shown in FIGS. 1 to 22, it was observed that abnormal pain was significantly decreased when the novel benzamide compound or salt thereof according to the present invention was used for subcutaneous administration or oral administration. In particular, it was observed that the compound represented by Formula 6 (VVZ-005), compound represented by Formula 23 (VVZ-024), compound represented by Formula 24 (VVZ-025), compound represented by Formula 31 (VVZ-032), compound represented by Formula 47 (VVZ-038), compounds represented by Formula 37 (VVZ-040), compound represented by Formula 38 (VVZ-041), compound represented by Formula 82 (VVZ-062), compound represented by Formula 41 (VVZ-068), and compound represented by Formula 83 (VVZ-078) exhibit analgesic efficacy substantially equal to 0° C. superior to GBP of a positive control.

Further, in order to determine whether the inventive compound exhibits pain-suppressive affects not only neuropathic pain but also other pains, the compound represented by Formula 6 (VVZ-005) and compound represented by Formula 41 (VVZ-068) among the compounds having excellent effects as described above were subjected to further experiments as follows.

Example 4

Determination of Pain Suppression Efficacy of Each Compound in Formalin Model

A formalin model is an experimental model representative of nociceptive pain and hyperalgesia in association with tissue damage and infection caused by direct subcutaneous injection of formalin on the sole of a foot of a rat. This model is a pain model having various pain features and derives so strong a pain that it cannot be cured or relieved by any substance except for morphine.

First, the test animal in Example 3-1, that is, a rat was used. 50 μl of 5% formalin (Samchun, Korea) was directly administered to the sole of a foot of the rat through intraplantar injection (i.pl.), to induce an infective response as well as tissue damage. The compound represented by Formula 6 (VVZ-005, used in an HCl salt form) and compound represented by Formula 41 (VVZ-068) were i.pl. administered at concentrations of 12.5, 25 and 50 mg/kg, respectively. As a positive control, 3 mg/kg of morphine was i.pl. administered. The efficacy of each drug was observed. By measuring a period of time to show typical pain behaviors such as licking and shaking, the extent of pain was assessed.

Figure 23:
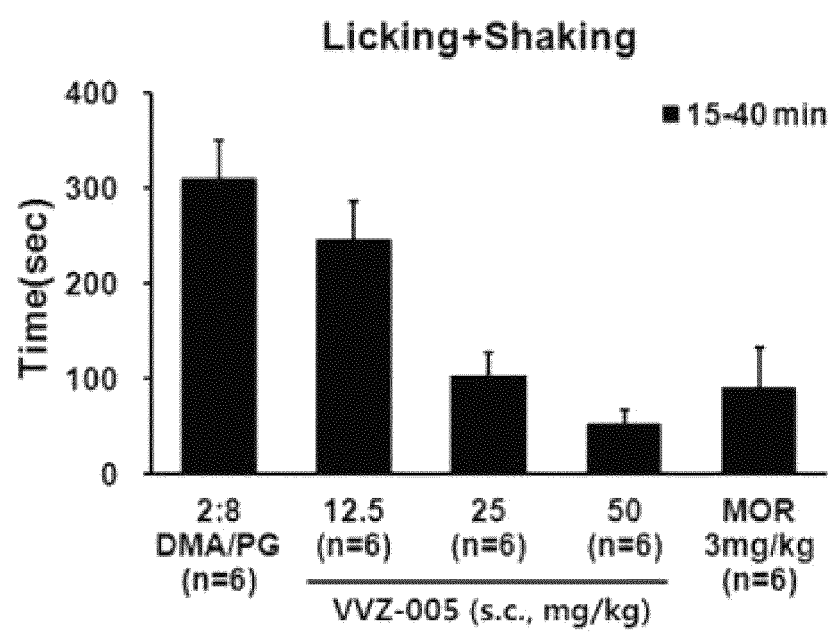
FIG. 23 is a graph showing a pattern of suppressing pain behavior induced by formalin in a compound VVZ-005 represented by Formula 6 in a formalin model.
Figure 24:
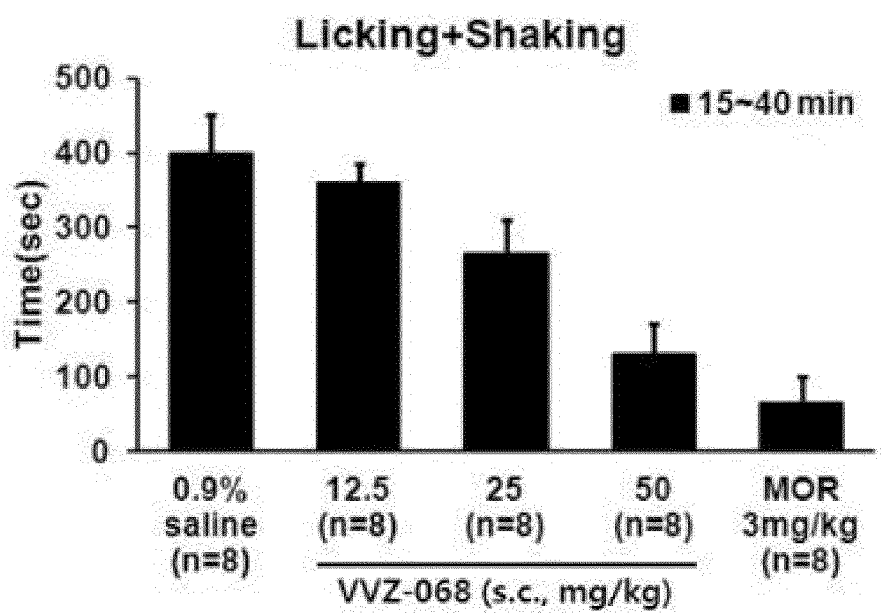
FIG. 24 is a graph showing a pattern of suppressing pain behavior induced by formalin in a compound VVZ-068 represented by Formula 41 in a formalin model.

As a result, it was found from FIGS. 23 and 24 that the inventive compound and its salt decreased pain behavior expressed by licking and shaking caused by formalin, in dose-dependent manner.

These results suggested that the inventive compound and pharmaceutically acceptable salt thereof may effectively act on suppression of various pains including, for example, nociceptive pain, chronic pain, etc. as well as neuropathic pain.

In order to identify that a mechanism, by which the inventive compound and pharmaceutically acceptable salts thereof have excellent analgesic efficacy on a number of various types of pains, is based on synergistic effects obtained by multi-target activity simultaneously acting on both of a GlyT2 target and a 5HT2A target, the following experiments were conducted.

Example 5

Synergistic Effect of 5HT2A Antagonist and GlyT2 Antagonist to Analgesic Efficacy in Neuropathic Pain Model (Chung Model)

The present example was conducted to identify that combined treatment using both of a 5HT2A antagonist (MDL 11,939) and a GlyT2 antagonist (ORG-25543) can induce synergistic effects with regard to analgesic efficacy expressed in a neuropathic pain model (Chung model).

Using the test animal in Example 3-1 and according to the method described in Example 3-2, MDL 11,939 and ORG-25543 were applied alone or as a combination thereof, followed by observation of pain relieving effect.

MDL 11,939 (Tocris Bioscience, USA) and ORG-25543 (CBvest inc, Korea) dissolved in 2:8 DMA/PG were i.pl. administered alone or as an instant combination thereof to the above animal model and, 30 minutes and 60 minutes after administration, the extent of pain suppression was assessed.

Figure 25:
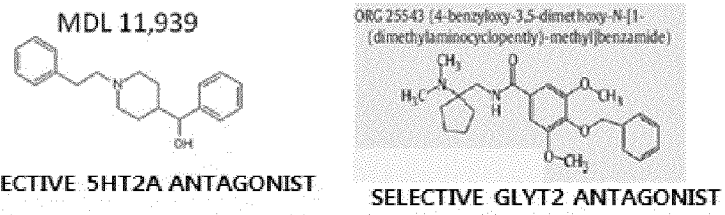
FIG. 25 is a graph showing synergistic analgesic effect when combined treatment is conducted using both 5HT2A antagonist (MDL, 11,939) and GlyT2 antagonist (ORG-25543) in a neuropathic pain model (i.e., Chung model).
Figure 25:
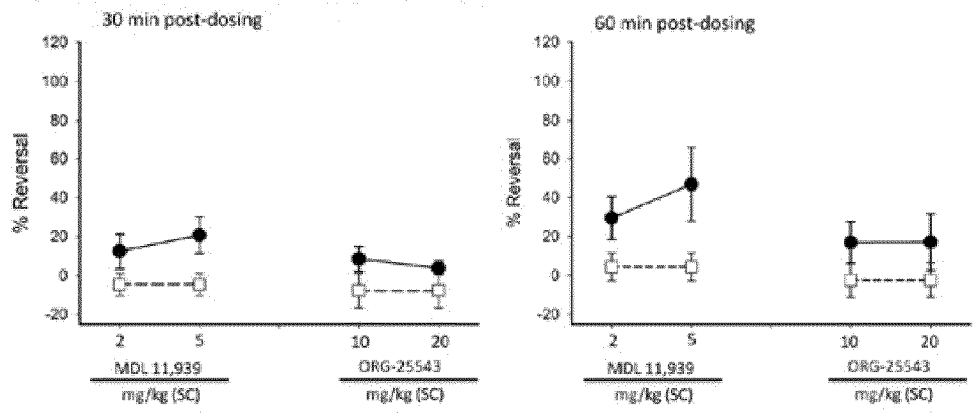
Figure 25:
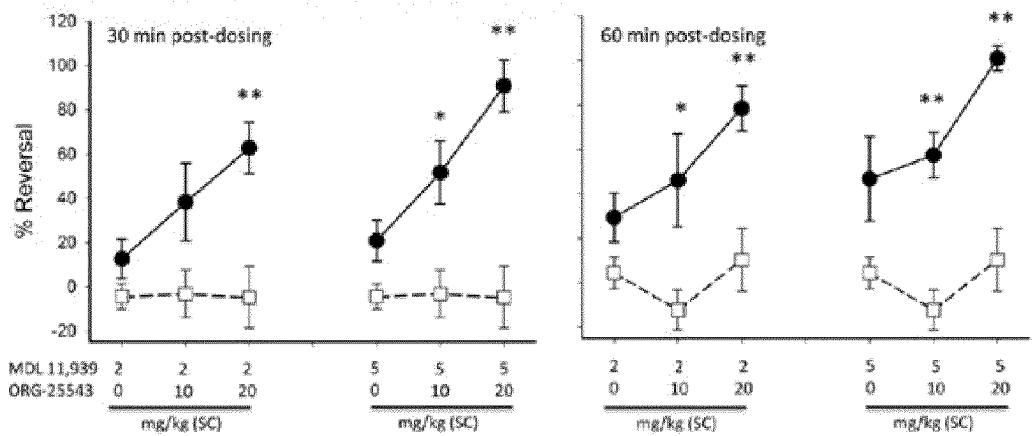

As a result, it was found from FIG. 25 that synergistic effects was expressed by a combination of a 5HT2A antagonist, that is, MDL 11,939 (2 or 5 mg/kg, s.c) and a GlyT2 antagonist, that is, ORG-25543 (10 or 20 mg/kg, s.c.) in the neuropathic pain model. For ORG-25543, treatment using this antagonist alone in the amount of 10 or 20 mg/kg did not show pain suppression efficacy (FIG. 25(a), single administration). In contrast, even with such a non-effective amount as described above, combined administration of ORG-25543 and MDL 11,939 exhibited analgesic efficacy to relieve physically abnormal pain derived by the neuropathic pain model in a dose-dependent manner (*p<0.05; **p<0.01) (FIG. 25(b), combined administration).

Example 6

Synergistic Effect of 5HT2A Antagonist and GlyT2 Antagonist to Analgesic Efficacy in Formalin Pain Model The present example was conducted to identify that combined treatment using a 5HT2A antagonist (MDL 11,939, Tocris Bioscience, USA) and a GlyT2 antagonist (ORG-25543) can induce synergistic effects with regard to analgesic efficacy expressed in a formalin-derived pain model.

Using the test animal in Example 3-1 and the formalin pain model described in Example 4, MDL 11,939 and ORG-25543 were applied alone or as a combination thereof, 10 minutes after formalin administration, followed by observation of pain relieving effect.

Figure 26:
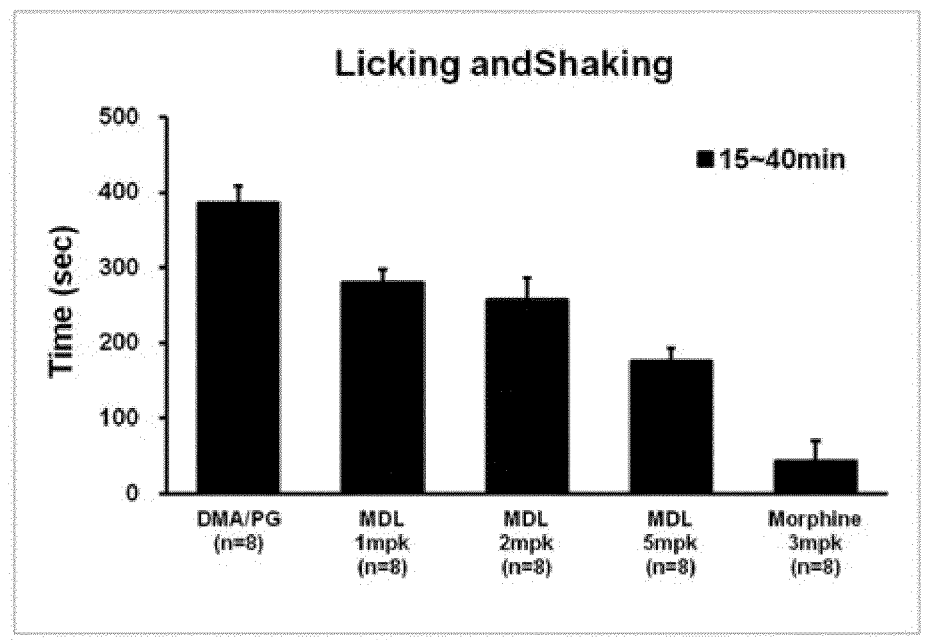
FIG. 26 is a graph showing synergistic analgesic effect when combined treatment is conducted using both 5HT2A antagonist (MDL 11,939) and GlyT2 antagonist (ORG-25543) in a formalin model.
Figure 26:
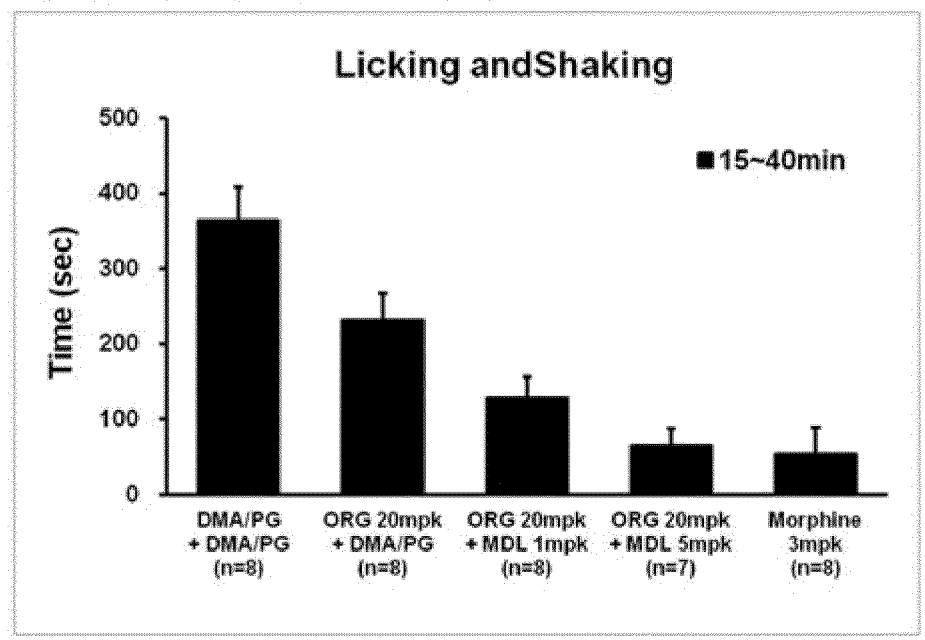

As a result, it was found from FIG. 26 that, compared to single administration of a 5HT2A antagonist, that is, MDL 11,939 (1, 2 or 5 mg/kg, s.c) or a GlyT2 antagonist, that is, ORG-25543 (20 mg/kg, s.c), respectively (FIG. 26(a)), combined administration of both antagonists (FIG. 26(b)) showed improved pain relieving effect (*p<0.05; **p<0.01; bar=average).

Further, with reference to a close correlation of peripheral bases between two senses, pain and itching, the mechanism and treatment concept established with regard to pain was also applied to itching. Although gabapentin, widely used as a neuropathic pain therapeutic agent, has been adopted for itching therapeutics in some examples known in the art, effective itching therapeutics still have to be developed. Hereinafter, further experiments were conducted to identify that a novel benzamide derivative and pharmaceutically acceptable salts thereof according to the present invention have anti-pruritic efficacy.

Example 7

Determination of Anti-Pruritic Efficacy of Each Compound in Itching Model

An itching-deriving substance may include histamine, serotonin, poly-L-arginine, etc. An animal model, that is, a rat with itching derived by intradermal injection of serotonin or poly-L-arginine on the dorsal skin of the rat was used.

Test animals in Example 3-1 were divided into two groups and theses groups had itching derived by intradermal injection of serotonin (25 µg/50 µl) and poly-L-arginine (200 µg/50 µl), respectively, on the dorsal skin of the animal. Next, the compound represented by Formula 6 (VVZ-005, used in an HCl salt form) and compound represented by Formula 41 (VVZ-068), respectively, were s.c. administered in an amount of 50 mg/kg and, alternatively, naloxone at a concentration of 5 mg/kg was intraperitoneally administered as a positive control. For these materials, drug efficacy was observed. By measuring number and duration of scratching at an itching-derived site, itching extent was assessed.

Figure 27:
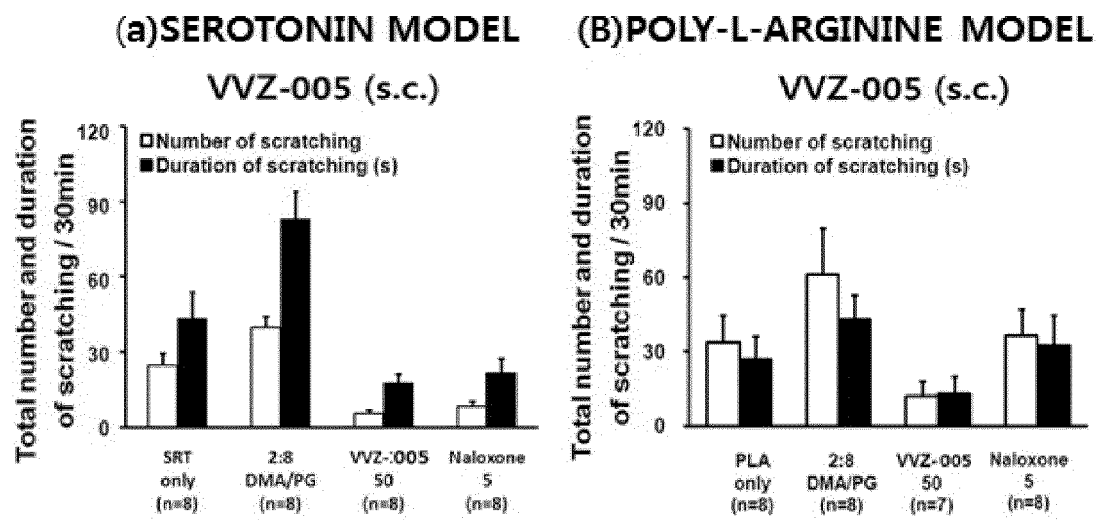
FIG. 27 is a graph showing a pattern of suppressing itching behavior induced by; (a) serotonin, and (b) poly-L-arginine of a compound represented by Formula 6 (VVZ-005) in an itching model.
Figure 28:
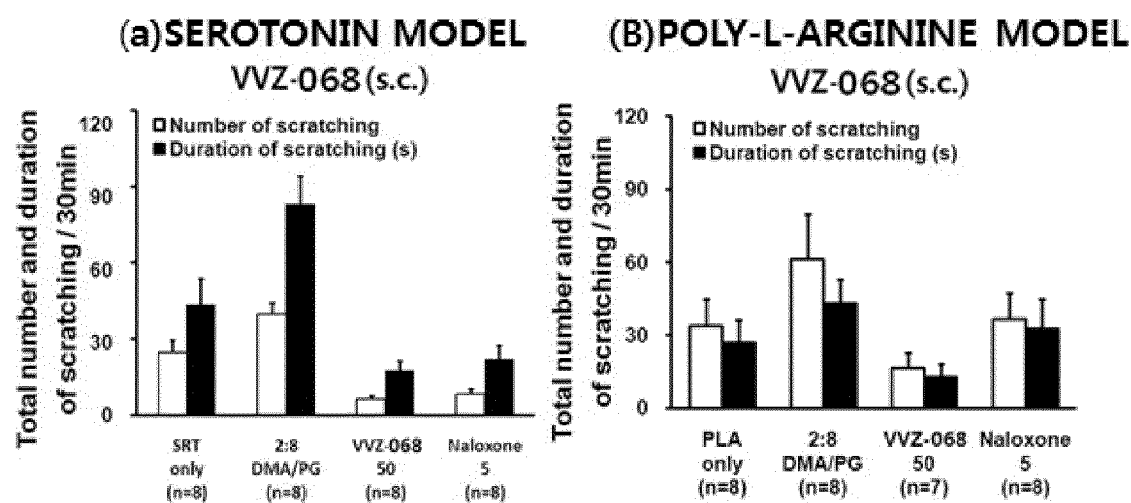
FIG. 28 is a graph showing a pattern of suppressing itching behavior induced by; (a) serotonin, and (b) poly-L-arginine of a compound represented by Formula 41 (VVZ-068) in an itching model.

As a result, it was found from FIGS. 27 and 28 that the inventive compound and its salt suppressed serotonin or poly-L-arginine-derived itching much more effectively, compared to the positive control, that is, naloxone administration. Herein, (a) in the above figures denotes the serotonin model while (b) denotes the poly-L-arginine model.

The above result suggested that the inventive compound and pharmaceutically acceptable salt may exhibit not only pain-suppressive effects but also anti-pruritic efficacy, and additionally, may effectively function as a composition for treatment and/or prevention of pruritus including atopic dermatitis.

Although the present invention has been described in connection with the exemplary embodiments illustrated in the drawings, it is only illustrative. It will be understood by those skilled in the art that various modifications and equivalents can be made to the present invention. Therefore, the true technical scope of the present invention should be defined by the appended claims.

The invention claimed is:

1. A benzamide derivative represented by Formula 1 below or a pharmaceutically acceptable salt thereof:

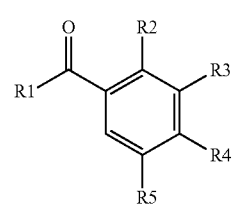

[Formula 1]

wherein:
 $R_1$ is $NHR_6$;
 $R_2$ is hydrogen, $(C_1-C_6)$ alkyl, or $(C_1-C_6)$ alkoxy;
 $R_3$ is hydrogen, $(C_1-C_6)$ alkyl or $(C_1-C_6)$ alkoxy having at least one hydrogen atom substituted or unsubstituted with halogen;

R₄ is hydroxyl group, (C₁-C₆) alkoxy, (C₄-C₆) aromatic cycloalkoxy, (C₃-C₆) aliphatic cycloalkoxy, or (C₁-C₆) alkylalkoxy substituted with at least one (C₄-C₆) aromatic ring or one (C₃-C₆) aliphatic ring;

R₅ is (C₁-C₆) alkyl, (C₁-C₆) alkoxy, or halogen; and

R₆ is CH₂R₁₁, wherein R₁₁ is a (C₅-C₆) aliphatic heterocyclic or aromatic heterocyclic group having at least one carbon atom replaced by O, wherein the aliphatic heterocyclic ring or aromatic heterocyclic ring of R₁₁ is substituted with at least one substituent selected from a group consisting of (C₁-C₆) alkyl, hydroxy, NR₂₁R₂₂, halogen, and (C₅-C₆) aliphatic heterocyclic or aromatic heterocyclic group having at least one carbon atom replaced by O or N, wherein R₂₁ and R₂₂ are independently each hydrogen, (C₁-C₆) alkyl, or benzyl.

2. The benzamide derivative or pharmaceutically acceptable salt thereof according to claim 1, wherein:

R₂ is hydrogen or methoxy (—OCH₃),

R₃ is hydrogen, methyl (—CH₃), methoxy (—OCH₃), or trifluoromethyl (—CF₃),

R₄ is butoxy (—O(CH₂)₃CH₃) or benzyloxy (—OCH₂C₆H₅), and

R₅ is methyl (—CH₃), methoxy (—OCH₃), or chlorine (—Cl).

3. The benzamide derivative or pharmaceutically acceptable salt thereof according to claim 1, wherein the compound represented by Formula 1 is selected from a group consisting of Formula 6, 35, 38, 40, 41, 43-46, and 73:

[Formula 6]

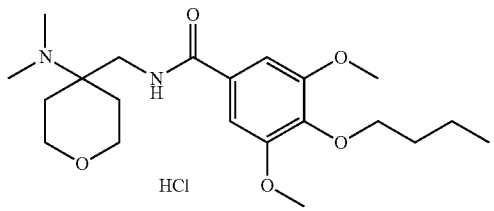

[Formula 35]

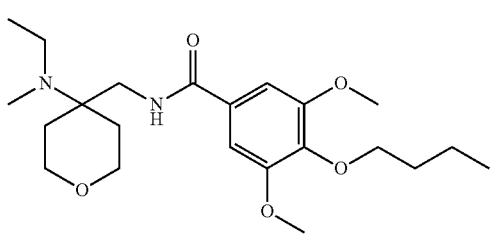

[Formula 38]

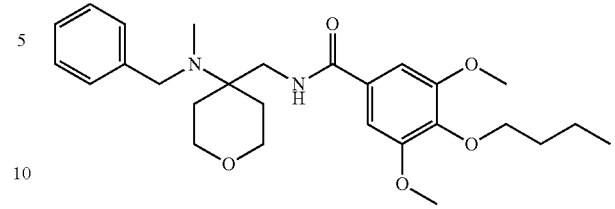

[Formula 40]

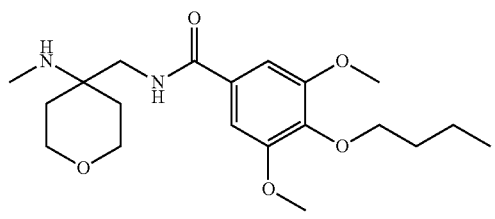

[Formula 41]

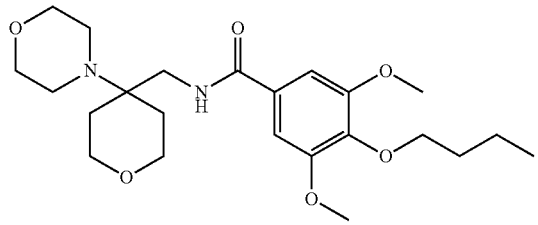

[Formula 43]

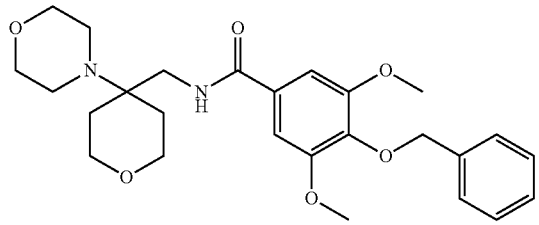

[Formula 44]

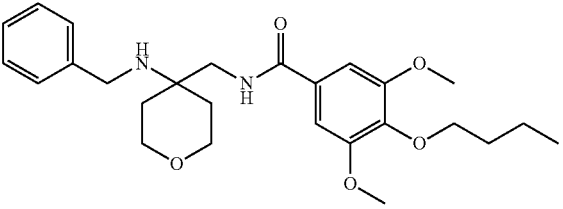

[Formula 45]

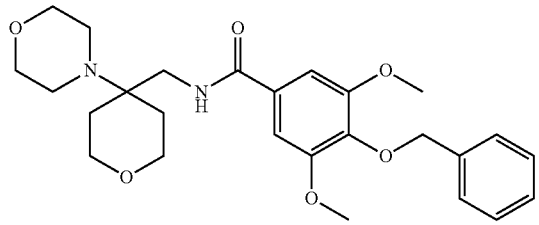

[Formula 46]

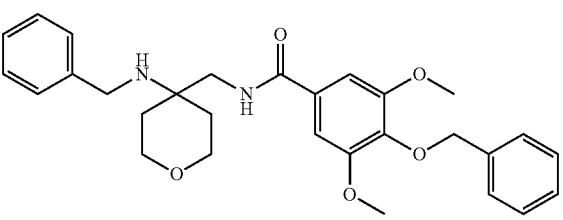

-continued

[Formula 73]

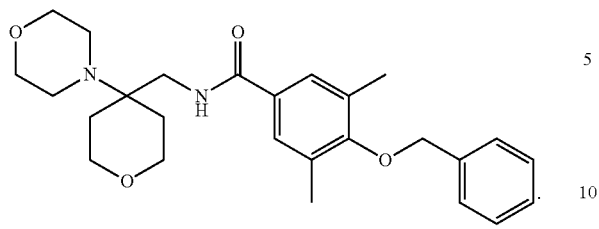

4. The benzamide derivative or pharmaceutically acceptable salt thereof according to claim 1, wherein the benzamide derivative or its pharmaceutically acceptable salt is an antagonist of Glycine Transporter 2 (GlyT2) and 5-hydroxytryptamine subtype 2 (5HT2) receptor simultaneously.

5. A composition for treatment of pain or pruritus, comprising the benzamide derivative or pharmaceutically acceptable salt thereof according to claim 1.

* * * * *